United States Patent
Geuijen et al.

(10) Patent No.: US 12,139,548 B2
(45) Date of Patent: *Nov. 12, 2024

(54) ANTIBODY THAT BINDS ErbB-2 AND ErbB-3

(71) Applicant: Merus N.V., Utrecht (NL)

(72) Inventors: Cecilia Anna Wilhelmina Geuijen, Utrecht (NL); Cornelis Adriaan De Kruif, Utrecht (NL); Mark Throsby, Utrecht (NL); Ton Logtenberg, Utrecht (NL); Alexander Berthold Hendrik Bakker, Utrecht (NL)

(73) Assignee: Merus N.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/047,933

(22) Filed: Oct. 19, 2022

(65) Prior Publication Data

US 2023/0242669 A1    Aug. 3, 2023

Related U.S. Application Data

(60) Continuation of application No. 17/675,431, filed on Feb. 18, 2022, which is a division of application No. 15/121,623, filed as application No. PCT/NL2015/050125 on Feb. 27, 2015, now Pat. No. 11,279,770.

(30) Foreign Application Priority Data

Feb. 28, 2014 (EP) .................................... 14157360
May 5, 2014 (EP) .................................... 14167066

(51) Int. Cl.
| | |
|---|---|
| A61K 39/00 | (2006.01) |
| A61K 31/185 | (2006.01) |
| A61K 31/337 | (2006.01) |
| A61K 31/436 | (2006.01) |
| A61K 31/4375 | (2006.01) |
| A61K 31/4439 | (2006.01) |
| A61K 31/519 | (2006.01) |
| A61K 39/395 | (2006.01) |
| C07K 16/30 | (2006.01) |
| C07K 16/32 | (2006.01) |

(52) U.S. Cl.
CPC ............ *C07K 16/32* (2013.01); *A61K 31/185* (2013.01); *A61K 31/337* (2013.01); *A61K 31/436* (2013.01); *A61K 31/4375* (2013.01); *A61K 31/4439* (2013.01); *A61K 31/519* (2013.01); *A61K 39/39558* (2013.01); *C07K 16/30* (2013.01); *A61K 2039/505* (2013.01); *C07K 2317/24* (2013.01); *C07K 2317/31* (2013.01); *C07K 2317/526* (2013.01); *C07K 2317/55* (2013.01); *C07K 2317/565* (2013.01); *C07K 2317/732* (2013.01); *C07K 2317/76* (2013.01); *C07K 2317/92* (2013.01)

(58) Field of Classification Search
CPC ................................................ A61K 2039/505
See application file for complete search history.

(56) References Cited

U.S. PATENT DOCUMENTS

| | | | |
|---|---|---|---|
| 4,801,687 A | 1/1989 | Ngo | |
| 4,816,567 A | 3/1989 | Cabilly et al. | |
| 5,151,504 A | 9/1992 | Croze | |
| 5,731,168 A | 3/1998 | Carter et al. | |
| 7,642,228 B2 | 1/2010 | Carter et al. | |
| 7,705,103 B2 | 4/2010 | Sherman et al. | |
| 8,349,574 B2 | 1/2013 | Bates et al. | |
| 8,592,562 B2 | 11/2013 | Kannan et al. | |
| 8,628,774 B2 | 1/2014 | Gurney et al. | |
| 9,220,775 B2 | 12/2015 | Chowdhury et al. | |
| 9,248,181 B2 | 2/2016 | De Kruif et al. | |
| 9,248,182 B2 | 2/2016 | De Kruif et al. | |
| 9,358,286 B2 | 6/2016 | De Kruif et al. | |
| 9,551,208 B2 | 1/2017 | Ma et al. | |
| 10,844,127 B2 * | 11/2020 | Logtenberg | C07K 16/32 |
| 11,279,770 B2 | 3/2022 | Geuijen et al. | |
| 11,780,925 B2 * | 10/2023 | Throsby | A61K 39/39558 |
| | | | 424/143.1 |
| 11,820,825 B2 * | 11/2023 | Logtenberg | C07K 16/32 |
| 2003/0078385 A1 | 4/2003 | Arathoon et al. | |
| 2004/0071696 A1 | 4/2004 | Adams et al. | |
| 2006/0212956 A1 | 9/2006 | Crocker et al. | |

(Continued)

FOREIGN PATENT DOCUMENTS

| | | |
|---|---|---|
| JP | 2011508604 A | 3/2011 |
| JP | 2012509259 A | 4/2012 |

(Continued)

OTHER PUBLICATIONS

Phillips et al. (Breast Cancer Res. Treat. Jan. 2022; 191 (2): 303-317).*

(Continued)

*Primary Examiner* — Stephen L Rawlings
(74) *Attorney, Agent, or Firm* — Sterne, Kessler, Goldstein & Fox P.L.L.C.

(57) ABSTRACT

The invention relates among others to antibodies comprising a first antigen-binding site that binds Erb B-2 and a second antigen-binding site that binds Erb B-3. The antibodies can typically reduce a ligand-induced receptor function of Erb B-3 on a Erb B-2 and Erb B-3 positive cell. Also described are method for the treatment and use of the antibodies in imaging and in the treatment of subjects having an Erb B-2, Erb B-3 or Erb B-2/3 positive tumor.

20 Claims, 100 Drawing Sheets

Specification includes a Sequence Listing.

(56) References Cited

U.S. PATENT DOCUMENTS

| | | | |
|---|---|---|---|
| 2009/0181022 A1 | 7/2009 | Nielsen et al. |
| 2009/0182127 A1 | 7/2009 | Kjaergaard et al. |
| 2009/0191559 A1 | 7/2009 | Huang et al. |
| 2010/0015133 A1 | 1/2010 | Igawa et al. |
| 2010/0183615 A1 | 7/2010 | Kufer et al. |
| 2010/0286374 A1 | 11/2010 | Kannan et al. |
| 2011/0077163 A1 | 3/2011 | Doranz |
| 2011/0195454 A1 | 8/2011 | McWhirter et al. |
| 2012/0107306 A1 | 5/2012 | Elis et al. |
| 2012/0270801 A1 | 10/2012 | Frejd et al. |
| 2012/0328623 A1 | 12/2012 | Takahashi |
| 2013/0071859 A1 | 3/2013 | Bates et al. |
| 2013/0115208 A1 | 5/2013 | Ho et al. |
| 2013/0156779 A1 | 6/2013 | Clarke et al. |
| 2013/0185821 A1 | 7/2013 | Babb et al. |
| 2013/0251703 A1 | 9/2013 | Elis et al. |
| 2013/0259867 A1 | 10/2013 | Amler et al. |
| 2013/0336981 A1 | 12/2013 | De Kruif et al. |
| 2014/0072579 A1 | 3/2014 | De Kruif et al. |
| 2014/0120096 A1 | 5/2014 | Bakker et al. |
| 2014/0140999 A1 | 5/2014 | De Kruif et al. |
| 2014/0141019 A1 | 5/2014 | Kharrat et al. |
| 2015/0013996 A1 | 1/2015 | Davies et al. |
| 2015/0139996 A1 | 5/2015 | De Kruif et al. |
| 2015/0196637 A1 | 7/2015 | De Kruif et al. |
| 2016/0229920 A1 | 8/2016 | Ward et al. |
| 2016/0367699 A1 | 12/2016 | Jackson et al. |
| 2017/0037145 A1 | 2/2017 | Geuijen et al. |
| 2017/0058035 A1 | 3/2017 | Logtenberg et al. |
| 2017/0166653 A1 | 6/2017 | Garner et al. |

FOREIGN PATENT DOCUMENTS

| | | |
|---|---|---|
| JP | 2014-508782 A | 4/2014 |
| JP | 2014-511383 A | 5/2014 |
| JP | 2017-507944 A | 3/2017 |
| WO | WO-0120694 A1 | 3/2001 |
| WO | WO-2004009618 A2 | 1/2004 |
| WO | WO-2004061104 A2 | 7/2004 |
| WO | WO-2005000894 A2 | 1/2005 |
| WO | WO-2005118635 A2 | 12/2005 |
| WO | WO-2006028936 A2 | 3/2006 |
| WO | WO-2006044908 A2 | 4/2006 |
| WO | WO-2006106905 A1 | 10/2006 |
| WO | WO-2007110205 A2 | 10/2007 |
| WO | WO-2007147901 A1 | 12/2007 |
| WO | WO-2008027236 A2 | 3/2008 |
| WO | WO-2008100624 A2 | 8/2008 |
| WO | WO-2008119353 A1 | 10/2008 |
| WO | WO-2008140493 A2 | 11/2008 |
| WO | WO-2009051974 A1 | 4/2009 |
| WO | WO-2009080251 A1 | 7/2009 |
| WO | WO-2009080252 A1 | 7/2009 |
| WO | WO-2009080253 A1 | 7/2009 |
| WO | WO-2009089004 A1 | 7/2009 |
| WO | WO-2009098596 A2 | 8/2009 |
| WO | WO-2009157771 A2 | 12/2009 |
| WO | WO-2010059315 A1 | 5/2010 |
| WO | WO-2010084197 A1 | 7/2010 |
| WO | WO-2010108127 A1 | 9/2010 |
| WO | WO-2010129304 A2 | 11/2010 |
| WO | WO-2010151792 A1 | 12/2010 |
| WO | WO-2011012637 A2 | 2/2011 |
| WO | WO-2011028952 A1 | 3/2011 |
| WO | WO-2011028953 A1 | 3/2011 |
| WO | WO-2011143545 A1 | 11/2011 |
| WO | WO-2012023053 A2 | 2/2012 |
| WO | WO-2012058768 A1 | 5/2012 |
| WO | WO 2012116317 A | 8/2012 |
| WO | WO 2012125573 A2 | 9/2012 |
| WO | WO-2012125864 A2 | 9/2012 |
| WO | WO-2012131555 A2 | 10/2012 |
| WO | WO-2013048883 A2 | 4/2013 |
| WO | WO-2013084151 A2 | 6/2013 |
| WO | WO-2013134686 A1 | 9/2013 |
| WO | WO-2013157953 A1 | 10/2013 |
| WO | WO-2013157954 A1 | 10/2013 |
| WO | WO-2014051433 A1 | 4/2014 |
| WO | WO-2014060365 A1 | 4/2014 |
| WO | WO-2014159580 A1 | 10/2014 |
| WO | WO-2014165855 A1 | 10/2014 |
| WO | WO-2014182970 A1 | 11/2014 |
| WO | WO-2015130172 A1 | 9/2015 |
| WO | WO-2015130173 A1 | 9/2015 |
| WO | WO-2016077734 A2 | 5/2016 |

OTHER PUBLICATIONS

Almagro, J.C. and Fransson, J., "Humanization of Antibodies," Frontiers in Bioscience 13:1619-1633, Frontiers In Bioscience Publications, United States (Jan. 2008).

Armour, K.L., et al., "Differential Binding to Human FcgammaRIIa and FcgammaRIIb Receptors by Human IgG Wildtype and Mutant Antibodies," Molecular Immunology 40(9):585-593, Pergamon Press, England (2003).

Arteaga, C.L., et al., "Treatment of Her2-positive Breast Cancer: Current Status and Future Perspectives," Nature Reviews Clinical Oncology 9(1):16-32, Nature Publishing Group, England (Nov. 2011).

Atwell, S., et al., "Stable Heterodimers from Remodeling the Domain Interface of a Homodimer Using a Phage Display Library," Journal of Molecular Biology 270(1):26-35, Elsevier, England (1997).

Bakker, A.B., et al., "C-type Lectin-like Molecule-1: a Novel Myeloid Cell Surface Marker Associated With Acute Myeloid Leukemia," Cancer Research 64(22):8443-8450, American Association for Cancer Research, United States (Nov. 2004).

Balko, J.M., et al., "The Receptor Tyrosine Kinase Erbb3 Maintains the Balance Between Luminal and Basal Breast Epithelium," Proceedings of the National Academy of Sciences of the United States of America 109(1):221-226, National Academy of Sciences, United States (Jan. 2012).

Bargou, R., et al., "Tumor Regression in Cancer Patients by Very Low Doses of a T Cell-engaging Antibody," Science 321(5891):974-977, American Association for the Advancement of Science, United States (Aug. 2008).

Bendig, M.M., et al., "The Production of Foreign Proteins in Mammalian Cells," Genetic Engineering 7:91-127, Academic Press, England (1988).

Bernard, A., et al., "A unique epitope on the CD2 molecule defined by the monoclonal antibody 9-1: epitope-specific modulation of the E-rosette receptor and effects on T-cell functions," Hum Immunol. 17(4):388-405, Elsevier, Netherlands (1986).

Bettler., et al., "Binding site For Ige Of The Human Lymphocyte Low-Affinity Fc Epsilon Receptor (Fc Epsilon RII/CD23) is Confined to the Domain Homologous With Animal Lectins," Proceedings of the National Academy of Sciences of the United States of America 86(18): 7118-7122, National Academy of Sciences, United States (Sep. 1989).

Bluemel, C., et al., "Epitope Distance to the Target Cell Membrane and Antigen Size Determine the Potency of T Cell-mediated Lysis by BiTE Antibodies Specific for a Large Melanoma Surface Antigen," Cancer Immunology, Immunotherapy 59(8):1197-1209, Springer Verlag, Germany (Aug. 2010).

Bogan, A., et al., "Anatomy of Hot Spots in Protein Interfaces," Journal of Molecular Biology, vol. 280, pp. 1-9 (1998).

Bostrom, J., et al., "Variants of the Antibody Herceptin that Interact with HER2 and VEGF at the Antigen Binding Site," Science 323(5921):1610-1614, American Association for the Advancement of Science, United States (Mar. 2009).

Boyer,C.M et al., "Relative Cytotoxic Activity of Immunotoxins Reactive With Different Epitopes on the Extracellular Domain of the C-Erbb-2 (Her-2/Neu) Gene Product P185," International Journal of Cancer, 82(4): 525-531, John Wiley & Sons, Inc (Aug. 1999).

Buday, L. et al., "Epidermal Growth Factor Regulates the Exchange Rate of Guanine Nucleotides on p21ras in Fibroblasts," Molecular and Cellular Biology, vol. 13{3}:1903-1910 {1993}.

(56) References Cited

OTHER PUBLICATIONS

Caldas, C., et al., "Humanization of the Anti-Cd18 Antibody 6.7: An Unexpected Effect of a Framework Residue in Binding to Antigen," Molecular Immunology 39(15):941-952, Pergamon Press, England (May 2003).

Capelle, M., et al., "Spectroscopic Characterization of Antibodies Adsorbed to Aluminium Adjuvants: Correlation With Antibody Vaccine Immunogenicity," Vaccine 23(14):1686-1694, Elsevier Science, Netherlands (Feb. 2005).

Carmon, K.S., et al., "R-Spondins Function as Ligands of the Orphan Receptors LGR4 and LGR5 to Regulate Wnt/β-Catenin Signaling," Proceedings of the National Academy of Sciences 108(28):11452-11457, National Academy of Sciences, United States (2011).

Carter, P., "Bispecific Human IgG by Design," Journal of Immunological Methods 248(1-2):7-15, Elsevier, Netherlands (2001).

Carter, P., et al., "Toward the Production of Bispecific Antibody Fragments for Clinical Applications," Journal of Hematotherapy, vol. 4, pp. 463-470 (1995).

Cartron, G., et al., "Therapeutic Activity of Humanized Anti-cd20 Monoclonal Antibody and Polymorphism in IgG Fc Receptor FcgammaRIIIa Gene," Blood 99(3):754-758, American Society of Hematology, United States (2002).

Casset, F., et al., "A Peptide Mimetic of an Anti-CD4 Monoclonal Antibody By Rational Design," Biochemical and Biophysical Research Communications 307(1):198-205, Academic Press, United States (Jul. 2003).

Chames, P. and Baty, D., "Bispecific Antibodies for Cancer Therapy: The Light at the End of the Tunnel?," MAbs 1(6):539-547, Taylor & Francis, United States (Nov.-Dec. 2009).

Chang, H-J., et al., "Loop-sequence features and stability determinants in antibody variable domains by high-throughput experiments," Structure 22(1):9-21, Cell Press, United States (2014).

Chatenoud, L., et al., "In Vivo Cell Activation Following OKT3 Administration. Systemic Cytokine Release and Modulation by Corticosteroids," Transplantation 49(4):697-702, Lippincott Williams & Wilkins, United States (Apr. 1990).

Chen, C.H., et al., "Effect of Duration of Osmotherapy on Blood-brain Barrier Disruption and Regional Cerebral Edema After Experimental Stroke," Journal of Cerebral Blood Flow and Metabolism 26(7):951-958, SAGE Publications, United States (Jul. 2006).

Chien, N.C., et al., "Significant Structural and Functional Change of an Antigen-Binding Site by a Distant Amino Acid Substitution: Proposal of a Structural Mechanism," Proceedings of the National Academy of Sciences USA 86(14):5532-5536, National Academy of Sciences, United States (1989).

Cui, H., et al., "Chemically Programmed Bispecific Antibodies That Recruit and Activate T Cells," The Journal of Biological Chemistry 287(34):28206-28214, American Society for Biochemistry and Molecular Biology, United States (Aug. 2012).

Davies, J. and Riechmann, L., "Antibody VH Domains as Small Recognition Units," Biotechnology 13(5):475-479, Nature Publishing Group, United States (1995).

Davis, J.H., et al., "SEEDbodies: Fusion Proteins Based on Strand-exchange Engineered Domain (SEED) CH3 Heterodimers in an Fc Analogue Platform for Asymmetric Binders or Immunofusions and Bispecific Antibodies.," Protein Engineering, Design & Selection 23(4):195-202, Oxford University Press, England (2010).

De Haard, H.J., et al., "A Large Non-immunized Human Fab Fragment Phage Library That Permits Rapid Isolation and Kinetic Analysis of High Affinity Antibodies," Journal of Biological Chemistry 274(26):18218-18230, American Society for Biochemistry and Molecular Biology, United States (Jun. 1999).

De Kruif, J., et al., "Selection and Application of Human Single Chain Fv Antibody Fragments from a Semi-Synthetic Phage Antibody Display Library with Designed CDR3 Regions," Journal of Molecular Biology 248(1):97-105, Elsevier, England (Apr. 1995).

De Kruif, J., et al., "Generation of Stable Cell Clones Expressing Mixtures of Human Antibodies," Biotechnology and Bioengineering 106(5):741-750, Wiley, United States (Aug. 2010).

De Lau, W., et al., "The R-spondin/Lgr5/Rnf43 Module: Regulator of Wnt Signal Strength," Genes and Development 28(4):305-316, Cold Spring Harbor Laboratory Press, United States (2014) (D31 as cited in Opposition of EP 2173379.

De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).

De Vries, S.J., et al., "The HADDOCK Web Server for Data-driven Biomolecular Docking," Nature Protocols 5(5):883-897, Nature Publishing Group, England (May 2010).

De Wildt, et al., Analysis of Heavy and Light Chain Pairings Indicates that Receptor Editing Shapes fhe Human Antibody Repertoire, Journal of Molecular Biology, 285(3):895-901, Elsevier,England(1999).

Deisenhofer, J., "Crystallographic refinement and atomic models of a human Fc fragment and its complex with fragment B of protein A from *Staphylococcus aureus* at 2.9- and 2.8-A resolution," Biochemistry 20(9):2361-2370, American Chemical Society, United States (1981).

Demeule, B., et al., "Characterization of Protein Aggregation: the Case of a Therapeutic Immunoglobulin," Biochimica et Biophysica Acta 1774(1):146-153, Elsevier Publisher, Netherlands (Jan. 2007 ).

Demeule, B., et al., "Detection and Characterization of Protein Aggregates by Fluorescence Microscopy," International Journal of Pharmaceutics 329(1-2):37-45, Elsevier/North-Holland Biomedical Press, Netherlands (Feb. 2007 ).

Devash, Y., et al., "Vertical Transmission of Human Immunodeficiency Virus Is Correlated With the Absence of High-affinity/avidity Maternal Antibodies to the Gp120 Principal Neutralizing Domain," Proceedings of the National Academy of Sciences of the United States of America 87(9):3445-3449, National Academy of Sciences, United States (May 1990).

Di, Z., et al., "Ultra high content image analysis and phenotype profiling of 3D cultured microtissues," PLoS One. Oct. 7, 2014;9{10}:e109688 {2011).

Dreier, T., et al., "Extremely Potent, Rapid and Costimulation-Independent Cytotoxic T-Cell Response against Lymphoma Cells Catalyzed By a Single-Chain Bispecific Antibody," International Journal of Cancer 100(6):690-697, Wiley-Liss, United States (2002).

Edwards, B.M., et al., "The Remarkable Flexibility of the Human Antibody Repertoire; Isolation of Over One Thousand Different Antibodies to a Single Protein, BLyS," Journal of Molecular Biology, 334(1):103-118, Elsevier, England (Nov. 2003).

Ellerson, J.R., et al., "Structure and Function of Immunoglobulin Domains. III. Isolation and Characterization of a Fragment Corresponding to the Cgamma2 Homology Region of Human Immunoglobin G1," Journal of Immunology 116(2):510-517, American Association of Immunologists, United States (Feb. 1976).

Ewer, M.S., et al., "Cardiotoxicity of Anticancer Treatments: What the Cardiologist Needs to Know," Nature Reviews Cardiology 7(10):564-575, Nature Publishing Group, England (Oct. 2010).

Farnan, D. and Moreno, G.T., "Multiproduct High-resolution Monoclonal Antibody Charge Variant Separations by pH Gradient Ion-exchange Chromatography," Analytical Chemistry 81(21):8846-8857, American Chemical Society, United States (2009).

Fu, W., et al., "Insights into HER2 signaling from step-by-step optimization of anti-HER2 antibodies," Mabs 6(4):978-990, Taylor Francis online, United States (2014).

Garrett, T.P., et al., "Crystal Structure of a Truncated Epidermal Growth Factor Receptor Extracellular Domain Bound to Transforming Growth Factor alpha," Cell 110(6):763-773, Cell Press, United States (Sep. 2002).

Geginat, J., et al., "Proliferation and Differentiation Potential of Human CD8+ Memory T-cell Subsets in Response to Antigen or Homeostatic Cytokines," Blood 101(11):4260-4266, American Society of Hematology, United States (Jun. 2003).

Genbank, "*Homo Sapiens* C-type Lectin Protein CLL-1 mRNA, Complete Cds," Accession No. AF247788.1, accessed at https://www.ncbi.nlm.nih.gov/nuccore/19716160/, Mar. 26, 2002, 1 page.

(56) References Cited

OTHER PUBLICATIONS

George, J., et al., "Differential Effects of Anti-β2-Glycoprotein I Antibodies on Endothelial Cells and on the Manifestations of Experimental Antiphospholipid Syndrome," Circulation 97(9): 900-906, American Heart Association, United States (1998).
Girlanda, S., et al., "MICA Expressed by Multiple Myeloma and Monoclonal Gammopathy of Undetermined Significance Plasma Cells Costimulates Pamidronate-activated Gammadelta Lymphocytes," Cancer Research, 65(16):7502-7508, American Association for Cancer Research, United States (Aug. 2005).
Giusti, A.M., et al., "Somatic diversification of S107 from an antiphosphocholine to an anti-DNA autoantibody is due to a single base change in its heavy chain variable region," Proceedings of the National Academy of Sciences 84(9):2926-2930, National Academy of Sciences, United States, (1987).
Greco, W.R., et al., "The Search for Synergy: a Critical Review From a Response Surface Perspective," Pharmacological Reviews 47(2):331-385, American Society for Pharmacology and Experimental Therapeutics, United States (Jun. 1995).
Greenspan, N.S. and Di Cera, E., "Defining Epitopes: It's not as Easy as it Seems," Nature Biotechnology 17(10):936-937, Nature Publishing Group, United States (1999).
Gulli, L.F., et al., "Epidermal Growth Factor-induced Apoptosis in A431 Cells Can Be Reversed by Reducing the Tyrosine Kinase Activity," Cell Growth & Differentiation 7(2):173-178, The Association, United States (Feb. 1996).
Gunasekaran, K., et al., "Enhancing Antibody Fc Heterodimer Formation Through Electrostatic Steering Effects: Applications to Bispecific Molecules and Monovalent IgG," Journal of Biological Chemistry 285(25):19637-19646, American Society for Biochemistry and Molecular Biology, United States (Jun. 2010).
Gussow, D. and Seemann, G., "Humanization of Monoclonal Antibodies," Methods in Enzymology 203:99-121, Elsevier Science, United States (1991).
Haagen, I.A., et al., "The Efficacy of CD3 X CD19 Bispecific Monoclonal Antibody (BsAB) in a Clonogenic Assay: The Effect of Repeated Addition of Bsab and Interleukin-2," Blood 85(11):3208-3212, American Society of Hematology, United States (Jun. 1995).
Hao, H.X., et al., "ZNRF3 Promotes Wnt Receptor Turnover in an R-Spondin-Sensitive Manner," Nature 485(7397):195-200, Nature Publishing Group, England (2012).
Hathaway, H., et al., "Detection of breast cancer cells using targeted magnetic nanoparticles and ultra-sensitive magnetic field sensors," Breast Cancer Research R108: 1-12, Springer Nature, United States (2011).
Hendsch, Z.S., et al., "Preferential Heterodimer Formation via Undercompensated Electrostatic Interactions," Journal of the American Chemical Society 123(6):1264-1265, American Chemical Society, United States (Feb. 2001).
Holm, P., et al., "Functional Mapping and Single Chain Construction of the Anti-cytokeratin 8 Monoclonal Antibody TS1," Molecular Immunology 44(6):1075-1084, Pergamon Press, England (Feb. 2007).
Horsten, H., et al., "Production of Non-Fucosylated Antibodies by Co-expression of Heterologous GDP-6-Deoxy-D-Lyxo-4-Hexulose Reductase," Glycobiology, 20(12):1607-1618, IRL Press at Oxford University Press, England, (Dec. 2010).
Idusogie, E.E., et al., "Mapping of the C1q Binding Site on Rituxan, A Chimeric Antibody with a Human IgG1 Fc," The Journal of Immunology 164(8):4178-4184, American Association of Immunologists, United States (2000).
Ionescu, R.M., et al., "Contribution of Variable Domains to the Stability of Humanized IgG1 Monoclonal Antibodies," Journal of Pharmaceutical Sciences 97(4):1414-1426, Elsevier, United States (Apr. 2008 ).
Jackson, C., et al., "Clinical Significance of HER-2 Splice Variants in Breast Cancer Progression and Drug Resistance," Int J. Cell Bio. 937584, Cell Press, United States (2013).
Jain, K.K., et al., "A Prospective Randomized Comparison of Epirubicin and Doxorubicin in Patients With Advanced Breast Cancer," Journal of Clinical Oncology 3(6):818-826, American Society of Clinical Oncology, United States (Jun. 1985).
Jiang, B., et al., "A Novel Peptide Isolated from a Phage Display Peptide Library with Trastuzumab Can Mimic Antigen Epitope of HER-2," The Journal of Biological Chemistry 280(6):4656-4662, The American Society for Biochemistry and Molecular Biology (2005).
Junttila, T.T., et al., "Ligand-Independent HER2/HER3/PI3K Complex Is Disrupted by Trastuzumab and Is Effectively Inhibited by the PI3K Inhibitor GDC-0941," Cancer Cell 15(5):429-440, Cell Press, United States (May 2009).
Junttila, T.T., et al., "Superior in Vivo Efficacy of Afucosylated Trastuzumab in the Treatment of HER2-amplified Breast Cancer," Cancer Research 70(11):4481-4489, American Association for Cancer Research, United States (Jun. 2010).
Kabat, E.A., et al., "Identical V Region Amino Acid Sequences and Segments of Sequences in Antibodies of Different Specificities. Relative Contributions of Vh and V1 Genes, Minigenes, and Complementarity-determining Regions to Binding of Antibody-combining Sites," Journal of Immunology 147(5):1709-1719, American Association of Immunologists, United States (Sep. 1991).
Kang J.C., et al., "Engineering Multivalent Antibodies to Target Heregulin-Induced HER3 Signaling in Breast Cancer Cells," Comparative Study 6(2):340-353, Landes Bioscience, United states (Apr. 2014).
Kipriyanov, S.M., et al., "Bispecific CD3 x CD19 Diabody for T Cell-Mediated Lysis of Malignant Human B Cells," International Journal of Cancer 77(5):763-772, Wiley-Liss, United States (1998).
Klein, C., et al., "Progress in Overcoming the Chain Association Issue in Bispecific Heterodimeric IgG Antibodies," MAbs 4(6):653-663, Taylor & Francis, United States (Nov.-Dec. 2012).
Kontermann, R.E., "Dual Targeting Strategies with Bispecific Antibodies," mAbs 4(2):182-197, Taylor and Francis, United States (2012), XP055566203.
Kruif, D.J., et al., "Human Immunoglobulin Repertoires Against Tetanus Toxoid Contain a Large and Diverse Fraction of High-affinity Promiscuous V(H) Genes," Journal of Molecular Biology 387(3):548-558, Elsevier, England (Apr. 2009).
Kumar, R., et al., "The Second Pdz Domain of Inad Is a Type I Domain Involved in Binding to Eye Protein Kinase C. Mutational Analysis and Naturally Occurring Variants," Journal of Biological Chemistry 276(27):24971-24977, American Society for Biochemistry and Molecular Biology, United States (Jul. 2001).
Lakowicz, J.R., "Principles of Fluorescence Spectroscopy," 3rd Edition, Kluwer Academic/Plenum Publisher, 469 pages (2006).
Landgraf, R., et al., "HER2 Therapy. HER2 (ERBB2): Functional Diversity from Structurally Conserved Building Blocks," Breast Cancer Research 9(1):202, BioMed Central Ltd, England (2007).
Lanzavecchia, A. and Staerz, U.D., "Lysis of Nonnucleated Red Blood Cells by Cytotoxic T Lymphocytes," European Journal of Immunology 17(7):1073-1074, Wiley-VCH, Germany (Jul. 1987).
Le Gall, F., et al., "Effect of Linker Sequences Between the Antibody Variable Domains on the Formation, Stability and Biological Activity of a Bispecific Tandem Diabody," Protein Engineering, Design & Selection 17(4):357-366, Oxford University Press, England (Apr. 2004).
Lee, B., et al., "The Interpretation of Protein Structures: Estimation of Static Accessibility," Journal of Molecular Biology 55(3):379-400, Elsevier, England (Feb. 1971).
Liesveld, J.L., et al., "Expression of IgG Fc Receptors in Myeloid Leukemic Cell Lines. Effect of Colony-stimulating Factors and Cytokines," Journal of Immunology 140(5):1527-1533, American Association of Immunologists, United States (Mar. 1988).
Liu, C and Lee, A., "ADCC Enhancement Technologies for Next Generation Therapeutic Antibody," Trends in Bio/Pharmaceutical Industry, 9 pages, 2009.
Liu, H., et al., "Heterogeneity of Monoclonal Antibodies," Journal of Pharmaceutical Sciences 97(7):2426-2447, Wiley-Liss, United States (Jul. 2008).
Liu, M.A., et al., "Heteroantibody Duplexes Target Cells for Lysis by Cytotoxic T Lymphocytes," Proceedings of the National Academy of Sciences of the United States of America 82(24):8648-8652, National Academy of Sciences, United States (1985).

(56) References Cited

OTHER PUBLICATIONS

Loffler, A., et al., "A Recombinant Bispecific Single-chain Antibody, CD19 X CD3, Induces Rapid and High Lymphoma-directed Cytotoxicity by Unstimulated T Lymphocytes," Blood 95(6):2098-2103, American Society of Hematology, United States (Mar. 2000).
Lotenberg, T., "Hub for organoids can we take it beyond the buzz" Retrieved from Internet: (https://www.innovationtorhealth.nl/index.php/page/getFileUIDIuid/82364b177dfed9754d785aafffb21363/crusedb/25).
MacCallum, R.M., et al., "Antibody-antigen Interactions: Contact Analysis and Binding Site Topography," Journal of Molecular Biology 262(5):732-745, Academic Press, England (Oct. 1996).
Mariuzza, R.A., et al., "The Structural Basis of Antigen-antibody Recognition," Annual Review of Biophysics and Biomolecular Structure 16:139-159, Annual Reviews, United States (1987).
Marks, J.D., et al., "By-passing Immunization. Human Antibodies from V-gene Libraries Displayed on Phage," Journal of Molecular Biology 222(3):581-597, Academic Press Limited, United States (Dec. 1991).
Marshall, A.S., et al., "Identification and Characterization of a Novel Human Myeloid Inhibitory C-type Lectin-like Receptor (MICL) That Is Predominantly Expressed on Granulocytes and Monocytes," The Journal of Biological Chemistry 279(15):14792-14802, American Society for Biochemistry and Molecular Biology, United States (Apr. 2004).
Marvin, J.S., et al., "Redesigning an Antibody Fragment for Faster Association With Its Antigen," Biochemistry 42(23):7077-7083, American Chemical Society, United States (Jun. 2003).
McPhee, F., et al., "Engineering Human Immunodeficiency Virus 1 Protease Heterodimers as Macromolecular Inhibitors of Viral Maturation," Proceedings of the National Academy of Sciences of the United States of America 93(21):11477-11481, National Academy of Sciences, United States (Oct. 1996).
Merchant, A.M., et al., "An Efficient Route to Human Bispecific IgG," Nature Biotechnology 16(7):677-681, Nature Publishing Group, United States (1998).
Merlino, G.T. et al, "Amplification and Enhanced Expression of the Epidermal Growth Factor Receptor Gene in A431Human Carcinoma Cells," Science, vol. 224(4647): 417-419 (1984).
Merus, www.merus.nl, press release, 2 pages, dated Jan. 7, 2013.
Merus, www.merus.nl, press release, 3 pages, dated Jun. 17, 2013.
Miller, S, "Protein-protein Recognition and the Association of Immunoglobulin Constant Domains," Journal of Molecular Biology 216(4):965-973, Elsevier Ltd (Dec. 1990).
Moore, P.A., et al., "Application of Dual Affinity Retargeting Molecules to Achieve Optimal Redirected T-cell killing of B-cell Lymphoma," Blood 117(17):4542-4551, American Society of Hematology, United States (Apr. 2011).
Moshaver, B., et al., "Identification of a Small Subpopulation of Candidate Leukemia-initiating Cells in the Side Population of Patients With Acute Myeloid Leukemia," Stem Cells 26(12):3059-3067, AlphaMed Press, United States (Dec. 2008).
Nieba, L., et al., "Disrupting the Hydrophobic Patches at the Antibody Variable/constant Domain Interface: Improved in Vivo Folding and Physical Characterization of an Engineered Scfv Fragment," Protein Engineering 10(4):435-444, Oxford University Press, England (Apr. 1997).
Nissim, A., et al., "Antibody Fragments From a 'single Pot' Phage Display Library as Immunochemical Reagents," The EMBO Journal, 13(3):692-698, (Feb. 1994).
Nohaile, M.J., et al., "Altering dimerization specificity by changes in surface electrostatics," Proceedings of the National Academy of Sciences 98(6):3109-3114, National Academy of Sciences, United States (2001).
Norde, W.J., et al., "Myeloid Leukemic Progenitor Cells Can Be Specifically Targeted by Minor Histocompatibility Antigen LRH-1-reactive Cytotoxic T Cells," Blood 113(10):2312-2323, American Society of Hematology, United States (Mar. 2009).

Ocana, A., et al., "HER3 Overexpression and Survival In Solid Tumors: A Meta-Analysis," Journal of the National Cancer Institute 105(4):266-273, Oxford University Press, United States (Feb. 2013).
Offner, S., et al., "Induction of Regular Cytolytic T Cell Synapses by Bispecific Single-chain Antibody Constructs on MHC Class I-negative Tumor Cells," Molecular Immunology 43(6):763-771, Pergamon Press, England (Feb. 2006).
Oganesyan, V., et al., "Structural Characterization of a Human Fc Fragment Engineered for Lack of Effector Functions," Acta Crystallographica. Section D, Biological Crystallography 64(Pt 6):700-704, Wiley-Blackwell, United States (Jun. 2008).
Ogiso, H., et al., "Crystal Structure of the Complex of Human Epidermal Growth Factor and Receptor Extracellular Domains," Cell 110(6):775-787, Cell Press, United States (Sep. 2002).
Omenn, G. S., et al., "A New Class of Protein Cancer Biomarket Candidates: Differentially-expressed splic variatns of ERBB2 (HER2/NEU) and ERBB1 (EGFR) in Breast Cancer Cell Lines," J. Proteomics: 103-112, Elsevier, Netherlands (2014).
Padlan, E.A., "X-Ray Crystallography of Antibodies," Advances in Protein Chemistry 49:57-133, Academic Press, United States (1996).
Papadea, C. and Check, I.J., "Human Immunoglobulin G and Immunoglobulin G Subclasses: Biochemical, Genetic, and Clinical Aspects," Critical Reviews in Clinical Laboratory Sciences 27(1):27-58, Informa Healthcare, England (1989).
Peng, R., et al., "Bleomycin Induces Molecular Changes Directly Relevant to Idiopathic Pulmonary Fibrosis: A Modelor "Active," Disease," Pios One, 8{4}: e59348, 15 pages {2013}.
Peng, W., et al., "Blockade of the PD-1 Pathway Enhances the Efficacy of Adoptive Cell Therapy against Cancer," Oncoimmunology 2(2):e22691, Taylor & Francis, United States (Feb. 2013).
Petterson, R.D., et al., "CD47 Signals T Cell Death," Journal of Immunolgy 15; 162 (12): 7031-7040, American Association of Immunologists, United States (Jun. 1999).
Press, O.W., et al., "Ricin A-chain containing immunotoxins directed against different epitopes on the CD2 molecule differ in their ability to kill normal and malignant T cells," Journal of Immunology 141(12):4410-4417, American Association of Immunologists, United States (1988).
Raffen, R., et al., "Reengineering Immunoglobulin Domain Interactions by Introduction of Charged Residues," Protein Engineering 11(4):303-309, Oxford University Press, England (Apr. 1998).
Reusch, U., et al., "Beyond mAbs with TandAbs," Innovations in Pharmaceutical Technology, 4 pages, (2011).
Ridgway, J.B., et al., "'Knobs-Into-Holes' Engineering of Antibody CH3 Domains for Heavy Chain Heterodimerization," Protein Engineering 9(7):617-621, Oxford University Press, England (1996).
Riemer, A.B., et al., "Matching of Trastuzumab (Herceptin) Epitope Mimics Onto the Surface of Her-2/neu—a New Method of Epitope Definition," Molecular Immunology 42(9):1121-1124, Pergamon Press, England (2005).
Robinson M.K., et al., "Targeting ErbB2 and ErbB3 with a bispecific single-chain FV Enhances targeting selectivity and induces a therapeutic effect in Vitro", British Journal of CA, Nature Publishing Group, GB 99(9):1415-1425, England, London (Oct. 2008).
Rudikoff, S., et al., "Single Amino Acid Substitution Altering Antigen-binding Specificity," Proceedings of the National Academy of Sciences of the United States of America 79(6):1979-1983, National Academy of Sciences, United States (Mar. 1982).
Sali, A., et al., "Comparative Protein Modelling By Satisfaction of Spatial Restraints," Journal of Molecular Biology 234(3):779-815, Elsevier, England (Dec. 1993).
Sal-Man, N. and Shai, Y., "Arginine mutations within a transmembrane domain of Tar, an *Escherichia coli* aspartate receptor, can drive homodimer dissociation and heterodimer association in vivo," Biochemical Journal 385(Pt1):29-36, Portland Press, United Kingdom (2005).
Sandercock et al., "Identification of anti-tumour biologics using primary tumour models, 3-D phenotypic screening and image-based multi-parametric profiling." Mol Cancer. Jul. 31, 2015;14:147. PMID 26227951.

(56) References Cited

OTHER PUBLICATIONS

Sato, T., et al., "Long-term Expansion of Epithelial Organoids From Human Colon, Adenoma, Adenocarcinoma, and Barrett's Epithelium," Gastroenterology 141(5):1762-1772, W.B. Saunders, United States (Nov. 2011).
Schaefer, G., et al., "A Two-in-one Antibody Against Her3 and Egfr Has Superior Inhibitory Activity Compared With Monospecific Antibodies," Cancer cell 20(4):472-486, Cell Press, United States (Oct. 2011).
Schiffer, M., et al., "Analysis of Immunoglobulin Domain Interactions. Evidence for a Dominant Role of Salt Bridges," Journal of Molecular Biology 203(3):799-802, Elsevier, England (Oct. 1988).
Schoeberl, B., et al., "An ErbB3 Antibody, MM-121, is Active in Cancers with Ligand-Dependent Activation," Cancer Research 70(6):2485-2494, American Association for Cancer Research, United States (Mar. 2010).
Selzer, T., et al., "Rational Design of Faster Associating and Tighter Binding Protein Complexes," Nature Structural & Molecular Biology 7(7):537-541, Nature Publishing Group, United States (Jul. 2000).
Sergina, N.V., et al., "Escape from HER-Family Tyrosine Kinase Inhibitor Therapy By The Kinase-Inactive HER3," Nature 445(7126):437-441, Nature Publishing Group, England (Jan. 2007).
Seshagiri, S., et al., "Recurrent R-spondin Fusions in Colon Cancer," Nature 488(7413):660-664, Nature Publishing Group, England (2012).
Shames, D.S., et al., "High Heregulin Expression Is Associated with Activated HER3 and May Define an Actionable Biomarker in Patients with Squamous Cell Carcinomas of the Head and Neck," PLoS One 8(2):e56765, Public Library of Science, United States (2013).
Sheinerman, F.B., et al., "Electrostatic Aspects of Protein-protein Interactions," Current Opinion in Structural Biology 10(2):153-159, Elsevier Science, England (Apr. 2000).
Sheridan, C., "Amgen Swallows Micromet to BiTE Into All Market," Nature Biotechnology 30(4):300-301, Nature America Publishing, United States (Apr. 2012).
Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).
Sinha, N., et al., "Differences in Electrostatic Properties at Antibody-antigen Binding Sites: Implications for Specificity and Cross-reactivity," Biophysical Journal 83(6):2946-2968, Cambridge, United States (Dec. 2002).
Sinha, N., et al., "Electrostatics in Protein Binding and Function," Current Protein and Peptide Science 3(6):601-614, Bentham Science Publishers, Netherlands (Dec. 2002).
Sluijter, B.J., et al., "4-1BB-mediated Expansion Affords Superior Detection of in Vivo Primed Effector Memory CD8+ T Cells from Melanoma Sentinel Lymph Nodes," Clinical Immunology 137(2):221-233, Academic Press, United States (Nov. 2010).
Spiess, C., et al., "Alternative Molecular Formats and Therapeutic Applications for Bispecific Antibodies," Molecular Immunology 67(2 Pt A):95-106, Pergamon Press, England (Oct. 2015).
Staerz, U.D., and Bevan, M.J., "Hybrid Hybridoma Producing a Bispecific Monoclonal Antibody that can Focus Effector T-cell Activity," Proceedings of the National Academy of Sciences USA 83(5):1453-1457, National Academy of Sciences, United States (1986).
Stancovski, I., et al., "Mechanistic aspects of the opposing effects of monoclonal antibodies to the ERBB2 receptor on tumor growth," Proceedings of the National Academy of Sciences USA 88(19):8691-8695, National Academy of Sciences, United States (1991).
Strelkauskas et al., Human Monoclonal Antibody: 2. Simultaneous Expression of IgG and IgM with Similar Binding Specificities by a Human Hybrid Clone, Hybridoma, 1987, pp. 479-487, vol. 6, No. 5, Mary Ann Liebert Inc., Publishers.

Suntharalingam, G., et al., "Cytokine Storm in a Phase 1 Trial of the Anti-CD28 Monoclonal Antibody TGN1412," The New England Journal of Medicine 355(10):1018-1028, Massachusetts Medical Society, United States (Sep. 2006).
Tahallah, N., et al., "The Effect of the Source Pressure on the Abundance of Ions of Noncovalent Protein Assemblies in an Electrospray Ionization Orthogonal Time-of-flight Instrument," Rapid Communications in Mass Spectrometry 15(8):596-601, John Wiley And Sons Ltd, England (2001).
Tanner, M., et al., "Characterization of a Novel Cell Line Established From a Patient With Herceptin-resistant Breast Cancer," Molecular Cancer Therapeutics 3(12):1585-1592, American Association for Cancer Research, United States (Dec. 2004).
Thery, J.C., et al., "Resistance to Human Epidermal Growth Factor Receptor Type 2-targeted Therapies," European Journal of Cancer 50(5):892-901, (Mar. 2014).
Troise, F., et al., "A novel ErbB2 epitope targeted by human antitumor immunoagents," FEBS Journal, 278: 1156-1166, John Wiley & Sons, United States (2011).
Uberall, I. et ai.,"The status and role of ErbB receptors in human cancer," Exp Mol Pathol., vol. 84:79-89 (2008).
UniProtKB Database "C-type lectin domain family 12 member A," UniProt accession No. Q5QGZ9, accessed at https://www.uniprot.org/uniprot/Q5QGZ9, accessed on Jan. 21, 2015.
Vajdos, F.F., et al., "Comprehensive Functional Maps of The Antigen-binding Site of an Anti-Erbb2 Antibody Obtained with Shotgun Scanning Mutagenesis," Journal of Molecular Biology 320(2):415-428, Academic Press, England (Jul. 2002).
Van De Wetering, M., et al., "Prospective Derivation of a Living Organoid Biobank of Colorectal Cancer Patients," Cell, vol. 161:933-945, Science direct (Jun. 2015).
Van Rhenen, A., et al., "The Novel AML Stem Cell Associated Antigen Cll-1 Aids in Discrimination Between Normal and Leukemic Stem Cells," Blood 110(7):2659-2666, American Society of Hematology, United States (Oct. 2007).
Volpi, C. C., et al., "The landscape of d16HER2 splice variant expression across HER2-positive cancers," Sci. Rep. 9(1):3545, Nature Publishing Group, United Kingdom (Mar. 2019).
Wadhwa, D., et al., "Trastuzumab Mediated Cardiotoxicity in the Setting of Adjuvant Chemotherapy for Breast Cancer: a Retrospective Study," Breast Cancer Research and Treatment 117(2):357-364, Kluwer Academic, Netherlands (Sep. 2009).
Wehrman, T.S., et al., "A System for Quantifying Dynamic Protein Interactions Defines a Role for Herceptin in Modulating ErbB2 Interactions," Proceedings of the National Academy of Sciences of the United States of America 103(50):19063-19068, National Academy of Sciences, United States (Dec. 2006).
Weidle, UH. et al., "The Intriguing Options of Multispecific Antibody Formats for Treatment of Cancer," Cancer Genomics & Proteomics, vol. 10: 1-18 {2013).
Wilson, T.R., et al., "Widespread Potential for Growth-factor-driven Resistance to Anticancer Kinase Inhibitors," Nature 487(7408):505-509, Nature Publishing Group, England (Jul. 2012).
Winkler, K., et al., "Changing the Antigen Binding Specificity by Single Point Mutations of an Anti-p24 (HIV-1) Antibody," The Journal of Immunology 165(8):4505-4514, The American Association of Immunologists, United States (2000).
Wu, H., et al., "Humanization of a Murine Monoclonal Antibody by Simultaneous Optimization of Framework and CDR Residues," Journal of Molecular Biology 294(1):151-162, Elsevier, England (Nov. 1999).
Xu, F., et al., "Antibody-Induced Growth Inhibition is Mediated Through Immunochemically and Functionally Distinct Epitopes on the Extracellular Domain of the c-erb-2 (HER-2/neu) Gene Product p185," International Journal of Cancer 53(3):401-408, Wiley-Liss, United States (1993).
Yarden, Y. et al., "The EGFR family and its ligands in human cancer: signalling mechanisms and therapeutic opportunities," European Journal of Cancer 37(Supp4): S3-S8, ResearchGate GmbH (Sep. 2001).
Yarden, Y., et al., "The ERBB Network: At Last, Cancer Therapy Meets Systems Biology," Nature Reviews Cancer 12(8):553-563, Nature Publishing Group, England (Jul. 2012).

(56) References Cited

OTHER PUBLICATIONS

Yonesaka, K., et al., "Activation of ERBB2 Signaling Causes Resistance to the Egfr-Directed Therapeutic Antibody Cetuximab," Science Translational Medicine 3(99):99ra86, American Association for the Advancement of Science, United States (Sep. 2011).

Yu, H., et al., "Plasma Levels of Insulin-like Growth Factor-I and Lung Cancer Risk: A Case-control Analysis," Journal of the National Cancer Institute 91(2):151-156, Oxford University Press, United States (Jan. 1999).

Zebisch M and Jones EY, "Crystal structure of R-spondin 2 in complex with the ectodomains of its receptors LGR5 and ZNRF3." J Struct Biol. Aug. 2015;191(2):149-55.

Zebisch M and Jones EY, "ZNRF3/RNF43—A direct linkage of extracellular recognition and E3 ligase activity to modulate cell surface signalling." Prog Biophys Mol Biol. Sep. 2015; 118(3): 112-8.

Zeidler, R., et al., "Simultaneous Activation of T Cells and Accessory Cells by a New Class of Intact Bispecific Antibody Results in Efficient Tumor Cell Killing," Journal of Immunology 163(3):1246-1252, American Association of Immunologists, United States (1999).

Zhang, H., et al., "ErbB Receptors: From Oncogenes to Targeted Cancer Therapies," Journal of Clinical Investigation 117(8):2051-2058, American Society for Clinical Investigation, United States (Aug. 2007).

Zhao, X., et al., "Targeting C-type Lectin-like Molecule-1 for Antibody-mediated Immunotherapy in Acute Myeloid Leukemia," Haematologica 95(1):71-78, Ferrata Storti Foundation, Italy (Jan. 2010).

Zhu, Z., et al., "Remodeling Domain Interfaces to Enhance Heterodimer Formation," Protein science 6(4):781-788, Cold Spring Harbor Laboratory Press, United States (Apr. 1997).

Yu, C-M., et al., "Rationalization and design of the complementarity determining region sequences in an antibody-antigen recognition interface," PLoS One 7(3):e33340, Public Library of Science, United States (Mar. 2012).

Office action mailed Nov. 27, 2017 in U.S. Appl. No. 15/121,623, inventor Geuijen; C.A.W., et al., 371(c) Date: Aug. 25, 2016, 54 pages.

Office action mailed Jul. 26, 2018 in U.S. Appl. No. 15/121,623, inventor Geuijen; C.A.W., et al., 371(c) Date: Aug. 25, 2016, 54 pages.

Office action mailed Jan. 15, 2020 in U.S. Appl. No. 15/121,623, inventor Geuijen; C.A.W., et al., 371(c) Date: Aug. 25, 2016, 35 pages.

Office action mailed Aug. 25, 2020 in U.S. Appl. No. 15/121,623, inventor Geuijen; C.A.W., et al., 371(c) Date: Aug. 25, 2016, 18 pages.

Office action mailed May 3, 2021 in U.S. Appl. No. 15/121,623, inventor Geuijen; C.A.W., et al., 371(c) Date: Aug. 25, 2016, 20 pages.

Co-pending U.S. Appl. No. 17/675,431, inventors Geuijen, C. A. W., et al., filed Feb. 18, 2022 (Not yet Published).

* cited by examiner

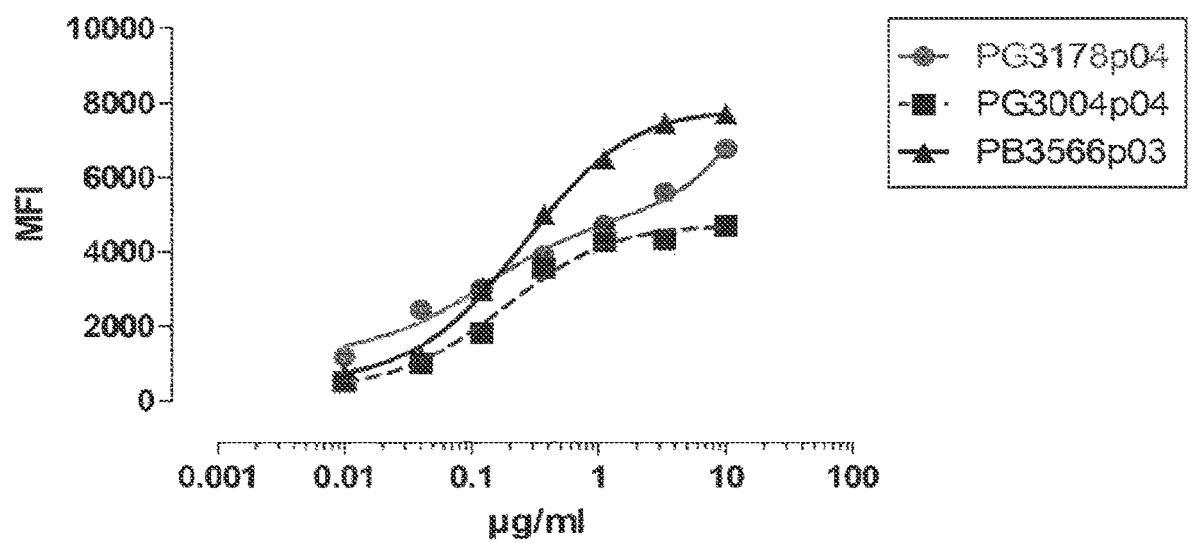
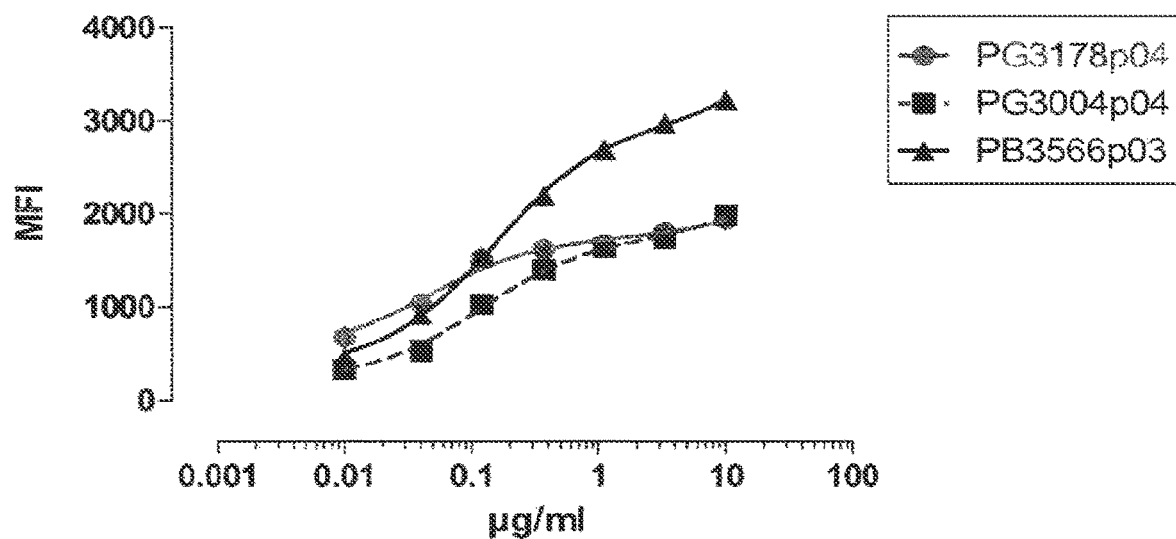
Fig. 6

Fig. 16A(a)

SEQ ID NO: 7 MF2926: heavy chain variable region sequence of an erbB-2 binding antibody Nucleic acid sequence (underlined sequence encodes end of leader peptide):

```
  1  GGCCCAGCCC GCCATGGCCC AGGTCCAGCT GCAGCAGTCT GGACCTGAGC TGGTGAAACC
 61  TGGGGCTTCA GTGATGATTT CCTGCAAGGC TTCTGGTTAC TCATTCACTG GCTACCACAT
121  GAACTGGGTG AAGCAAAGTC CTGAAAAGAG CCTTGAGTGG ATTGGAGACA TAAATCCTAG
181  CATTGGTACG ACTGCCCACA ACCAGATTTT CAGGGCCAAG GCCACAATGA CTGTTGACAA
241  ATCCTCCAAC ACAGCCTACA TGCAGCTCAA GAGCCTGACA TCTGAAGACT CTGGAGTCTT
301  TTACTGTGTT AGAAGAGGGG ACTGGTCCTT CGATGTCTGG GGCACAGGGA CCACGGTCAC
361  CGTCTCCAGT
```

Amino acid sequence:

SEQ ID NO: 8 QVQLQQSGPELVKPGASVMISCKASGYSFTGYHMNWVKQSPEKSLEWIGDINPSIGT
TAHNQIFRAKATMTVDKSSNTAYMQLKSLTSEDSGVFYCVRRGDWSFDVWGTGTTV
TVSS

SEQ ID NO: 9 CDR1: GYHMNWVKQSPEKSLE

SEQ ID NO: 10 CDR2: NQIFRA

SEQ ID NO: 11 CDR3: RGDWSFDV

Fig. 16A(b)

SEQ ID NO: 12 MF2930: heavy chain variable region sequence of an erbB-2 binding antibody Nucleic acid sequence (underlined sequence encodes end of leader peptide):

```
  1 GGCCCAGCCG GCCATGGCCG AGGTCCAGCT GCAGCAGTCT GGGGCTGAAC TGGTGAAGCC
 61 TGGAGCCTCA GTGATGATGT CCTGTAAGGT TTCTGGCTAC ACCTTCACTT CCTATCCTAT
121 AGCGTGGATG AAGCAGGTTC ATGGAAAGAG CCTAGAGTGG ATTGGAAATT TCATCCTTA
181 CAGTGATGAT ACTAAGTACA ATGAAAACTT CAAGGCCAAG GCCACATTGA CTGTAGAAAA
241 ATCCTCTAGC ACAGTCTACT TGGAGCTCAG CCGATTAACA TCTGATGACT CTGCTGTTTA
301 TTACTGTGCA AGAAGTAACC CATTATATTA CTTTGCTATG GACTACTGGG GTCAAGGAAC
361 CTCGGTCACC GTCTCCAGT
```

Amino acid sequence:

SEQ ID NO: 13 EVQLQQSGAELVKPGASVMMSCKVSGYTFTSYPIAWMKQVHGKSLEWIGNFHPYSD
DTKYNENFKGKATLTVEKSSSTVYLELSRLTSDDSAVYYCARSNPLYYFAMDYWGQG
TSVTVSS

SEQ ID NO: 14 CDR1:      SYPIAWMKQVHGKSLE

SEQ ID NO: 15 CDR2:      NENFKG

SEQ ID NO: 16 CDR3:      SNPLYYFAMDY

Fig. 16A(c)

SEQ ID NO: 17 MF1849: heavy chain variable region sequence of an erbB-2 binding antibody Nucleic acid sequence (underlined sequence encodes end of leader peptide):

```
  1 GGCCCAGCCG GCCATGGCCC AGGTGCAGCT GGTGGAGTCT GGGGAGGCG TGGTCCAGCC
 61 TGGGAGGTCC CTGAGACTCT CCTGTGCAGC CTCTGGATTC ACCTTCAGTA GCTATGGCAT
121 GCACTGGGTC CGCCAGGCTC CAGGCAAGGG GCTGGAGTGG GTGGCAGTTA TATCATATGA
181 TGGAAGTAAT AAATACTATG CAGACTCCGT GAAGGGCCGA TTCACCATCT CCAGAGACAA
241 TTCCAAGAAC ACGCTGTATC TGCAAATGAA CAGCCTGAGA GCTGAGGACA CGGCCGTGTA
301 TTACTGTGCA AAAGGTGACT ACGGTTCTTA CTCTTCTTAC GCCTTTGATT ATGGGGCCA
361 AGGTACCCTG GTCACCGTCT CCAGT
```

Amino acid sequence:

SEQ ID NO: 18 QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCAKGDYGSYSSYAFDYWG
QGTLVTVSS

| | | |
|---|---|---|
| SEQ ID NO: 19 CDR1: | SYGMH | |
| SEQ ID NO: 20 CDR2: | VISYDGSNKYYADSVKG | |
| SEQ ID NO: 21 CDR3: | GDYGSYSSYAFDY | |

Fig. 16A(d)

SEQ ID NO: 22 MF2973: heavy chain variable region sequence of an erbB-2 binding antibody Nucleic acid sequence (underlined sequence encodes end of leader peptide):

```
  1 GGCCCAGCCG GCCATGGCCC AGGTGCAGCT GAAGCAGTCT GGGGCTGAGC TGGTGAGGCC
 61 TGGGGCTTCA GTGAAGTTGT CCTGCAAGGC TTCTGGCTAC ATTTTCACTG GCTACTATAT
121 AAACTGGTTG AGGCAGAGGC CTGGACAGGG ACTTGAATGG ATTGCAAAAA TTTATCCTGG
181 AAGTGGTAAT ACTTACTACA ATGAGAAGTT CACGGGCAAG GCCACACTGA CTGCAGAAGA
241 ATCCTCCAGC ACTGCCTACA TGCAGCTCAG CAGCCTGACA TCTGAGGACT CTGCTGTCTA
301 TTTCTGTGCA AGAGGGCCCC ACTATGATTA CGACGGCCCC TGGTTTGTTT ACTGGGGCCA
361 AGGGACTCTG GTCACCGTCT CCAGT
```

Amino acid sequence:

SEQ ID NO: 23 QVQLKQSGAELVRPGASVKLSCKASGYIFTGYYINWLRQRPGQGLEWIAKIYPGSGNT
YYNEKFRGKATLTAEESSSTAYMQLSSLTSEDSAVYFCARGPHYDYDGPWFVYWGQ
GTLVTVSS

SEQ ID NO: 24 CDR1: GYYINWLRQRPGQGLE

SEQ ID NO: 25 CDR2: NEKFRG

SEQ ID NO: 26 CDR3: GPHYDYDGPWFVY

Fig. 16A(e)

SEQ ID NO: 27 MF3004: heavy chain variable region sequence of an erbB-2 binding antibody Nucleic acid sequence (underlined sequence encodes end of leader peptide):

```
  1 GGCCCAGCCG GCCATGGCCC AGGTGCAGCT GAAGCAGTCT GGGGCTGAGC TGGTGAGGCC
 61 TGGGGCTTCA GTGAAGCTGT CCTGCAAGGC TTCTGGCTAC ACTTTCACTG GCTACTATAT
121 AAACTGGGTG AAGCAGAGGC CTGGACAGGG ACTTGAGTGG ATTGCAAGGA TTTATCCTGG
181 AAGTGGTTAT ACTTACTACA ATGAGAAGTT CAAGGGCAAG GCCACACTGA CTGCAGAAGA
241 ATCCTCCAGC ACTGCCTACA TGCACCTCAG CAGCCTGACA TCTGAGGACT CTGCTGTCTA
301 TTTCTGTGCA AGACCCCACT ATGGTTACGA CGACTGGTAC TTCGGTGTCT GGGGCACAGG
361 CACCACGGTC ACCGTCTCCA GT
```

Amino acid sequence:

SEQ ID NO: 28 QVQLKQSGAELVRPGASVKLSCKASGYTFTGYYINWVKQRPGQGLEWIARIYPGSGY
TYYNEKFKGKATLTAEESSSTAYMHLSSLTSEDSAVYFCARPHYGYDDWYFGVWGT
GTTVTVSS

SEQ ID NO: 29 CDR1:     GYYINWVKQRPGQGLE

SEQ ID NO: 30 CDR2:     NEKFKG

SEQ ID NO: 31 CDR3:     PHYGYDDWYFGV

Fig. 16A(f)

SEQ ID NO: 32 MF2971: heavy chain variable region sequence of an erbB-2 binding antibody Nucleic acid sequence (underlined sequence encodes end of leader peptide):

```
  1 GGCCCAGCCG GCCATGGCCC AGGTGCAGCT GAAGCAGTCT GGGGCTGAGC TGGTGAGGCC
 61 TGGGGCTTCA GTGAAACTGT CCTGCAAGGC TTCTGGCTAC ACTTTCACTG CCTACTATAT
121 AAACTGGGTG AAGCAGAGGC CTGGACAGGG ACTTGAGTGG ATTGCAAGGA TTTATCCTGG
181 AAGTGGCTAT ACTTACTACA ATGAGATTTT CAAGGGCAGG GCCACACTGA CTGCAGACGA
241 ATCCTCCAGC ACTGCCTACA TGCAACTCAG CAGCCTGACA TCTGAGGACT CTGCTGTCTA
301 TTTCTGTGCA AGACCTCCGG TCTACTATGA CTCGGCCTGG TTTGCTTACT GGGGCCAAGG
361 GACTCTGGTC ACCGTCTCCA GT
```

Amino acid sequence:

SEQ ID NO: 33 QVQLKQSGAELVRPGASVKLSCKASGYTFTAYYINWVKQRPGQGLEWIARIYPGSGY
TYYNEIFKGRATLTADESSSTAYMQLSSLTSEDSAVYFCARPPVYYDSAWFAYWGQG
TLVTVSS

SEQ ID NO: 34 CDR1: AYYINWVKQRPGQGLE

SEQ ID NO: 35 CDR2: NEIFKG

SEQ ID NO: 36 CDR3: PPVYYDSAWFAY

Fig. 16A(g)

SEQ ID NO: 37 MF3025: heavy chain variable region sequence of an erbB-2 binding antibody Nucleic acid sequence (underlined sequence encodes end of leader peptide):

```
  1 GGCCCAGCCG GCCATGGCCC AGGTGCAGCT CAAGCAGTCT GGGGCTGAGC TGGTGAGGCC
 61 TGGGACTTCA GTGAAGCTGT CCTGCAAGGC TTCTGGCTAC ACTTTCACTG GCTACTATAT
121 AAACTGGGTG AAGCAGAGGC CTGGACAGGG ACTTGAGTGG ATTGCAAGGA TTTATCCTGG
181 AAGTGGTTAT ACTTACTACA ATGAGAAGTT CAAGGGCAAG GCCACACTGA CTGCAGAAGA
241 ATCCTCCAAC ACTGCCTATA TGCACCTCAG CAGCCTGACA TCTGAGGACT CTGCTGTCTA
301 TTTCTGTGCA AGGCCCCACT ATGGTTACGA CGACTGGTAC TTCGCTGTCT GGGGCACAGG
361 GACCACGGTC ACCGTCTCCA GT
```

Amino acid sequence:

SEQ ID NO: 38  QVQLKQSGAELVRPGTSVKLSCKASGYTFTGYYINWVKQRPGQGLEWIARIYPGSGY
TYYNEKFKGKATLTAEESSNTAYMHLSSLTSEDSAVYFCARPHYGYDDWYFAVWGT
GTTVTVSS

SEQ ID NO: 39 CDR1:    GYYINWVKQRPGQGLE

SEQ ID NO: 40 CDR2:    NEKFKG

SEQ ID NO: 41 CDR3:    PHYGYDDWYFAV

Fig. 16A(h)

SEQ ID NO: 42 MF2916: heavy chain variable region sequence of an erbB-2 binding antibody Nucleic acid sequence (underlined sequence encodes end of leader peptide):

```
  1 GGCCCAGCCG GCCATGGCCC AGGTCCAGCT GCAGCAGTCT GGGGCTGAGC TGGTGAGGCC
 61 TGGGGCTTCA GTGAAGCTGT CCTGCAAGGC TTCTGGCTAC ACTTTCACTG GCTACTATAT
121 AAACTGGGTG AAGCAGAGGC CTGGACAGGG ACTTGAGTGG ATTGCAAGGA TTTATCCTGG
181 CAGTGGTCAT ACTTCCTACA ATGAGAAGTT CAAGGGCAAG GCCACACTGA CTACAGAAAA
241 ATCCTCCAGC ACTGCCTACA TGCAGCTCAG CAGCCTGACA TCTGAGGACT CTGCTGTCTA
301 TTTCTGTGCA AGACCTATCT ACTTTGATTA CGCAGGGGGG TACTTCGATG TCTGGCGCAC
361 AAGAACCTCG GTCACCGTCT CCAGT
```

Amino acid sequence:

SEQ ID NO: 43 QVQLQQSGAELVRPGASVKLSCKASGYTFTGYYINWVKQRPGQGLEWIARIYPGSGH
TSYNEKFKGKATLTTEKSSSTAYMQLSSLTSEDSAVYFCARPIYFDYAGGYFDVWGTR
TSVTVSS

SEQ ID NO: 44 CDR1: GYYINWVKQRPGQGLE

SEQ ID NO: 45 CDR2: NEKFKG

SEQ ID NO: 46 CDR3: PIYFDYAGGYFDV

Fig. 16A(i)

SEQ ID NO: 47 MF3958: heavy chain variable region sequence of an erbB-2 binding antibody Nucleic acid sequence (underlined sequence encodes end of leader peptide):

```
  1 GGCCCAGCCG GCCATGGCCC AGGTGCAGCT GGTGCAGTCT GGCGCCGAAG TGAAGAAACC
 61 TGGCGCCAGC GTGAAGCTGA GCTGCAAGGC CAGCGGCTAC ACCTTCACCG CCTACTACAT
121 CAACTGGGTC CGACAGGCCC CAGGCCAGGG CCTGGAATGG ATCGGCAGAA TCTACCCCGG
181 CTCCGGCTAC ACCAGCTACG CCCAGAAGTT CCAGGGCAGA GCCACCCTGA CCGCCGACGA
241 GAGCACCAGC ACCGCCTACA TGGAACTGAG CAGCCTGCGG AGCGAGGATA CCGCCGTGTA
301 CTTCTGCGCC AGACCCCCCG TGTACTACGA CAGCGCTTGG TTTGCCTACT GGGGCCAGGG
361 CACCCTGGTC ACCGTCTCCA GT
```

Amino acid sequence:

SEQ ID NO: 48 QVQLVQSGAEVKKPGASVKLSCKASGYTFTAYYINWVRQAPGQGLEWIGRIYPGSGY
TSYAQKFQGRATLTADESTSTAYMELSSLRSEDTAVYFCARPPVYYDSAWFAYWGQG
TLVTVSS

SEQ ID NO: 49 CDR1: AYYIN

SEQ ID NO: 50 CDR2: RIYPGSGYTSYAQKFQG

SEQ ID NO: 51 CDR3: PPVYYDSAWFAY

Fig. 16A(j)

SEQ ID NO: 52 MF3031: heavy chain variable region sequence of an erbB-2 binding antibody Nucleic acid sequence (underlined sequence encodes end of leader peptide):

```
  1 GGCCCAGCCG GCCATGGCCC AGGTCCAGCT GCAGCAGTCT GGGGCTGAGC TGGTGAGGCC
 61 TGGGGCTTCA GTGAAGCTGT CCTGCAAGGC TTCTGGCTAC ACTTTCACTG CCTACTATAT
121 AAACTGGGTG AAGCAGAGGC CTGGACAGGG ACTTGAGTGG ATTGCAAAGA TTTATCCTGG
181 AAGTGGTTAT ACTTACTACA ATGAGAATTT CAGGGGCAAG GCCACACTGA CTGCAGAAGA
241 ATCCTCCAGT ACTGCCTACA TACAACTCAG CAGCCTGACA TCTGAGGACT CTGCTGTCTA
301 TTTCTGTGCA AGAGGCGTCT ATGATTACGA CGGGGCCTGG TTTGCTTACT GGGGCCAAGG
361 GACTCTGGTC ACCGTCTCCA GT
```

Amino acid sequence:

SEQ ID NO: 53 QVQLQQSGAELVRPGASVKLSCKASGYTFTAYYINWVKQRPGQGLEWIAKIYPGSGY
TYYNENFRGKATLTAEESSSTAYIQLSSLTSEDSAVYFCARGVYDYDGAWFAYWGQG
TLVTVSS

| | |
|---|---|
| SEQ ID NO: 54 CDR1: | AYYINWVKQRPGQGLE |
| SEQ ID NO: 55 CDR2: | NENFRG |
| SEQ ID NO: 56 CDR3: | GVYDYDGAWFAY |

Fig. 16A(k)

SEQ ID NO: 57 MF3991: heavy chain variable region sequence of an erbB-2 binding antibody Nucleic acid sequence (underlined sequence encodes end of leader peptide):

```
  1 GGCCCAGCCG GCCATGGCCC AGGTGCAGCT GGTGCAGTCT GGCGCCGAAG TGAAGAAACC
 61 TGGCGCCAGC GTGAAGCTGA GCTGCAAGGC CAGCGGCTAC ACCTTCACCG CCTACTACAT
121 CAACTGGGTC CGACAGGCCC CAGGCCAGGG CCTGGAATGG ATCGGCAGAA TCTACCCCGG
181 CTCCGGCTAC ACCAGCTACG CCCAGAAGTT CCAGGCCAGA GCCACCCTGA CCGCCGACGA
241 GAGCACCAGC ACCGCCTACA TGGAACTGAG CAGCCTGCGG AGCGAGGATA CCGCCGTGTA
301 CTTCTGCGCC AGACCCCACT ACGGCTACGA CGACTGGTAC TTCGGCGTGT GGGGCCAGGG
361 CACCCTGGTC ACCGTCTCCA GT
```

Amino acid sequence:

SEQ ID NO: 58 QVQLVQSGAEVKKPGASVKLSCKASGYTFTAYYINWVRQAPGQGLEWIGRIYPGSGY
TSYAQKFQGRATLTADESTSTAYMELSSLRSEDTAVYFCARPHYGYDDWYFGVWGQ
GTLVTVSS

SEQ ID NO: 59 CDR1: AYYIN

SEQ ID NO: 60 CDR2: RIYPGSGYTSYAQKFQG

SEQ ID NO: 61 CDR3: PHYGYDDWYFGV

Fig. 16B(a)

SEQ ID NO: 62 MF3178: heavy chain variable region sequence of an erbB-3 binding antibody Nucleic acid sequence (underlined sequence encodes end of leader peptide):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCTGTGTA
301 TTACTGTGCA AGACATCATG GTTCTCGTCA TTTCTGGTCT TACTGGGGCT TTGATTATTG
361 GGGCCAAGGT ACCCTGGTCA CCGTCTCCAG T
```

Amino acid sequence:

SEQ ID NO: 63  QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCARDHGSRHFWSYWGF
DYWGQGTLVTVSS

SEQ ID NO: 64 CDR1:    GYYMH

SEQ ID NO: 65 CDR2:    WINPNSGGTNYAQKFQG

SEQ ID NO: 66 CDR3:    DHGSRHFWSYWGFDY

Fig. 16B(b)

SEQ ID NO: 67 MF3176: heavy chain variable region sequence of an erbB-3 binding antibody Nucleic acid sequence (underlined sequence encodes end of leader peptide):

```
  1 GGCCCAGCCG GCCATGGCCG AGGTGCAGCT GTTGGAGTCT GGGGGAGGCT TGGTACAGCC
 61 TGGGGGGTCC CTGAGACTCT CCTGTGCAGC CTCTGGATTC ACCTTTAGCA GCTATGCCAT
121 GAGCTGGGTC CGCCAGGCTC CAGGGAAGGG GCTGGAGTGG GTCTCAGCTA TTAGTGGTAG
181 TGGTGGTAGC ACATACTACG CAGACTCCGT GAAGGGCCGG TTCACCATCT CCAGAGACAA
241 TTCCAAGAAC ACGCTGTATC TGCAAATGAA CAGCCTGAGA GCCGAGGACA CGGCTGTGTA
301 TTACTGTGCA AGACATTGGT GGTACCCGCC GTACTACTGG GGCTTTGATT ATGGGGCCA
361 AGGTACCCTG GTCACCGTCT CCAGT
```

Amino acid sequence:

SEQ ID NO: 68 EVQLLESGGGLVQPGGSLRLSCAASGFTFSSYAMSWVRQAPGKGLEWVSAISGSGGS
TYYADSVKGRFTISRDNSKNTLYLQMNSLRAEDTAVYYCARDWWYPPYYWGFDYWG
QGTLVTVSS

SEQ ID NO: 69 CDR1:      SYAMS

SEQ ID NO: 70 CDR2:      AISGSGGSTYYADSVKG

SEQ ID NO: 71 CDR3:      DWWYPPYYWGFDY

Fig. 16B(c)

SEQ ID NO: 72 MF3163: heavy chain variable region sequence of an erbB-3 binding antibody Nucleic acid sequence (underlined sequence encodes end of leader peptide):

```
  1 GGCCCAGCCG GCCATGGCCC AGGTGCAGCT GGTGCAGTCT GGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCCGTGTA
301 TTACTGTGCA AAAGATTCTT ACTCTCGTCA TTTCTACTCT TGGTGGGCCT TTGATTATTG
361 GGGCCAAGGT ACCCTGGTCA CCGTCTCCAG T
```

Amino acid sequence:

SEQ ID NO: 73 QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCAKDSYSRHFYSWWAF
DYWGQGTLVTVSS

| | | |
|---|---|---|
| SEQ ID NO: 74 CDR1: | GYYMH |
| SEQ ID NO: 75 CDR2: | WINPNSGGTNYAQKFQG |
| SEQ ID NO: 76 CDR3: | DSYSRHFYSWWAFDY |

Fig. 16B(d)

SEQ ID NO: 77 MF3099: heavy chain variable region sequence of an erbB-3 binding antibody Nucleic acid sequence (underlined sequence encodes end of leader peptide):

```
  1 GGCCCAGCCG GCCATGGCCG AGGTCCAGCT GCAGCAGCCT GGGGCTGAGC TGGTGAGGCC
 61 TGGGACTTCA GTGAAGTTGT CCTGCAAGGC TTCTGGCTAC ACCTTCACCA GCTACTGGAT
121 GCACTGGGTA AAGCAGACGC CTGGACAAGG CCTTGAGTGG ATCGGAATTC TTGATCCTTC
181 TGATAGTTAT ACTACCTACA ATCAAAAGTT CAAGGGCAAG GCCACATTAA CAGTAGACAC
241 ATCCTCCAGC ATAGCCTACA TGCAGCTCAG CAGCCTGACA TCTGAGGACT CTGCGCTCTA
301 TTACTGTGCA AGAGGGGCAG ATTACGACGA GGGAGGTGCT ATGGACTACT GGGGTCAAGG
361 AACCTCGGTC ACCGTCTCCA GT
```

Amino acid sequence:

SEQ ID NO: 78 EVQLQQPGAELVRPGTSVKLSCKASGYTFTSYWMHWVKQRPGQGLEWIGILDPSDSY
TTYNQKFKGKATLTVDTSSSIAYMQLSSLTSEDSALYYCARGGDYDEGGAMDYWGQ
GTSVTVSS

| | | |
|---|---|---|
| SEQ ID NO: 79 | CDR1: | SYWMH |
| SEQ ID NO: 80 | CDR2: | ILDPSDSYTTYNQKFKG |
| SEQ ID NO: 81 | CDR3: | GGDYDEGGAMDY |

Fig. 16B(e)

SEQ ID NO: 82 MF3307: heavy chain variable region sequence of an erbB-3 binding antibody Nucleic acid sequence (underlined sequence encodes end of leader peptide):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGCACAC
241 GTCCATCAGC ACAGCCTACA TGGAGCTGAG CAGGCTGAGA TCTGACGACA CGGCCGTGTA
301 TTACTGTGCA AGAGGTTCTC GTAAACGTCT GTCTAACTAC TTCAACGCCT TTGATTATTG
361 GGGCCAAGGT ACCCTGGTCA CCGTCTCCAG T
```

Amino acid sequence:

SEQ ID NO: 83 QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCARGSRKRLSNYFNAFD
YWGQGTLVTVSS

| | | |
|---|---|---|
| SEQ ID NO: 84 CDR1: | GYYMH | |
| SEQ ID NO: 85 CDR2: | WINPNSGGTNYAQKFQG | |
| SEQ ID NO: 86 CDR3: | GSRKRLSNYFNAFDY | |

Fig. 16C a) Common Light Chain

SEQ ID NO: 87  DIQMTQSPSSLSASVGDRVTITCRASQSISSYLNWYQQKPGKAPKLLIYAASSLQSGVP
SRFSGSGSGTDFTLTISSLQPEDFATYYCQQSYSTPPTFGQGTKVEIKRTVAAPSVFIFP
PSDEQLKSGTASVVCLLNNFYPREAKVQWKVDNALQSGNSQESVTEQDSKDSTYSLS
STLTLSKADYEKHKVYACEVTHQGLSSPVTKSFNRGEC

Fig. 16D heavy chain for erbB-2 binding

SEQ ID NO: 88  QVQLVQSGAEVKKPGASVKLSCKASGYTFTAYYINWVRQAPGQGLEWIGRIYPGSGY
TSYAQKFQGRATLTADESTSTAYMELSSLRSEDTAVYFCARPPVYYDSAWFAYWGQG
TLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCDKTHTC
PPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAK
GQPREPQVYTDPPSREEMTKNQVSLTCEVKGFYPSDIAVEWESNGQPENNYKTTPPV
LDSDGSFFLYSKLTVDKSRWQQGNVFSCSVMHEALHNHYTQKSLSLSPG heavy chain for erbB-3 binding SEQ ID NO: 89  QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCARDHGSRHFWSYWGF
DYWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPI
EKTISKAKGQPREPQVYTKPPSREEMTKNQVSLKCLVKGFYPSDIAVEWESNGQPEN
NYKTTPPVLDSDGSFFLYSKLTVDKSRWQQGNVFSCSVMHEALHNHYTQKSLSLSPG

Fig. 16E(a)

HER2-specific Ab sequences

SEQ ID NO: 90 MF2889: heavy chain variable region sequence of an erbB-2 binding antibody Nucleic acid sequence (underlined sequence encodes end of leader peptide):

```
  1   GGCCCAGCCG GCCATGGCCG AGGTCCAGCT GCAGCAGTCT GGAGCTGAGC TGGTAAGGCC
 61   TGGGACTTCA GTGAAGGTGT CCTGCAAGGC TTCTGGATAC GCCTTCACTA ATTATTTGAT
121   AGAGTGGGTA AAGCAGAGGC CTGGCCAGGG CCTTGAGTGG ATTGGAGTGA TTTATCCTGA
181   AGGTGGTGGT ACTATCTACA ATGAGAAGTT CAAGGGCAAG GCAACACTGA CTGCAGACAA
241   ATCCTCCAGC ACTGCCTACA TGCAGCTCAG CGGCCTGACA TCTGAGGACT CTGCGGTCTA
301   TTTCTGTGCA AGAGGAGACT ATGATTACAA ATATGCTATG GACTACTGGG GTCAAGGAAC
361   CTCCGTCACC GTCTCCACT
```

Amino acid sequence:

SEQ ID NO: 91 EVQLQQSGAELVRPGTSVKVSCKASGYAFTNYLIEWVKQRPGQGLEWIGVIYPEGGG
TIYNEKFKGKATLTADKSSSTAYMQLSGLTSEDSAVYFCARGDYDYKYAMDYWGQG
TSVTVSS

SEQ ID NO: 92 CDR1: NYLIE

SEQ ID NO: 93 CDR2: VIYPEGGGTIYNEKFKG

SEQ ID NO: 94 CDR3: GDYDYKYAMDY

Fig. 16E(b)

SEQ ID NO: 95 MF2913: heavy chain variable region sequence of an erbB-2 binding antibody Nucleic acid sequence (underlined sequence encodes end of leader peptide):

```
  1 GGCCCAGCCG GCCATGGCCG AGGTCAAGCT GCAGCAGTCT GGACCTGAGC TGGTGAAGCC
 61 TGGCGCTTCA GTGAAGATAT CCTGCAAGGC TTCTGGTTAC TCATTCACTG ACTACAAAAT
121 GGACTGGGTG AAGCAGAGCC ATGGAAAGAG CCTCGAATGG ATTGGAAATA TTAATCCTAA
181 CAGTGGTGGT GTTATCTACA ACCAGAAGTT CAGGGGCAAG GTCACATTGA CTGTTGACAG
241 GTCCTCCAGC GCAGCCTACA TGGAGCTCCG CAGCCTGACA TCTGAGGACA CTGCAGTCTA
301 TTATTGTTCA AGAGGACTGT GGGATGCTAT GGACTCCTGG GGTCAAGGAA CCTCGGTCAC
361 CGTCTCCAGT
```

Amino acid sequence:

SEQ ID NO: 96 EVKLQQSGPELVKPGASVKISCKASGYSFTDYKMDWVKQSHGKSLEWIGNINPNSGG
VIYNQKFRGKVTLTVDRSSSAAYMELRSLTSEDTAVYYCSRGLWDAMDSWGQGTSVT
VSS

SEQ ID NO: 97 CDR1:     DYKMDWVKQSHGKSLE

SEQ ID NO: 98 CDR2:     NQKFRG

SEQ ID NO: 99 CDR3:     GLWDAMDS

Fig. 16E(c)

SEQ ID NO: 100 MF1847: heavy chain variable region sequence of an erbB-2 binding antibody Nucleic acid sequence (underlined sequence encodes end of leader peptide):

```
  1   GGCCCAGCCG GCCATGGCCC AGGTGCAGCT GGTGGAGTCT GGGGGAGGCG TGGTCCAGCC
 61   TGGGAGGTCC CTGAGACTCT CCTGTGCAGC CTCTGGATTC ACCTTCAGTA GCTATGGCAT
121   GCACTGGGTC CGCCAGGCTC CAGGCAAGGG GCTGGAGTGG GTGGCAGTTA TATCATATGA
181   TGGAAGTAAT AAATACTATG CAGACTCCGT GAAGGGCCGA TTCACCATCT CCAGAGACAA
241   TTCCAAGAAC ACGCTGTATC TGCAAATGAA CAGCCTGAGA GCTGAGGACA CGGCCGTCTA
301   TTACTGTGCA AAAGGTTGGT GGCATCCGCT GCTGTCTGGC TTTGATTATT GGGGCCAAGG
361   TACCCTGGTC ACCGTCTCCA GT
```

Amino acid sequence:

SEQ ID NO: 101 QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCAKGWWHPLLSGFDYWG
QGTLVTVSS

SEQ ID NO: 102 CDR1:    SYGMH

SEQ ID NO: 103 CDR2:    VISYDGSNKYYADSVKG

SEQ ID NO: 104 CDR3:    GWWHPLLSGFDY

Fig. 16E(d)

SEQ ID NO: 105 MF3001: heavy chain variable region sequence of an erbB-2 binding antibody Nucleic acid sequence (underlined sequence encodes end of leader peptide):

```
  1   GGCCCAGCCG GCCATGGCCG AGGTCCAGCT GCAGCAGTCT GGGGCTGAAC TGGCAAAACC

61   TGGGGCCTCA GTGAAGCTGT CCTGCAACAC TTCTGGCTAC AACTTTCCTA TCTACTGGAT

121   GCACTGGGTA AAACAGAGGC CTGGACGGGG TCTGGAATGG ATTGGATACA TTAATCCTAG

181   TACTGGTTAT ATTAAGAACA ATCAGAAGTT CAAGGACAAG GCCACCTTGA CTGCAGACAA

241   ATCCTCCAAC ACAGCCTACA TGCAGCTCAA CAGCCTGACA TATGAGGACT CTGCAGTCTA

301   TTACTGTACA AGAGAAGGGA TAACTGGGTT TACTTACTGG GGCCAAGGGA CTCTGGTCAC

361   CGTCTCCAGT
```

Amino acid sequence:

SEQ ID NO: 106 EVQLQQSGAELAKPGASVKLSCKTSGYNFPIYWMHWVKQRPGRGLEWIGYINPSTGY
IKNNQKFKDKATLTADKSSNTAYMQLNSLTYEDSAVYYCTREGITGFTYWGQGTLVT
VSS

SEQ ID NO: 107 CDR1:    IYWMHWVKQRPGRGLE

SEQ ID NO: 108 CDR2:    NQKFKD

SEQ ID NO: 109 CDR3:    EGITGFTY

Fig. 16E(e)

SEQ ID NO: 110 MF1898: heavy chain variable region sequence of an erbB-2 binding antibody Nucleic acid sequence (underlined sequence encodes end of leader peptide):

```
  1 GCCCCAGCCG GCCATGGCCC AGGTGCAGCT GGTGGAGTCT GGGGGAGGCG TGGTCCAGCC
 61 TGGGAGGTCC CTGAGACTCT CCTGTGCAGC CTCTGGATTC ACCTTCAGTA GCTATGGCAT
121 GCACTGGGTC CGCCAGGCTC CAGGCAAGGG GCTGGAGTGG GTGGCAGTTA TATCATATGA
181 TGGAAGTAAT AAATACTATG CAGACTCCGT GAAGGGCCGA TTCACCATCT CCAGAGACAA
241 TTCCAAGAAC ACGCTGTATC TGCAAATGAA CAGCCTGAGA GCTGAGGACA CGGCCGTGTA
301 TTACTGTGCA AAAGATGGTT TCCGTCGTAC TACTCTGTCT GGCTTTGATT ATTGGGGCCA
361 AGGTACCCTG GTCACCGTCT CCAGT
```

Amino acid sequence:

SEQ ID NO: 111 QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCAKDGFRRTTLSGFDYW
GQGTLVTVSS

SEQ ID NO: 112 CDR1: SYGMH

SEQ ID NO: 113 CDR2: VISYDGSNKYYADSVKG

SEQ ID NO: 114 CDR3: DGFRRTTLSGFDY

Fig. 16E(f)

SEQ ID NO: 115 MF3003 heavy chain variable region sequence of an erbB-2 binding antibody Nucleic acid sequence (underlined sequence encodes end of leader peptide):

```
  1  GGCCCAGCCG GCCATGGCCC AGGTGCAGCT GAAGCAGTCT GGACCTGAGC TGGTGAAGCC
 61  TGGGGCCTCA GTGAAGATTT CCTGCAAGGC TTCTGGCGAC GCATTCAGTT ACTCCTGGAT
121  GAACTGGGTG AAGCAGAGGC CTGGAAAGGG TCTTGAGTGG ATTGGACGGA TTTATCCTGG
181  AGATGGAGAT ATTAACTACA ATGGGAAGTT CAAGGGCAAG GCCACACTGA CTGCAGACAA
241  ATCCTCCAGC ACAGCCCACC TGCAACTCAA CAGCCTGACA TCTGAGGACT CTGCGGTCTA
301  CTTCTGTGCA AGAGGACAGC TCGGACTAGA GGCCTGGTTT GCTTATTGGG GCCAGGGGAC
361  TCTGGTCACC GTCTCCAGT
```

Amino acid sequence:

SEQ ID NO: 116 QVQLKQSGPELVKPGASVKISCKASGDAFSYSWMNWVKQRPGKGLEWIGRIYPGDG
DINYNGKFKGKATLTADKSSSTAHLQLNSLTSEDSAVYFCARGQLGLEAWFAYWGQ
GTLVTVSS

SEQ ID NO: 117 CDR1:     YSWMNWVKQRPGKGLE

SEQ ID NO: 118 CDR2:     NGKFKG

SEQ ID NO: 119 CDR3:     GQLGLEAWFAY

Fig. 16E(g)

HER3-specific Ab sequences

SEQ ID NO: 120 MF6058: heavy chain variable region sequence of an erbB-3 binding antibody Nucleic acid sequence (underlined sequence encodes end of leader peptide):

```
  1 CCCCCAGCCC GCCATCCCCC ACCTCCACCT CGTCCACTCT CCGCCTCACC TCAACAAGCC
 61 TGGGCCTCA GTGAAGGTCA CGTGCAAGGC TTCTGGATAC ACCTTCACCG GCTACTATAT
121 GCACTGGGTG CGACAGGCCC CTGGACAAGC TCTTGAGTGG ATGGGATGGA TCAACCCTCA
181 AAGTGGTGGC ACAAACTATG CAAACAACTT TCACCCACG CTCTCTATGA CCACCCACAC
241 GTCCACAAGC ACAGCCTACA TGCAGCTGAG CAGGCTGAGA TCTGACGACA CGGCTACGTA
301 TTACTGTGCA AGAGATCATG GTTCTCGTCA TTTCTGGTCT TACTGGGGCT TTGATTATTG
361 GGGCCAAGGT ACCCTGGTCA CCGTCTCCAG T
```

Amino acid sequence:

SEQ ID NO: 121 QVQLVQSGADVKKPGASVKVTCKASGYTFTGYYMHWVRQAPGQALEWMGWINPQS
GGTNYAKKFQGRVSMTRETSTSTAYMQLSRLRSDDTATYYCARDHGSRHFWSYWGF
DYWGQGTLVTVSS

| | | |
|---|---|---|
| SEQ ID NO: 122 CDR1: | GYYMH | |
| SEQ ID NO: 123 CDR2: | WINPQSGGTNYAKKFQG | |
| SEQ ID NO: 124 CDR3: | DHGSRHFWSYWGFDY | |

Fig. 16E(h)

SEQ ID NO: 125 MF6061: heavy chain variable region sequence of an erbB-3 binding antibody Nucleic acid sequence (underlined sequence encodes end of leader peptide):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 CCACTGGGTG CGACAGGCCC CTCCACAAGG CCTTGACTGG ATGGATCCA TCAACCCTCA
181 GAGTGGTGGC ACAAACTATG CACAGAAGTT TAAGGGCAGG GTCACGATGA CCAGGGACAC
241 GTCCACCAGC ACAGCCTACA TGGAGCTGAG CAGGCTGAGA TCTGACGACA CGGCTGTGTA
301 TTACTGTGCA AGAGATCATG GTTCTCGTCA TTTCTGGTCT TACTGGGGCT TTGATTATTG
361 GGGCCAAGGT ACCCTGGTCA CCGTCTCCAG T
```

Amino acid sequence:

SEQ ID NO: 126 QVQLVQSGAEVKKPGASVKVSCKASGYTFTGYYMHWVRQAPGQGLEWMGWINPQS
GGTNYAQKFKGRVTMTRDTSTSTAYMELSRLRSDDTAVYYCARDHGSRHFWSYWGF
DYWGQGTLVTVSS

SEQ ID NO: 127 CDR1: GYYMH

SEQ ID NO: 128 CDR2: WINPQSGGTNYAQKFKG

SEQ ID NO: 129 CDR3: DHGSRHFWSYWGFDY

Fig. 16E(i)

SEQ ID NO: 130 MF6065: heavy chain variable region sequence of an erbB-3 binding antibody Nucleic acid sequence (underlined sequence encodes end of leader peptide):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCT CTTACTATAT
121 CCACTGGGTG CGACAGGCCC CTCCACAACG CCTTGAGTGG ATGGGATGGA TCAACCCTCA
181 GGGGGGTTCT ACAAACTATG CACAGAAGTT TCAGGGCAGG GTCACGATGA CCAGGGACAC
241 GTCCACCAGC ACAGTGTACA TGGAGCTGAG CAGGCTGAGA TCTGAGGACA CGGCTGTGTA
301 TTACTGTGCA AGAGATCATG GTCTCGTCA TTTCTGGTCT TACTGGGGCT TTGATTATTG
361 GGGCCAAGGT ACCCTGGTCA CCGTCTCCAG T
```

Amino acid sequence:

SEQ ID NO: 131 QVQLVQSGAEVKKPGASVKVSCKASGYTFTSYYMHWVRQAPGQGLEWMGWINPQG
GSTNYAQKFQGRVTMTRDTSTSTVYMELSRLRSEDTAVYYCARDHGSRHFWSYWGF
DYWGQGTLVTVSS

SEQ ID NO: 132 CDR1:   SYYMH

SEQ ID NO: 133 CDR2:   WINPQGGSTNYAQKFQG

SEQ ID NO: 134 CDR3:   DHGSRHFWSYWGFDY

```
              139                                                              186
SEQ ID NO: 135 LCYQDTILWKDIFHKNNQLALTLIDTNRSRACHPCSPMCKGSRCWGES
```

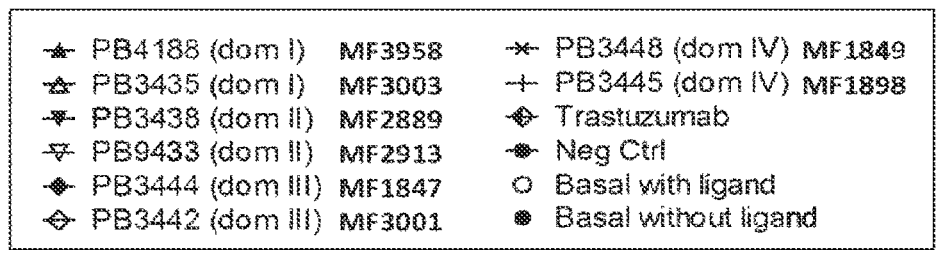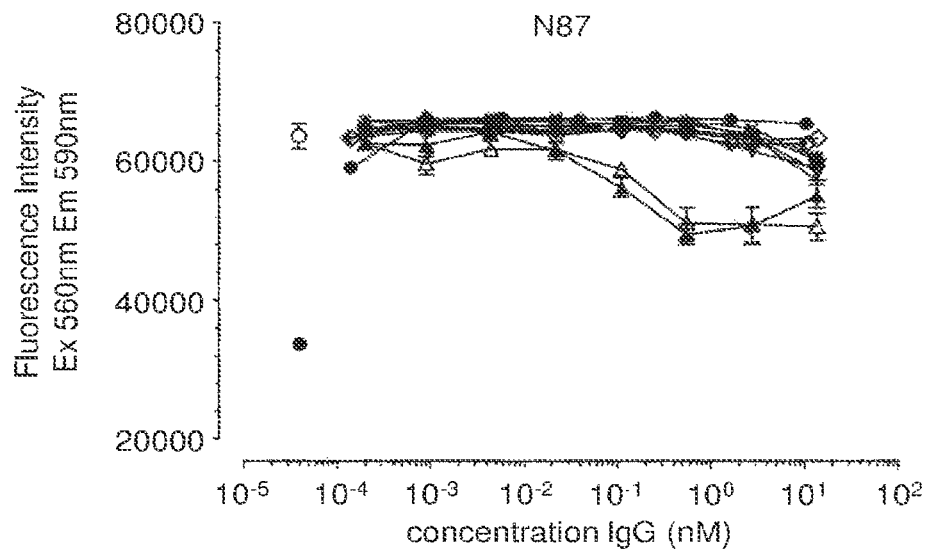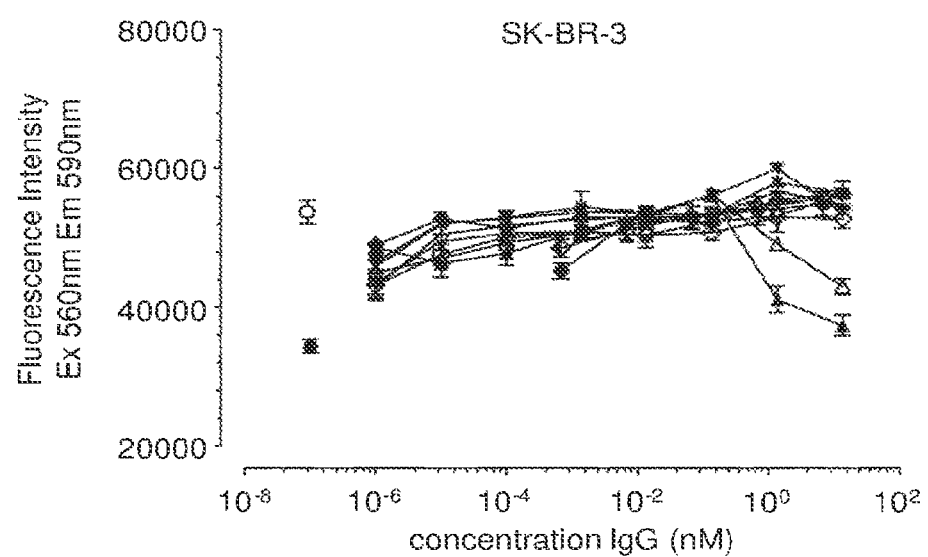
Fig. 28A

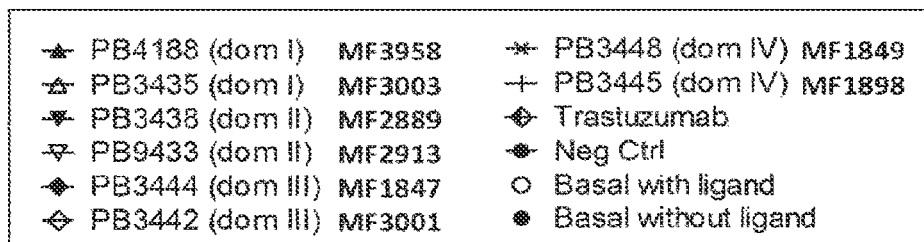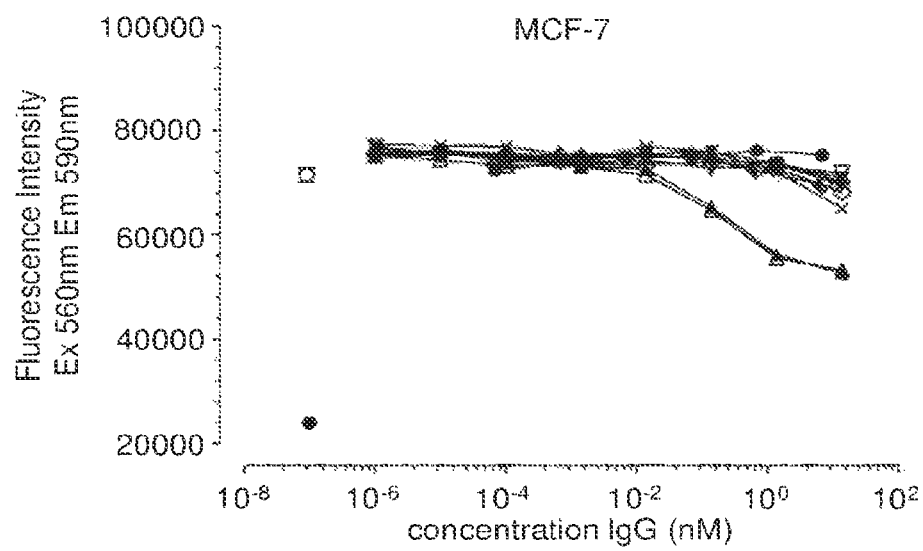
Fig. 28B

Fig. 37A

Amino acid alignment of MF3178 variants

```
                                                     CDR1                    CDR2
                   1        10        20        30              40        50        60
SEQ ID NO: 62 MF3178  QVQLVQSGAEVKKPGASVKVSCKASGYTFT  GYYMH  WVRQAPGQGLEWMG  WINPNSGGTNYAQKFQG
SEQ ID NO: 136 MF6055 .........D....................  .....  .........A....  ....S.......K....
SEQ ID NO: 138 MF6056 .........D........T...........  .....  .........A....  ....S.......K....
SEQ ID NO: 140 MF6057 .........D........T...........  .....  ..............  ....Q............
SEQ ID NO: 142 MF6058 .........D........T...........  .....  .........A....  ....Q.......K....
SEQ ID NO: 144 MF6059 ..............................  .....  ..............  ....G..S.........
SEQ ID NO: 146 MF6060 .........D....................  .....  .........A....  ....Q.......K....
SEQ ID NO: 148 MF6061 ..............................  .....  ..............  ....Q...........K.
SEQ ID NO: 150 MF6062 ..............................  .....  ..............  ....G..S.........
SEQ ID NO: 152 MF6063 ..............................  .....  ..............  ....Q.......K....
SEQ ID NO: 154 MF6064 ..............................  .....  ........K.....  ....Q............
SEQ ID NO: 156 MF6065 ..............................  S....  ..............  ....QG.S.........
SEQ ID NO: 158 MF6066 ..............................  .....  ..............  ....Q..S.........
SEQ ID NO: 160 MF6067 ..............................  .....  ..............  ....Q............
SEQ ID NO: 162 MF6068 ..............................  .....  ..............  ....Q............
SEQ ID NO: 164 MF6069 ..............................  .....  ..............  ....Q............
SEQ ID NO: 166 MF6070 ..............................  S....  ..............  ....SG.S.........
SEQ ID NO: 168 MF6071 ..............................  .....  ..............  ....S..S.........
SEQ ID NO: 170 MF6072 ..............................  .....  ..............  ....S............
SEQ ID NO: 172 MF6073 ..............................  .....  ..............  ....S............
SEQ ID NO: 174 MF6074 ..............................  .....  ..............  ....S............

CDR3
                    70        80        90       100        110       120
SEQ ID NO: 62 MF3178  RVTMTRDTSISTAYMELSRLRSDDTAVYYCAR  DHGSRHFWSYWGFDY  WGQGTLVTVSS
SEQ ID NO: 136 MF6055 ......E..T.....................T......  ...............  ...........
SEQ ID NO: 138 MF6056 ..S...E..T.....Q...............F......  ...............  ...........
SEQ ID NO: 140 MF6057 .........T.....Q......................  ...............  ...........
SEQ ID NO: 142 MF6058 ..S...E..T.....Q...............T......  ...............  ...........
SEQ ID NO: 144 MF6059 ......................................  ...............  ...........
SEQ ID NO: 146 MF6060 ......E..T.....................T......  ...............  ...........
SEQ ID NO: 148 MF6061 .........T............................  ...............  ...........
SEQ ID NO: 150 MF6062 .........T............................  ...............  ...........
SEQ ID NO: 152 MF6063 .........T............................  ...............  ...........
SEQ ID NO: 154 MF6064 .........T............................  ...............  ...........
SEQ ID NO: 156 MF6065 .........T..V.........E...............  ...............  ...........
SEQ ID NO: 158 MF6066 .........T........S...E...............  ...............  ...........
SEQ ID NO: 160 MF6067 .........T..V.....S...................  ...............  ...........
SEQ ID NO: 162 MF6068 .........T............................  ...............  ...........
SEQ ID NO: 164 MF6069 ......................................  ...............  ...........
SEQ ID NO: 166 MF6070 .........T..V.........E...............  ...............  ...........
SEQ ID NO: 168 MF6071 .........T........S...E...............  ...............  ...........
SEQ ID NO: 170 MF6072 .........T..V.....S...................  ...............  ...........
SEQ ID NO: 172 MF6073 .........T............................  ...............  ...........
SEQ ID NO: 174 MF6074 ......................................  ...............  ...........
```

Fig. 37B

Nucleic acid alignment of MF3178 variants (*without* end of leader sequence)

```
SEQ ID NO: 62   MF3178  CAGGTGCAGCTGGTGCAGTCTGGGGCTGAGGTGAAGAAGCCTGGGGCCTCAGTGAAGGTCTCCTGCAAG
SEQ ID NO: 142  MF6058  ..................................C...........................A.G......
SEQ ID NO: 150  MF6061  .........................................................................
SEQ ID NO: 156  MF6065  .........................................................................

CDR1
SEQ ID NO: 62   MF3178  GCTTCTGGATACACCTTCACC  GGCTACTATATGCAC  TGGGTGCGACAGGCCCCTGGACAAGGGCTTG
SEQ ID NO: 142  MF6058  .....................  ...............  ..............................CT....
SEQ ID NO: 150  MF6061  .....................  ...............  .........................................
SEQ ID NO: 156  MF6065  .....................  .TCT............  .........................................

CDR2
SEQ ID NO: 62   MF3178  AGTGGATGGGA  TGGATCAACCCTAACAGTGGTGGCACAAACTATGCACAGAAGTTTCAGGGC  AGGGT
SEQ ID NO: 142  MF6058  ...........  ...........C.A........................A...........  .....
SEQ ID NO: 150  MF6061  ...........  ...........C.G........................A...........  .....
SEQ ID NO: 156  MF6065  ...........  ...........C.GG.G...TCT...........................  .....

SEQ ID NO: 62   MF3178  CACGATGACCAGGGACACGTCCATCAGCACAGCCTACATGGAGCTGAGCAGGCTGAGATCTGACGACAC
SEQ ID NO: 142  MF6058  .T.T..........G........CA..............C..............................
SEQ ID NO: 150  MF6061  .......................C.............................................
SEQ ID NO: 156  MF6065  ......................C.........TG...............................G.....

CDR3
SEQ ID NO: 62   MF3178  GGCTGTGTATTACTGTGCAAGA  GATCATGGTTCTCGTCATTTCTGGTCTACTGGGGCTTTGATTAT
SEQ ID NO: 142  MF6058  ....AC................  .............................................
SEQ ID NO: 150  MF6061  ......................  .............................................
SEQ ID NO: 156  MF6065  ......................  .............................................

SEQ ID NO: 62   MF3178  TGGGGCCAAGGTACCCTGGTCACCGTCTCCAGT
SEQ ID NO: 142  MF6058  .................................
SEQ ID NO: 150  MF6061  .................................
SEQ ID NO: 156  MF6065  .................................
```

Fig. 37C

DNA sequences of MF3178 variants (without end of leader sequence)

SEQ ID NO: 136 MF6055

>MF6055_VH
caggtgcagctggtgcagtctggggctgacgtgaagaagcctggggcctcagtgaaggtctcctgcaagg
cttctggatacaccttcaccggctactatatgcactgggtgcgacaggcccctggacaagctcttgagtg
gatgggatggatcaacccttctagtggtggcacaaactatgcaaagaagtttcagggcagggtcacgatg
accagggagacgtccacaagcacagcctacatggagctgagcaggctgagatctgacgacacggctacgt
attactgtgcaagagatcatggttctcgtcatttctggtcttactggggctttgattattggggccaagg
taccctggtcaccgtctccagt

SEQ ID NO: 138 MF6056

>MF6056_VH
caggtgcagctggtgcagtctggggctgacgtgaagaagcctggggcctcagtgaaggtcacgtgcaagg
cttctggatacaccttcaccggctactatatgcactgggtgcgacaggcccctggacaagctcttgagtg
gatgggatggatcaacccttctagtggtggcacaaactatgcaaagaagtttcagggcagggtctctatg
accagggagacgtccacaagcacagcctacatgcagctgagcaggctgagatctgacgacacggctacgt
attactgtgcaagagatcatggttctcgtcatttctggtcttactggggctttgattattggggccaagg
taccctggtcaccgtctccagt

SEQ ID NO: 140 MF6057

>MF6057_VH
caggtgcagctggtgcagtctggggctgatgtgaagaagcctggggcctcagtgaaggtcacgtgcaagg
cttctggatacaccttcaccggctactatatgcactgggtgcgacaggcccctggacaagggcttgagtg
gatgggatggatcaaccctcagagtggtggcacaaactatgcacagaagtttcagggcagggtcacgatg
accagggacacgtccatcagcacagcctacatgcagctgagcaggctgagatctgacgacacggctgtgt
attactgtgcaagagatcatggttctcgtcatttctggtcttactggggctttgattattggggccaagg
taccctggtcaccgtctccagt

SEQ ID NO: 142 MF6058

>MF6058_VH
caggtgcagctggtgcagtctggggctgacgtgaagaagcctggggcctcagtgaaggtcacgtgcaagg
cttctggatacaccttcaccggctactatatgcactgggtgcgacaggcccctggacaagctcttgagtg
gatgggatggatcaaccctcaaagtggtggcacaaactatgcaaagaagtttcagggcagggtctctatg
accagggagacgtccacaagcacagcctacatgcagctgagcaggctgagatctgacgacacggctacgt
attactgtgcaagagatcatggttctcgtcatttctggtcttactggggctttgattattggggccaagg
taccctggtcaccgtctccagt

Fig. 37D

SEQ ID NO: 144 MF6059

>MF6059_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctggcagtggttctacaaactatgcacagaagtttcagggcagggtcacgatg
accagggacacgtccatcagcacagcctacatggagctgagcaggctgagatctgacgacacggctgtgt
attactgtgcaagagatcatggttctcgtcatttctggtcttactggggctttgattattggggccaagg
taccctggtcaccgtctccagt

SEQ ID NO: 146 MF6060

>MF6060_VH
caggtgcagctggtgcagtctggggctgacgtgaagaagcctggggcctcagtgaaggtctcctgcaagg
cttctggatacaccttcaccggctactatatgcactgggtgcgacaggcccctggacaagctcttgagtg
gatgggatggatcaaccctcaaagtggtggcacaaactatgcaaagaagtttcagggcagggtcacgatg
accagggagacgtccacaagcacagcctacatggagctgagcaggctgagatctgacgacacggctacgt
attactgtgcaagagatcatggttctcgtcatttctggtcttactggggctttgattattggggccaagg
tacccggtcaccgtctccagt

SEQ ID NO: 148 MF6061

>MF6061_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcacagaagtttaagggcagggtcacgatg
accagggacacgtccaccagcacagcctacatggagctgagcaggctgagatctgacgacacggctgtgt
attactgtgcaagagatcatggttctcgtcatttctggtcttactggggctttgattattggggccaagg
tacccggtcaccgtctccagt

SEQ ID NO: 150 MF6062

>MF6062_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctggcagtggttctacaaactatgcacagaagtttcagggcagggtcacgatg
accagggacacgtccacaagcacagcctacatggagctgagcaggctgagatctgacgacacggctgtgt
attactgtgcaagagatcatggttctcgtcatttctggtcttactggggctttgattattggggccaagg
tacccggtcaccgtctccagt

Fig. 37E

SEQ ID NO: 152 MF6063

>MF6063_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcaaagaagtttcagggcagggtcacgatg
accagggacacgtccaccagcacagcctacatggagctgagcaggctgagatctgacgacacggctgtgt
attactgtgcaagagatcatggttctcgtcatttctggtcttactggggctttgattattggggccaagg
taccctggtcaccgtctccagt

SEQ ID NO: 154 MF6064

>MF6064_VH
caggtgcagctggtgcagtctggggctgaggtgaagaagcctggggcctcagtgaaggtctcctgcaagg
cttctggatacaccttcaccggctactatatgcactgggtgcgacaggcccctggaaagggcttgagtg
gatgggatggatcaaccctcagagtggtggcacaaactatgcacagaagtttcagggcagggtcacgatg
accagggacacgtccacgagcacagcctacatggagctgagcaggctgagatctgacgacacggctgtgt
attactgtgcaagagatcatggttctcgtcatttctggtcttactggggctttgattattggggccaagg
taccctggtcaccgtctccagt

SEQ ID NO: 156 MF6065

>MF6065_VH
caggtgcagctggtgcagtctggggctgaggtgaagaagcctggggcctcagtgaaggtctcctgcaagg
cttctggatacaccttcacctcttactatatgcactgggtgcgacaggcccctggacaagggcttgagtg
gatgggatggatcaaccctcagggggttctacaaactatgcacagaagtttcagggcagggtcacgatg
accagggacacgtccaccagcacagtgtacatggagctgagcaggctgagatctgaggacacggctgtgt
attactgtgcaagagatcatggttctcgtcatttctggtcttactggggctttgattattggggccaagg
taccctggtcaccgtctccagt

SEQ ID NO: 158 MF6066

>MF6066_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggttctacaaactatgcacagaagtttcagggcagggtcacgatg
accagggacacgtccaccagcacagcctacatggagctgagctctgagatctgaggacacggctgtgt
attactgtgcaagagatcatggttctcgtcatttctggtcttactggggctttgattattggggccaagg
taccctggtcaccgtctccagt

Fig. 37F

SEQ ID NO: 160 MF6067

>MF6067_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcacagaagtttcagggcagggtcacgatg
accagggacacgtccaccagcacagtctacatggagctgagctctctgagatctgacgacacggctgtgt
attactgtgcaagagatcatggttctcgtcatttctggtcttactggggctttgattattggggccaagg
taccctggtcaccgtctccagt

SEQ ID NO: 162 MF6068

>MF6068_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcacagaagtttcagggcagggtcacgatg
accagggacacgtccaccagcacagcctacatggagctgagcaggctgagatctgacgacacggctgtgt
attactgtgcaagagatcatggttctcgtcatttctggtcttactggggctttgattattggggccaagg
taccctggtcaccgtctccagt

SEQ ID NO: 164 MF6069

>MF6069_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcacagaagtttcagggcagggtcacgatg
accagggacacgtccatcagcacagcctacatggagctgagcaggctgagatctgacgacacggctgtgt
attactgtgcaagagatcatggttctcgtcatttctggtcttactggggctttgattattggggccaagg
taccctggtcaccgtctccagt

SEQ ID NO: 166 MF6070

>MF6070_VH
caggtgcagctggtgcagtctggggctgaggtgaagaagcctggggcctcagtgaaggtctcctgcaagg
cttctggatacaccttcacctcttactatatgcactgggtgcgacaggcccctggacaagggcttgagtg
gatgggatggatcaaccttctgggggttctacaaactatgcacagaagtttcagggcagggtcacgatg
accagggacacgtccaccagcacagtgtacatggagctgagcaggctgagatctgaggacacggctgtgt
attactgtgcaagagatcatggttctcgtcatttctggtcttactggggctttgattattggggccaagg
taccctggtcaccgtctccagt

Fig. 37G

SEQ ID NO: 168 MF6071

>MF6071_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaacccttctagtggttctacaaactatgcacagaagtttcagggcagggtcacgatg
accagggacacgtccaccagcacagcctacatggagctgagctctctgagatctgaggacacggctgtgt
attactgtgcaagagatcatggttctcgtcatttctggtcttactggggcttttgattattggggccaagg
taccctggtcaccgtctccagt

SEQ ID NO: 170 MF6072

>MF6072_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaacccttctagtggtggcacaaactatgcacagaagtttcagggcagggtcacgatg
accagggacacgtccaccagcacagtctacatggagctgagctctctgagatctgacgacacggctgtgt
attactgtgcaagagatcatggttctcgtcatttctggtcttactggggcttttgattattggggccaagg
taccctggtcaccgtctccagt

SEQ ID NO: 172 MF6073

>MF6073_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaacccttctagtggtggcacaaactatgcacagaagtttcagggcagggtcacgatg
accagggacacgtccaccagcacagcctacatggagctgagcaggctgagatctgacgacacggctgtgt
attactgtgcaagagatcatggttctcgtcatttctggtcttactggggcttttgattattggggccaagg
taccctggtcaccgtctccagt

SEQ ID NO: 174 MF6074

>MF6074_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaacccttctagtggtggcacaaactatgcacagaagtttcagggcagggtcacgatg
accagggacacgtccatcagcacagcctacatggagctgagcaggctgagatctgacgacacggctgtgt
attactgtgcaagagatcatggttctcgtcatttctggtcttactggggcttttgattattggggccaagg
taccctggtcaccgtctccagt

ANTIBODY THAT BINDS ErbB-2 AND ErbB-3

RELATED APPLICATIONS

This application is a continuation of U.S. Application No. 17,675,431, filed Feb. 18, 2022, which is a division of U.S. application Ser. No. 15/121,623 filed Aug. 25, 2016, now U.S. Pat. No. 11,279,770, which is the National Stage of International Application No. PCT/NL2015/050125, which claims priority to EP Application No. 14157360.0 filed Feb. 28, 2014 and EP Application No. 14167066.1 filed May 5, 2014.

REFERENCE TO SEQUENCE LISTING SUBMITTED ELECTRONICALLY

The content of the electronically submitted sequence listing (Name: 4096_0100004_Seqlisting_ST26.xml; Size: 207,303 Bytes; and Date of Creation: Sep. 25, 2023) is herein incorporated by reference in its entirety.

The invention relates to the field of antibodies. In particular it relates to the field of therapeutic (human) antibodies for the treatment of diseases involving aberrant cells. More in particular it relates to antibodies that bind ErbB-2 and ErbB-3 and their use in the binding of ErbB-2 and ErbB-3 positive cells, particularly tumor cells.

The human epidermal growth factor receptor family (HER, also collectively referred to as the ErbB signaling network) is a family of transmembrane receptor tyrosine kinases (RTK). The family includes the epidermal growth factor receptor (EGFR), also known as ErbB-1 (or HER1), and the homologous receptors ErbB-2 (HER2), ErbB-3 (HER3) and ErbB-4 (HER4). The receptors (reviewed in Yarden and Pines 2012) are widely expressed on epithelial cells. Upregulation of HER receptors or their ligands, such as heregulin (HRG) or epidermal growth factor (EGF), is a frequent event in human cancer (Wilson, Fridlyand et al. 2012). Overexpression of ErbB-1 and ErbB-2 in particular occurs in epithelial tumors and is associated with tumor invasion, metastasis, resistance to chemotherapy, and poor prognosis (Zhang, Berezov et al. 2007). In the normal breast, ErbB-3 has been shown to be important in the growth and differentiation of luminal epithelium. For instance, loss/inhibition of ErbB-3 results in selective expansion of the basal over the luminal epithelium (Balko, Miller et al. 2012). Binding of ligand to the extracellular domain of the RTKs induces receptor dimerization, both between the same (homodimerization) and different (heterodimerization) receptor subtypes. Dimerization can activate the intracellular tyrosine kinase domains, which undergo autophosphorylation and, in turn, can activate a number of downstream pro-proliferative signaling pathways, including those mediated by mitogen-activated protein kinases (MAPK) and the prosurvival pathway Akt (reviewed in Yarden and Pines, 2012). No specific endogenous ligand has been identified for ErbB-2, which is therefore assumed to normally signal through heterodimerization (Sergina, Rausch et al. 2007). ErbB-3 can be activated by engagement of its ligands. These ligands include but are not limited to neuregulin (NRG) and heregulin (HRG).

Various modes of activation of signaling of the ErbB receptor family have been identified. Among these are ligand dependent and ligand independent activation of signaling. Over-expressed ErbB-2 is able to generate oncogenic signaling through the ErbB-2:ErbB-3 heterodimer even in the absence of the ErbB-3 ligand (Junttila, Akita et al. 2009). ErbB-2 activity can be inhibited by ErbB-2 specific antibodies. Such ErbB-2 specific antibodies are for instance used in the treatment of ErbB-2 positive (HER2+) tumors. A problem with such treatments is that often tumors escape the ErbB-2 specific treatment and continue to grow even in the presence of the inhibiting antibody. It has been observed that ErbB-2 positive tumors, such as breast, ovarian, cervical and gastric tumors can escape treatment by the selective outgrowth of a subpopulation of tumor cells that exhibit upregulated ErbB-3 expression (Ocana, Vera-Badillo et al. 2013) and/or ErbB-3 ligand expression (Wilson, Fridlyand et al. 2012). Also activating mutations in the ErbB-3 receptor have been identified.

The anti-ErbB-2 monoclonal antibody trastuzumab (HERCEPTIN®) and the ErbB-1 specific cetuximab (ERBITUX™) are among several monoclonal antibodies approved for clinical application. Trastuzumab has a proven survival benefit in metastatic breast cancer (Arteaga, Sliwkowski et al. 2011). The precise mechanism of action of trastuzumab has not been unequivocally established. Suggested modes of action are the inhibition of RTK signaling and the recruitment of antibody dependent cellular cytotoxicity (ADCC). Other mechanisms of action that have been described include blocking proteolytic cleavage of the ErbB-2 extracellular domain, inhibition of angiogenic factors and enhancement of receptor endocytosis. Other agents that interfere with ErbB-2 signaling have been approved or are under development for treatment of breast and other ErbB-2 overexpression cancers. For example, the chemical compound lapatinib inhibits both ErbB-1 and ErbB-2 tyrosine kinase activity and is used in first line treatment of ErbB-2 amplified breast cancer.

In patients with HER2+ metastatic breast cancer, resistance to trastuzumab either as single-agent or in combination with chemotherapy, commonly occurs within months of starting therapy. Only a fraction of patients with HER2+ metastatic breast cancer respond to single agent trastuzumab, suggesting de novo mechanisms of resistance in advanced cancers. These mechanisms include, among others, signaling from other HER family of receptors and compensatory signaling from RTKs outside of the HER family (Thery et al., Resistance to human epidermal growth factor receptor type 2-targeted therapies, Eur J Cancer (2014), Vol. 50, Issue 5, pages 892-901 (http://dx.doi.org/10.1016/j.ejca.2014.01.003)). For example, overexpression of HER3 or its ligands along with HER2 leads to the formation of HER-2/HER-3 heterodimers and acquired resistance to trastuzumab. Thus, the antibody trastuzumab is thought to be ineffective in blocking signaling driven by ErbB-3 ligands (Wehrman, Raab et al. 2006, Junttila, Akita et al. 2009, Thery et al. 2014).

Recently the monoclonal antibody pertuzumab was approved for use in combination with trastuzumab on the basis of an extra 5 months progression-free survival benefit (Baselga, Cortes et al. 2012). Pertuzumab also binds ErbB-2 but at a different position than trastuzumab.

Other strategies to treat ErbB-2 positive tumors are directed towards ErbB-3. ErbB-3 binding monoclonal antibodies have demonstrated activity in preclinical studies (Schoeberl, Faber et al. 2010). Some ErbB-3 binding monoclonal antibodies can inhibit proliferation and growth of a variety of cancers.

Another strategy involves binding of both the ErbB-2 and ErbB-3 receptor. The molecule MM-111, is an artificial biological molecule containing two single chain Fv (scFv) fragments that bind ErbB-2 and ErbB-3. The two scFv are associated with a mutated human serum albumin (HSA) protein to increase the half-life of the molecule. In preclinical testing the molecule was shown to inhibit ErbB-3 signaling and proliferation. This effect was predominantly measured on ErbB-3 positive cell lines that expressed relatively high amounts of ErbB-2.

SUMMARY OF THE INVENTION

The invention provides a bispecific antibody comprising a first antigen-binding site that binds ErbB-2 and a second antigen-binding site that binds ErbB-3, and wherein the antibody can reduce a ligand-induced receptor function of ErbB-3 on a ErbB-2 and ErbB-3 positive cell. Said first antigen-binding site is preferably present in a variable domain comprising a VH chain with the amino acid sequence of VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001; MF3003 or MF1898 as depicted in FIG. 16A or FIG. 16E. Said second antigen-binding site is preferably present in a variable domain comprising a VH chain with the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 as depicted in FIG. 16B or FIG. 16E or FIG. 37. The immunoglobulin light chain in the variable domain preferably comprises the amino acid sequence of FIG. 16C.

An antibody of the invention is, unless otherwise specifically specified, preferably a bispecific antibody.

The invention further provides a pharmaceutical composition comprising an antibody according to the invention.

Further provided is an antibody according to the invention that further comprises a label, preferably a label for in vivo imaging.

The invention also provides a method for the treatment of a subject having a ErbB-2, ErbB-3 or ErbB-2/ErbB-3 positive tumor or at risk of having said tumor comprising administering to the subject a bispecific antibody according to the invention. Also provided is a bispecific antibody according to the invention for use in the treatment of a subject having or at risk of having an ErbB-2, ErbB-3 or ErbB-2/ErbB-3 positive tumor.

DETAILED DESCRIPTION OF THE INVENTION

The invention provides a bispecific antibody comprising a first antigen-binding site that binds ErbB-2 and a second antigen-binding site that binds ErbB-3, wherein the bispecific antibody reduces or can reduce a ligand-induced receptor function of ErbB-3 on a ErbB-2 and ErbB-3 positive cell.

As used herein, the term "antigen-binding site" refers to a site derived from and preferably as present on a bispecific antibody which is capable of binding to antigen. An unmodified antigen-binding site is typically formed by and present in the variable domain of the antibody. The variable domain contains said antigen-binding site. A variable domain that binds an antigen is a variable domain comprising an antigen-binding site that binds the antigen.

In one embodiment an antibody variable domain of the invention comprises a heavy chain variable region (VH) and a light chain variable region (VL). The antigen-binding site can be present in the combined VH/VL variable domain, or in only the VH region or only the VL region. When the antigen-binding site is present in only one of the two regions of the variable domain, the counterpart variable region can contribute to the folding and/or stability of the binding variable region, but does not significantly contribute to the binding of the antigen itself.

As used herein, antigen-binding refers to the typical binding capacity of an antibody to its antigen. An antibody comprising an antigen-binding site that binds to ErbB-2, binds to ErbB-2 and, under otherwise identical conditions, at least 100-fold lower to the homologous receptors ErbB-1 and ErbB-4 of the same species. An antibody comprising an antigen-binding site that binds to ErbB-3, binds to ErbB-3 and, under otherwise identical conditions, not to the homologous receptors ErbB-1 and ErbB-4 of the same species. Considering that the ErbB-family is a family of cell surface receptors, the binding is typically assessed on cells that express the receptor(s). Binding of an antibody to an antigen can be assessed in various ways. One way is to incubate the antibody with the antigen (preferably cells expressing the antigen), removing unbound antibody (preferably by a wash step) and detecting bound antibody by means of a labeled antibody that binds to the bound antibody.

Antigen binding by an antibody is typically mediated through the complementarity regions of the antibody and the specific three-dimensional structure of both the antigen and the variable domain allowing these two structures to bind together with precision (an interaction similar to a lock and key), as opposed to random, non-specific sticking of antibodies. As an antibody typically recognizes an epitope of an antigen, and as such epitope may be present in other compounds as well, antibodies according to the present invention that bind ErbB-2 and/or ErbB-3 may recognize other proteins as well, if such other compounds contain the same epitope. Hence, the term "binding" does not exclude binding of the antibodies to another protein or protein(s) that contain the same epitope. Such other protein(s) is preferably not a human protein. An ErbB-2 antigen-binding site and an ErbB-3 antigen-binding site as defined in the present invention typically do not bind to other proteins on the membrane of cells in a post-natal, preferably adult human. A bispecific antibody according to the present invention is typically capable of binding ErbB-2 and ErbB-3 with a binding affinity of at least $1 \times 10e-6$ M, as outlined in more detail below.

The term "interferes with binding" as used herein means that the antibody is directed to an epitope on ErbB-3 and the antibody competes with ligand for binding to ErbB-3. The antibody may diminish ligand binding, displace ligand when this is already bound to ErbB-3 or it may, for instance through steric hindrance, at least partially prevent that ligand can bind to ErbB-3.

The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Specific binding, is defined as binding with affinities (KD) of at least $1 \times 10e-6$ M, more preferably $1 \times 10e-7$ M, more preferably higher than $1 \times 10e-9$ M. Typically, antibodies for therapeutic applications have affinities of up to $1 \times 10e-10$ M or higher. Antibodies such the bispecific antibodies of the present invention comprise the constant domains (Fc part) of a natural antibody. An antibody of the invention is typically a bispecific full length antibody, preferably of the human IgG subclass. Preferably, an antibody of the present invention is of the human IgG1 subclass. Such antibodies of the invention have good ADCC properties, have favorable half life upon in vivo administration to humans and CH3 engineering technology exists that can provide for modified heavy chains that preferentially form heterodimers over homodimers upon co-expression in clonal cells.

An antibody of the invention is preferably a "full length" antibody. The term 'full length' according to the invention is defined as comprising an essentially complete antibody, which however does not necessarily have all functions of an intact antibody. For the avoidance of doubt, a full length antibody contains two heavy and two light chains. Each chain contains constant (C) and variable (V) regions, which can be broken down into domains designated CH1, CH2, CH3, VH, and CL, VL. An antibody binds to antigen via the variable domains contained in the Fab portion, and after binding can interact with molecules and cells of the immune system through the constant domains, mostly through the Fc portion. The terms 'variable domain', 'VH/VL pair', 'VH/VL' are used herein interchangeably. Full length antibodies according to the invention encompass antibodies wherein mutations may be present that provide desired characteristics. Such mutations should not be deletions of substantial portions of any of the regions. However, antibodies wherein one or several amino acid residues are deleted, without essentially altering the binding characteristics of the resulting antibody are embraced within the term "full length antibody". For instance, an IgG antibody can have 1-20 amino acid residue insertions, deletions or a combination thereof in the constant region. For instance, ADCC activity of an antibody can be improved when the antibody itself has a low ADCC activity, by slightly modifying the constant region of the antibody (Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489)

Full length IgG antibodies are preferred because of their favourable half life and the need to stay as close to fully autologous (human) molecules for reasons of immunogenicity. An antibody of the invention is preferably a bispecific IgG antibody, preferably a bispecific full length IgG1 antibody. IgG1 is favoured based on its long circulatory half life in man. In order to prevent any immunogenicity in humans it is preferred that the bispecific IgG antibody according to the invention is a human IgG1.

The term 'bispecific' (bs) means that one part of the antibody (as defined above) binds to one epitope on an antigen whereas a second part binds to a different epitope. The different epitope is typically present on a different antigen. According to the present invention, said first and second antigens are in fact two different proteins. A preferred bispecific antibody is an antibody that comprises parts of two different monoclonal antibodies and consequently binds to two different types of antigen. One arm of the bispecific antibody typically contains the variable domain of one antibody and the other arm contains the variable domain of another antibody. The heavy chain variable regions of the bispecific antibody of the invention are typically different from each other, whereas the light chain variable regions are preferably the same in the bispecific antibodies of the invention. A bispecific antibody wherein the different heavy chain variable regions are associated with the same, or a common, light chain is also referred to as a bispecific antibody with a common light chain. Further provided is therefore a bispecific antibody according to the invention, wherein both arms comprise a common light chain.

Preferred bispecific antibodies can be obtained by co-expression of two different heavy chains and a common light chain in a single cell. When wildtype CH3 domains are used, co-expression of two different heavy chains and a common light chain will result in three different species, AA, AB and BB. To increase the percentage of the desired bispecific product (AB) CH3 engineering can be employed, or in other words, one can use heavy chains with compatible heterodimerization domains, as defined hereunder.

The term 'compatible heterodimerization domains' as used herein refers to protein domains that are engineered such that engineered domain A' will preferentially form heterodimers with engineered domain B' and vice versa, whereas homodimerization between A'-A' and B'-B' is diminished.

The term 'common light chain' according to the invention refers to light chains which may be identical or have some amino acid sequence differences while the binding specificity of the full length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common VL', 'single light chain', 'single VL', with or without the addition of the term 'rearranged' are all used herein interchangeably. It is an aspect of the present invention to use as common light chain a human light chain that can combine with different heavy chains to form antibodies with functional antigen binding domains (WO2004/009618, WO2009/157771, Merchant et al. 1998 and Nissim et al. 1994). Preferably, the common light chain has a germline sequence. A preferred germline sequence is a light chain variable region that is frequently used in the human repertoire and has good thermodynamic stability, yield and solubility. A preferred germline light chain is O12, preferably the rearranged germline human kappa light chain IgVκ1-39*01/IGJκ1*01 or a fragment or a functional equivalent (i.e. same IgVκ1-39 gene segment but different IGJκ gene segment) thereof (nomenclature according to the IMGT database worldwide web at imgt.org).

Further provided is therefore a bispecific antibody according to the invention, wherein said common light chain is a germline light chain, preferably a rearranged germline human kappa light chain comprising the IgVK1-39 gene segment, most preferably the rearranged germline human kappa light chain IgVK1-39*01/IGJK1*01. The terms rearranged germline human kappa light chain IgVκ1-39*01/IGJK1*01, IGKV1-39/IGKJ1, huVκ1-39 light chain or in short huVκ1-39 are used interchangeably throughout the application. Obviously, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions. The light chain of the present invention can also be a light chain as specified herein above, having 1-5 amino acid insertions, deletions, substitutions or a combination thereof.

Also contemplated are antibodies wherein a VH is capable of specifically recognizing a first antigen and the VL, paired with the VH in a immunoglobulin variable domain, is capable of specifically recognizing a second antigen. The resulting VH/VL pair will bind either antigen 1 or antigen 2. Such so called "two-in-one antibodies", described in for instance WO 2008/027236, WO 2010/108127 and Schaefer et al (Cancer Cell 20, 472-486, October 2011), are different from bispecific antibodies of the invention and are further referred to as "two-in-one" antibodies. Such "two-in-one" antibodies have identical arms and are not antibodies of the present invention.

The term 'ErbB-2' as used herein refers to the protein that in humans is encoded by the ERBB-2 gene. Alternative names for the gene or protein include CD340; HER-2; HER-2/neu; MLN 19; NEU; NGL; TKR1. The ERBB-2 gene is frequently called HER2 (from human epidermal growth factor receptor 2). Where reference is made herein to ErbB-2, the reference refers to human ErbB-2. An antibody comprising an antigen-binding site that binds ErbB-2, binds human ErbB-2. The ErbB-2 antigen-binding site may, due to sequence and tertiary structure similarity between human and other mammalian orthologs, also bind such an ortholog but not necessarily so. Database accession numbers for the human ErbB-2 protein and the gene encoding it are (NP_001005862.1, NP_004439.2 NC_000017.10 NT_010783.15 NC_018928.2). The accession numbers are primarily given to provide a further method of identification of ErbB-2 as a target, the actual sequence of the ErbB-2 protein bound the antibody may vary, for instance because of a mutation in the encoding gene such as those occurring in some cancers or the like. The ErbB-2 antigen binding site binds ErbB-2 and a variety of variants thereof, such as those expressed by some ErbB-2 positive tumor cells.

The term 'ErbB-3' as used herein refers to the protein that in humans is encoded by the ERBB-3 gene. Alternative names for the gene or protein are HER3; LCCS2; MDA-BF-1; c-ErbB-3; c-erbb-3; erbb-3-S; p180-Erbb-3; p45-sErbb-3; and p85-sErbb-3. Where reference is made herein to ErbB-3, the reference refers to human ErbB-3. An antibody comprising an antigen-binding site that binds ErbB-3, binds human ErbB-3. The ErbB-3 antigen-binding site, may, due to sequence and tertiary structure similarity between human and other mammalian orthologs, also bind such an ortholog but not necessarily so. Database accession numbers for the human ErbB-3 protein and the gene encoding it are (NP_001005915.1 NP_001973.2, NC_000012.11 NC_018923.2 NT_029419.12). The accession numbers are primarily given to provide a further method of identification of ErbB-3 as a target, the actual sequence of the ErbB-3 protein bound by an antibody may vary, for instance because of a mutation in the encoding gene such as those occurring in some cancers or the like. The ErbB-3 antigen binding site binds ErbB-3 and a variety of variants thereof, such as those expressed by some ErbB-2 positive tumor cells.

A bispecific antibody of the invention that comprises a first antigen-binding site that binds ErbB-2 and a second antigen-binding site that binds ErbB-3, can reduce or reduces a ligand-induced receptor function of ErbB-3 on an ErbB-2 and ErbB-3 positive cell. In the presence of excess ErbB-2, ErbB-2/ErbB-3 heterodimers may provide a growth signal to the expressing cell in the absence of detectable ligand for the ErbB-3 chain in the heterodimer. This ErbB-3 receptor function is herein referred as a ligand-independent receptor function of ErbB-3. The ErbB-2/ErbB-3 heterodimer also provide a growth signal to the expressing cell in the presence of an ErbB-3 ligand. This ErbB-3 receptor function is herein referred to as a ligand-induced receptor function of ErbB-3.

The term "ErbB-3 ligand" as used herein refers to polypeptides which bind and activate ErbB-3. Examples of ErbB-3 ligands include, but are not limited to neuregulin 1 (NRG) and neuregulin 2, betacellulin, heparin-binding epidermal growth factor, and epiregulin. The term includes biologically active fragments and/or variants of a naturally occurring polypeptide.

In a preferred embodiment of the invention the ligand-induced receptor function of ErbB-3 is ErbB-3 ligand-induced growth of an ErbB-2 and ErbB-3 positive cell. In a preferred embodiment said cell is an MCF-7 cell (ATCC® HTB-22™); an SKBR3 (ATCC® HTB-30™) cell; an NCI-87 (ATCC® CRL-5822™) cell; a BxPC-3-luc2 cell (Perkin Elmer 125058), a BT-474 cell (ATCC® HTB-20™) or a JIMT-1 cell (DSMZ no.: ACC 589).

In a preferred embodiment the ErbB-2 and ErbB-3 positive cell comprises at least 50.000 ErbB-2 receptors on the cell surface. In a preferred embodiment at least 100.000 ErbB-2 receptors. In one preferred embodiment, the ErbB-2 and ErbB-3 positive cell comprises at least 1.000.000 ErbB-2 receptors on the cell surface. In another preferred embodiment the ErbB-2 and ErbB-3 positive cell comprises no more than 1.000.000 ErbB-2 receptors on the cell surface. Currently used therapies such as trastuzumab (HERCEPTIN®) and pertuzumab are only prescribed for patients with malignant ErbB-2 positive cells that have more than 1.000.000 ErbB-2 receptors on their cell surface, in order to obtain a clinical response. Patients with ErbB-2 positive tumor cells with more than 1.000.000 ErbB-2 receptors on their cell surface are typically classified as ErbB-2 [+++]. Patients are for instance classified using the HERCEPTEST™ and/or HER2 FISH (PHARMDX™), marketed both by Dako Denmark A/S, and/or using a HERMARK® assay, marketed by Monogram Biosciences. Trastuzumab and pertuzumab are only prescribed to ErbB-2 [+++] patients because patients with lower ErbB-2 concentrations typically do not exhibit a sufficient clinical response when treated with trastuzumab and pertuzumab. The invention, however, provides bispecific antibodies that also have an improved binding affinity for cells with a lower ErbB-2 receptor concentration, as compared to trastuzumab. As shown in the Examples, proliferation of such cells with lower ErbB2 expression is effectively counteracted with an antibody according to the invention. Such lower ErbB-2 receptor concentration is present on malignant cells of patients that are classified as ErbB-2 [++] or ErbB-2 [+]. Also, relapsed ErbB-2 positive tumors often have an ErbB-2 receptor concentration of lower than 1.000.000 receptors per cell. Such ErbB-2 [++] or ErbB-2 [+] patients, as well as patients with a relapsed ErbB-2 positive tumor, are therefore preferably treated with a bispecific antibody according to the present invention. Further provided is therefore a bispecific antibody comprising a first antigen-binding site that binds ErbB-2 and a second antigen-binding site that binds ErbB-3, wherein the antibody can reduce ligand-induced growth of an ErbB-2 and ErbB-3 positive cell that has less than 1.000.000 ErbB-2 cell-surface receptors. Also provided is a method for the treatment of a subject having a ErbB-2, ErbB-3 or ErbB-2/ErbB-3 positive tumor or at risk of having said tumor, wherein said tumor has less than 1.000.000 ErbB-2 cell-surface receptors per cell, the method comprising administering to the subject a bispecific antibody or pharmaceutical composition according to the invention. A bispecific antibody according to the invention for use in the treatment of a subject having or at risk of having an ErbB-2, ErbB-3 or ErbB-2/ErbB-3 positive tumor, wherein said tumor has less than 1.000.000 ErbB-2 cell-surface receptors per cell, is also herewith provided. Said antibody according to the present invention is typically capable of reducing a ligand-induced receptor function, preferably ligand induced growth, of ErbB-3 on a ErbB-2 and ErbB-3 positive cell. Said antibody according to the invention preferably comprises a first antigen-binding site that binds domain I of ErbB-2 and a second antigen-binding site that binds domain III of ErbB-3. In one preferred embodiment, the affinity of said second antigen-binding site for an ErbB-3 positive cell is equal to, or higher than, the affinity of said first antigen-binding site for an ErbB-2 positive cell, as explained herein below in more detail. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM.

In one preferred embodiment, said antibody according to the invention comprises an antigen-binding site that binds at least one amino acid of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181.

In one preferred embodiment, said antibody according to the invention preferably comprises an antigen-binding site that binds at least one amino acid of domain III of ErbB-3 selected from the group consisting of R426 and surface-exposed amino acid residues that are located within 11.2 Å from R426 in the native ErbB-3 protein.

To establish whether a tumor is positive for ErbB-3 the skilled person can for instance determine the ErbB-3 amplification and/or staining in immunohistochemistry. At least 10% tumor cells in a biopt should be positive. The biopt can also contain 20%, 30% 40% 50% 60% 70% or more positive cells.

As used herein the ligand-induced receptor function is reduced by at least 20%, preferably at least 30, 40, 50 60, or at least 70% in a particularly preferred embodiment the ligand-induced receptor function is reduced by 80, more preferably by 90%. The reduction is preferably determined by determining a ligand-induced receptor function in the presence of a bispecific antibody of the invention, and comparing it with the same function in the absence of the antibody, under otherwise identical conditions. The conditions comprise at least the presence of an ErbB-3 ligand. The amount of ligand present is preferably an amount that induces half of the maximum growth of an ErbB-2 and ErbB-3 positive cell line. The ErbB-2 and ErbB-3 positive cell line for this test is preferably the MCF-7 cell line (ATCC® HTB-22™), the SKBR3 cell line (ATCC® HTB-30™) cells, the JIMT-1 cell line (DSMZ ACC 589) or the NCI-87 cell line (ATCC® CRL-5822™). The test and/or the ligand for determining ErbB-3 ligand-induced receptor function is preferably a test for ErbB-3 ligand induced growth reduction as specified in the examples.

The ErbB-2 protein contains several domains (see for reference FIG. 1 of Landgraf, R Breast Cancer Res. 2007; 9(1): 202-). The extracellular domains are referred to as domains I-IV. The place of binding to the respective domains of antigen-binding sites of antibodies described herein has been mapped (see examples). A bispecific antibody of the invention with an antigen-binding site (first antigen-binding site) that binds domain I or domain IV of ErbB-2 (first antigen-binding site) comprises a heavy chain variable region that maintains significant binding specificity and affinity for ErbB-2 when combined with various light chains. Bispecific antibodies with an antigen-binding site (first antigen-binding site) that binds domain I or domain IV of ErbB-2 (first antigen-binding site) and an antigen-binding site for ErbB-3 (second antigen-binding site) were found to be more effective in reducing a ligand-induced receptor function of ErbB-3 when compared to a bispecific antibody comprising an antigen-binding site (first antigen-binding site) that binds to another extra-cellular domain of ErbB-2. A bispecific antibody comprising an antigen-binding site (first antigen-binding site) that binds ErbB-2, wherein said antigen-binding site binds to domain I or domain IV of ErbB-2 is preferred. Preferably said antigen-binding site binds to domain IV of ErbB-2. A bispecific antibody with an antigen-binding site (first antigen-binding site) that binds ErbB-2, and that further comprises ADCC was found to be more effective than other ErbB-2 binding antibodies that did not have significant ADCC activity, particularly in vivo. A bispecific antibody according to the invention which exhibits ADCC is therefore preferred. It was found that antibodies wherein said first antigen-binding site binds to domain IV of ErbB-2 had intrinsic ADCC activity. A domain I binding ErbB-2 binding antibody that has low intrinsic ADCC activity can be engineered to enhance the ADCC activity Fc regions mediate antibody function by binding to different receptors on immune effector cells such as macrophages, natural killer cells, B-cells and neutrophils. Some of these receptors, such as CD16A (FcγRIIIA) and CD32A (FcγRIIA), activate the cells to build a response against antigens. Other receptors, such as CD32B, inhibit the activation of immune cells. By engineering Fc regions (through introducing amino acid substitutions) that bind to activating receptors with greater selectivity, antibodies can be created that have greater capability to mediate cytotoxic activities desired by an anti-cancer Mab.

One technique for enhancing ADCC of an antibody is afucosylation. (See for instance Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489). Further provided is therefore a bispecific antibody according to the invention, which is afucosylated. Alternatively, or additionally, multiple other strategies can be used to achieve ADCC enhancement, for instance including glycoengineering (Kyowa Hakko/Biowa, GlycArt (Roche) and Eureka Therapeutics) and mutagenesis (Xencor and Macrogenics), all of which seek to improve Fc binding to low-affinity activating FcγRIIIa, and/or to reduce binding to the low affinity inhibitory FcγRIIb.

Several in vitro methods exist for determining the efficacy of antibodies or effector cells in eliciting ADCC. Among these are chromium-51 [Cr51] release assays, europium [Eu] release assays, and sulfur-35 [S35] release assays. Usually, a labeled target cell line expressing a certain surface-exposed antigen is incubated with antibody specific for that antigen. After washing, effector cells expressing Fc receptor CD16 are typically co-incubated with the antibody-labeled target cells. Target cell lysis is subsequently typically measured by release of intracellular label, for instance by a scintillation counter or spectrophotometry. A preferred test is detailed in the Examples.

One advantage of the present invention is the fact that binding of antibodies according to the invention such as for instance PB4188 to ErbB-2 and ErbB-3 positive cells results in internalization that is to the same extent as compared to trastuzumab. If a combination of trastuzumab and pertuzumab is used, internalization of these antibodies is enhanced. This enhanced internalization, however, results in reduced ADCC. An antibody according to the present invention resulting in internalization that is essentially to the same extent as compared to trastuzumab is, therefore, preferred over a combination of trastuzumab and pertuzumab because with such antibody the ADCC activity is better maintained.

An antibody of the invention comprising an antigen-binding site that binds ErbB-3, interferes with binding of an ErbB-3 ligand to ErbB-3. Such antibodies are more effective in reducing a ligand-induced receptor function of ErbB-3 on an ErbB-2 and ErbB-3 positive cell line, particularly in the context of an bi-specific antibody that also comprises an antigen-binding site that binds ErbB-2.

Preferred embodiments of the current invention provide a bispecific antibody comprising a first antigen-binding site that binds ErbB-2 and a second antigen-binding site that binds ErbB-3, wherein said first antigen-binding site binds domain I of ErbB-2. As shown in the Examples, bispecific antibodies having these characteristics are well capable of binding ErbB-2 and ErbB-3 positive cells and counteracting their activity (such as the ligand-induced receptor function of ErbB-3 and the ligand-induced growth of an ErbB-2 and ErbB3 positive cell). Moreover, bispecific antibodies according to the invention comprising a first antigen-binding site that binds domain I of ErbB-2 are particularly suitable for use in combination with existing anti-ErbB-2 therapies like trastuzumab and pertuzumab, because trastuzumab and pertuzumab bind different domains of ErbB-2. Trastuzumab binds domain IV of ErbB-2 and pertuzumab binds domain II of ErbB-2. Hence, bispecific antibodies according to the invention that bind domain I of ErbB-2 are preferred because they do not compete with trastuzumab and pertuzumab for the same epitope.

Another preferred embodiment provides a bispecific antibody comprising a first antigen-binding site that binds ErbB-2 and a second antigen-binding site that binds ErbB-3, wherein said second antigen-binding site binds domain III of ErbB-3. Such antibody according to the invention is particularly suitable for combination therapy with currently used anti-ErbB-3 binding molecules that do not bind domain III of ErbB-3, such as MM-121 (Merrimack Pharmaceuticals; also referred to as #Ab6) and RG7116 (Roche) that bind domain I of ErbB-3, because then the different binding molecules do not compete with each other for the same epitope.

Preferably, a bispecific antibody is provided that comprises a first antigen-binding site that binds ErbB-2 and a second antigen-binding site that binds ErbB-3, wherein said first antigen-binding site binds domain I of ErbB-2 and said second antigen-binding site binds domain III of ErbB-3. Such antibody is particularly suitable for combination therapy with anti-ErbB-2 binding molecules that do not bind domain I of ErbB-2, such as trastuzumab and pertuzumab, and with anti-ErbB-3 binding molecules that do not bind domain III of ErbB-3, such as MM-121 (#Ab6) and RG7116.

One preferred embodiment provides a bispecific antibody that comprises a first antigen-binding site that binds ErbB-2 and a second antigen-binding site that binds ErbB-3, wherein said first antigen-binding site binds domain I of ErbB-2 and said second antigen-binding site binds domain III of ErbB-3 and wherein the antibody can reduce a ligand-induced receptor function of ErbB-3 on a ErbB-2 and ErbB-3 positive cell. Said antibody can preferably reduce ligand-induced growth of an ErbB-2 and ErbB-3 positive cell.

Further embodiments of the invention provide a bispecific antibody comprising a first antigen-binding site that binds ErbB-2 and a second antigen-binding site that binds ErbB-3, wherein the affinity (KD) of said second antigen-binding site for an ErbB-3 positive cell is equal to, or higher than, the affinity of said first antigen-binding site for an ErbB-2 positive cell. Contrary to prior art bispecific compounds such as for instance MM-111 from Merrimack Pharmaceuticals, which have a higher affinity for ErbB-2 than for ErbB-3, the present invention provides bispecific antibodies which have an ErbB-3-specific arm with an affinity for ErbB-3 on cells that is higher than the affinity of the ErbB-2-specific arm for ErbB-2 on cells. Such bispecific antibodies are better capable of binding ErbB-3, despite the low cell surface concentration of ErbB-3. This provides the advantage that the functional activity against ErbB-3 is enhanced as compared to prior art compounds, meaning that these bispecific antibodies according to the invention are better capable of counteracting ErbB-3 activity (such as ligand-induced growth).

As used herein, the term "affinity" refers to the KD value.

The affinity (KD) of said second antigen-binding site for an ErbB-3 positive cell is preferably lower than or equal to 2.0 nM, more preferably lower than or equal to 1.5 nM, more preferably lower than or equal to 1.39 nM, more preferably lower than or equal to 0.99 nM. In one preferred embodiment, the affinity of said second antigen-binding site for ErbB-3 on SK-BR-3 cells is lower than or equal to 2.0 nM, more preferably lower than or equal to 1.5 nM, more preferably lower than or equal to 1.39 nM, preferably lower than or equal to 0.99 nM. In one embodiment, said affinity is within the range of 1.39-0.59 nM. In one preferred embodiment, the affinity of said second antigen-binding site for ErbB-3 on BT-474 cells is lower than or equal to 2.0 nM, more preferably lower than or equal to 1.5 nM, more preferably lower than or equal to 1.0 nM, more preferably lower than 0.5 nM, more preferably lower than or equal to 0.31 nM, more preferably lower than or equal to 0.23 nM. In one embodiment, said affinity is within the range of 0.31-0.15 nM. The above-mentioned affinities are preferably as measured using steady state cell affinity measurements, wherein cells are incubated at 4° C. using radioactively labeled antibody, where after cell-bound radioactivity is measured, as described in the Examples.

The affinity (KD) of said first antigen-binding site for an ErbB-2 positive cell is preferably lower than or equal to 5.0 nM, more preferably lower than or equal to 4.5 nM, more preferably lower than or equal to 3.9 nM. In one preferred embodiment, the affinity of said first antigen-binding site for ErbB-2 on SK-BR-3 cells is lower than or equal to 5.0 nM, preferably lower than or equal to 4.5 nM, more preferably lower than or equal to 4.0 nM, more preferably lower than or equal to 3.5 nM, more preferably lower than or equal to 3.0 nM, more preferably lower than or equal to 2.3 nM. In one embodiment, said affinity is within the range of 3.0-1.6 nM. In one preferred embodiment, the affinity of said first antigen-binding site for ErbB-2 on BT-474 cells is lower than or equal to 5.0 nM, preferably lower than or equal to 4.5 nM, more preferably lower than or equal to 3.9 nM. In one embodiment, said affinity is within the range of 4.5-3.3 nM. The above-mentioned affinities are preferably as measured using steady state cell affinity measurements, wherein cells are incubated at 4° C. using radioactively labeled antibody, where after cell-bound radioactivity is measured, as described in the Examples.

In one preferred embodiment, a bispecific antibody according to the invention is provided, wherein the affinity (KD) of said bispecific antibody for BT-474 cells is lower than or equal to 5.0 nM, preferably lower than or equal to 4.5 nM, more preferably lower than or equal to 4.0 nM, more preferably lower than or equal to 3.5 nM, more preferably lower than or equal to 3.7 nM, preferably lower than or equal to 3.2 nM. In one embodiment, said affinity is within the range of 3.7-2.7 nM. In one preferred embodiment, a bispecific antibody according to the invention is provided, wherein the affinity of said bispecific antibody for SK-BR-3 cells is lower than or equal to 5.0 nM, preferably lower than or equal to 4.5 nM, more preferably lower than or equal to 4.0 nM, more preferably lower than or equal to 3.5 nM, more preferably lower than or equal to 3.0 nM, preferably lower than or equal to 2.5 nM, more preferably lower than or equal to 2.0 nM. In one embodiment, said affinity is within the range of 2.4-1.6 nM. Again, the above-mentioned affinities are preferably as measured using steady state cell affinity measurements, wherein cells are incubated at 4° C. using radioactively labeled antibody, where after cell-bound radioactivity is measured, as described in the Examples.

Further preferred embodiments of the invention provide a bispecific antibody comprising a first antigen-binding site that binds ErbB-2 and a second antigen-binding site that binds ErbB-3, wherein the affinity (KD) of said second antigen-binding site for an ErbB-3 positive cell is equal to, or higher than, the affinity of said first antigen-binding site for an ErbB-2 positive cell, and wherein the antibody can reduce a ligand-induced receptor function of ErbB-3 on a ErbB-2 and ErbB-3 positive cell. Said antibody can preferably reduce ligand-induced growth of an ErbB-2 and ErbB-3 positive cell.

The above-mentioned antibodies according to the invention with a high affinity for ErbB-3 preferably bind domain I of ErbB2 and/or domain III of ErbB-3. Further provided is, therefore, a bispecific antibody according to the invention that comprises a first antigen-binding site that binds domain I of ErbB-2 and a second antigen-binding site that binds ErbB-3, wherein the affinity (KD) of said second antigen-binding site for an ErbB-3 positive cell is equal to, or higher than, the affinity of said first antigen-binding site for an ErbB-2 positive cell. Also provided is a bispecific antibody according to the invention that comprises a first antigen-binding site that binds ErbB-2 and a second antigen-binding site that binds domain III of ErbB-3, wherein the affinity of said second antigen-binding site for an ErbB-3 positive cell is equal to, or higher than, the affinity of said first antigen-binding site for an ErbB-2 positive cell. In a particularly preferred embodiment a bispecific antibody according to the invention is provided that comprises a first antigen-binding site that binds domain I of ErbB-2 and a second antigen-binding site that binds domain III of ErbB-3, wherein the affinity of said second antigen-binding site for an ErbB-3 positive cell is equal to, or higher than, the affinity of said first antigen-binding site for an ErbB-2 positive cell.

Said second antigen-binding site preferably binds domain III of ErbB-3 and has an affinity (KD) for an ErbB-3 positive cell that is lower than or equal to 2.0 nM, more preferably lower than or equal to 1.5 nM, preferably lower than or equal to 1.39 nM, more preferably lower than or equal to 0.99 nM. In one preferred embodiment, said second antigen-binding site binds domain III of ErbB-3 and has an affinity for ErbB-3 on SK-BR-3 cells that is lower than or equal to 2.0 nM, more preferably lower than or equal to 1.5 nM, preferably lower than or equal to 1.39 nM, more preferably lower than or equal to 0.99 nM. In one embodiment, said affinity is within the range of 1.39-0.59 nM. In one preferred embodiment, said second antigen-binding site binds domain III of ErbB-3 and has an affinity for ErbB-3 on BT-474 cells that is lower than or equal to 2.0 nM, more preferably lower than or equal to 1.5 nM, more preferably lower than or equal to 1.0 nM, more preferably lower than or equal to 0.5 nM, more preferably lower than or equal to 0.31 nM, more preferably lower than or equal to 0.23 nM. In one embodiment, said affinity is within the range of 0.31-0.15 nM.

Said first antigen-binding site preferably binds domain I of ErbB-2 and has an affinity (KD) for an ErbB-2 positive cell that is lower than or equal to 5.0 nM, more preferably lower than or equal to 4.5 nM, more preferably lower than or equal to 3.9 nM. In one preferred embodiment, said first antigen-binding site binds domain I of ErbB-2 and has an affinity for ErbB-2 on SK-BR-3 cells that is lower than or equal to 5.0 nM, more preferably lower than or equal to 4.5 nM, more preferably lower than or equal to 4.0 nM, more preferably lower than or equal to 3.5 nM, more preferably lower than or equal to 3.0 nM, more preferably lower than or equal to 2.5 nM, more preferably lower than or equal to 2.3 nM. In one embodiment, said affinity is within the range of 3.0-1.6 nM. The affinity of said bispecific antibody for SK-BR-3 cells is preferably lower than or equal to 5.0 nM, more preferably lower than or equal to 4.5 nM, more preferably lower than or equal to 4.0 nM, more preferably lower than or equal to 3.5 nM, more preferably lower than or equal to 3.0 nM, more preferably lower than or equal to 2.5 nM, more preferably lower than or equal to 2.4 nM, more preferably lower than or equal to 2.0 nM. In one embodiment, said affinity is within the range of 2.4-1.6 nM.

In one preferred embodiment, said first antigen-binding site binds domain I of ErbB-2 and has an affinity (KD) for ErbB-2 on BT-474 cells that is lower than or equal to 5.0 nM, more preferably lower than or equal to 4.5 nM, preferably lower than or equal to 3.9 nM. In one embodiment, said affinity is within the range of 4.5-3.3 nM. The affinity of said bispecific antibody for BT-474 cells is preferably lower than or equal to 5.0 nM, more preferably lower than or equal to 4.5 nM, more preferably lower than or equal to 4.0 nM, more preferably lower than or equal to 3.7 nM, more preferably lower than or equal to 3.2 nM. In one embodiment, said affinity is within the range of 3.7-2.7 nM.

Again, the above-mentioned affinities are preferably as measured using steady state cell affinity measurements, wherein cells are incubated at 4° C. using radioactively labeled antibody, where after cell-bound radioactivity is measured, as described in the Examples.

Another preferred embodiment provides a bispecific antibody according to the invention comprising a first antigen-binding site that binds ErbB-2 and a second antigen-binding site that binds ErbB-3, wherein the antibody can reduce a ligand-induced receptor function of ErbB-3 on a ErbB-2 and ErbB-3 positive cell, wherein said bispecific antibody does not significantly affect the survival of cardiomyocytes. Cardiotoxicity is a known risk factor in ErbB-2 targeting therapies and the frequency of complications is increased when trastuzumab is used in conjunction with anthracyclines thereby inducing cardiac stress. For instance, the combination of doxycycline (DOX) with trastuzumab induces severe cardiac side effects. Clinical studies have estimated that 5% to 10% of patients who receive trastuzumab in the adjuvant setting of breast cancer develop cardiac dysfunction (Guarneri et al., J Clin Oncol., 1985, 3:818-26; Ewer M S et al., Nat Rev Cardiol 2010; 7:564-75). However, in a retrospective study, it was demonstrated that the risk for developing asymptomatic cardiac dysfunction is actually as high as about 25% when trastuzumab is used in the adjuvant setting with DOX (Wadhwa et al., Breast Cancer Res Treat 2009; 117:357-64). As shown in the Examples, the present invention provides antibodies that target ErbB-2 and that do not, or to a significantly lesser extent as compared to trastuzumab and pertuzumab, affect the survival of cardiomyocytes. This provides an important advantage since cardiotoxicity is reduced. This is already advantageous for people who do not suffer from an impaired cardiac function, and even more so for people who do suffer from an impaired cardiac function, or who are at risk thereof, such as for instance subjects suffering from congestive heart failure (CHF), left ventricular dysfunction (LVD) and/or a ≥10% decreased Left Ventricular Ejection Fraction (LVEF), and/or subjects who have had a myocardial infarction. Antibodies according to the invention that do not significantly affect the survival of cardiomyocytes are, therefore, preferred. In vitro, the function of cardiomyocytes is for instance measured by determining the viability of cardiomyocytes, by determining BNP (B-type natriuretic peptide, which is a cardiac biomarker), by determining QT prolongation, and/or by determining mitochondrial membrane potential.

Said antibody according to the invention preferably comprises a first antigen-binding site that binds domain I of ErbB-2 and a second antigen-binding site that binds domain III of ErbB-3. One embodiment provides an antibody according to the invention that does not significantly affect the survival of cardiomyocytes, comprising a first antigen-binding site that binds ErbB-2 and a second antigen-binding site that binds ErbB-3, wherein the affinity of said second antigen-binding site for an ErbB-3 positive cell is equal to, or higher than, the affinity of said first antigen-binding site for an ErbB-2 positive cell. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM.

In one preferred embodiment said antibody that does not significantly affect the survival of cardiomyocytes comprises:
  at least the CDR3 sequence, preferably at least the CDR1, CDR2 and CDR3 sequences, or at least the heavy chain variable region sequence, of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences; and/or
  at least the CDR3 sequence, preferably at least the CDR1, CDR2 and CDR3 sequences, or at least the heavy chain variable region sequence, of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences. In one preferred embodiment, said antibody is PB4188.

Another aspect of the present invention provides an antibody according to the invention, comprising a first antigen-binding site that binds ErbB-2 and a second antigen-binding site that binds ErbB-3, wherein said antibody comprises an antigen-binding site that binds at least one amino acid residue of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181. The amino acid residue numbering is that of Protein Data Bank (PDB) ID #1S78. As shown in the Examples, antibodies binding this region of domain I of ErbB-2 exhibit particularly good binding characteristics and they are capable of counteracting the activity of ErbB-2 positive cells (such as ligand-induced receptor function of ErbB-3 on a ErbB-2 and ErbB-3 positive cell, and/or ligand-induced growth of such cell). Moreover, such antibodies are particularly suitable for combination therapy with currently known anti-ErbB-2 monoclonal antibodies like trastuzumab (that binds domain IV of ErbB-2) and pertuzumab (that binds domain II of ErbB-2) because they bind different domains of ErbB-2. Hence, these antibodies can be used simultaneously without competition for the same epitope. The term "surface-exposed amino acid residues that are located within about 5 amino acid positions from T144, T164, R166, P172, G179, S180 or R181" refers to amino acid residues that are in the primary amino acid sequence located within about the first five amino acid residues adjacent to the recited residues and that are at least in part exposed to the outside of the protein, so that they can be bound by antibodies (see for instance FIG. 21B). Preferably, said amino acid residue located within about 5 amino acid positions from T144, T164, R166, P172, G179, S180 or R181 is selected from the group consisting of L139, C140, Y141, Q142, D143, I145, L146, W147, K148, D149, L159, T160, L161, I162, D163, N165, S167, R168, A169, C170, H171, C173, S174, P175, M176, C177, K178, C182, W183, G184, E185 and S186. Preferably, said antibody comprises an antigen-binding site that binds at least 2 or at least 3 amino acid residues of domain I of ErbB-2 selected from the group consisting of T144, T164, R166, P172, G179, S180 and R181, and surface-exposed amino acid residues that are located within 5 amino acid positions from T144, T164, R166, P172, G179, S180 or R181.

In one preferred embodiment, a bispecific antibody according to the invention is provided, wherein said antibody comprises an antigen-binding site that binds at least T144, R166 and R181 of domain I of ErbB-2. Another embodiment provides a bispecific antibody according to the invention, wherein said antibody comprises an antigen-binding site that binds at least T144, R166, P172, G179 and R181 of domain I of ErbB-2. Another embodiment provides a bispecific antibody according to the invention, wherein said antibody comprises an antigen-binding site that binds at least T144, T164, R166, P172, G179, S180 and R181 of domain I of ErbB-2.

Another aspect of the present invention provides an antibody comprising a first antigen-binding site that binds ErbB-2 and a second antigen-binding site that binds ErbB-3, wherein said antibody comprises an antigen-binding site that binds at least one amino acid of domain III of ErbB-3 selected from the group consisting R426 and surface-exposed amino acid residues that are located within 11.2 Å from R426 in the native ErbB-3 protein. The amino acid residue numbering is that of Protein Data Bank (PDB) ID #4P59. As shown in the Examples, antibodies binding this region of domain III of ErbB-3 exhibit particularly good binding characteristics and they are capable of counteracting the activity of ErbB-3 positive cells (such as ligand-induced receptor function of ErbB-3 on a ErbB-2 and ErbB-3 positive cell, and/or ligand-induced growth of such cell). The term "surface-exposed amino acid residues that are located within 11.2 Å from R426 in the native ErbB-3 protein" refers to amino acid residues that are in the tertiary structure of the ErbB-3 protein spationally positioned within 11.2 Å from R426 and that are at least in part exposed to the outside of the protein, so that they can be bound by antibodies. Preferably, said amino acid residues that are located within 11.2 Å from R426 in the native ErbB-3 protein are selected from the group consisting of L423, Y424, N425, G427, G452, R453, Y455, E480, R481, L482, D483 and K485 (see for instance FIG. 21C and Table 15). In one preferred embodiment, a bispecific antibody according to the invention is provided, wherein said antibody comprises an antigen-binding site that binds at least R426 of domain III of ErbB-3. Preferably, said antibody comprises an antigen-binding site that binds at least R426 of domain III of ErbB-3.

A bispecific antibody of the invention is preferably afucosylated in order to enhance ADCC activity. A bispecific antibody of the invention preferably comprises a reduced amount of fucosylation of the N-linked carbohydrate structure in the Fc region, when compared to the same antibody produced in a normal CHO cell.

A bispecific antibody of the present invention is preferably used in humans. To this end a bispecific antibody of the invention is preferably a human or humanized antibody.

Tolerance of a human to a polypeptide is governed by many different aspects. Immunity, be it T-cell mediated, B-cell mediated or other is one of the variables that are encompassed in tolerance of the human for a polypeptide. The constant region of a bispecific antibody of the present invention is preferably a human constant region. The constant region may contain one or more, preferably not more than 10, preferably not more than 5 amino-acid differences with the constant region of a naturally occurring human antibody. It is preferred that the constant part is entirely derived from a naturally occurring human antibody. Various antibodies produced herein are derived from a human antibody variable domain library. As such these variable domains are human. The unique CDR regions may be derived from humans, be synthetic or derived from another organism. The variable region is considered a human variable region when it has an amino acid sequence that is identical to an amino acid sequence of the variable region of a naturally occurring human antibody, but for the CDR region. The variable region of an ErbB-2 binding VH, an ErbB-3 binding VH, or a light chain in an antibody of the invention may contain one or more, preferably not more than 10, preferably not more than 5 amino-acid differences with the variable region of a naturally occurring human antibody, not counting possible differences in the amino acid sequence of the CDR regions. Such mutations occur also in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3-D structure of the murine heavy chain variable region; deimmunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope.

Such deimmunized murine heavy chain variable regions are less immunogenic in humans than the original murine heavy chain variable region. Preferably a variable region or domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

A bispecific antibody according to the invention preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. In a preferred embodiment the invention provides an antibody according to the invention wherein said constant region is selected from the group of IgG, IgA, IgM, IgD, and IgE constant regions, more preferably said constant region comprises an IgG constant region, more preferably an IgG1 constant region, preferably a mutated IgG1 constant region. Some variation in the constant region of IgG1 occurs in nature, such as for instance the allotypes G1 m1, 17 and G1m3, and/or is allowed without changing the immunological properties of the resulting antibody. Typically between about 1-10 amino acid insertions, deletions, substitutions or a combination thereof are allowed in the constant region.

The invention in one embodiment provides an antibody comprising a variable domain that binds ErbB-2, wherein said antibody comprises at least the CDR3 sequence of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or wherein said antibody comprises a heavy chain CDR3 sequence that differs in at most three, preferably in at most two, preferably in no more than one amino acid from a CDR3 sequence of a VH selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E. Said antibody preferably comprises at least the CDR3 sequence of MF1849, MF2971, MF3958, MF3004 or MF3991, most preferably at least the CDR3 sequence of MF3958.

Said antibody preferably comprises at least the CDR1, CDR2 and CDR3 sequences of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or heavy chain CDR1, CDR2 and CDR3 sequences that differ in at most three, preferably in at most two, preferably in at most one amino acid from the CDR1, CDR2 and CDR3 sequences of MF2926, MF2930, MF1849; MF2973, MF3004, MF3958, MF2971, MF3025, MF2916, MF3991, MF3031, MF2889, MF2913, MF1847, MF3001, MF3003 or MF1898. Said antibody preferably comprises at least the CDR1, CDR2 and CDR3 sequences of MF1849, MF2971, MF3958, MF3004 or MF3991, most preferably at least the CDR1, CDR2 and CDR3 sequences of MF3958.

The invention also provides an antibody comprising a variable domain that binds ErbB-3, wherein said antibody comprises at least the CDR3 sequence of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37, or wherein said antibody comprises a heavy chain CDR3 sequence that differs in at most three, preferably in no more than two, preferably in no more than one amino acid from a CDR3 sequence of a VH selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37. Said antibody preferably comprises at least the CDR3 sequence of MF3178, MF3176, MF3163, MF6058, MF6061 or MF6065, most preferably at least the CDR3 sequence of MF3178.

Said antibody preferably comprises at least the CDR1, CDR2 and CDR3 sequences of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37, or heavy chain CDR1, CDR2 and CDR3 sequences that differ in at most three, preferably in at most two, preferably in at most one amino acid from the CDR1, CDR2 and CDR3 sequences of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074. Said antibody preferably comprises at least the CDR1, CDR2 and CDR3 sequences of MF3178, MF3176, MF3163, MF6058, MF6061 or MF6065, most preferably at least the CDR1, CDR2 and CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR3 sequence of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or a heavy chain CDR3 sequence that differs in at most three, preferably in at most two, preferably in no more than one amino acid from a CDR3 sequence of a VH selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, and wherein said second antigen-binding site comprises at least the CDR3 sequence of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37, or a heavy chain CDR3 sequence that differs in at most three, preferably in at most two, preferably in no more than one amino acid from a CDR3 sequence of a VH selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37. Said first antigen-binding site preferably comprises at least the CDR3 sequence of MF1849, MF2971, MF3958, MF3004 or MF3991, most preferably at least the CDR3 sequence of MF3958 and said second antigen-binding site preferably comprises at least the CDR3 sequence of MF3178, MF3176, MF3163, MF6058, MF6061 or MF6065, most preferably at least the CDR3 sequence of MF3178.

Said first antigen-binding site preferably comprises at least the CDR1, CDR2 and CDR3 sequences of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or heavy chain CDR1, CDR2 and CDR3 sequences that differ in at most three, preferably in at most two, preferably in at most one amino acid from the CDR1, CDR2 and CDR3 sequences of MF2926, MF2930, MF1849; MF2973, MF3004, MF3958, MF2971, MF3025, MF2916, MF3991, MF3031, MF2889, MF2913, MF1847, MF3001, MF3003 or MF1898, and said second antigen-binding site preferably comprises at least the CDR1, CDR2 and CDR3 sequences of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37, or heavy chain CDR1, CDR2 and CDR3 sequences that differ in at most three, preferably in at most two, preferably in at most one amino acid from the CDR1, CDR2 and CDR3 sequences of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 as depicted in FIG. 16B or FIG. 16E or FIG. 37. Said first antigen-binding site preferably comprises at least the CDR1, CDR2 and CDR3 sequences of MF1849, MF2971, MF3958, MF3004 or MF3991, most preferably at least the CDR1, CDR2 and CDR3 sequences of MF3958, and said second antigen-binding site preferably comprises at least the CDR1, CDR2 and CDR3 sequences of MF3178, MF3176, MF3163, MF6058, MF6061 or MF6065, most preferably at least the CDR1, CDR2 and CDR3 sequence of MF3178.

One preferred embodiment provides a bispecific antibody comprising a first antigen-binding site that binds ErbB-2 and a second antigen-binding site that binds ErbB-3, wherein said first antigen-binding site comprises at least the CDR3 sequence of MF3958, or a CDR3 sequence that differs in at most three, preferably in at most two, preferably in no more than one amino acid from the CDR3 sequence of MF3958, and wherein said second antigen-binding site comprises at least the CDR3 sequence of MF3178, or a CDR3 sequence that differs in at most three, preferably in at most two, preferably in no more than one amino acid from the CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR1, CDR2 and CDR3 sequences of MF3958, or CDR1, CDR2 and CDR3 sequences that differ in at most three, preferably in at most two, preferably in at most one amino acid from the CDR1, CDR2 and CDR3 sequences of MF3958, and wherein said second antigen-binding site comprises at least the CDR1, CDR2 and CDR3 sequence of MF3178, or CDR1, CDR2 and CDR3 sequences that differ in at most three, preferably in at most two, preferably in at most one amino acid from the CDR1, CDR2 and CDR3 sequences of MF3178.

The invention in one embodiment provides a bispecific antibody comprising a first antigen-binding site that binds ErbB-2 and a second antigen-binding site that binds ErbB-3, wherein said first antigen-binding site comprises at least the CDR3 sequence of MF3958 and wherein said second antigen-binding site comprises at least the CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR1, CDR2 and CDR3 sequences of MF3958 and wherein said second antigen-binding site comprises at least the CDR1, CDR2 and CDR3 sequence of MF3178.

CDR sequences are for instance varied for optimization purposes, preferably in order to improve binding efficacy or the stability of the antibody. Optimization is for instance performed by mutagenesis procedures where after the stability and/or binding affinity of the resulting antibodies are preferably tested and an improved ErbB-2 or ErbB-3-specific CDR sequence is preferably selected. A skilled person is well capable of generating antibody variants comprising at least one altered CDR sequence according to the invention. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine.

The invention in one embodiment provides an antibody comprising a variable domain that binds ErbB-2, wherein the VH chain of said variable domain comprises the amino acid sequence of VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898 as depicted in FIG. 16A or FIG. 16E; or comprises the amino acid sequence of VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898 as depicted in FIG. 16A or FIG. 16E having at most 15, preferably 1, 2, 3, 4, 5, 6, 7, 8, 9 or 10 more preferably at most 1, 2, 3, 4 or 5, amino acid insertions, deletions, substitutions or a combination thereof with respect to the above mentioned VH chain sequence of FIG. 16A or FIG. 16E. The VH chain of the variable domain that binds ErbB-2 preferably comprises the amino acid sequence of:

MF1849; or

MF2971 or a humanized version thereof, wherein said humanized version preferably comprises the amino acid sequence of MF3958; or MF3004 or a humanized version thereof, wherein said humanized version preferably comprises the amino acid sequence of MF3991;

as depicted in FIG. 16A. In one embodiment, the VH chain of the variable domain that binds ErbB-2 comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991, wherein the recited VH sequences have at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 16A. In a preferred embodiment the VH chain of the variable domain that binds ErbB-2 comprises the amino acid sequence of MF3958; or comprises the amino acid sequence of MF3958 depicted in FIG. 16A having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. The antibody comprising a variable domain that binds ErbB-2 is preferably a bispecific antibody that preferably further comprises a variable domain that binds ErbB-3. The VH chain of the variable domain that binds Erb-B3 preferably comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 as depicted in FIG. 16B or FIG. 16E or FIG. 37; or comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 as depicted in FIG. 16B or FIG. 16E or FIG. 37 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence of FIG. 16B or FIG. 16E or FIG. 37. The VH chain of the variable domain that binds Erb-B3 preferably comprises the amino acid sequence of MF3178, MF3176, MF3163, MF6058, MF6061 or MF6065; or comprises the amino acid sequence of MF3178, MF3176, MF3163, MF6058, MF6061 or MF6065 having at most 15, preferably 1, 2, 3, 4, 5, 6, 7, 8, 9 or 10, more preferably in at most 1, 2, 3, 4 or 5, amino acid insertions, deletions, substitutions or a combination thereof with respect to the respective VH chain sequence of FIG. 16B or FIG. 37. In a preferred embodiment the VH chain of the variable domain that binds ErbB-3 comprises the amino acid sequence of MF3178; or comprises the amino acid sequence of MF3178 depicted in FIG. 16B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. Preferably, the above-mentioned amino acid insertions, deletions and substitutions are not present in the CDR3 region. The above-mentioned amino acid insertions, deletions and substitutions are also preferably not present in the CDR1 and CDR2 regions. The above-mentioned amino acid insertions, deletions and substitutions are also preferably not present in the FR4 region.

The invention further provides an antibody comprising a variable domain that binds ErbB-3, wherein the VH chain of said variable region comprises the amino acid sequence of VH chain MF3178; MF3176; MF3163; MF3099; MF3307; MF6055; MF6056; MF6057; MF6058; MF6059; MF6060 MF6061; MF6062; MF6063; MF6064; MF 6065; MF6066; MF6067; MF6068; MF6069; MF6070; MF6071; MF6072; MF6073 or MF6074 as depicted in FIG. 16B or FIG. 16E or FIG. 37, or comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 as depicted in FIG. 16B or FIG. 16E or FIG. 37 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to said VH chain sequence. The VH chain of the variable domain that binds ErbB3 preferably comprises the amino acid sequence of VH chain MF3178, MF3176, MF3163, MF6058, MF6061 or MF6065; or comprises the amino acid sequence of VH chain MF3178, MF3176, MF3163, MF6058, MF6061 or MF6065 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to said VH chain sequence. In a preferred embodiment the VH chain of the variable domain that binds ErbB-3 comprises the amino acid sequence of VH chain MF3178 depicted in FIG. 16B; or comprises the amino acid sequence of VH chain MF3178 depicted in FIG. 16B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. The antibody comprising a variable domain that binds ErbB-3, is preferably a bispecific antibody that preferably further comprises a variable domain that binds ErbB-2. The VH chain of the variable domain that binds ErbB-2 preferably comprises the amino acid sequence of a VH chain of FIG. 16A or FIG. 16E. The VH chain of the variable domain that binds ErbB-2 preferably comprises the amino acid sequence of MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991 as depicted in FIG. 16A. In one embodiment, the recited Erb-B2 binding VH sequences have at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 16A. In one preferred embodiment, said ErbB-2 binding VH chain of FIG. 16A comprises the amino acid sequence of MF3958; or comprises the amino acid sequence of MF3958 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. Preferably, the above-mentioned amino acid insertions, deletions and substitutions are not present in the CDR3 region. The above-mentioned amino acid insertions, deletions and substitutions are also preferably not present in the CDR1 and CDR2 regions. The above-mentioned amino acid insertions, deletions and substitutions are also preferably not present in the FR4 region.

Further provided is an antibody according to the invention, wherein said antibody comprises an ErbB-2 specific heavy chain variable region sequence selected from the group consisting of the heavy chain variable region sequences of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or wherein said antibody comprises a heavy chain variable region sequence that differs in at most 15, preferably in 1, 2, 3, 4, 5, 6, 7, 8, 9 or 10, more preferably in at most 1, 2, 3, 4 or 5, amino acids from the heavy chain variable region sequences of MF2926, MF2930, MF1849; MF2973, MF3004, MF3958, MF2971, MF3025, MF2916, MF3991, MF3031, MF2889, MF2913, MF1847, MF3001, MF3003 or MF1898.

Further provided is an antibody according to the invention, wherein said antibody comprises an ErbB-3 specific heavy chain variable region sequence selected from the group consisting of the heavy chain variable region sequences of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37, or wherein said antibody comprises a heavy chain variable region sequence that differs in at most 15, preferably in 1, 2, 3, 4, 5, 6, 7, 8, 9 or 10, more preferably in at most 1, 2, 3, 4 or 5, amino acids from the heavy chain variable region sequences of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074.

The invention in one embodiment provides an antibody comprising two antigen-binding sites that bind ErbB-2, wherein at least one of said antigen-binding sites binds domain I of ErbB-2. Preferably, both antigen-binding sites bind domain I of ErbB-2. Such antibody according to the invention is particularly suitable for combination therapy with currently used anti-ErbB-2 binding molecules that do not bind domain I of ErbB-2, such as trastuzumab that binds domain IV of ErbB-2 and pertuzumab that binds domain II of ErbB-2, because then the different binding molecules do not compete with each other for the same epitope.

Further provided is an antibody comprising two antigen-binding sites that bind ErbB-2, wherein at least one of said antigen-binding sites binds domain I of ErbB-2 and wherein the affinity (KD) of said at least one antigen-binding site for an ErbB-2 positive cell is lower than or equal to 5.0 nM, preferably lower than or equal to 4.5 nM, more preferably lower than or equal to 3.9 nM. Preferably, both antigen-binding sites bind domain I of ErbB-2. In one preferred embodiment, the affinity of said at least one antigen-binding site for ErbB-2 on SK-BR-3 cells is lower than or equal to 5.0 nM, preferably lower than or equal to 4.5 nM, more preferably lower than or equal to 4.0 nM, more preferably lower than or equal to 3.5 nM, more preferably lower than or equal to 3.0 nM, more preferably lower than or equal to 2.3 nM. In one embodiment, said affinity is within the range of 3.0-1.6 nM. In one preferred embodiment, the affinity of said at least one antigen-binding site for ErbB-2 on BT-474 cells is lower than or equal to 5.0 nM, preferably lower than or equal to 4.5 nM, more preferably lower than or equal to 3.9 nM. In one embodiment, said affinity is within the range of 4.5-3.3 nM.

The above-mentioned affinities are preferably as measured using steady state cell affinity measurements, wherein cells are incubated at 4° C. using radioactively labeled antibody, where after cell-bound radioactivity is measured, as described in the Examples.

The invention further provides an antibody comprising two variable domains that bind ErbB-2, wherein a VH chain of said variable domains comprises the amino acid sequence of the VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898 as depicted in FIG. 16A or FIG. 16E; or the amino acid sequence of the VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898 VH-chains as depicted in FIG. 16A or FIG. 16E, having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 16A or FIG. 16E. Said VH preferably comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991 as depicted in FIG. 16A; or comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991 as depicted in FIG. 16A having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 16A. The variable domains of the antibody preferably comprise identical VH chains, preferably having a sequence as depicted in FIG. 16A or FIG. 16E. An antibody with variable domains with identical VH chains is not a bispecific antibody. VH chains are identical for the present invention if they comprise the same VH chain sequence as depicted in FIG. 16A or FIG. 16E or FIG. 37, or the same VH chain sequence but for 1, 2, 3, 4 or 5 amino acid insertions, deletions, substitutions or a combination thereof with respect to the respective sequence depicted in FIG. 16A or FIG. 16E or FIG. 37.

The invention in one embodiment provides an antibody comprising two antigen-binding sites that bind ErbB-3, wherein at least one of said antigen-binding sites binds domain III of ErbB-3. Preferably, both antigen-binding sites bind domain III of ErbB-3. Such antibody according to the invention is particularly suitable for combination therapy with currently used anti-ErbB-3 binding molecules that do not bind domain III of ErbB-3, such as MM-121 (#Ab6) and RG7116 that bind domain I of ErbB-3, because then the different binding molecules do not compete with each other for the same epitope.

Further provided is an antibody comprising two antigen-binding sites that bind ErbB-3, wherein at least one of said antigen-binding sites binds domain III of ErbB-3 and wherein the affinity (KD) of said at least one antigen-binding site for an ErbB-3 positive cell is lower than or equal to 2.0 nM, preferably lower than or equal to 1.5 nM, more preferably lower than or equal to 1.39 nM, more preferably lower than or equal to 0.99 nM. Preferably, both antigen-binding sites bind domain III of ErbB-3. In one preferred embodiment, the affinity of said at least one antigen-binding site for ErbB-3 on SK-BR-3 cells is lower than or equal to 2.0 nM, preferably lower than or equal to 1.5 nM, more preferably lower than or equal to 1.39 nM, more preferably lower than or equal to 0.99 nM. In one embodiment, said affinity is within the range of 1.39-0.59 nM. In one preferred embodiment, the affinity of said at least one antigen-binding site for ErbB-3 on BT-474 cells is lower than or equal to 2.0 nM, more preferably lower than or equal to 1.5 nM, more preferably lower than or equal to 1.0 nM, more preferably lower than or equal to 0.5 nM, more preferably lower than or equal to 0.31 nM, more preferably lower than or equal to 0.23 nM. In one embodiment, said affinity is within the range of 0.31-0.15 nM.

Again, the above-mentioned affinities are preferably as measured using steady state cell affinity measurements, wherein cells are incubated at 4° C. using radioactively labeled antibody, where after cell-bound radioactivity is measured, as described in the Examples.

The invention further provides an antibody comprising two variable domains that each bind ErbB3 wherein a VH of the variable domains comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 as depicted in FIG. 16B or FIG. 16E or FIG. 37; or comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to any of said VH chain sequences. Said VH preferably comprises the amino acid sequence of VH chain MF3178, MF3176, MF3163, MF6058, MF6061 or MF6065; or comprises the amino acid sequence of VH chain MF3178, MF3176, MF3163, MF6058, MF6061 or MF6065 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to any of said VH chain sequences. Said VH preferably comprises the amino acid sequence of VH chain MF3178; or comprises the amino acid sequence of VH chain MF3178 depicted in FIG. 16B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the MF3178 VH chain sequence. The variable domains of the antibody preferably comprise identical VH chains, preferably having a sequence as depicted in FIG. 16B or FIG. 16E or FIG. 37. An antibody with variable domains with identical VH chains is not a bispecific antibody. The VH chains are identical if they comprise the same VH chain sequence as depicted in FIG. 16B or FIG. 16E or FIG. 37, or the same VH chain sequence but for 1, 2, 3, 4 or 5 amino acid insertions, deletions, substitutions or a combination thereof with respect to the VH chain sequence of FIG. 16B or FIG. 16E or FIG. 37.

Monospecific antibodies according to the present invention that are specific for ErbB-3 have the advantage that they have a better functional activity against ErbB-3, as compared to prior art compounds such as for instance MM-121 (#Ab6), meaning that these antibodies according to the invention are better capable of counteracting ErbB-3 activity (such as a ligand-induced receptor function of ErbB-3 and/or ligand-induced growth of an ErbB-2 and ErbB-3 positive cell). This is for instance shown in Table 7 and FIG. 38.

In a preferred embodiment the invention provides a bispecific antibody comprising a variable domain that binds ErbB-2, wherein the VH chain of said variable domain comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991, as depicted in FIG. 16A; or comprises the amino acid sequence of VH chain MF1849 or MF2971 or a humanized version thereof, wherein said humanized version preferably comprises the amino acid sequence of MF3958; or MF3004 or a humanized version thereof, wherein said humanized version preferably comprises the amino acid sequence of MF3991, as depicted in FIG. 16A having at most 15, preferably 1, 2, 3, 4, 5, 6, 7, 8, 9 or 10, more preferably at most 1, 2, 3, 4 or 5, amino acid insertions, deletions, substitutions or a combination thereof with respect to said VH. Such bispecific antibody according to this embodiment further preferably comprises a variable domain that binds ErbB-3. The VH chain of the variable domain that binds ErbB-3 preferably comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 as depicted in FIG. 16B or FIG. 16E or FIG. 37, or most preferably comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 as depicted in FIG. 16B or FIG. 16E or FIG. 37, having at most 15, preferably 1, 2, 3, 4, 5, 6, 7, 8, 9 or 10, more preferably at most 1, 2, 3, 4 or 5, amino acid insertions, deletions, substitutions or a combination thereof with respect to any of said VH chain sequences of FIG. 16B or FIG. 16E or FIG. 37. The VH chain of the variable domain that binds ErbB-3 preferably comprises the amino acid sequence of VH chain MF3178 as depicted in FIG. 16B or comprises the amino acid sequence of VH chain MF3178 depicted in FIG. 16B having at most 15, preferably 1, 2, 3, 4, 5, 6, 7, 8, 9 or 10 more preferably at most 1, 2, 3, 4 or 5, amino acid insertions, deletions, substitutions or a combination thereof with respect to the VH chain sequence of FIG. 16B.

The invention preferably provides a bispecific antibody comprising a variable domain that binds ErbB-2 and a variable domain that binds ErbB-3, wherein the VH chain of the variable domain that binds ErbB-2 comprises the amino acid sequence of VH chain MF3958 as depicted in FIG. 16A; or the amino acid sequence of VH chain MF3958 as depicted in FIG. 16A having at most 15, preferably 1, 2, 3, 4, 5, 6, 7, 8, 9 or 10, more preferably at most 1, 2, 3, 4 or 5, amino acid insertions, deletions, substitutions or a combination thereof with respect said VH; and wherein the VH chain of the variable domain that binds ErbB-3 comprises the amino acid sequence of VH chain MF3178 as depicted in FIG. 16B; or the amino acid sequence of VH chain MF3178 depicted in FIG. 16B having at most 15, preferably 1, 2, 3, 4, 5, 6, 7, 8, 9 or 10 more preferably at most 1, 2, 3, 4 or 5, amino acid insertions, deletions, substitutions or a combination thereof with respect to the VH chain sequence of FIG. 16B.

The invention preferably provides a bispecific antibody comprising a variable domain that binds ErbB-2 and a variable domain that binds ErbB-3, wherein the VH chain of the variable domain that binds ErbB-2 comprises the amino acid sequence of VH chain MF3991 as depicted in FIG. 16A; or the amino acid sequence of VH chain MF3991 as depicted in FIG. 16A having at most 15, preferably 1, 2, 3, 4, 5, 6, 7, 8, 9 or 10, more preferably at most 1, 2, 3, 4 or 5, amino acid insertions, deletions, substitutions or a combination thereof with respect said VH; and wherein the VH chain of the variable domain that binds ErbB-3 comprises the amino acid sequence of VH chain MF3178 as depicted in FIG. 16B; or the amino acid sequence of VH chain MF3178 depicted in FIG. 16B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence of FIG. 16B.

When compared to the sequence in FIG. 16, the behavior of a VH chain typically starts to become noticeably different when it has more than 15 amino acid changes with respect to the amino acid sequence of a VH chain as depicted in FIG. 16. A VH chain having at most 15, preferably 1, 2, 3, 4, 5, 6, 7, 8, 9 or 10 amino acid insertions, deletions, substitutions or a combination thereof with respect to the VH chain depicted in FIG. 16, preferably has 1, 2, 3, 4 or 5 amino acid insertions, deletions, substitutions or a combination thereof with respect to the VH chain depicted in FIG. 16, preferably 1, 2, 3 or 4 insertions, deletions, substitutions or a combination thereof, preferably 1, 2 or 3 insertions, deletions, substitutions or a combination thereof, more preferably 1 or 2 insertions, deletions, substitutions or a combination thereof, and preferably 1 insertion, deletion, substitution or a combination thereof with respect to the VH chain depicted in FIG. 16. The one or more amino acid insertions, deletions, substitutions or a combination thereof are preferably not in the CDR1, CDR2 and CDR3 region of the VH chain. They are also preferably not present in the FR4 region. An amino acid substitution is preferably a conservative amino acid substitution.

In a preferred embodiment the invention provides a bispecific antibody comprising an amino acid sequence as depicted in FIG. 16D, or a bispecific antibody of FIG. 16D having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the sequence of FIG. 16D, wherein the at most 15, preferably 1, 2, 3, 4, 5, 6, 7, 8, 9 or 10 amino acid substitutions are preferably conservative amino acid substitutions. The insertions, deletions, substitutions or a combination thereof are preferably not in the CDR3 region of the VH chain, preferably not in the CDR1, CDR2 and CDR3 region of the VH chain, and preferably not in the FR4 region.

Rational methods have evolved toward minimizing the content of non-human residues in the human context. Various methods are available to successfully graft the antigen-binding property of a bispecific antibody onto another antibody. The binding properties of antibodies rest predominantly in the exact sequence of the CDR3 region, often supported by the sequence of the CDR1 and CDR2 regions in the variable domain combined with the appropriate structure of the variable domain as a whole. Various methods are presently available to graft CDR regions onto a suitable variable domain of another antibody. Some of these methods are reviewed in J. C. Almagrol and J. Fransson (2008) Frontiers in Bioscience 13, 1619-1633, which is included by reference herein. The invention therefore further provides a human or humanized bispecific antibody comprising a first antigen-binding site that binds ErbB-2 and a second antigen-binding site that binds ErbB-3, wherein the variable domain comprising the ErbB-2 binding site comprises a VH CDR3 sequence as depicted in FIG. 16A or FIG. 16E, and wherein the variable domain comprising the ErbB-3 binding site comprises a VH CDR3 region as depicted in FIG. 16B or FIG. 16E or FIG. 37. The VH variable region comprising the ErbB-2 binding site preferably comprises the sequence of the CDR1 region, CDR2 region and the CDR3 region of a VH chain in FIG. 16A or FIG. 16E. The VH variable region comprising the ErbB-3 binding site preferably comprises the sequence of the CDR1 region, CDR2 region and the CDR3 region of a VH chain in FIG. 16B or FIG. 16E or FIG. 37. CDR grafting may also be used to produce a VH chain with the CDR regions of a VH of FIG. 16 or FIG. 37, but having a different framework. The different framework may be of another human VH, or a different mammal.

The mentioned at most 15, preferably 1, 2, 3, 4, 5, 6, 7, 8, 9 or 10 amino acid substitutions are preferably conservative amino acid substitutions. The insertions, deletions, substitutions or a combination thereof are preferably not in the CDR3 region of the VH chain, preferably not in the CDR1, CDR2 or CDR3 region of the VH chain and preferably not in the FR4 region.

The light chain of a variable domain comprising a variable heavy chain sequence as depicted in FIG. 16 or FIG. 37, is preferably germline light chain O12, preferably the rearranged germline human kappa light chain IgVκ1-39*01/IGJκ1*01 or a fragment or a functional derivative thereof (nomenclature according to the IMGT database worldwide web at imgt.org). The terms rearranged germline human kappa light chain IgVκ1-39*01/IGJκ1*01, IGKV1-39/IGKJ1, huVκ1-39 light chain or in short huVκ1-39 are used. The light chain can have 1, 2, 3, 4 or 5 amino acid insertions, deletions, substitutions or a combination thereof. The mentioned 1, 2, 3, 4 or 5 amino acid substitutions are preferably conservative amino acid substitutions, the insertions, deletions, substitutions or a combination thereof are preferably not in the CDR3 region of the VL chain, preferably not in the CDR1, CDR2 or CDR3 region or FR4 region of the VL chain.

Various methods are available to produce bispecific antibodies. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection. The ratio of bispecific to other antibodies that are produced by the cell can be increased in various ways. In a preferred embodiment of the invention, the ratio is increased by expressing not two different light chains but two essentially identical light chains in the cell. This concept is in the art also referred to as the "common light chain" method. When the essentially identically light chains work together with the two different heavy chains allowing the formation of variable domains with different antigen-binding sites and concomitant different binding properties, the ratio of bispecific antibody to other antibody that is produced by the cell is significantly improved over the expression of two different light chains. The ratio of bispecific antibody that is produced by the cell can be further improved by stimulating the pairing of two different heavy chains with each other over the pairing of two identical heavy chains. The art describes various ways in which such heterodimerization of heavy chains can be achieved. One way is to generate 'knob into hole' bispecific antibodies. See US Patent Application 20030078385 (Arathoon et al.—Genentech). Another and preferred method is described in U.S. provisional application 61/635,935, which has been followed up by US regular application Ser. No. 13/866,747 and PCT application No. PCT/NL2013/050294 (WO 2013/157954 A1), which are incorporated herein by reference. Methods and means are disclosed for producing bispecific antibodies from a single cell, whereby means are provided that favor the formation of bispecific antibodies over the formation of monospecific antibodies. These methods can also be favorably employed in the present invention. Thus the invention provides a method for producing a bispecific antibody according to the invention (from a single cell), wherein said bispecific antibody comprises two CH3 domains that are capable of forming an interface, said method comprising providing in said cell a) a first nucleic acid molecule encoding a 1st CH3 domain comprising heavy chain, b) a second nucleic acid molecule encoding a 2nd CH3 domain comprising heavy chain, wherein said nucleic acid molecules are provided with means for preferential pairing of said 1st and 2nd CH3 domain comprising heavy chains, said method further comprising the step of culturing said host cell and allowing for expression of said two nucleic acid molecules and harvesting said bispecific antibody from the culture. Said first and second nucleic acid molecules may be part of the same nucleic acid molecule, vector or gene delivery vehicle and may be integrated at the same site of the host cell's genome. Alternatively, said first and second nucleic acid molecules are separately provided to said cell.

A preferred embodiment provides a method for producing a bispecific antibody according to the invention (from a single cell), wherein said bispecific antibody comprises two CH3 domains that are capable of forming an interface, said method comprising providing:

a cell having a) a first nucleic acid molecule encoding a heavy chain comprising an antigen binding site that binds ErbB-2 and that contains a 1st CH3 domain, and b) a second nucleic acid molecule encoding a heavy chain comprising an antigen-binding site that binds ErbB-3 and that contains a 2nd CH3 domain, wherein said nucleic acid molecules are provided with means for preferential pairing of said 1st and 2nd CH3 domains, said method further comprising the step of culturing said cell and allowing for expression of said two nucleic acid molecules and harvesting said bispecific IgG antibody from the culture. In a particularly preferred embodiment, said cell also has a third nucleic acid molecule encoding a common light chain. Said first, second and third nucleic acid molecule may be part of the same nucleic acid molecule, vector or gene delivery vehicle and may be integrated at the same site of the host cell's genome. Alternatively, said first, second and third nucleic acid molecules are separately provided to said cell. A preferred common light chain is O12, preferably the rearranged germline human kappa light chain IgVκ1 39*01/IGJκ1*01, as described above. Means for preferential pairing of said $1^{st}$ and said $2^{nd}$ CH3 domain are preferably the corresponding mutations in the CH3 domain of the heavy chain coding regions. The preferred mutations to produce essentially only bispecific antibodies are the amino acid substitutions L351K and T366K (numbering according to Kabat) in the first CH3 domain and the amino acid substitutions L351D and L368E in the second CH3 domain, or vice versa. Further provided is therefore a method according to the invention for producing a bispecific antibody, wherein said first CH3 domain comprises the amino acid substitutions L351K and T366K (numbering according to Kabat) and wherein said second CH3 domain comprises the amino acid substitutions L351D and L368E, said method further comprising the step of culturing said cell and allowing for expression of said nucleic acid molecules and harvesting said bispecific antibody from the culture. Also provided is a method according to the invention for producing a bispecific antibody, wherein said first CH3 domain comprises the amino acid substitutions L351D and L368E (numbering according to Kabat) and wherein said second CH3 domain comprises the amino acid substitutions L351K and T366K, said method further comprising the step of culturing said cell and allowing for expression of said nucleic acid molecules and harvesting said bispecific antibody from the culture. Antibodies that can be produced by these methods are also part of the present invention. The CH3 heterodimerization domains are preferably IgG1 heterodimerization domains. The heavy chain constant regions comprising the CH3 heterodimerization domains are preferably IgG1 constant regions.

In one embodiment the invention provides a nucleic acid molecule encoding an antibody heavy chain variable region according to the invention. The nucleic acid molecule (typically an in vitro, isolated or recombinant nucleic acid) preferably encodes a heavy chain variable region as depicted in FIG. 16A or FIG. 16B or FIG. 37, or a heavy chain variable region as depicted in FIG. 16A or FIG. 16B or FIG. 37 having 1, 2, 3, 4 or 5 amino acid insertions, deletions, substitutions or a combination thereof. In a preferred embodiment the nucleic acid molecule comprises a sequence as depicted in FIG. 16 or FIG. 37. In another preferred embodiment the nucleic acid molecule encodes the same amino acid sequence as the nucleic acid depicted in FIG. 16 or FIG. 37, but has a different sequence because it encodes one or more different codons. For instance, such nucleic acid molecule is codon optimized for antibody producer cells, such as for instance Chinese hamster ovary (CHO) cells, NS0 cells or PER-C6™ cells. The invention further provides a nucleic acid sequence encoding a heavy chain of FIG. 16D or FIG. 37.

A nucleic acid molecule as used in the invention is typically but not exclusively a ribonucleic acid (RNA) or a deoxyribonucleic acid (DNA). Alternative nucleic acids are available for a person skilled in the art. A nucleic acid according to the invention is for instance comprised in a cell. When said nucleic acid is expressed in said cell, said cell produces an antibody according to the invention. Therefore, the invention in one embodiment provides a cell comprising an antibody according to the invention and/or a nucleic acid according to the invention. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Preferably said cell (typically an in vitro, isolated or recombinant cell) produces said antibody. In a preferred embodiment said cell is a hybridoma cell, a CHO cell, an NS0 cell or a PER-C6™ cell. In a particularly preferred embodiment said cell is a CHO cell. Further provided is a cell culture comprising a cell according to the invention. Various institutions and companies have developed cell lines for the large scale production of antibodies, for instance for clinical use. Non-limiting examples of such cell lines are CHO cells, NS0 cells or PER.C6™ cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, an NS0 cell or another cell type known for its suitability for antibody production for clinical purposes. In a particularly preferred embodiment said cell is a human cell. Preferably a cell that is transformed by an adenovirus E1 region or a functional equivalent thereof. A preferred example of such a cell line is the PER.C6™ cell line or equivalent thereof. In a particularly preferred embodiment said cell is a CHO cell or a variant thereof. Preferably a variant that makes use of a Glutamine synthetase (GS) vector system for expression of an antibody.

The invention further provides a composition, preferably a pharmaceutical composition, comprising an antibody according to the invention. The pharmaceutical composition preferably comprises a (pharmaceutically acceptable) excipient or carrier. In a preferred embodiment the pharmaceutical composition comprises 5-50 mM Histidine, 100-300 mM Trehalose, 0.1-03 g/L PolySorbate20 or a combination thereof. The pH is preferably set at pH=5.5-6.5. In a preferred embodiment the pharmaceutical composition comprises 25 mM Histidine, 220 mM Trehalose, 0.2 g/L PolySorbate20 or a combination thereof. The pH is preferably set at pH=5.5-6.5, most preferably at pH=6.

An antibody of the invention preferably further comprises a label, preferably a label for in vivo imaging. Such a label is typically not necessary for therapeutic applications. In for instance a diagnostic setting, a label can be helpful. For instance in visualizing target cells in the body. Various labels are suited and many are well known in the art. In a preferred embodiment the label is a radioactive label for detection. In another preferred embodiment, the label is an infrared label. Preferably the infrared label is suited for in vivo imaging. Various infrared labels are available to the person skilled in the art. Preferred infrared labels are for instance, IRDye 800; IRDye 680RD; IRDye 680LT; IRDye 750; IRDye 700DX; IRDye 800RS IRDye 650; IRDye 700 phosphoramidite; IRDye 800 phosphoramidite (LI-COR USA; 4647 Superior Street; Lincoln, Nebraska).

The invention further provides a method for the treatment of a subject having a ErbB-2, ErbB-3 or ErbB-2/ErbB-3 positive tumor or at risk of having said tumor comprising administering to the subject an antibody or pharmaceutical composition according to the invention. Before start of said treatment, the method preferably comprises determining whether said subject has, or is at risk of, such ErbB-2, ErbB-3 or ErbB-2/ErbB-3 positive tumor. In some embodiments, the subject is classified as [+] or [++] for ErbB-2. In another embodiment the subject is classified as [+++] for ErbB-2. The invention further provides an antibody of the invention for use in the treatment of a subject having or at risk of having an ErbB-2, ErbB-3 or ErbB-2/ErbB-3 positive tumor. Alternatively formulated, the invention provides a use of an antibody according to the invention for the manufacture of a medicament or prophylactic agent for the treatment of an ErbB-2, ErbB-3 or ErbB-2/ErbB-3 positive tumor. As used herein, the term treatment encompasses prophylaxis.

The tumor is preferably an ErbB-2, ErbB-3 or ErbB-2/ErbB-3 positive cancer. Preferably said positive cancer is a breast cancer, such as early-stage breast cancer. However, the invention can be applied to a wide range of ErbB-2, ErbB-3 or ErbB-2/ErbB-3 positive cancers, like gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, melanoma, and the like. Said antibody according to the present invention is typically capable of reducing a ligand-induced receptor function, preferably ligand induced growth, of ErbB-3 on a ErbB-2 and ErbB-3 positive cell. Said antibody according to the invention preferably comprises a first antigen-binding site that binds domain I of ErbB-2 and a second antigen-binding site that binds domain III of ErbB-3. In one preferred embodiment, the affinity (KD) of said second antigen-binding site for an ErbB-3 positive cell is equal to, or higher than, the affinity of said first antigen-binding site for an ErbB-2 positive cell. Further provided is therefore an antibody comprising a first antigen-binding site that binds ErbB-2 and a second antigen-binding site that binds ErbB-3 for use in the treatment of a subject having or at risk of having an ErbB-2, ErbB-3 or ErbB-2/ErbB-3 positive tumor, preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma, wherein the affinity of said second antigen-binding site for an ErbB-3 positive cell is equal to, or higher than, the affinity of said first antigen-binding site for an ErbB-2 positive cell. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM. In one preferred embodiment, said antibody is antibody PB4188.

In one preferred embodiment, said antibody according to the invention comprises an antigen-binding site that binds at least one amino acid of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181.

In one preferred embodiment, said antibody according to the invention preferably comprises an antigen-binding site that binds at least one amino acid of domain III of ErbB-3 selected from the group consisting R426 and surface-exposed amino acid residues that are located within 11.2 Å from R426 in the native ErbB-3 protein.

Further provided is therefore an antibody comprising a first antigen-binding site that binds ErbB-2 and a second antigen-binding site that binds ErbB-3 for use in the treatment of a subject having or at risk of having an ErbB-2, ErbB-3 or ErbB-2/ErbB-3 positive tumor, preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma, wherein said antibody according to the invention comprises an antigen-binding site that binds at least one amino acid of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181, and/or wherein said antibody according to the invention preferably comprises an antigen-binding site that binds at least one amino acid of domain III of ErbB-3 selected from the group consisting of R426 and surface-exposed amino acid residues that are located within 11.2 Å from R426 in the native ErbB-3 protein.

The subject is preferably a human subject. The subject is preferably a subject eligible for monoclonal antibody therapy using an ErbB-2 specific antibody such as trastuzumab. In a preferred embodiment the subject comprises a tumor, preferably an ErbB-2/ErbB-3 positive cancer, preferably a tumor/cancer with an ErbB-2 therapy resistant phenotype and/or a heregulin resistance phenotype, preferably a monoclonal antibody resistant phenotype. A tumor involving such phenotype can escape treatment with a current anti-HER2 regimen, such as (but not limited to) monoclonal antibody therapy against ErbB-2.

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred. The dosage can be in the range of the dosing regime for trastuzumab or lower.

The present invention describes among others antibodies that target the ErbB-2 and ErbB-3 receptors and result in potent proliferation inhibition of cancer cell lines in vitro and tumor growth inhibition in vivo, even in the presence of an escape mechanism such as for instance upregulation of NRG1-β1. A diverse panel of human and murine Fab binding arms specific for either ErbB-2 or ErbB-3 were identified. These were produced as bispecific antibodies by cloning them into complementary expression vectors that contain mutations in the CH3 region that drives heterodimerization of heavy chains. More than 500 bispecific antibodies were produced at small scale and tested in binding and functional assays on three different cancer cell lines. Various bispecific antibodies were selected and tested in an orthotopic xenograft model using the BxPC3 cell line. This cell line expresses both the ErbB-2 and ErbB-3 receptors and is partially dependent on the ErbB-3 ligand for growth. BxPC3 models are a robust and stringent screening model. Furthermore, a strong anti-tumor activity in vivo has been confirmed using a xenograft model using the JIMT-1 cell line. JIMT-1 cells are derived from a pleural metastasis of a 62-year old patient with breast cancer who was clinically resistant to trastuzumab. JIMT-1 cells grow as an adherent monolayer and form xenograft tumors in nude mice. JIMT-1 cells have an amplified HER-2 oncogene, which showed no identifiable mutations in its coding sequence. JIMT-1 cells overexpress HER-2 mRNA and protein, and the levels of HER-1, HER-3, and HER-4 mRNA and protein are similar to the trastuzumab-sensitive cell line SKBR-3 (Tanner et al, Mol Cancer Ther 2004).

Importantly, a better anti-tumor effect was obtained using an antibody according to the invention as compared to the currently used monoclonal antibodies trastuzumab and pertuzumab, as well as the chemical compound lapatinib.

Antibodies of the invention can be produced at levels >50 mg/L after transient transfection in suspension 293F cells. The bispecific antibodies can be purified to greater than 98% purity with yields >70%. Analytical characterization studies show bispecific IgG1 antibody profiles that are comparable to bivalent monospecific IgG1. In terms of functional activity a bispecific antibody of the invention can demonstrate superior potency compared to trastuzumab+ pertuzumab in vitro and in vivo.

Preferred embodiments of the invention provide combination therapy. In one embodiment, an antibody according to the invention is combined with trastuzumab or pertuzumab, since these antibodies bind different ErbB-2 epitopes so that they do not compete for the same epitope with an antibody according to the invention, as shown in the Examples. In another embodiment, an antibody according to the invention is combined with MM-121 (#Ab6) or RG7116 (Roche), since these antibodies bind different ErbB-3 epitopes so that they do not compete for the same epitope with an antibody according to the invention, as shown in the Examples.

In another preferred embodiment, a binding compound that is specific for ErbB-2 and ErbB-3 is combined with an inhibitor of a component of the PI3Kinase pathway and/or with an inhibitor of a component of the MAPK pathway, such as for instance with a tyrosine kinase inhibitor, a PI3Ka inhibitor, an Akt inhibitor, an mTOR inhibitor or an Src inhibitor. In one embodiment a binding compound that is specific for ErbB-2 and ErbB-3 is combined with a microtubuli disrupting drug or with an inhibitor of a histone deacetylase (HDAC). Surprisingly, the inventors have found a synergistic effect when these combinations are used. Further provided is therefore a method for the treatment of a subject having a ErbB-2, ErbB-3 or ErbB-2/ErbB-3 positive tumor or at risk of having said tumor, the method comprising administering to the subject:
  a binding compound that is specific for ErbB-2 and ErbB-3, and
  one or more compounds selected from the group consisting of an inhibitor of a component of the PI3Kinase pathway, an inhibitor of a component of the MAPK pathway, a microtubuli disrupting drug, and an inhibitor of a histone deacetylase (HDAC). Said inhibitor preferably comprises a tyrosine kinase inhibitor, a PI3Ka inhibitor, an Akt inhibitor, an mTOR inhibitor or an Src inhibitor. Said tyrosine kinase inhibitor is preferably afatinib, lapatinib and/or neratinib. Said PI3Ka inhibitor is preferably BYL719. In one embodiment, said Akt inhibitor is MK-2206. In one preferred embodiment, said mTOR inhibitor is everolimus. In one preferred embodiment, said Src inhibitor is saracatinib. In one preferred embodiment, said microtubuli disrupting drug is paclitaxel. In one preferred embodiment, said HDAC inhibitor is vorinostat. In one preferred embodiment, said binding compound that is specific for ErbB-2 and ErbB-3 is MM-111 (Merrimack Pharmaceuticals). In one preferred embodiment, said binding compound that is specific for ErbB-2 and ErbB-3 is a bispecific antibody. In one preferred embodiment, said binding compound that is specific for ErbB-2 and ErbB-3 is a bispecific antibody according to the invention.

Further provided is therefore a method for the treatment of a subject having a ErbB-2, ErbB-3 or ErbB-2/ErbB-3 positive tumor or at risk of having said tumor, the method comprising administering to the subject:
  a bispecific antibody comprising a first antigen-binding site that binds ErbB-2 and a second antigen-binding site that binds ErbB-3, and
  one or more compounds selected from the group consisting of an inhibitor of a component of the PI3Kinase pathway, an inhibitor of a component of the MAPK pathway, a microtubuli disrupting drug, and an HDAC inhibitor.

Also provided is a bispecific antibody comprising a first antigen-binding site that binds ErbB-2 and a second antigen-binding site that binds ErbB-3 for use in the treatment of a ErbB-2, ErbB-3 or ErbB-2/ErbB-3 positive tumor, wherein said treatment comprises administering said bispecific antibody and at least one compound selected from the group consisting of an inhibitor of a component of the PI3Kinase pathway, an inhibitor of a component of the MAPK pathway, a microtubuli disrupting drug, and an HDAC inhibitor to a subject having a ErbB-2, ErbB-3 or ErbB-2/ErbB-3 positive tumor. Preferably, a bispecific antibody according to the invention having a first antigen-binding site that binds domain I of ErbB-2 and a second antigen-binding site that binds domain III of ErbB-3 is combined with one or more compounds selected from the group consisting of an inhibitor of a component of the PI3Kinase pathway, an inhibitor of a component of the MAPK pathway, a microtubuli disrupting drug, and an HDAC inhibitor. Said inhibitor preferably comprises a tyrosine kinase inhibitor, a PI3Ka inhibitor, an Akt inhibitor, an mTOR inhibitor or an Src inhibitor. Said tyrosine kinase inhibitor is preferably afatinib, lapatinib and/or neratinib. Said PI3Ka inhibitor is preferably BYL719. In one embodiment, said Akt inhibitor is MK-2206. In one preferred embodiment, said mTOR inhibitor is everolimus. In one preferred embodiment, said Src inhibitor is saracatinib. In one preferred embodiment, said microtubuli disrupting drug is paclitaxel. In one preferred embodiment, said HDAC inhibitor is vorinostat.

Said ErbB-2, ErbB-3 or ErbB-2/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. In one embodiment, said ErbB-2, ErbB-3 or ErbB-2/ErbB-3 positive tumor has less than 1.000.000 ErbB-2 cell-surface receptors per tumor cell.

In one embodiment, an antibody according to the present invention that is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and paclitaxel, more preferably with at least one compound selected from the group consisting of afatinib, lapatinib, neratinib, BYL719, MK-2206, everolimus, saracatinib, vorinostat and paclitaxel, is typically capable of reducing a ligand-induced receptor function, preferably ligand induced growth, of ErbB-3 on a ErbB-2 and ErbB-3 positive cell. Said antibody according to the invention preferably comprises a first antigen-binding site that binds domain I of ErbB-2 and a second antigen-binding site that binds domain III of ErbB-3. In one preferred embodiment, the affinity (KD) of said second antigen-binding site for an ErbB-3 positive cell is equal to, or higher than, the affinity of said first antigen-binding site for an ErbB-2 positive cell. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM.

In one preferred embodiment, an antibody according to the invention that is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and paclitaxel, more preferably with at least one compound selected from the group consisting of afatinib, lapatinib, neratinib, BYL719, MK-2206, everolimus, saracatinib, vorinostat and paclitaxel, comprises an antigen-binding site that binds at least one amino acid of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181.

In one preferred embodiment, an antibody according to the invention that is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and paclitaxel, more preferably with at least one compound selected from the group consisting of afatinib, lapatinib, neratinib, BYL719, MK-2206, everolimus, saracatinib, vorinostat and paclitaxel, comprises an antigen-binding site that binds at least one amino acid of domain III of ErbB-3 selected from the group consisting of R426 and surface-exposed amino acid residues that are located within 11.2 Å from R426 in the native ErbB-3 protein.

Preferably, a bispecific antibody according to the invention comprising at least the CDR3 sequence, preferably at least the CDR1, CDR2 and CDR3 sequences, of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, and/or comprising at least the CDR3 sequence, preferably at least the CDR1, CDR2 and CDR3 sequences, of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37 is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and paclitaxel, more preferably with at least one compound selected from the group consisting of afatinib, lapatinib, neratinib, BYL719, MK-2206, everolimus, saracatinib, vorinostat and paclitaxel In one preferred embodiment a bispecific antibody according to the invention comprising:
  an ErbB-2 specific heavy chain variable region sequence selected from the group consisting of the heavy chain variable region sequences of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or comprising an ErbB-2 specific heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the heavy chain variable region sequences of MF2926, MF2930, MF1849; MF2973, MF3004, MF3958, MF2971, MF3025, MF2916, MF3991, MF3031, MF2889, MF2913, MF1847, MF3001, MF3003 or MF1898, and
  an ErbB-3 specific heavy chain variable region sequence selected from the group consisting of the heavy chain variable region sequences of MF3178; MF3176; MF3163; MF3099; MF3307; MF6055; MF6056;

MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37, or comprising an ErbB-3 specific heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the heavy chain variable region sequences of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074, is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and paclitaxel, more preferably with at least one compound selected from the group consisting of afatinib, lapatinib, neratinib, BYL719, MK-2206, everolimus, saracatinib, vorinostat and paclitaxel. In one preferred embodiment, antibody PB4188 is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and paclitaxel, more preferably with at least one compound selected from the group consisting of afatinib, lapatinib, neratinib, BYL719, MK-2206, everolimus, saracatinib, vorinostat and paclitaxel.

Preferred embodiments of the invention provide uses of antibodies according to the invention under heregulin stress conditions. Heregulin is a growth factor that is involved in growth of ErbB-3 positive tumor cells. Typically, when the tumor cells express high levels of heregulin (referred to as heregulin stress), currently known therapies like trastuzumab, pertuzumab and lapatinib are no longer capable of inhibiting tumor growth. This phenomenon is called heregulin resistance. Surprisingly, however, an antibody according to the invention is also capable of counteracting growth of tumor cells that express high levels of heregulin. As used herein, an expression level of heregulin is considered high if a cell has a heregulin expression level that is at least 60%, preferably at least 70%, more preferably at least 80%, more preferably at least 85%, more preferably at least 90% or 95% of the heregulin expression level of BXPC3 or MCF7 cells. Heregulin expression levels are for instance measured using qPCR with tumor RNA (such as for instance described in Shames et al. PLOS ONE, February 2013, Vol. 8, Issue 2, pp 1-10 and in Yonesaka et al., Sci. transl. Med., Vol. 3, Issue 99 (2011); pp 1-11), or using protein detection methods, like for instance ELISA, preferably using blood, plasma or serum samples (such as for instance described in Yonesaka et al., Sci. transl. Med., Vol. 3, Issue 99 (2011); pp 1-11). Further provided is therefore an antibody according to the invention for use in the treatment of a subject having or at risk of having an ErbB-2, ErbB-3 or ErbB-2/ErbB-3 positive tumor, wherein said cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells. Said antibody according to the invention preferably comprises a first antigen-binding site that binds domain I of ErbB-2. Also provided is a method for the treatment of a subject having a ErbB-2, ErbB-3 or ErbB-2/ErbB-3 positive tumor, wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells, the method comprising administering to the subject an antibody or pharmaceutical composition according to the invention. One preferred embodiment provides a use of an antibody according to the invention for the preparation of a medicament for the treatment of an ErbB-2, ErbB-3 or ErbB-2/ErbB-3 positive tumor, wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells. Said ErbB-2, ErbB-3 or ErbB-2/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Further provided is therefore an antibody according to the invention for use in the treatment of a subject having or at risk of having breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma, preferably breast cancer, wherein cells of said cancer have a heregulin expression level that is at least 60%, preferably at least 70%, more preferably at least 80%, more preferably at least 85%, more preferably at least 90% or 95% of the heregulin expression level of BXPC3 or MCF7 cells. Said antibody according to the invention preferably comprises a first antigen-binding site that binds domain I of ErbB-2.

High heregulin levels are typically present during the formation of metastases (i.e. the migration, invasion, growth and/or differentiation of tumor cells or tumor initiating cells). Typically, tumor initiating cells are identified based on stem cell markers such as for instance CD44, CD24, CD133 and/or ALDH1. These processes can therefore barely be counteracted with currently known therapies like trastuzumab and pertuzumab. Since an antibody according to the invention is capable of counteracting growth and/or differentiation of tumor cells or tumor initiating cells that express high levels of heregulin, such antibody according to the invention is also particularly suitable for counteracting the formation of metastases. Further provided is therefore a method for counteracting the formation of a metastasis in a subject having a ErbB-2, ErbB-3 or ErbB-2/ErbB-3 positive tumor, wherein said ErbB-2, ErbB-3 or ErbB-2/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells, comprising administering to the subject a bispecific antibody comprising a first antigen-binding site that binds ErbB-2 and a second antigen-binding site that binds ErbB-3. Also provided is a bispecific antibody comprising a first antigen-binding site that binds ErbB-2 and a second antigen-binding site that binds ErbB-3 for use in the treatment or prevention of the formation of metastases, wherein said ErbB-2, ErbB-3 or ErbB-2/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Further provided is a use of a bispecific antibody according to the invention for the preparation of a medicament for the treatment or prevention of the formation of metastases, wherein said ErbB-2, ErbB-3 or ErbB-2/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Said ErbB-2, ErbB-3 or ErbB-2/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Further provided is therefore a bispecific antibody according to the invention comprising a first antigen-binding site that binds ErbB-2 and a second antigen-binding site that binds ErbB-3 for use in the treatment or prevention of the formation of metastases of breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma cells, preferably breast cancer cells, wherein said cells have a heregulin expression level that is at least 60%, preferably at least 70%, more preferably at least 80%, more preferably at least 85%, more preferably at least 90% or 95% of the heregulin expression level of BXPC3 or MCF7 cells. Said antibody according to the present invention is typically capable of reducing a ligand-induced receptor function, preferably ligand induced growth, of ErbB-3 on a ErbB-2 and ErbB-3 positive cell. Said antibody according to the invention preferably comprises a first antigen-binding site that binds domain I of ErbB-2 and a second antigen-binding site that binds domain III of ErbB-3. In one preferred embodiment, the affinity (KD) of said second antigen-binding site for an ErbB-3 positive cell is equal to, or higher than, the affinity of said first antigen-binding site for an ErbB-2 positive cell. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM.

In one preferred embodiment, said antibody according to the invention comprises an antigen-binding site that binds at least one amino acid of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181.

In one preferred embodiment, said antibody according to the invention preferably comprises an antigen-binding site that binds at least one amino acid of domain III of ErbB-3 selected from the group consisting of R426 and surface-exposed amino acid residues that are located within 11.2 Å from R426 in the native ErbB-3 protein.

One preferred embodiment provides a method according to the invention for the treatment of a subject having a ErbB-2, ErbB-3 or ErbB-2/ErbB-3 positive tumor wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells, or an antibody according to the invention for use in such treatment, wherein said antibody comprises at least the CDR3 sequence, preferably at least the CDR1, CDR2 and CDR3 sequences, or at least the heavy chain variable region sequence, of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E.

One preferred embodiment provides a method according to the invention for the treatment of a subject having a ErbB-2, ErbB-3 or ErbB-2/ErbB-3 positive tumor wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells, or an antibody according to the invention for use in such treatment, wherein said antibody comprises at least the CDR3 sequence, preferably at least the CDR1, CDR2 and CDR3 sequences, or at least the heavy chain variable region sequence, of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37. One embodiment provides antibody PB4188 for use in the treatment of a subject having a ErbB-2, ErbB-3 or ErbB-2/ErbB-3 positive tumor, wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells.

As already described, antibodies according to the present invention are particularly suitable for treating ErbB-2 positive tumor cells with less than 1.000.000 ErbB-2 receptors on their cell surface. Patients with such tumors, who are typically classified as ErbB-2 [++] or ErbB-2 [+], include patients with primary tumors as well as patients with relapsed ErbB-2 positive tumors. Currently used therapies such as trastuzumab (HERCEPTIN®) and pertuzumab are only prescribed for patients with malignant ErbB-2 positive cells that have more than 1.000.000 ErbB-2 receptors on their cell surface, which are classified as ErbB-2 [+++]. Patients that are classified as ErbB-2 [++] or ErbB-2 [+] are therefore preferably treated with an antibody according to the present invention. Further provided is therefore a method or antibody for use according to the invention, wherein said subject has an ErbB-2 or ErbB-2/ErbB-3 positive tumor that has less than 1.000.000 ErbB-2 cell-surface receptors per tumor cell. One preferred embodiment provides a bispecific antibody according to the invention comprising a first antigen-binding site that binds ErbB-2 and a second antigen-binding site that binds ErbB-3 for use in the treatment or prevention of the formation of metastases, wherein said ErbB-2, ErbB-3 or ErbB-2/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells, and wherein said tumor cell has less than 1.000.000 ErbB-2 cell-surface receptors.

In another preferred embodiment, an antibody according to the invention is used for counteracting an ErbB-2, ErbB-3 or ErbB-2/ErbB-3 positive tumor in a subject who has an impaired cardiac function, or who is at risk thereof. With an impaired cardiac function is meant that the subject has a cardiac function, such as for instance the left ventricular ejection fraction (LVEF), that is lower than 90%, preferably lower than 85% or lower than 80%, preferably lower than 75% or lower than 70%, as compared to a healthy cardiac function. Said healthy cardiac function is, for instance, the average cardiac function (such as for instance the average LVEF) of the healthy population. Alternatively, said healthy cardiac function is the function (such as the LVEF) as measured in a patient before the start of anti-tumor therapy with an antibody according to the invention.

Cardiac function is for instance monitored by a physical examination of the subject and by an examination of the LVEF, using for instance an echocardiogram or a MUGA scan.

ErbB-2 is involved in growth, repair, and survival of adult cardiomyocytes as part of a signalling network that involves the heregulin receptor complex HER2:HER4. As described herein before, cardiotoxicity is a known risk factor in ErbB-2 targeting therapies and the frequency of complications is increased when trastuzumab is used in conjunction with anthracyclines thereby inducing cardiac stress. For instance, the combination of doxycycline with trastuzumab induces severe cardiac side effects. Despite the increasing number of clinical cases of trastuzumab-induced cardiac dysfunction, its mechanism of action is unknown. In view of the cardiotoxicity of currently known therapies against ErbB-2, ErbB-3 or ErbB-2/ErbB-3 positive tumors, it is of particular advantage to use an antibody according to the invention. As shown in the Examples, antibodies have now been provided that do not, or to a significantly lesser extent as compared to trastuzumab and pertuzumab, affect the survival of cardiomyocytes. This provides an important advantage since cardiotoxicity is reduced. This is already advantageous for people who do not suffer from an impaired cardiac function, and even more so for people who do suffer from an impaired cardiac function, such as for instance subjects suffering from congestive heart failure (CHF), left ventricular dysfunction (LVD) and/or a decreased Left Ventricular Ejection Fraction (LVEF), and/or subjects who have had a myocardial infarction. Further provided is therefore a bispecific antibody according to the invention for use in the treatment of a subject having or at risk of having an ErbB-2, ErbB-3 or ErbB-2/ErbB-3 positive tumor, wherein said subject has a cardiac function that is lower than 90%, preferably lower than 85% or lower than 80% or lower than 75% or lower than 70%, as compared to a healthy cardiac function. Said cardiac function preferably includes the LVEF. Said ErbB-2, ErbB-3 or ErbB-2/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Said antibody according to the invention preferably comprises a first antigen-binding site that binds domain I of ErbB-2 and a second antigen-binding site that binds domain III of ErbB-3. One preferred embodiment provides a method according to the invention for the treatment of a subject having a ErbB-2, ErbB-3 or ErbB-2/ErbB-3 positive tumor wherein the subject has a cardiac function that is lower than 90%, preferably lower than 85%, preferably lower than 80%, preferably lower than 75% or lower than 70%, as compared to a healthy cardiac function, or an antibody according to the invention for use in such treatment, wherein said antibody comprises:

at least the CDR3 sequence, preferably at least the CDR1, CDR2 and CDR3 sequences, or at least the heavy chain variable region sequence, of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences; and/or at least the CDR3 sequence, preferably at least the CDR1, CDR2 and CDR3 sequences, or at least the heavy chain variable region sequence, of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences. In one preferred embodiment, said antibody is PB4188.

In one embodiment, said bispecific antibody is for use in the treatment of a subject under heregulin stress conditions, as explained in more detail elsewhere. Further provided is therefore a bispecific antibody according to the invention for use in the treatment of a subject having or at risk of having an ErbB-2, ErbB-3 or ErbB-2/ErbB-3 positive tumor, wherein said subject has a cardiac function that is lower than 90%, preferably lower than 85%, preferably lower than 80%, preferably lower than 75% or lower than 70%, as compared to a healthy cardiac function, and wherein said cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells. Said cardiac function preferably includes the LVEF. Also provided is a method for the treatment of a subject having a ErbB-2, ErbB-3 or ErbB-2/ErbB-3 positive tumor, wherein the subject has a cardiac function that is lower than 90%, preferably lower than 85%, preferably lower than 80%, preferably lower than 75%, preferably lower than 70%, as compared to a healthy cardiac function, and wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells, the method comprising administering to the subject a bispecific antibody or pharmaceutical composition according to the invention. One preferred embodiment provides a use of a bispecific antibody according to the invention for the preparation of a medicament for the treatment of an ErbB-2, ErbB-3 or ErbB-2/ErbB-3 positive tumor in a subject who has a cardiac function, preferably a LVEF, that is lower than 90%, preferably lower than 85%, preferably lower than 80%, preferably lower than 75% or lower than 70%, as compared to a healthy cardiac function, preferably a healthy LVEF, wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells.

Also provided is a bispecific antibody comprising a first antigen-binding site that binds ErbB-2 and a second antigen-binding site that binds ErbB-3 for use in the treatment or prevention of the formation of metastases, wherein said subject has a cardiac function that is lower than 90%, preferably lower than 85%, preferably lower than 80%, preferably lower than 75%, preferably lower than 70% as compared to a healthy cardiac function. Further provided is a use of a bispecific antibody according to the invention for the preparation of a medicament for the treatment or prevention of the formation of metastases, wherein said subject has a cardiac function that is lower than 90%, preferably lower than 85%, preferably lower than 80%, preferably lower than 75% or lower than 70% as compared to a healthy cardiac function. Said ErbB-2, ErbB-3 or ErbB-2/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Said cardiac function preferably includes the LVEF. In one preferred embodiment, said antibody is antibody PB4188.

In another embodiment, use is made of antibodies according to the invention for counteracting phosphorylation of various factors of the prosurvival pathway Akt (also referred to as the PI3 kinase pathway) and the MAP kinase pathway. These are downstream pro-proliferative signaling pathways of HER3. Surprisingly, the inventors have succeeded in significantly inhibiting phosphorylation of Akt, ERK1/2 and S6 ribosomal protein (S6-RP) with an antibody according to the present invention, whereas trastuzumab and pertuzumab do not have these strong anti-phosphorylation effects. Counteracting phosphorylation of factors of the pro-proliferative PI3 kinase and MAP kinase pathways is advantageous, since this counteracts growth of an ErbB-3 positive tumor cell. Further provided is therefore a use of an antibody according to the invention for counteracting, preferably inhibiting, phosphorylation of Akt, ERK1/2 and/or S6-RP. Importantly, phosphorylation of Akt can be significantly reduced or even completely blocked with an antibody of the invention, both in vitro and in vivo, as shown in the Examples. A preferred embodiment therefore provides a use of an antibody according to the invention for counteracting, preferably inhibiting, phosphorylation of Akt. Also provided is a use of an antibody according to the invention for counteracting the formation of a HER3-p85 complex. Since the formation of a HER3-p85 complex is the first phase in Akt activation, it is advantageous to counteracting the formation of said HER3-p85 complex. Said antibody according to the invention is preferably a bispecific antibody comprising a first antigen-binding site that binds domain I ErbB-2 and a second antigen-binding site that binds domain III of ErbB-3. Said antibody preferably comprises an antigen-binding site that binds at least one amino acid of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181. Additionally, or alternatively, said antibody preferably comprises an antigen-binding site that binds at least one amino acid of domain III of ErbB-3 selected from the group consisting of F409 and R426 and surface-exposed amino acid residues that are located within 11.2 Å from R426 in the native ErbB-3 protein. In one embodiment, said antibody comprises at least one CDR1, CDR2 and CDR3 sequence, or at least one VH sequence, as depicted in FIG. 16 or FIG. 37. In one embodiment, said antibody is PB4188.

For the purpose of clarity and a concise description features are described herein as part of the same or separate embodiments, however, it will be appreciated that the scope of the invention may include embodiments having combinations of all or some of the features described.

BRIEF DESCRIPTION OF THE DRAWINGS

FIG. 6: FACS analysis of a bispecific HER2×HER3 antibody and its parental monoclonal antibodies on MCF-7 and BxPC3-luc2 HER2 expressing cells. MFI, mean fluorescence intensity.

FIG. 16A-16E: Nucleic acid and amino acid sequences of VH-chains, common light chain and heavy chains of antibodies of the invention. Where in this figure a leader sequence is indicated this is not part of the VH chain or antibody, but is typically cleaved of during processing of the protein in the cell that produces the protein.

a) HER3 crystal structure (PDB #4P59) showing epitope residue Arg 426 in gray spheres and all surface exposed residues within an 11.2 Å radius from Arg 426 in black spheres. b) Solvent exposed surface of epitope region with Arg 426 and distant residues shown in gray and all surface exposed residues within a 11.2 Å radius from Arg 426 shown in black. c) Residues in the epitope region Arg 426 in light gray and surrounding residues (all labeled) in dark gray. Figures and analyses were made with Yasara (www.yasara.org).

Figure 22:
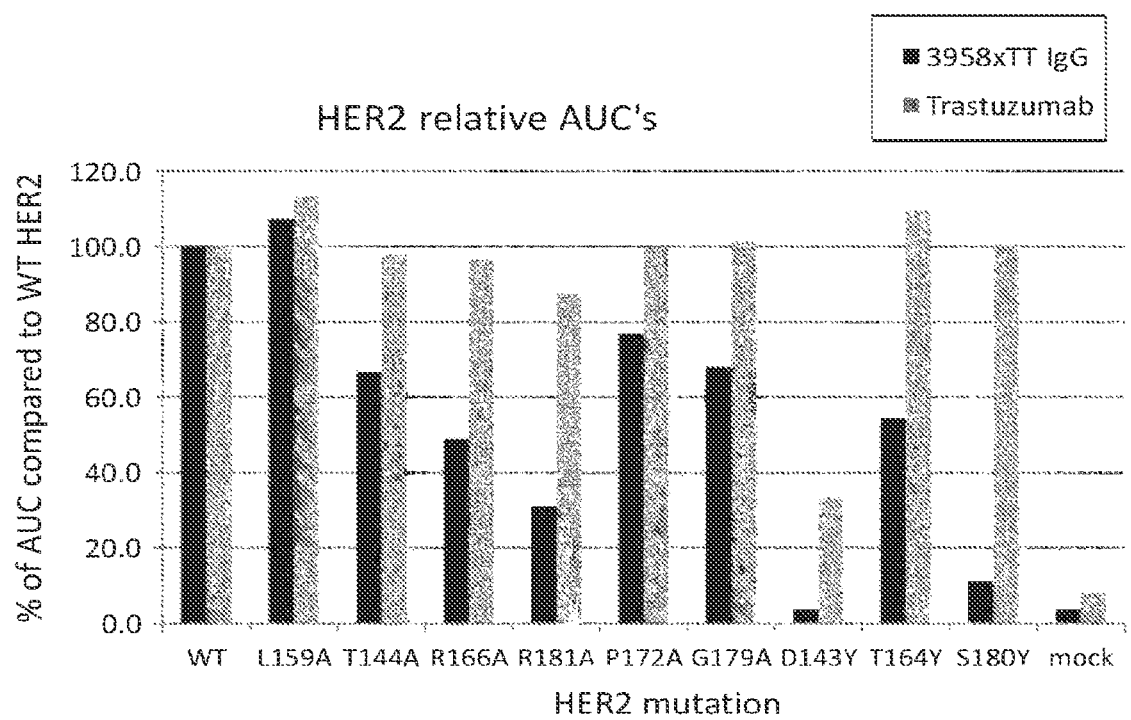

FIG. 22: Confirmation of critical binding residues for Fab arm 3958 to HER2. Trastuzumab was included as a control antibody. Binding was determined in a FACS titration and binding is expressed as AUC in comparison to trastuzumab binding. D143Y is not considered to be part of the 3958 epitope as binding of Trastuzumab to this mutant is also blocked.

Figure 23:
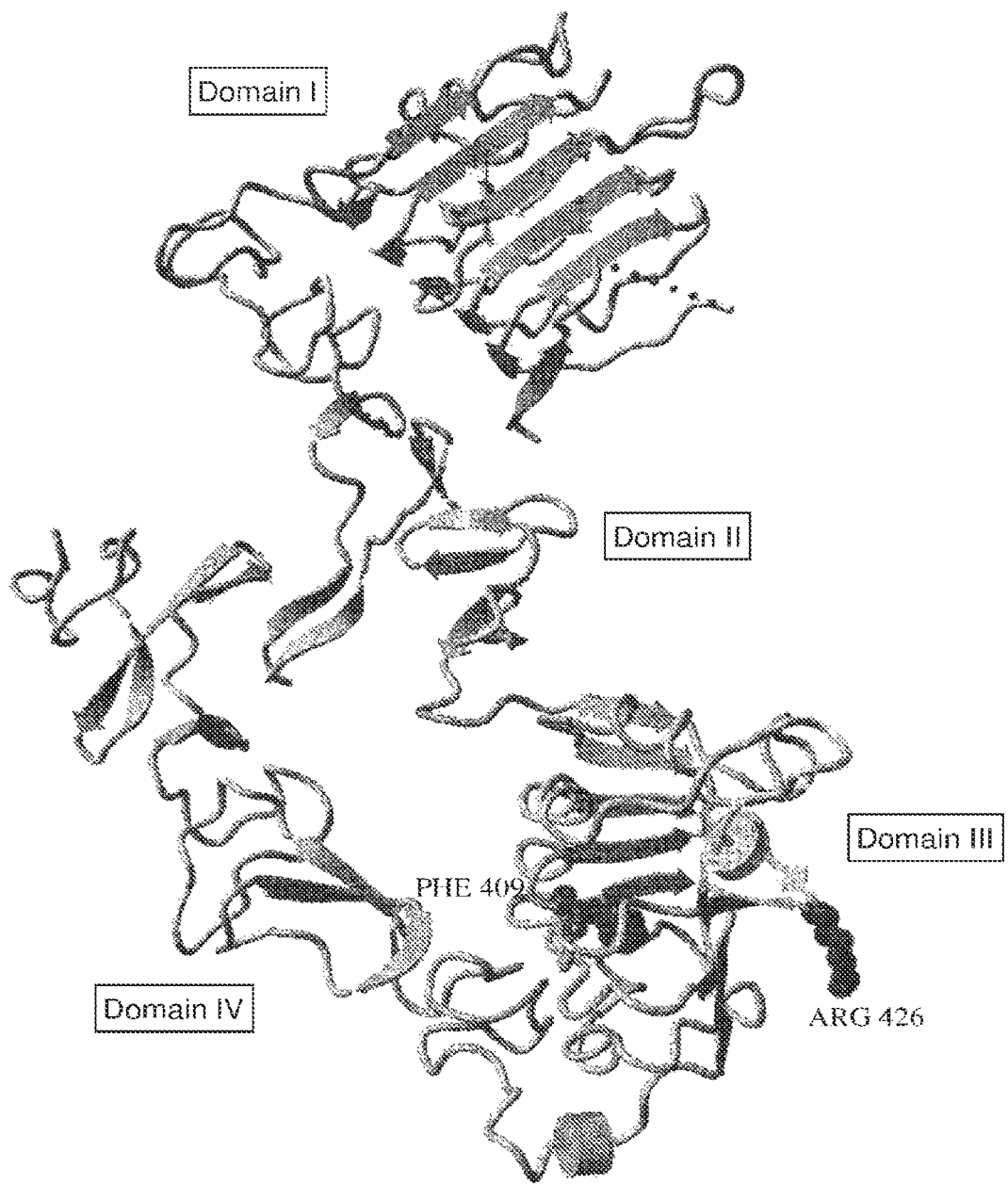

FIG. 23: Critical residues for PG3178 binding represented in the HER3 crystal structure. Critical residues identified for PG3178binding are represented as black spheres on the HER3 crystal structure (PDB ID #4P59).

Figure 24:
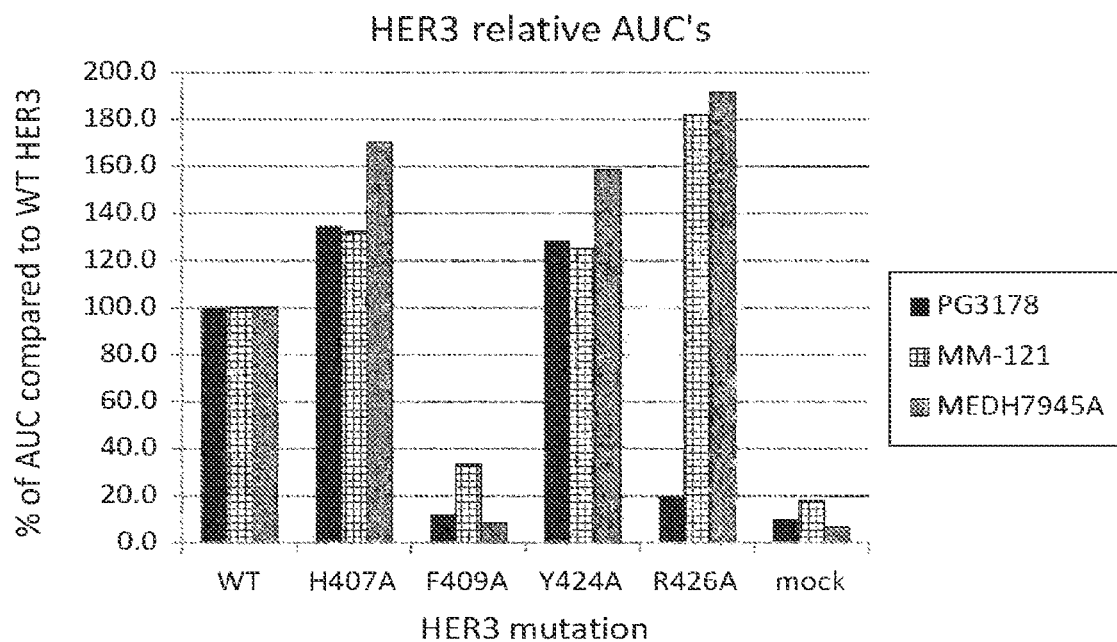

FIG. 24: Confirmation of R426 as a critical binding residue for PG3175 to HER3. Two anti-HER3 antibodies were included as control antibodies. Binding was determined in a FACS titration and binding is expressed as AUC in comparison to binding to WT HER3.

Figure 25:
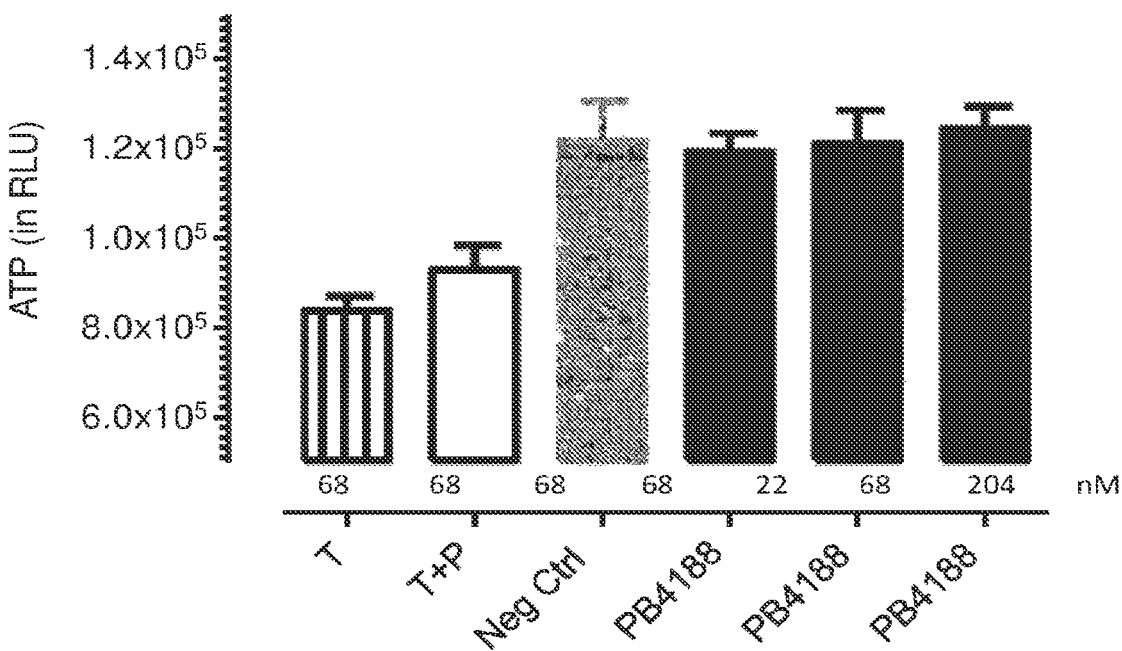

FIG. 25: Absence of PB4188 toxicity under cardiac stress in vitro. Incubation of cardiomyocytes with PB4188 or monospecific benchmark antibodies in the presence 3 μM of the anthracyclin doxorubicin. Viability of the cardiomyocytes was determined by quantification of ATP and expressed in relative light units (RLU). T, trastuzumab; P, pertuzumab.

Figure 26:
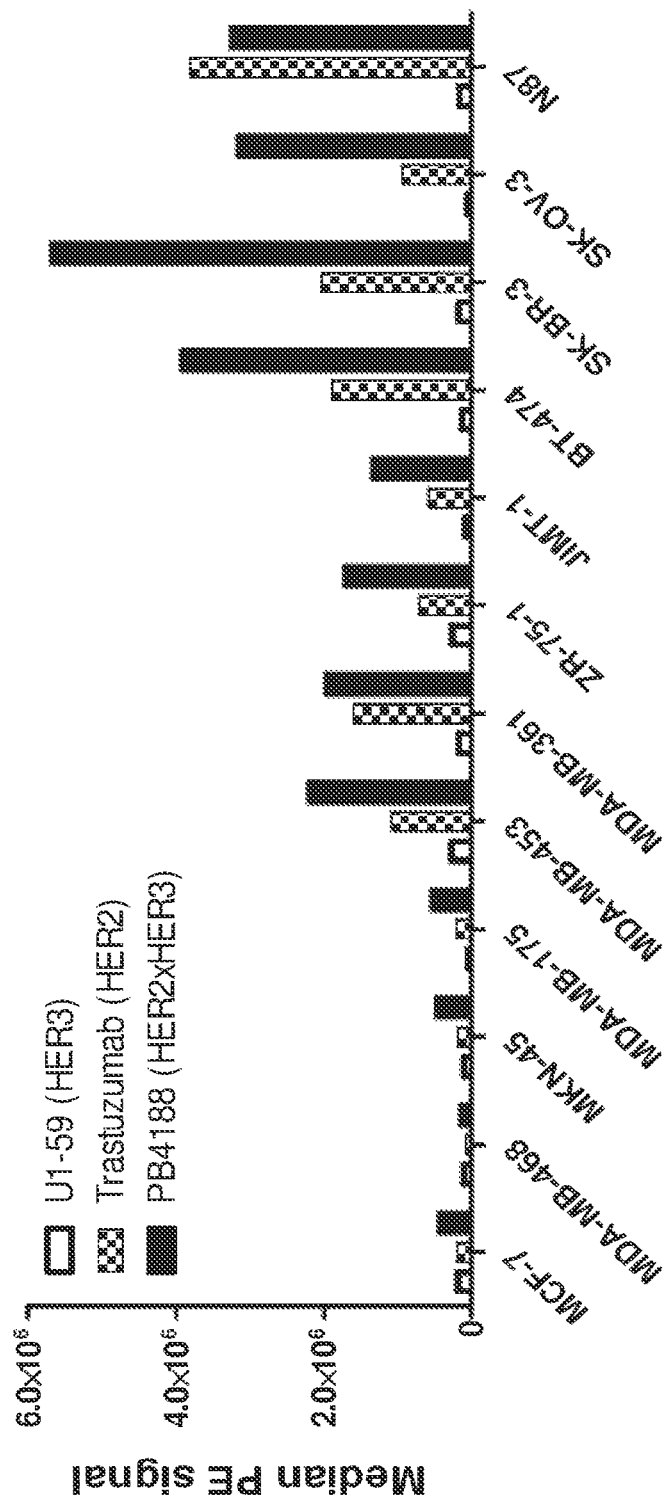

FIG. 26: Binding of PB4188 in comparison to trastuzumab and a HER3 antibody to HER2 amplified cells. FACS titrations were performed on the indicated cell lines expressing different HER2 levels. Area under the curve of Median PE signal values were plotted per cell line.

Figure 27:
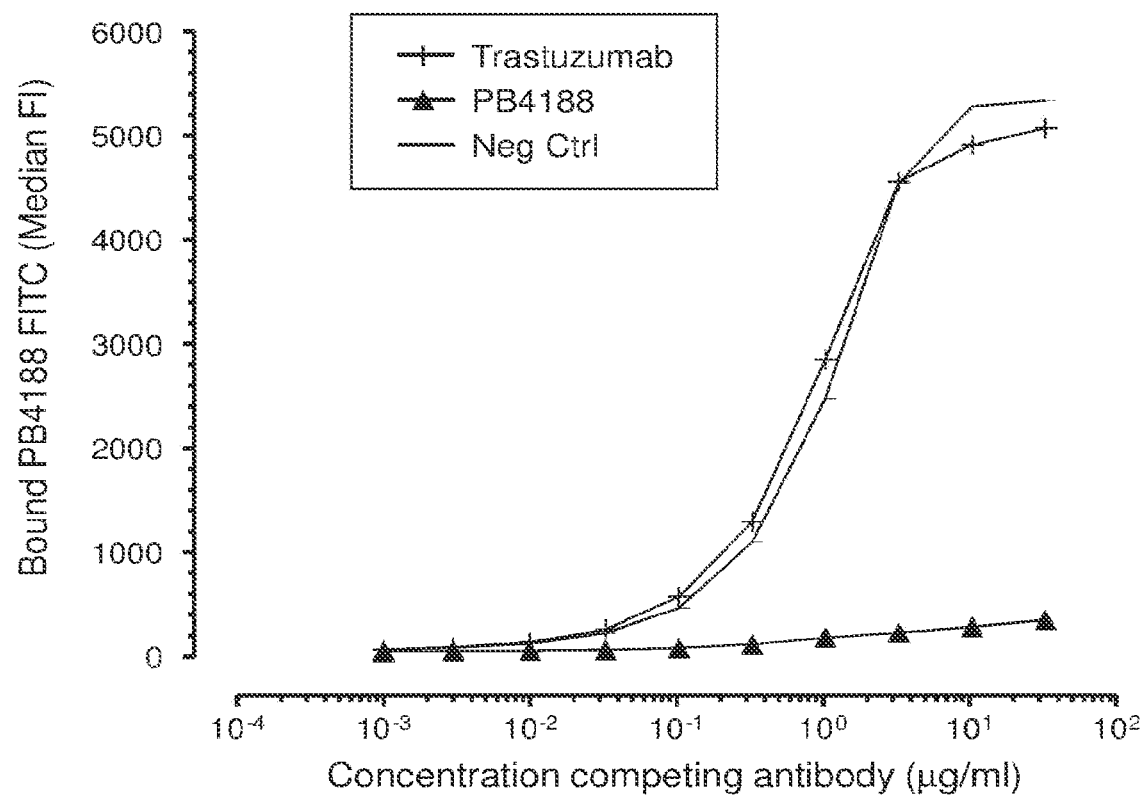

FIG. 27: Binding of a serial titration of PB4188$^{FITC}$ to SKBR-3 cells pre-incubated with a saturated concentration of PB4188, trastuzumab or a negative control antibody. PB4188$^{FITC}$ binds as effectively to SKBR-3 in the presence of trastuzumab or control antibody.

FIGS. 28A and 28B: Inhibition of cell proliferation under HRG stress conditions by HER2×HER3 bispecific antibodies composed of the same HER3 Fab arm and different HER2 arms that are directed against the four HER2 domains.

Figure 29:
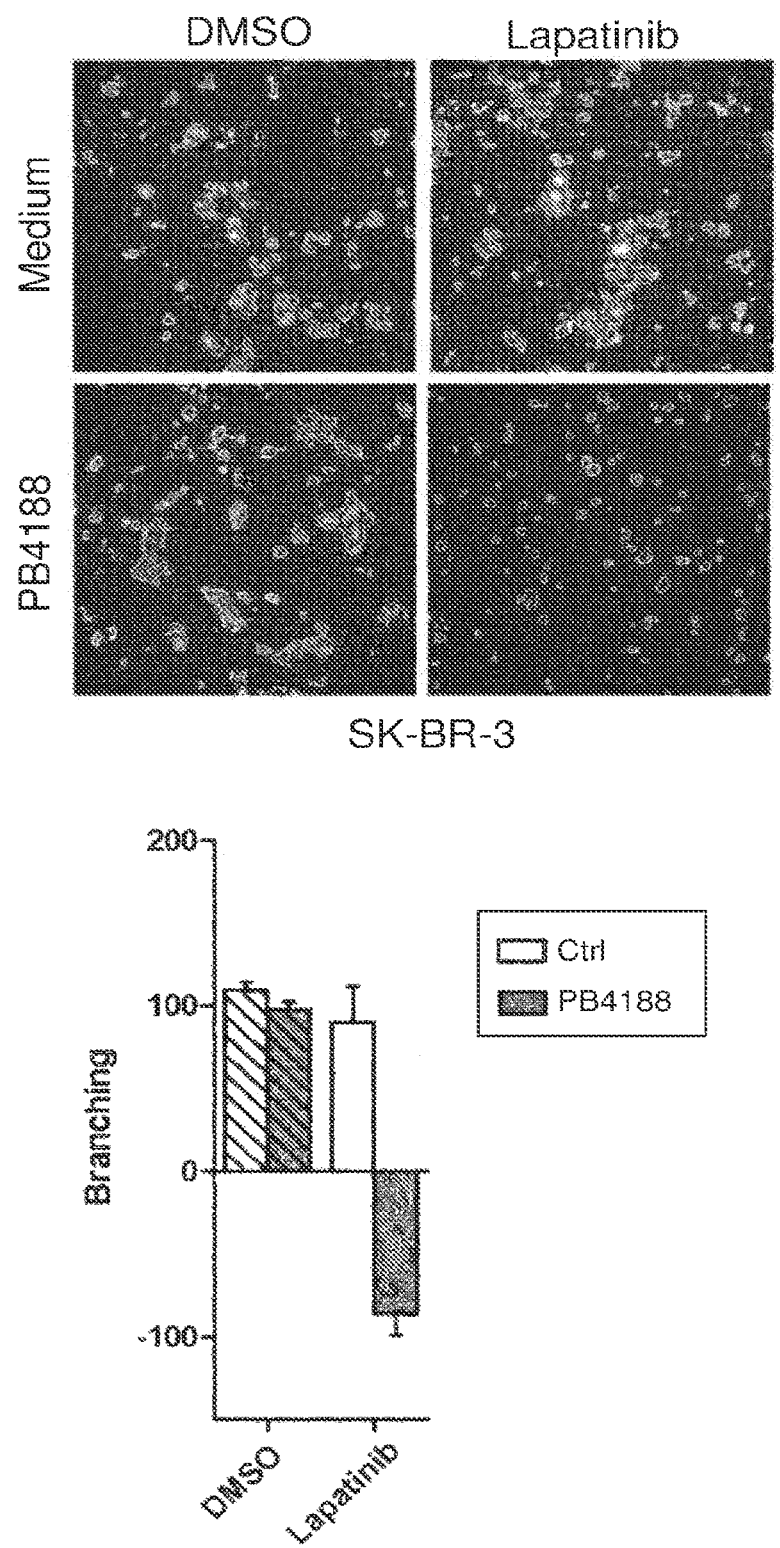
Figure 30A:
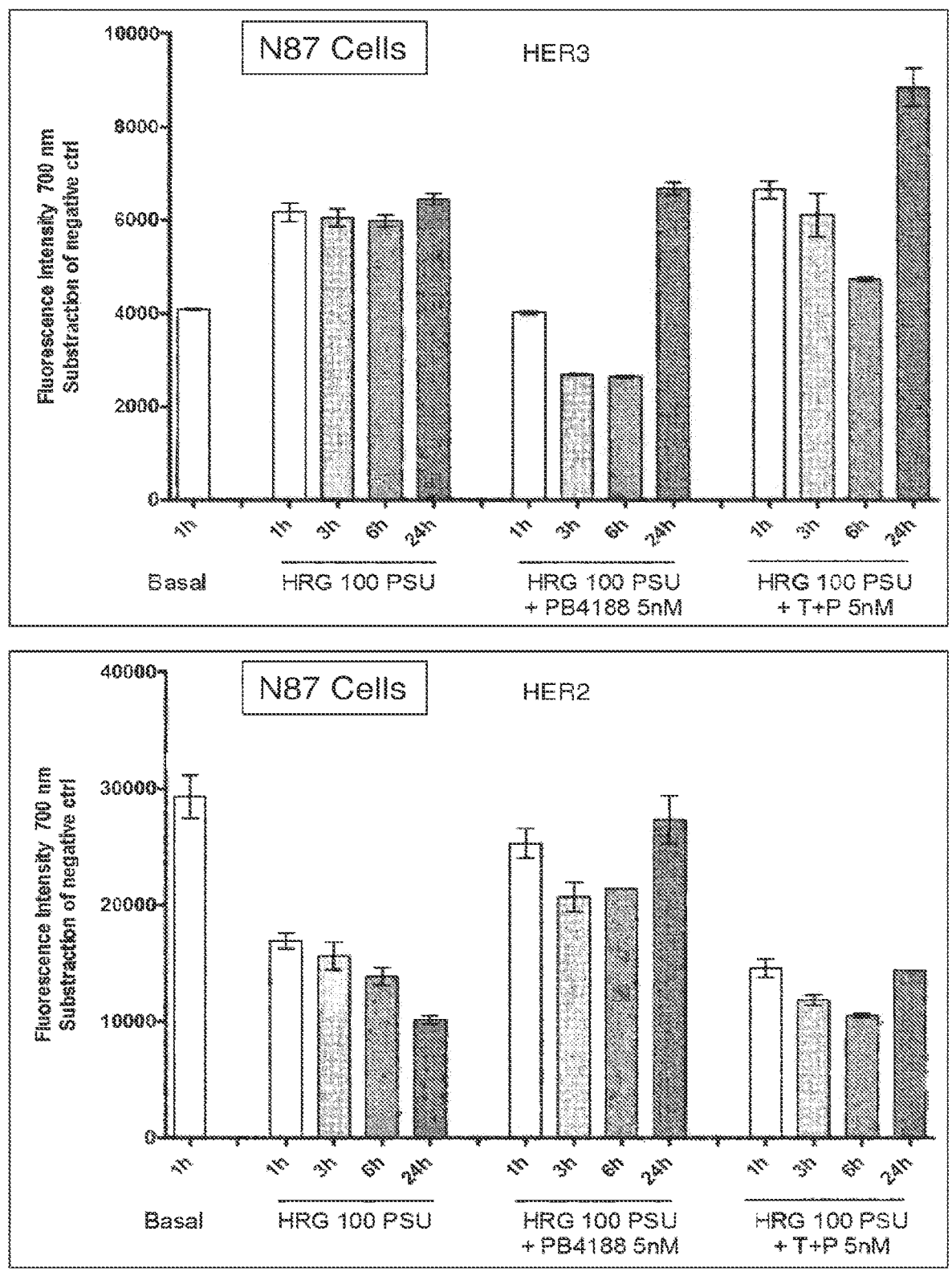
Figure 30A:
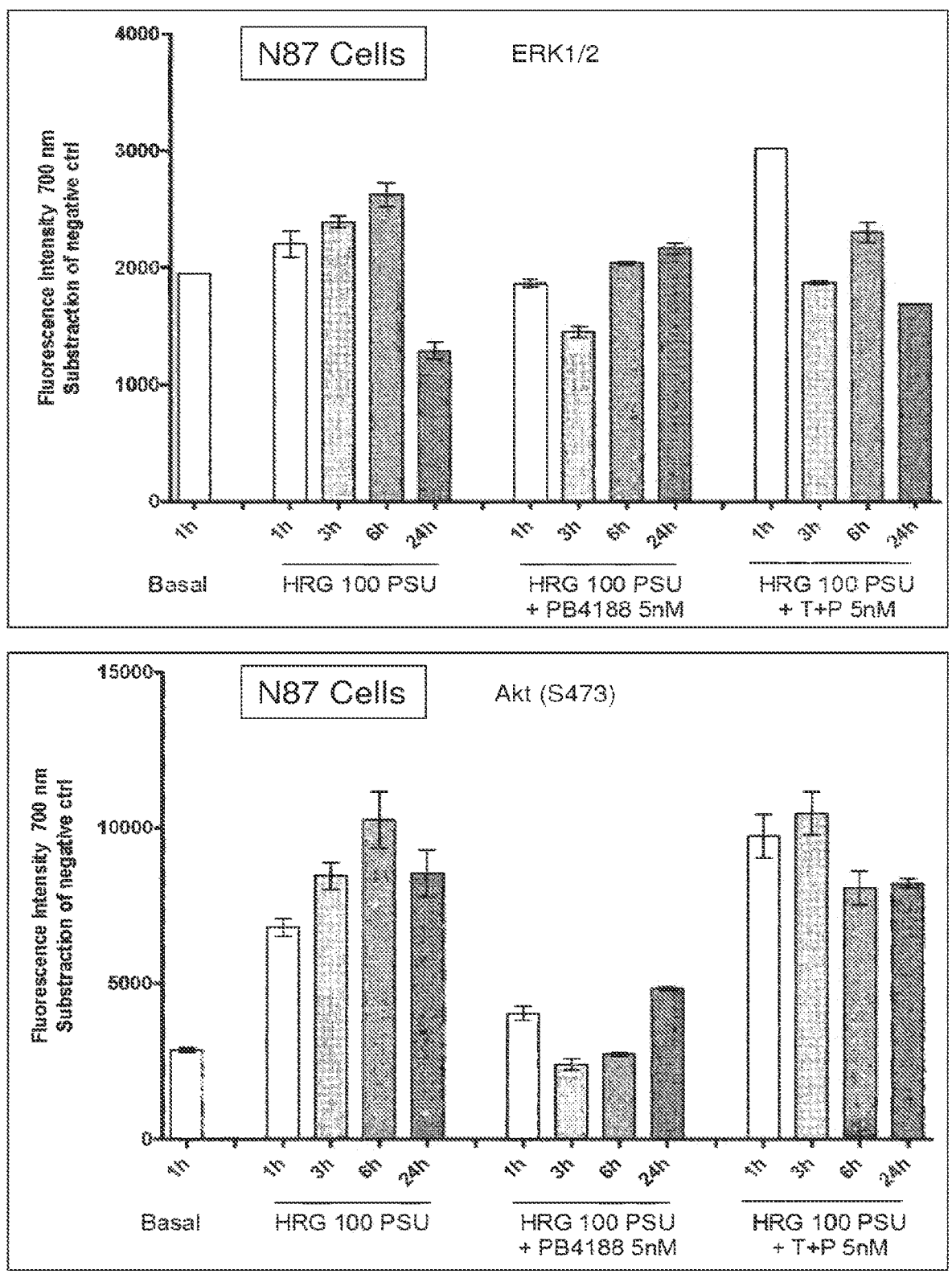
Figure 30A:
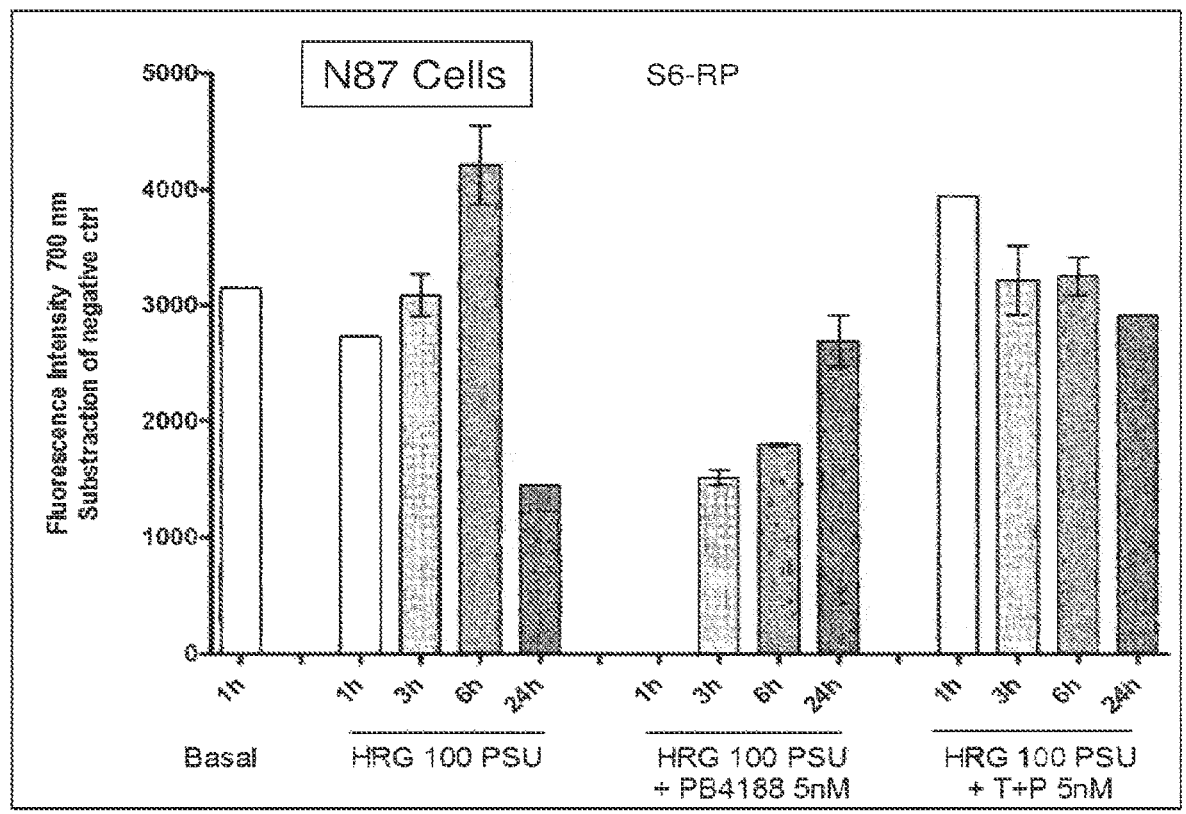
Figure 30B:
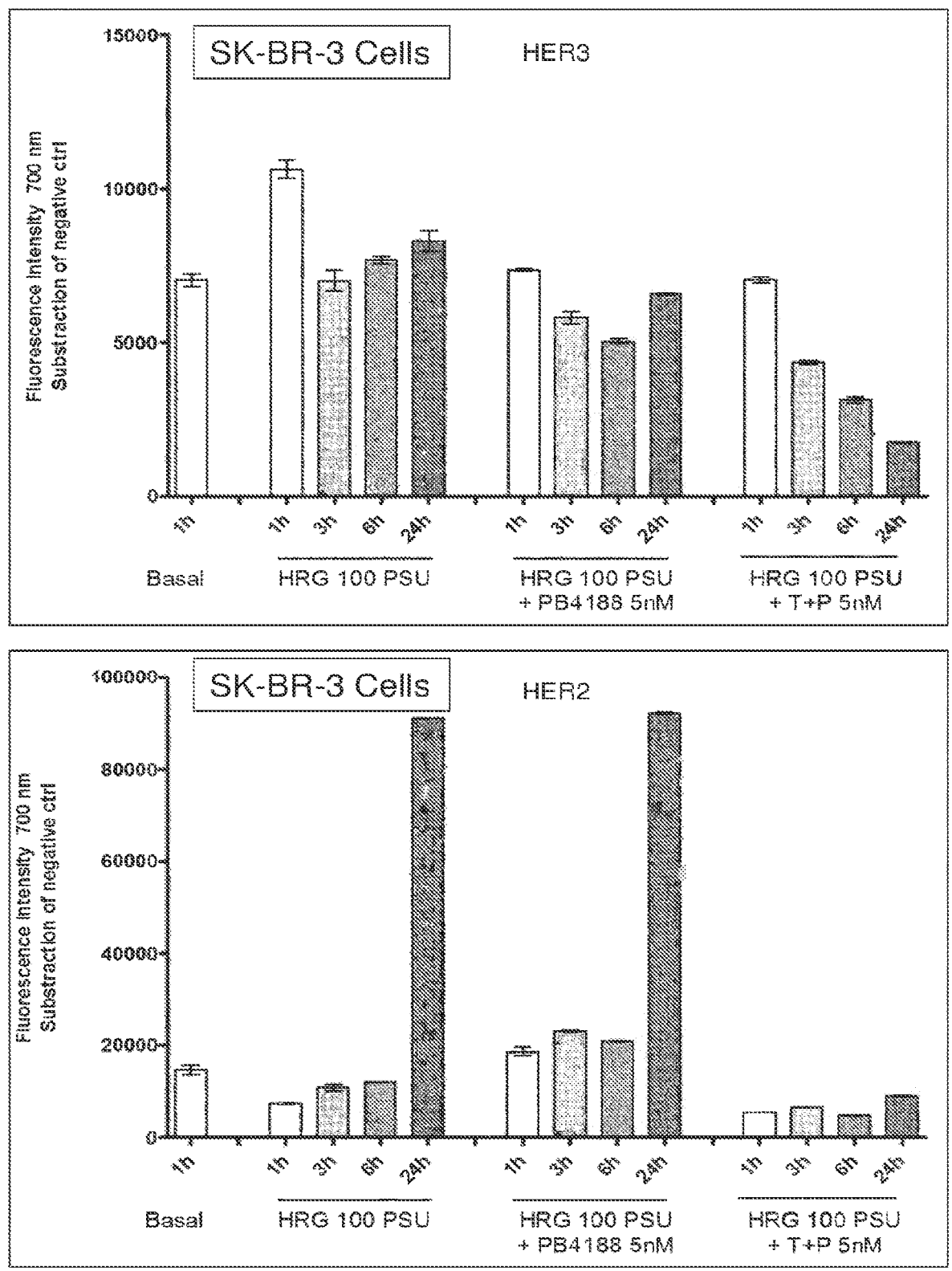
Figure 30B:
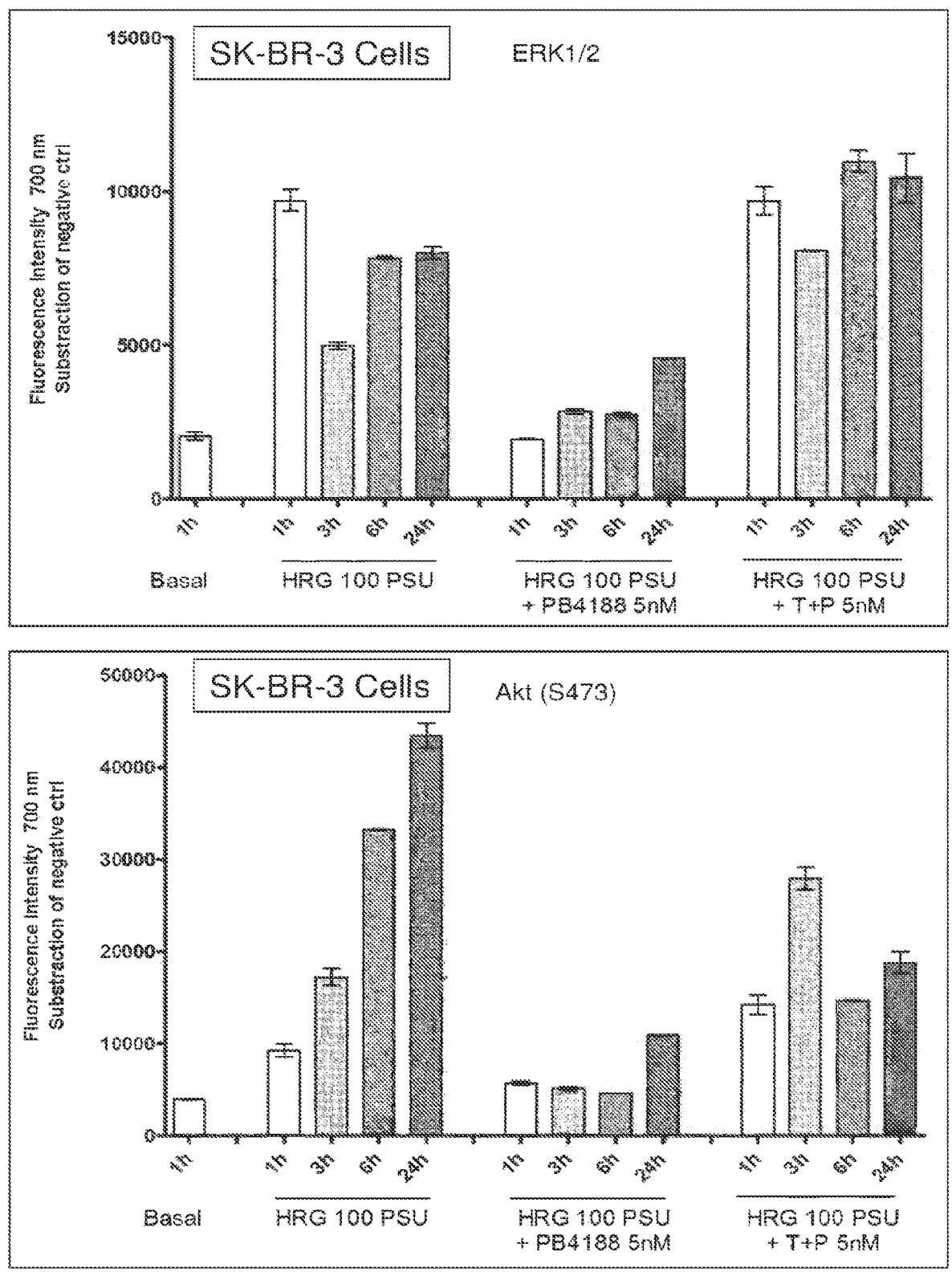
Figure 30B:
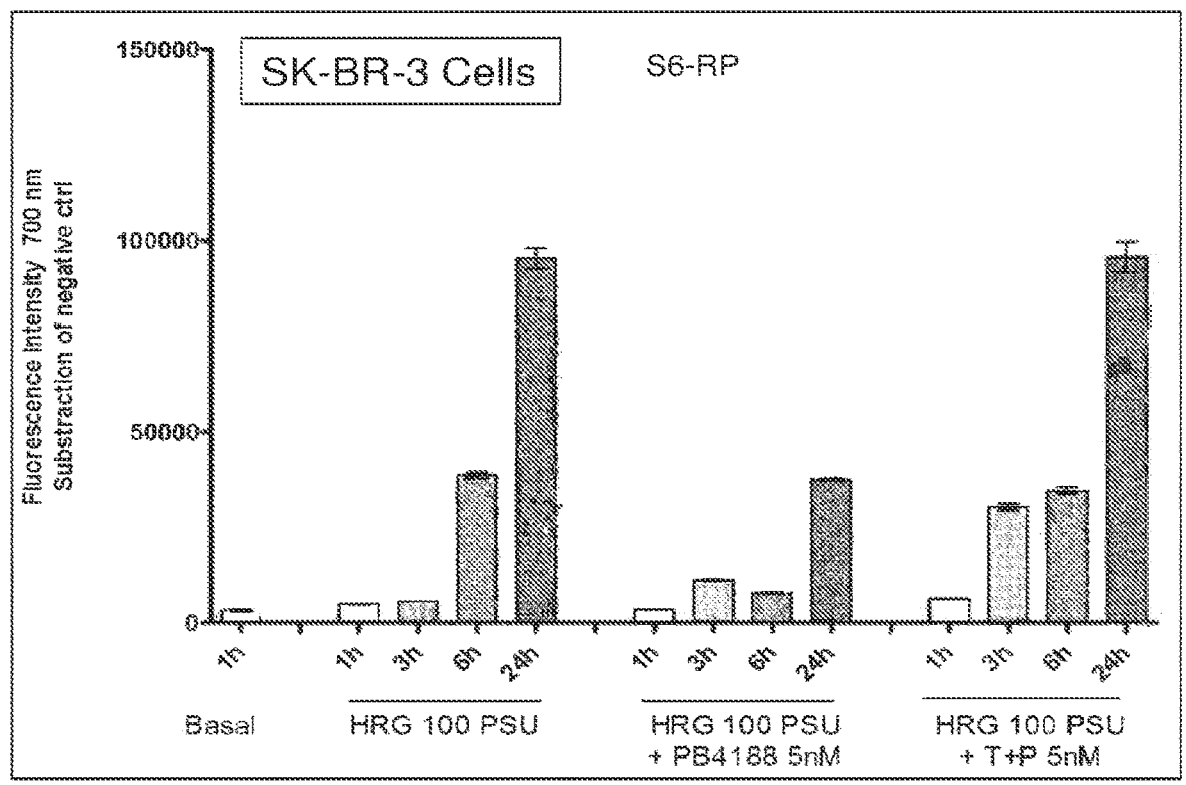

FIG. 29: Synergistic combination of PB4188 with lapatinib on the growth and morphology of SKBR-3 cells. Left, microscopical views of cells treated under different conditions; right morphological changes plotted graphically in relation to the treatment conditions FIGS. 30A and 30B: Inhibition of HRG mediated phosphorylation of N87 and SKBR-3 cells by PB4188 in a time course experiment. Trastuzumab+Pertuzumab and HRG alone were included as controls.

Figure 31:
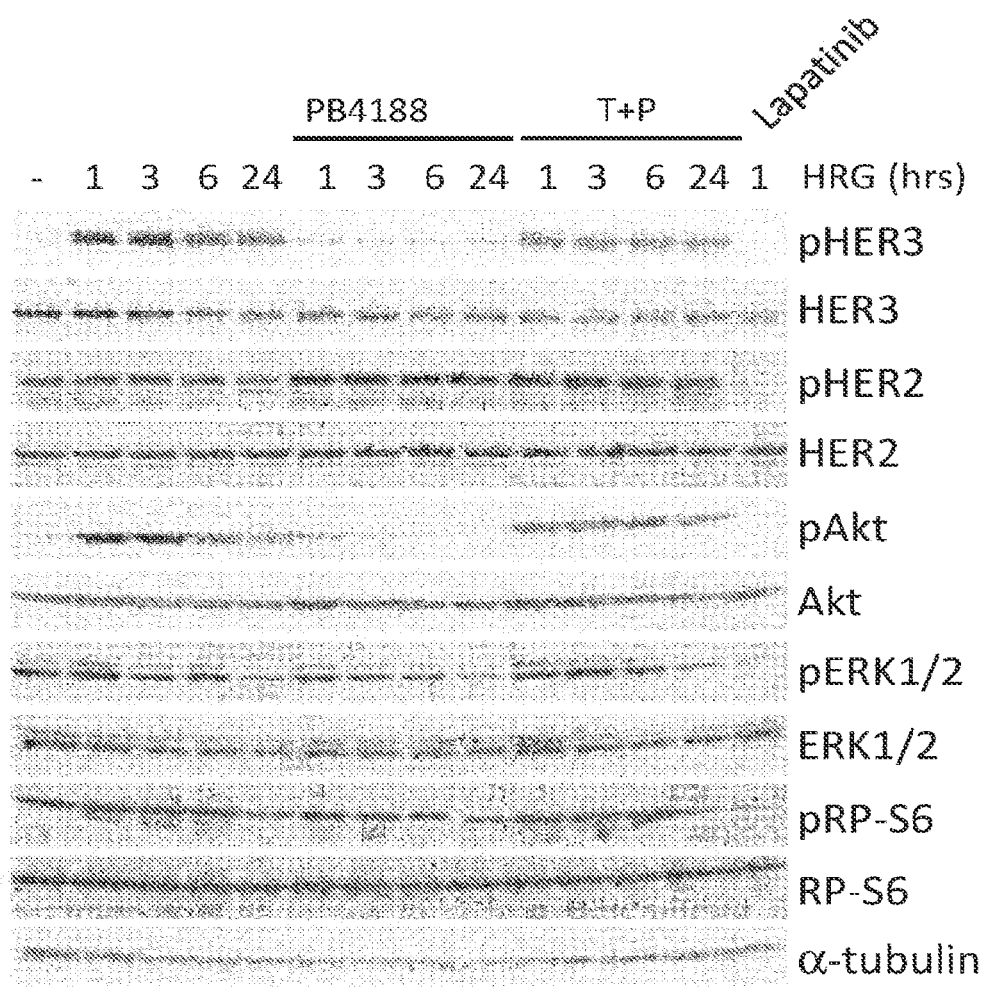

FIG. 31: Inhibition of HRG mediated phosphorylation of N87 cells by PB4188 in a time course experiment. Trastuzumab+Pertuzumab and lapatinib were included as controls.

Figure 32:
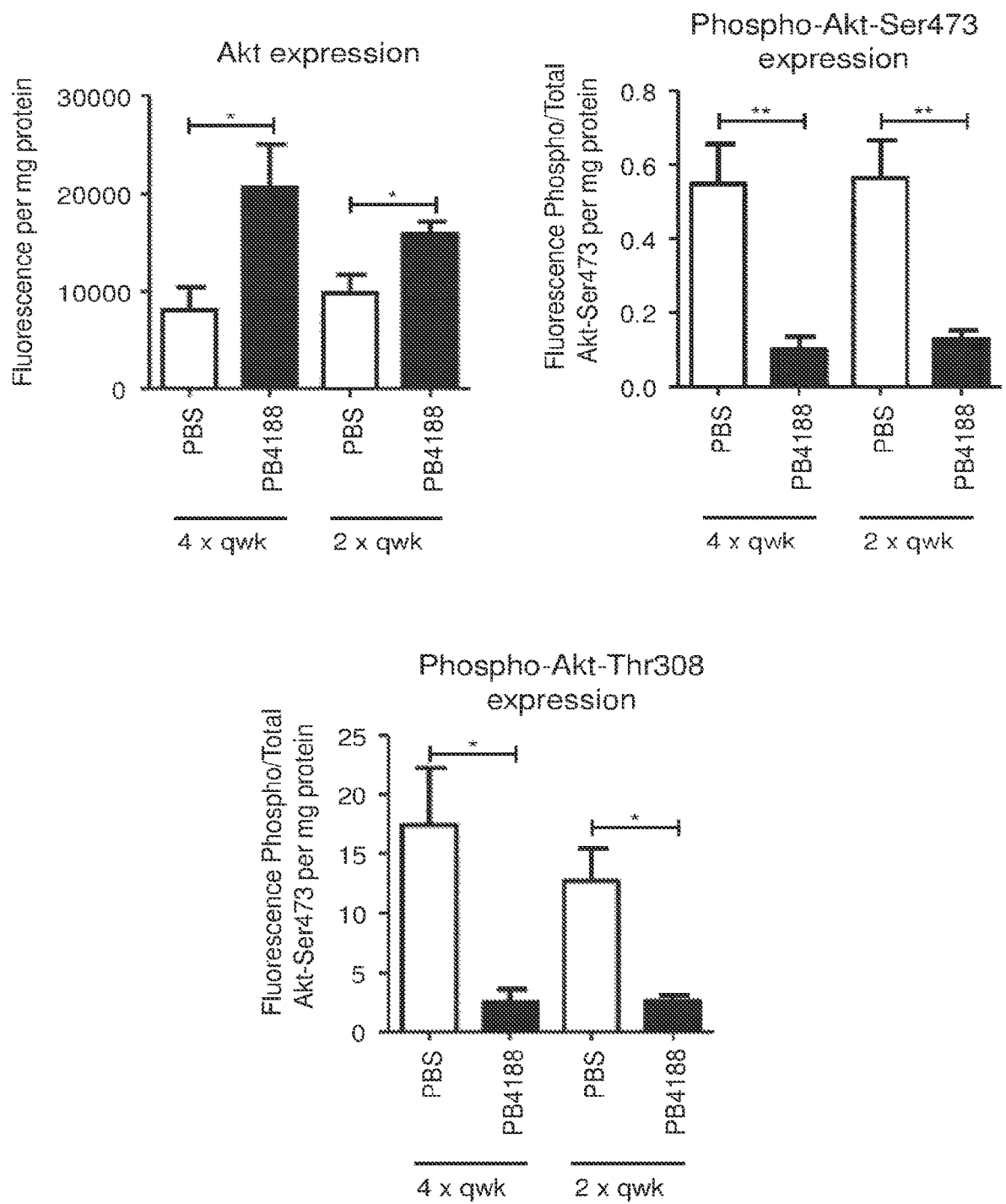

FIG. 32: Changes in Akt levels and Akt phosphorylation were assessed 4 H after a two weekly of four weekly dose of PB4188. Phosphorylation levels in tumor lysates were assessed by Luminex assays. Analysis were performed in duplicate and five tumors were analyzed per group.

Figure 33:
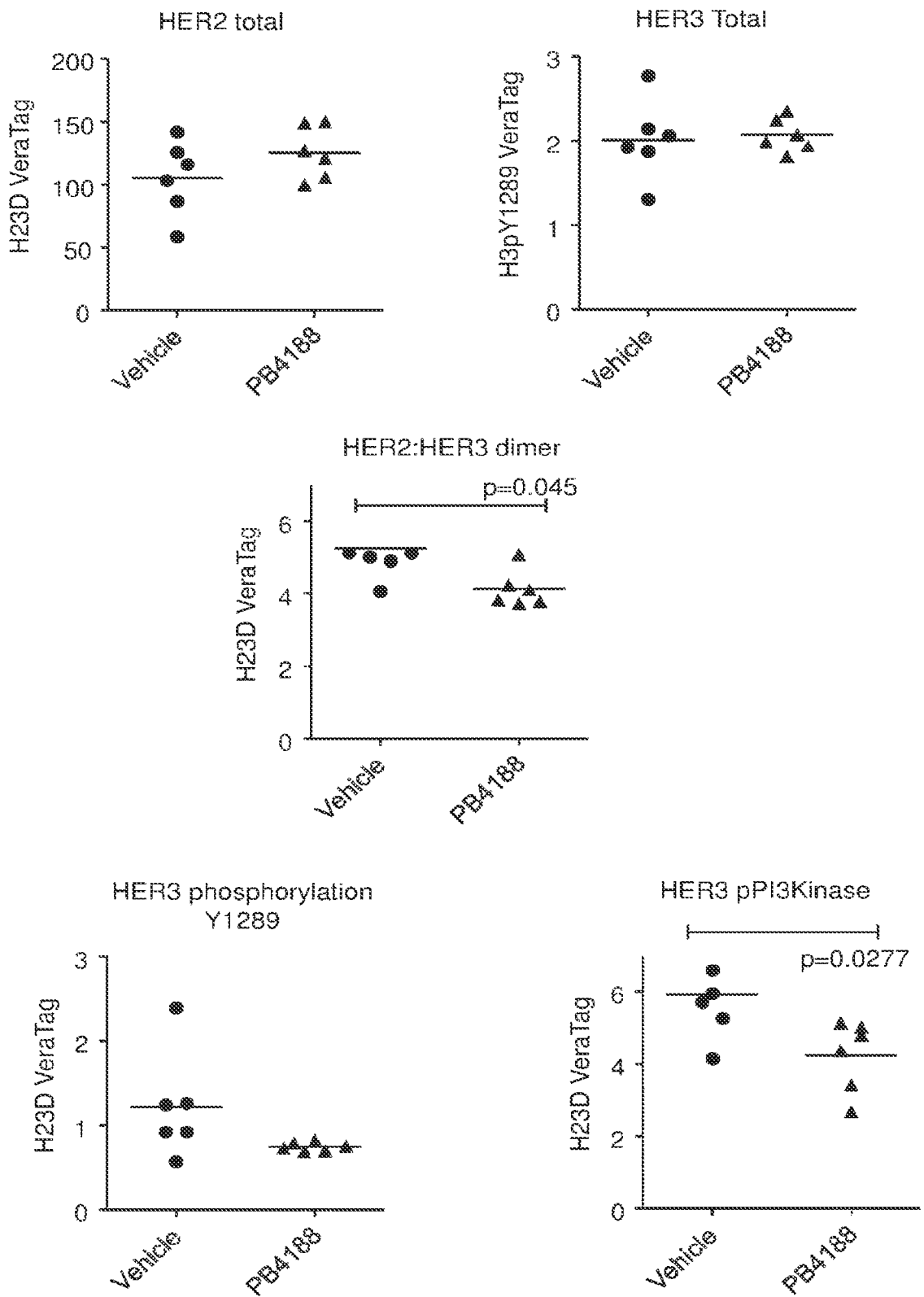

FIG. 33: In vivo mediated effect of PB4188 on HER2: HER3 mediated signaling as analyzed by Vera Tag analysis on JIMT-1 tumor material. Tumors were analyzed 4H after dosing, tumors derived from PBS treated animals were included as controls.

Figure 34A:
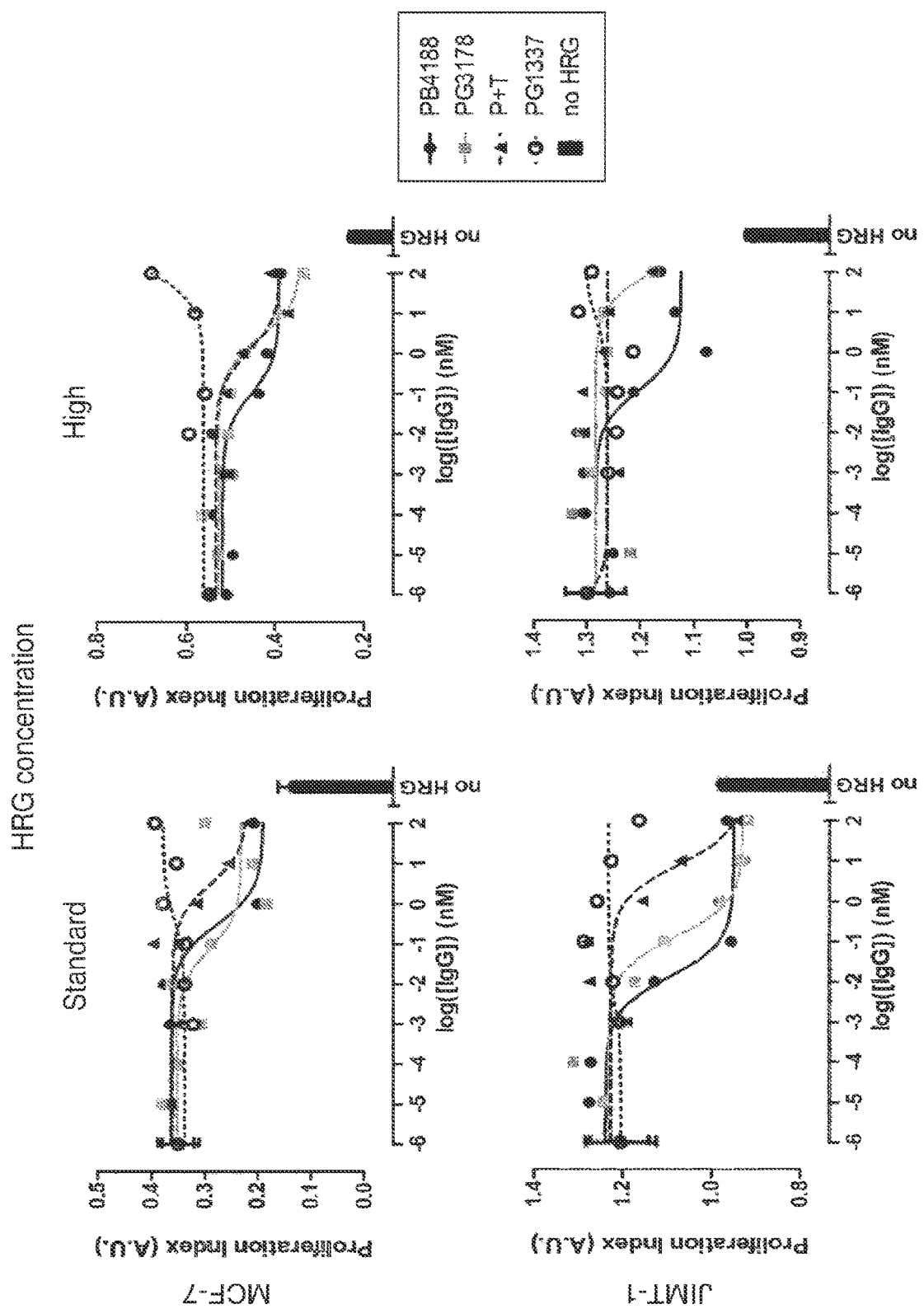
Figure 34B:
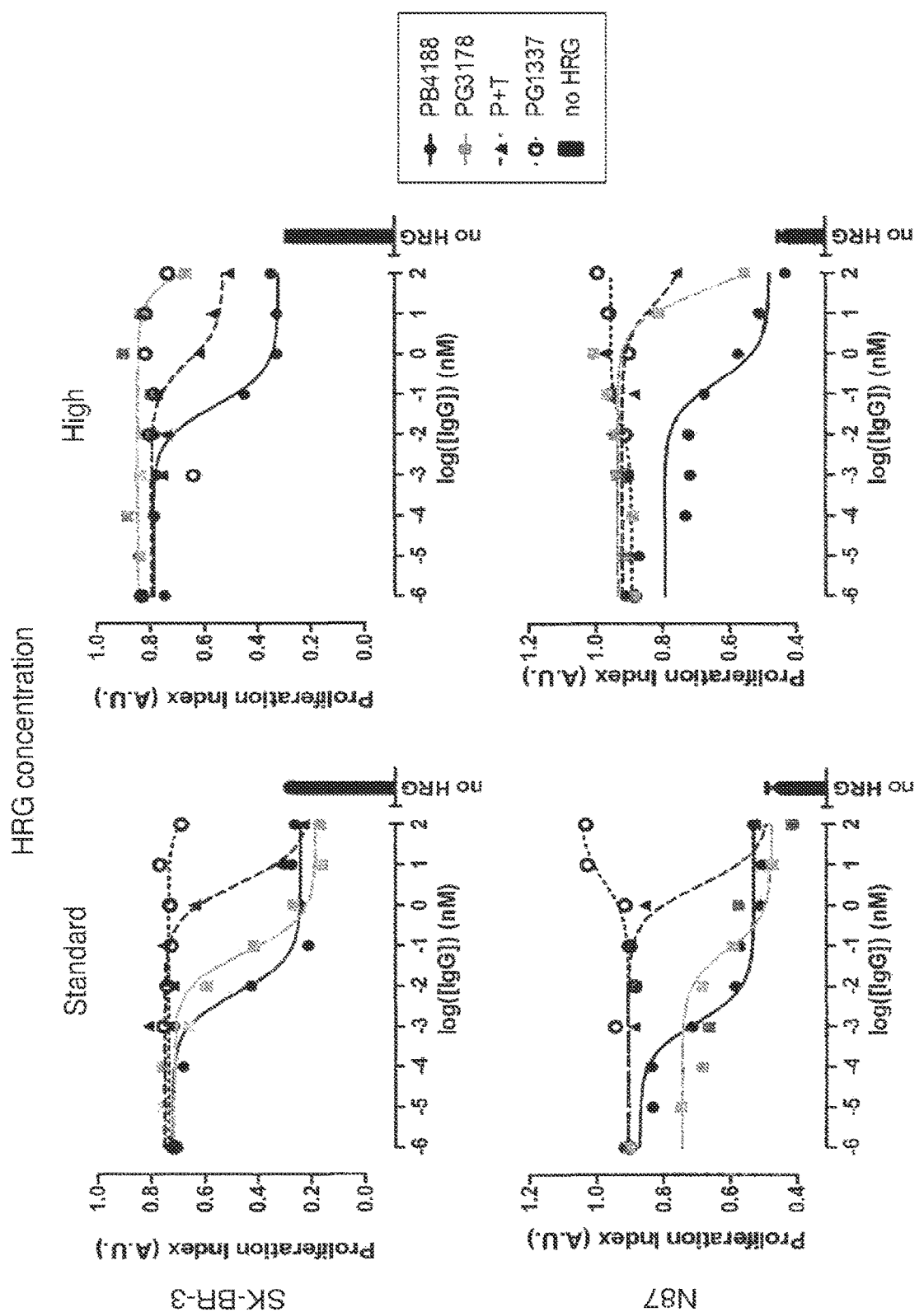
Figure 35A:
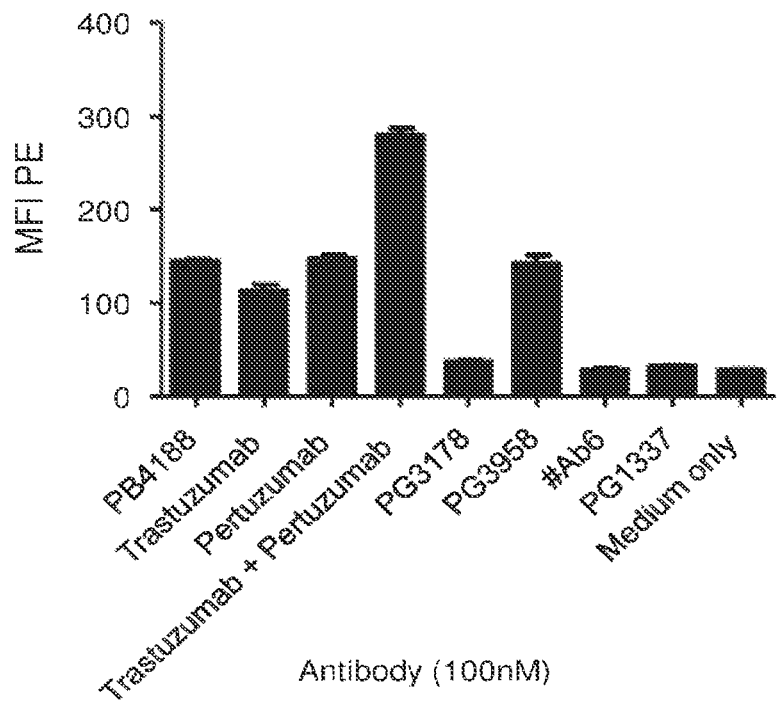
Figure 35B:
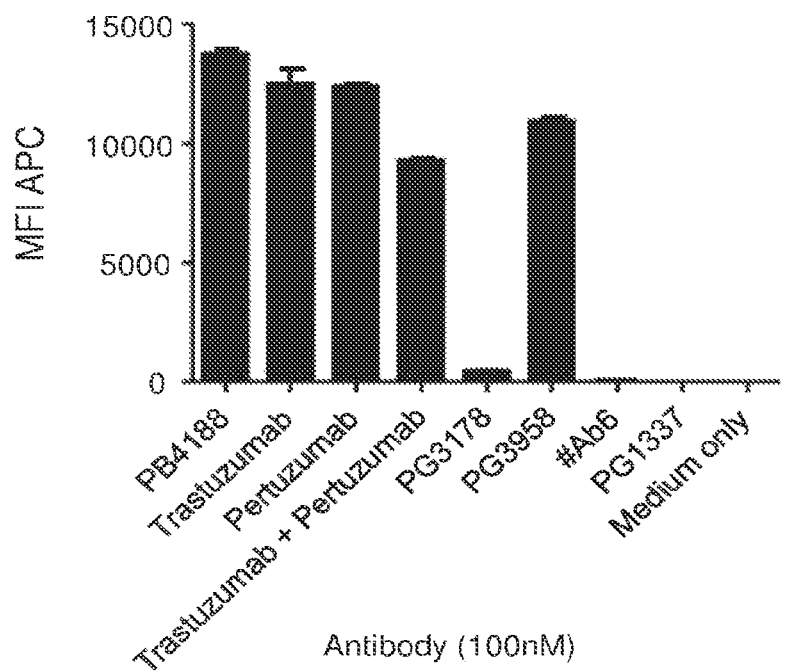
Figure 35C:
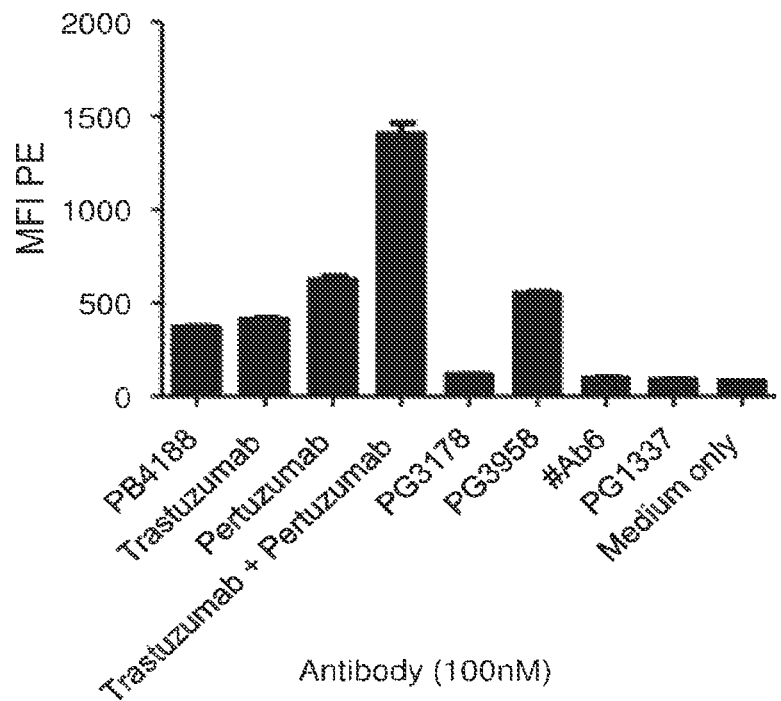
Figure 35D:
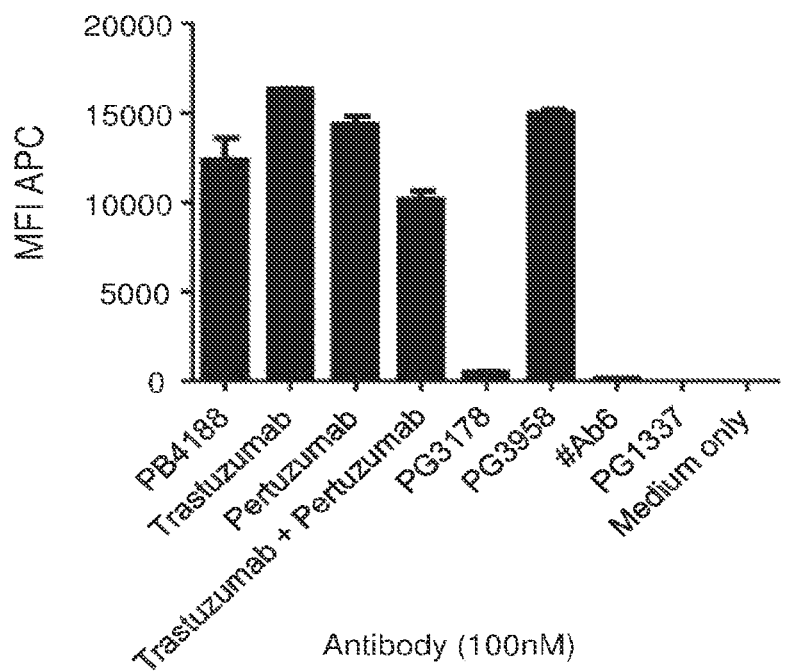

FIGS. 34A and 34B: PB4188 reduces cell cycle progression. Cell seeded in assay medium were incubated with titration of antibodies in the presence of a standard (1 ng/ml) or high (100 ng/ml) concentration of HRG. 24 hrs later (or 48 hrs for MCF-7 cells), cells were analyzed for their distribution in the different phases of the cell cycle (G0/G1, S or G2/M phases). Proliferation index was calculated as the ratio between the percentage of cells in the S and G2/M phases and the percentage of cells in the G0/G1 phase. P+T, pertuzumab+trastruzumab.

FIG. 35A-35D: Internalization of antibodies labelled with pH-sensitive dye in HER2-overexpressing cancer cells. N87 (35A, 35B) and SKBR-3 (35C, 35D) seeded in assay medium supplemented with 1 ng/ml HRG were incubated for 24 hrs with 100 nM pH-sensitive dye-labelled antibodies. After harvesting, cells were stained with APC-labelled anti-human IgG secondary antibody to detect cell surface-bound antibodies. Cells were analyzed by FACS for fluorescence in the PE (35A, 35C) to determine internalization and APC (35B, 35D) channels to determine surface binding of the antibodies.

Figure 36:
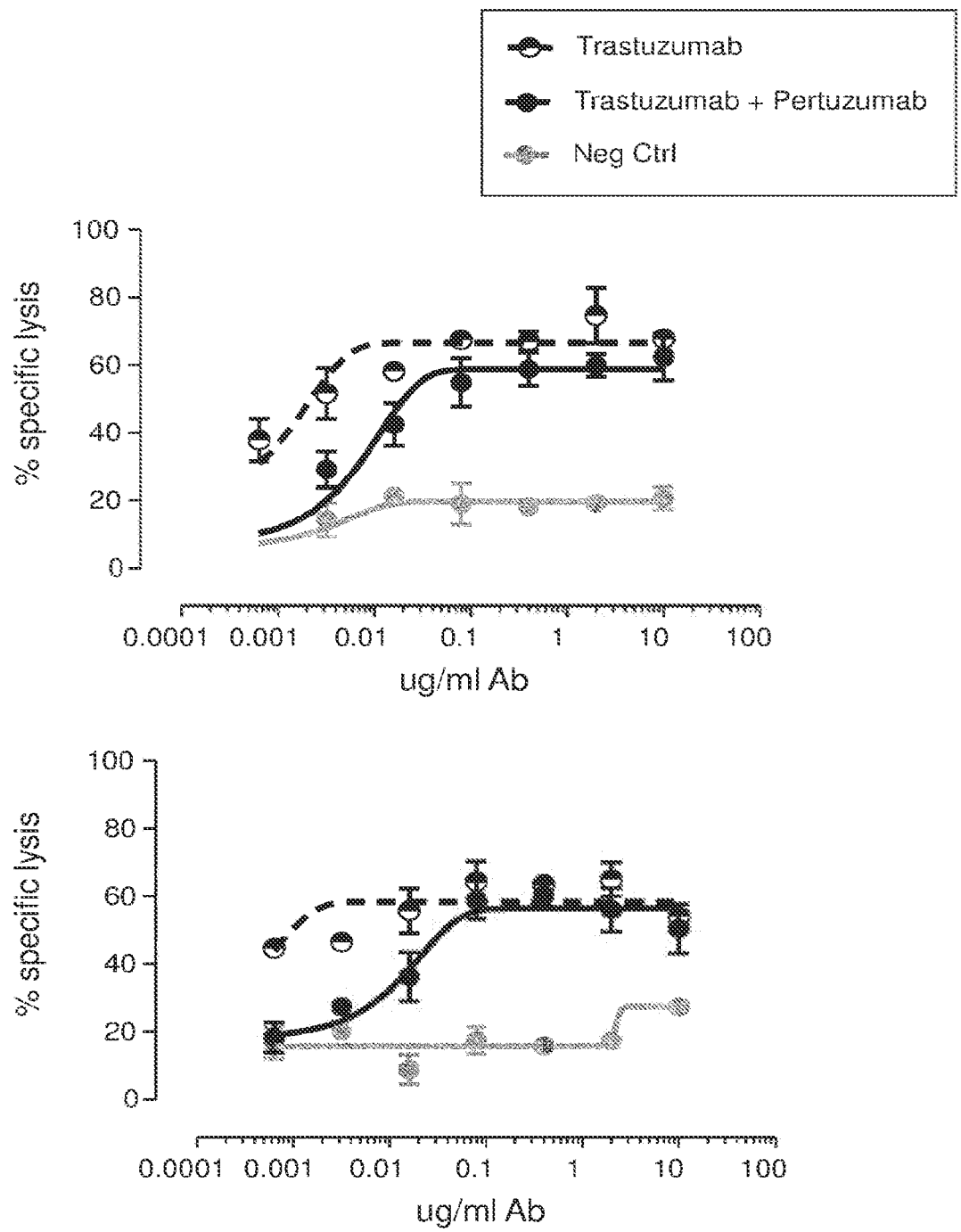

FIG. 36: ADCC activity of Trastuzumab versus Trastuzumab+Pertuzumab with cells derived from two different donors.

FIG. 37A-37G: Amino acid and nucleotide alignments of the F3178 variants. CDR regions are indicated.

Figure 38:
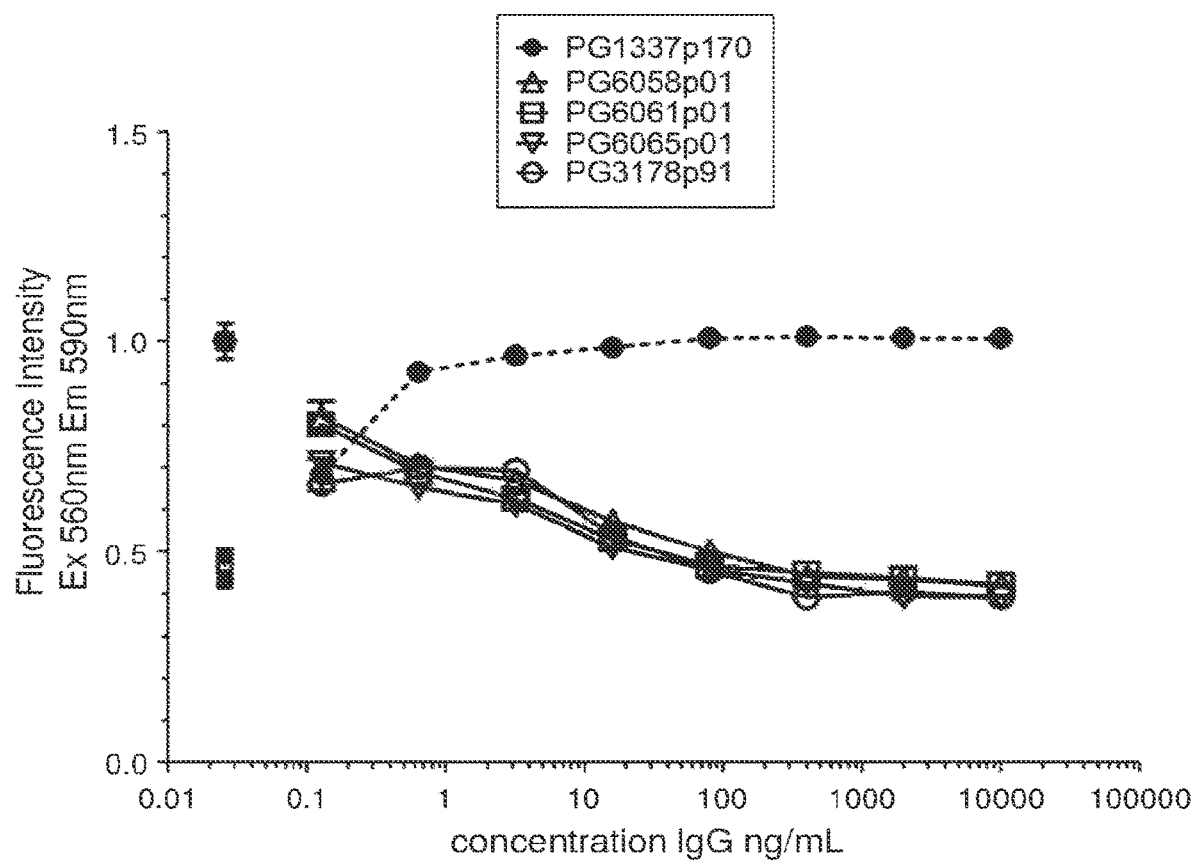

FIG. 38: Titration curves of HER3 monoclonal antibodies in the HRG dependent N87 assay. PG6058, PG6061 and PG6065 are variants of PG3178. PG1337 is a negative control specific for tetanus toxoid. Data were normalized to basal proliferation with ligand present on each plate.

Figure 39A:
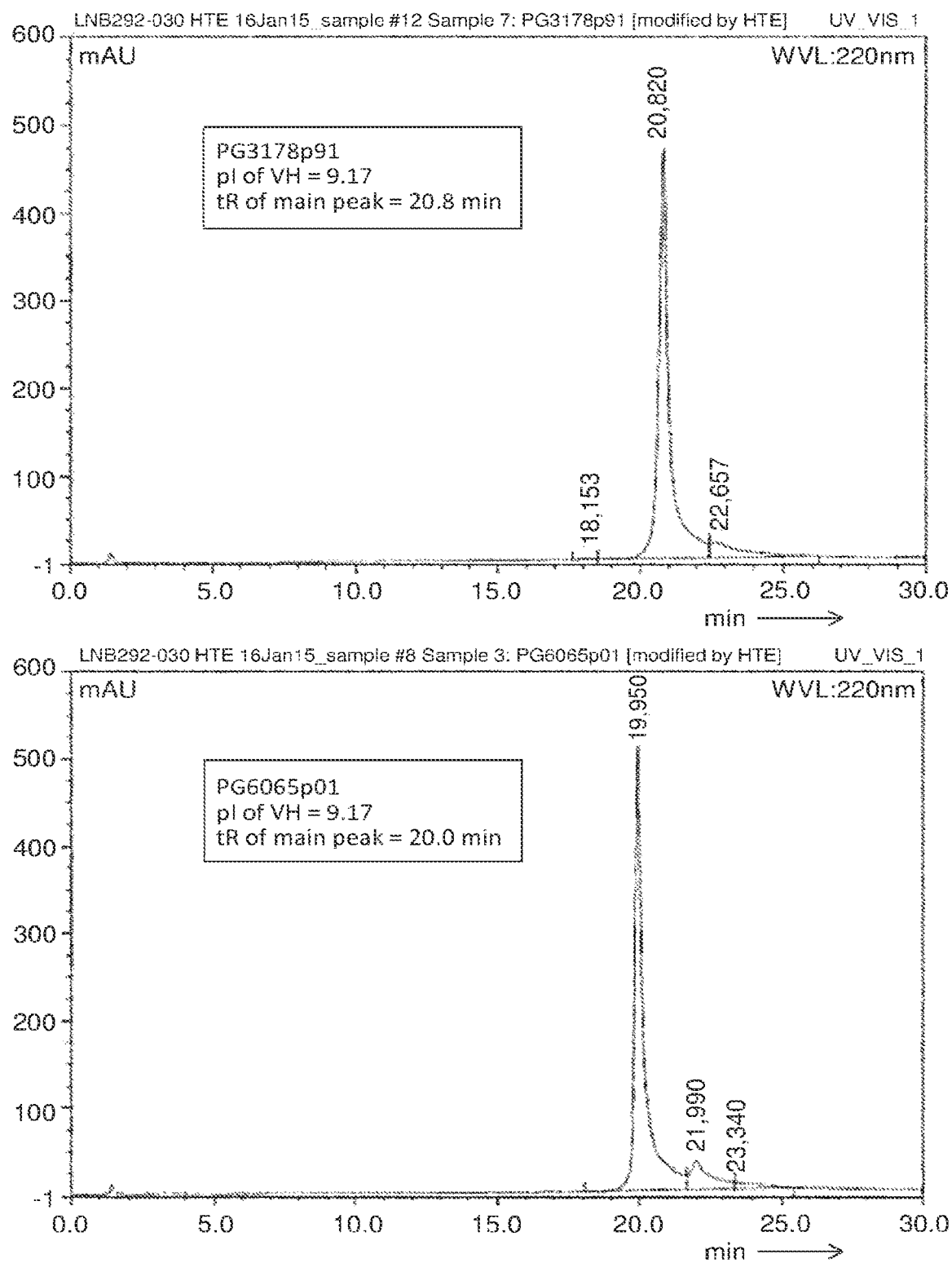
Figure 39B:
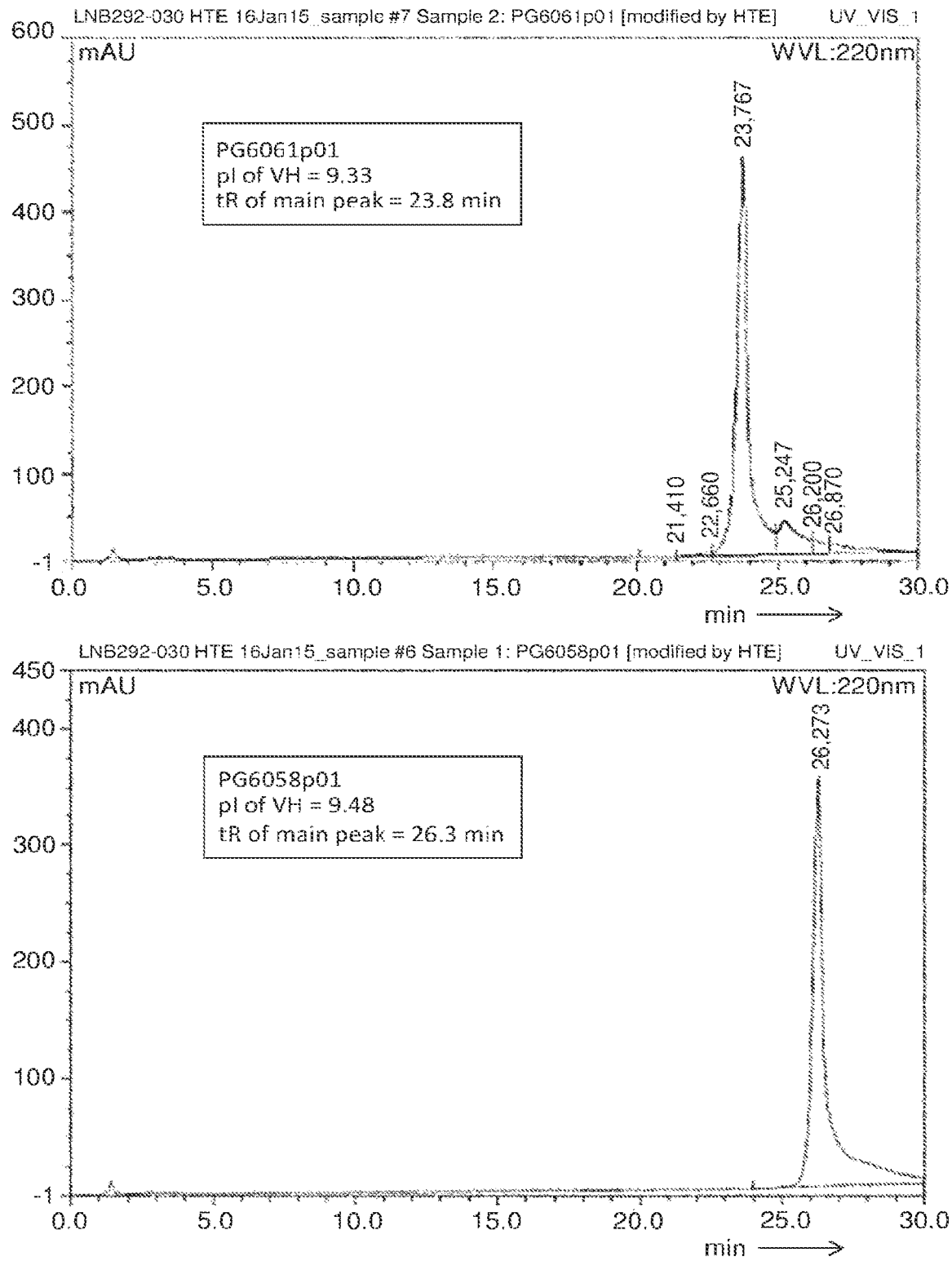

FIGS. 39A and 39B: CIEX-HPLC profiles of HER3 monoclonal antibodies. PG6058, PG6061 and PG6065 are variants of PG3178. The calculated iso-electric point (pI) of the VH region and the retention time (tR) of the main peak are given for each antibody.

Figure 40A:
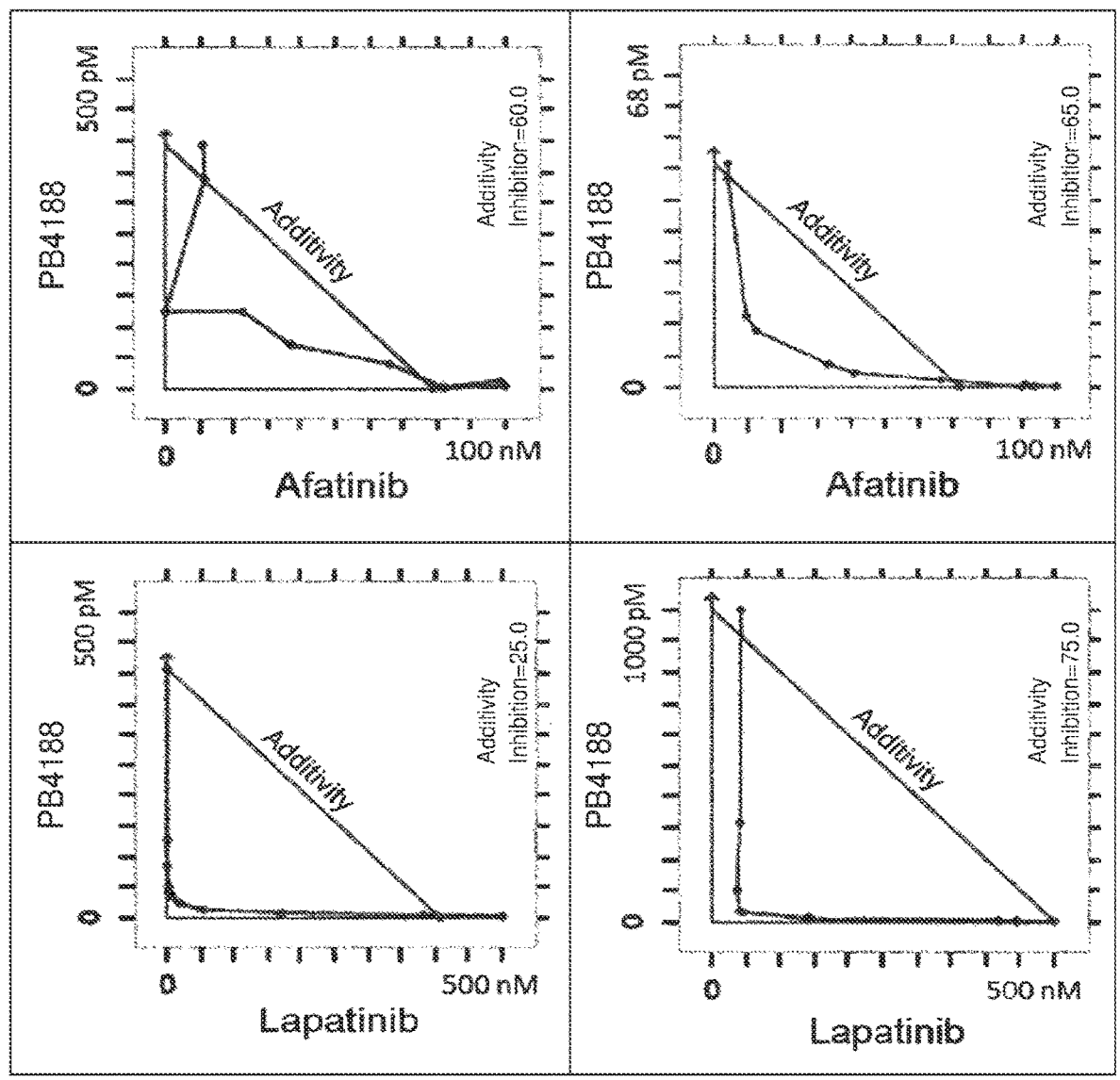
Figure 40A:
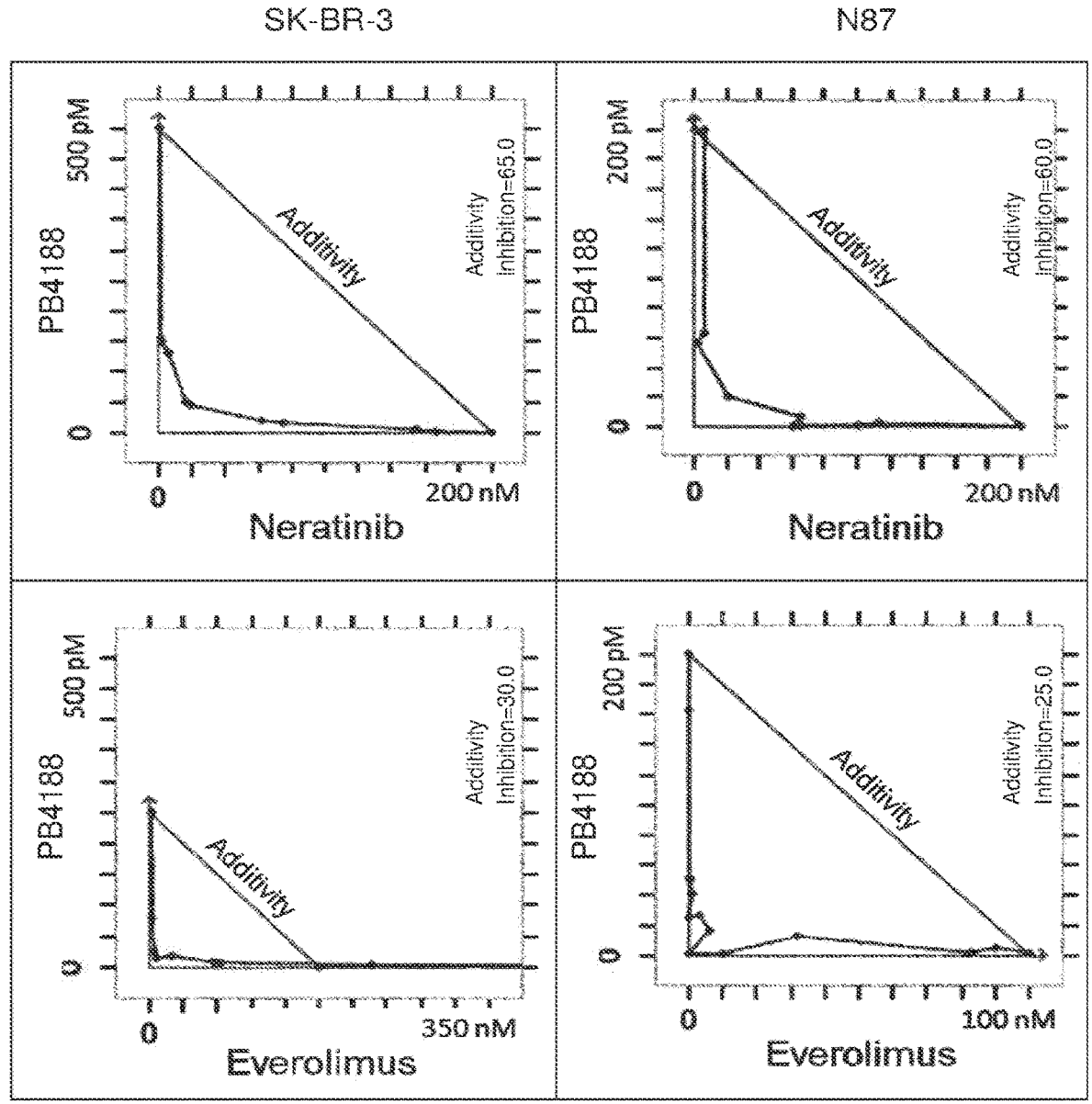
Figure 40A:
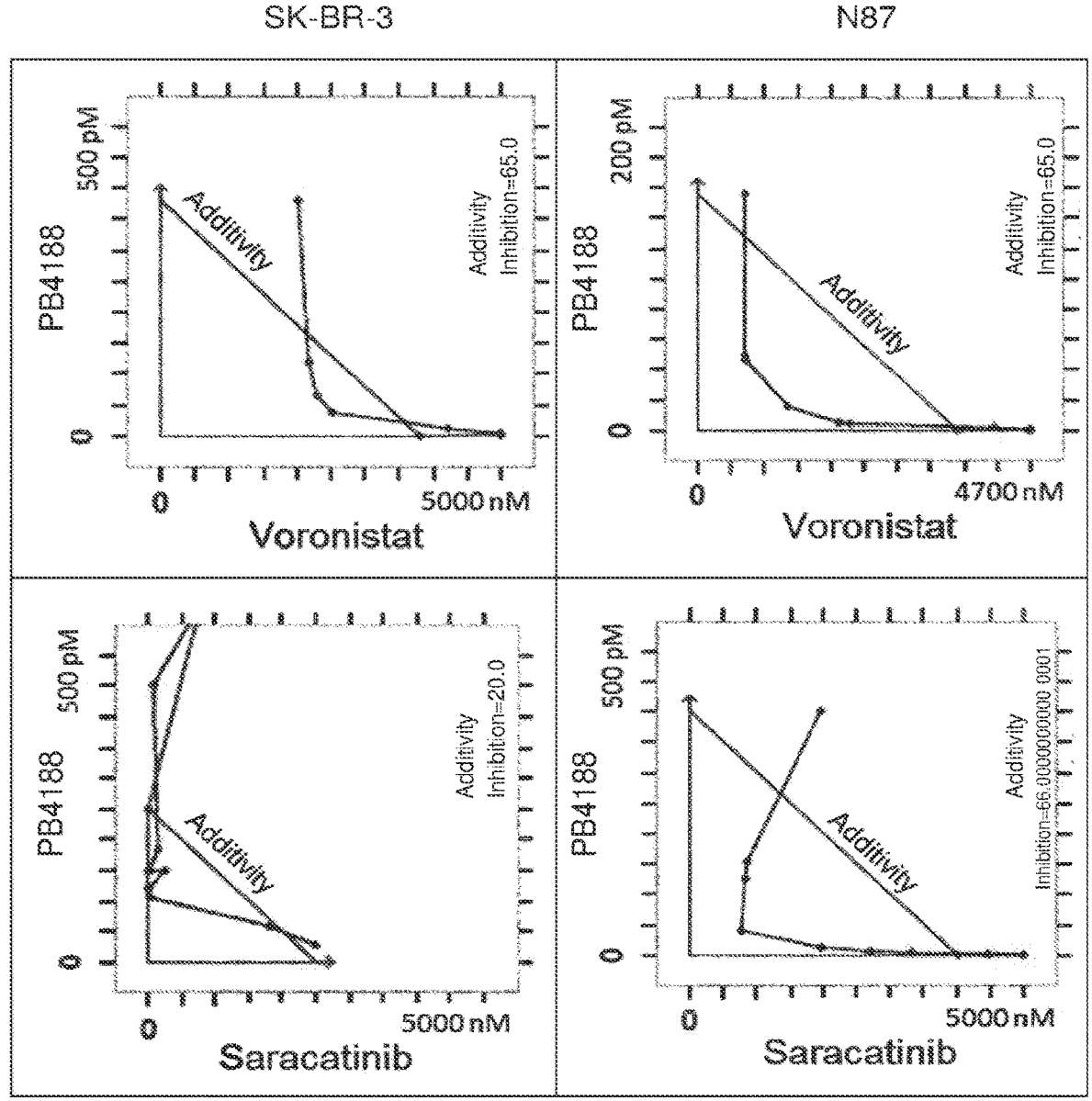
Figure 40A:
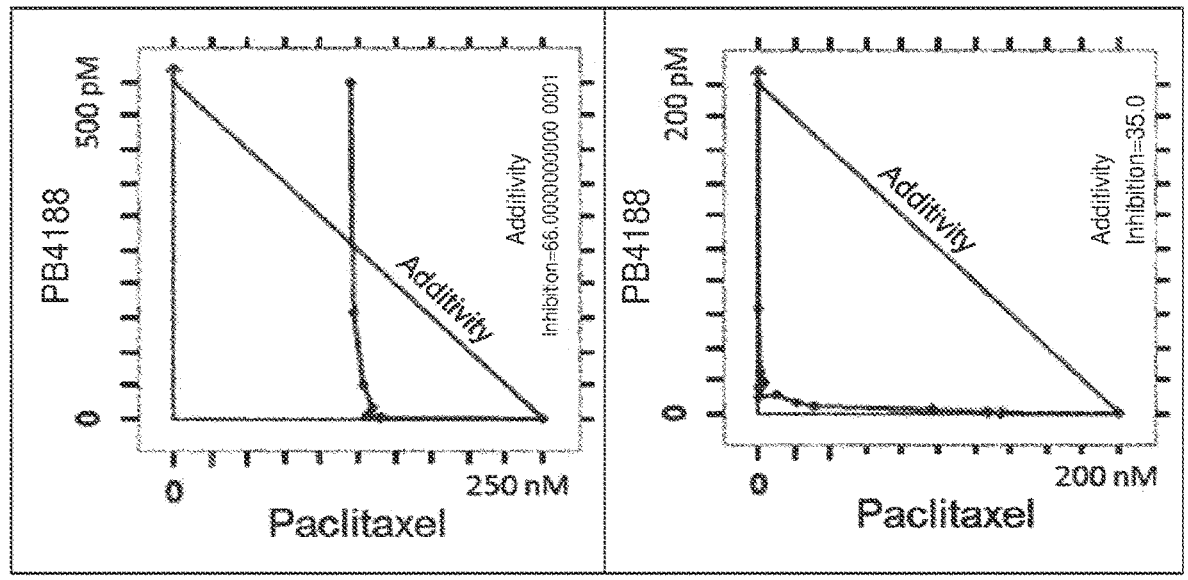
Figure 40B:
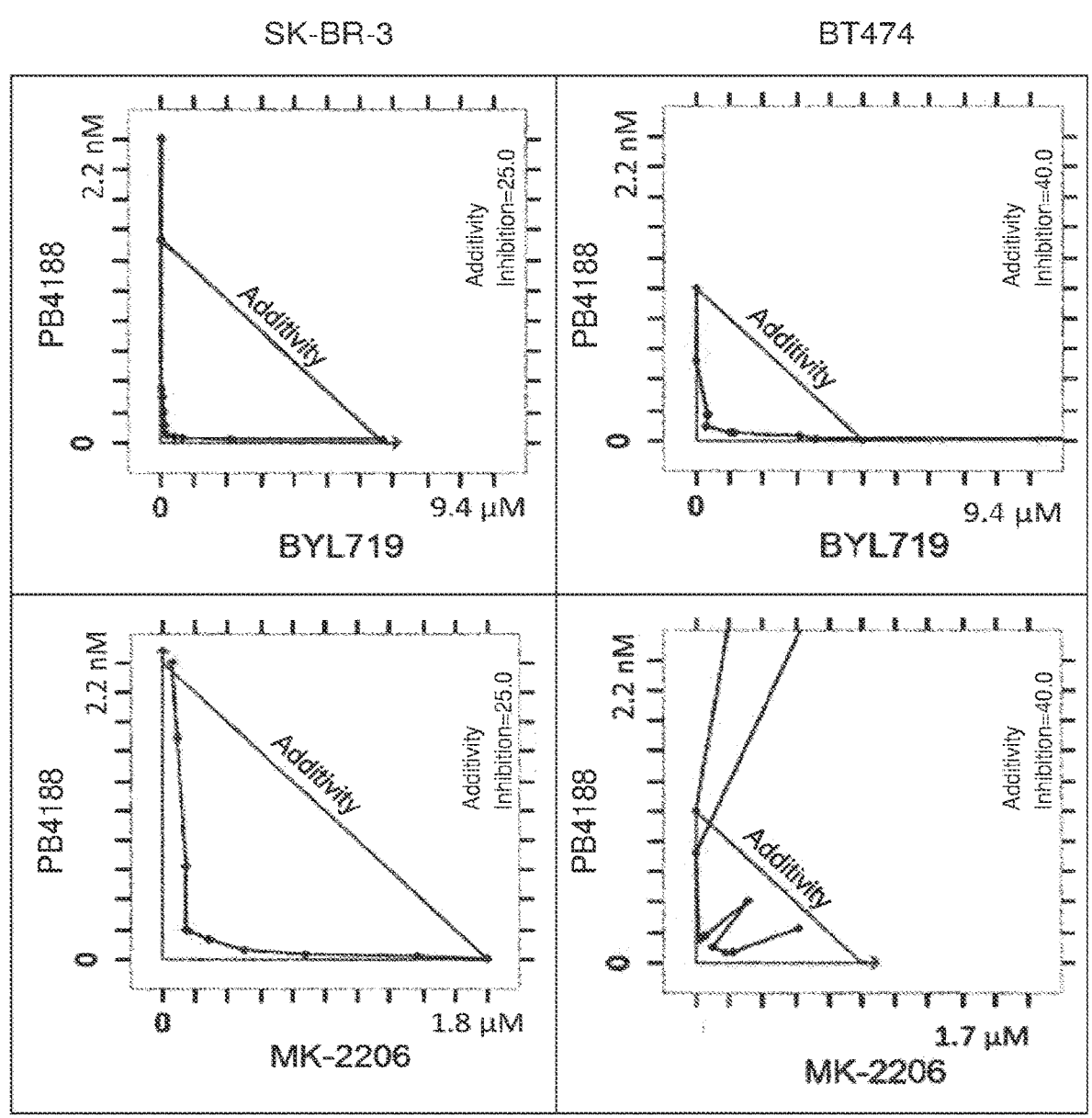

FIGS. 40A and 40B: In vitro drug combination isobolograms with PB4188 on HER2 amplified cell lines at HRG stress concentrations (40A) or grown in MATRIGEL® (40B).

EXAMPLES

Methods, Materials and Screening for Antibodies
Cell Lines:

BxPC-3-luc2 (Perkin Elmer 125058), N87 (ATCC® CRL-5822™), SK-BR-3 (ATCC® HTB-30™), BT-474 (ATCC® HTB-20™), JIMT-1 (DSMZ ACC 589), L929 (Sigma Aldrich 85011425), K562 (DSMZ ACC10), HEK293T (ATCC®-CRL-11268™) CHO-K1 (DSMZ ACC110), MCF-7 (DSMZ ACC 115), MDA-MB-468 (#300279-513, Cell line services) SK-OV-3 (ATCC® HTB-77™), MDA-MB-175 (ATCC-HTB-25), MDA-MB-453 (ATCC-HTB-131), MDA-MB-361 (ATCC-HTB-27), ZR-75-1 (ATCC-CRL-1500) and MKN-45 (DSMZ ACC409) cell lines were purchased from ATCC, DSMZ or Sigma Aldrich and routinely maintained in growth media supplemented with 10% heat inactivated fetal bovine serum (FBS). HEK293F Freestyle cells were obtained from INVITROGEN® and routinely maintained in 293 FreeStyle medium.

Generation of Recombinant Human, Chicken, Rat and Swapped Domain Vectors (Cloning of HER)

Human HER2. Full length Human HER2 was amplified by PCR from cDNA derived from RNA isolated from the breast cancer cell line JIMT-1. The primers used for the amplification of human HER2 were as follows. Forward primer:

(SEQ ID NO: 1)
AAGCTGGCTAGCACCATGGAGCTGGCGGCCTTGTGC.

Reversed primer: AATAATTCTAGACTGGCACGTCCAGACCCAGG (SEQ ID NO: 2). The full-length amplified product was digested with NheI and XbaI and subsequently cloned in the corresponding sites of pcDNA3.1 (INVITROGEN®). The sequence was verified by comparison with the NCBI Reference Sequence NM_004448.2. To generate constructs solely expressing the human HER2 extracellular domain (ECD) for transfection and immunization purposes the HER2 transmembrane domain and ECD were PCR amplified and recloned in pVax1. For transfection purposes another construct was generated in pDisplay by amplifying the HER2 ECD domain, in this construct the HER2 ECD domain is fused to the PDGFR transmembrane domain.

Human HER3. The full length human cDNA clone of HER3 was obtained from Origene. To generate constructs solely expressing the human HER3 ECD for transfection and immunization purposes the HER3 transmembrane domain and ECD were PCR amplified and recloned in pVax1. In addition another construct was generated in pVax1 whereby the HER3 ECD domain was fused to the PDGFR transmembrane domain. All sequences were verified by comparison with the NCBI Reference NM_001982.3

Cynomolgus HER2 extracellular domain was PCR amplified from cynomolgus cDNA—Monkey) Normal Colon Tissue (Biochain). The primers used for the amplification of cynomolgus HER2 were as follows: Forward primer: AAGCTGGCTAGCACCATG-GAGCTGGCGGCCTGGTAC (SEQ ID NO: 3). Reversed primer: AATAATTCTAGACTGGCACGTCCAGACCCAGG (SEQ ID NO: 4). The full-length amplified product was digested with NheI-XbaI and subsequently cloned in the corresponding sites of pcDNA3.1. The clone was sequenced and aligned with sequences available of rhesus monkeys (XM_002800451) to check correctness of the ErbB-2 clone.

Cynomolgus HER3 extracellular domain was PCR amplified from cynomolgus cDNA—Monkey) Normal Colon Tissue (Biochain). The primers used for the amplification of cynomolgus HER3 were as follows: Forward primer: AAGCTGGCTAGCACCAT-GAGGGCGAACGGCGCTCTG (SEQ ID NO: 5), Reversed primer: AATAATTCTAGAT-TACGTTCTCTGGGCATTAGC (SEQ ID NO: 6). The full-length amplified product was digested with NheI-XbaI and subsequently cloned in the corresponding sites of pcDNA3.1. The clone was sequenced and aligned with sequences available of rhesus monkeys (ENSM-MUP00000027321) to check correctness of the HER3 clone.

The chicken HER2 sequence was based on the reference sequence NM_001044661.1. Chimeric swapped domain constructs were generated by swapping domains I until IV of the chicken HER2 sequence for the human I domains I until IV. Sequences containing a myc tag were optimized for expression in mammalian cells and synthesized at Geneart.

The rat HER3sequence was based on the reference sequence NM_001044661.1. Chimeric swapped domain constructs were generated by swapping domains I until IV of the rat HER3 sequence for the human I domains I until IV. Sequences containing a myc tag were optimized for expression in mammalian cells and synthesized at Geneart.

Generation of HER2 and HER3 Over-Expressing Cell Lines

To generate cell lines that express high levels of HER3 on the cell surface a mammalian expression vector was generated by excising the full length HER3 by a NotI and KpnI digestion. Subsequently the fragment was cloned in the corresponding sites of the pcDNA3.1(−)/hygro vector. A full length HER2 and HER3 expression vector encoding a neomycin resistance gene was used to generate cell lines that express high levels of HER2 on the cell surface. Prior to transfection the plasmids were linearized by a SSpI and FspI digestion. Both vectors were transfected separately into K562 cells and stable pools were generated following antibiotic selection. The resultant cell lines (K562-HER2 and K562-HER3) expressed high levels of HER2 and HER3 on their cell surface.

Immunizations

HER2immunizations. Four different immunization strategies were applied. For cohort #A, six C57Bl/6 mice were immunized with $2 \times 10^6$ L929 cells transiently transfected with HER2 in 200 µl via intraperitoneal injection. Subsequently, mice were boosted with 20 µg Erbb-2-Fc (RND systems) protein dissolved in 125 µl TITERMAX™ Gold via intraperitoneal injection on day 14, followed by boosts with $2 \times 10^6$ L929 cells transiently transfected with HER2 in 200 µl on days 28 and 42. For cohort #C, six C57Bl/6 mice were immunized with $2 \times 10^6$ L929 cells transiently transfected with HER2 via intraperitoneal injection. Subsequently, mice were boosted with $2 \times 10^6$ L929 cells transiently transfected with HER2 in 200 µl via intraperitoneal injection on day 14, followed by a protein boosts with 20 µg Erbb-2-Fc protein dissolved in 125 µl TITERMAX™ Gold via intraperitoneal injection on day 35 and a final boost with 20 µg Erbb-2-Fc protein dissolved in 200 µl PBS via intraperitoneal injection on day 49. For cohort #E, six C57Bl/6 mice were immunized with 20 µg Erbb-2-Fc protein dissolved in 125 µl TITERMAX™ Gold via intraperitoneal injection. Subsequently, protein boosts with 20 µg Erbb-2-Fc protein dissolved in 125 µl TITERMAX™ Gold via intraperitoneal injection were made at day 14 and 28 and a final boost with 20 µg Erbb-2-Fc protein dissolved in 200 µl PBS via intraperitoneal injection on day 42. For cohort #G, six C57Bl/6 mice were immunized by DNA vaccination at Genovac (Freiburg, Germany) according to their protocols. The endotoxin-free provided vectors used for the DNA vaccination encoded the transmembrane and extracellular part of HER2 cloned in pVax1. Subsequently, DNA boosts were given at day 14, 28 and 66.

HER3immunizations. Four different immunization strategies were applied. For cohort #B, six (C57Bl/6) mice were immunized with $2 \times 10^6$ L929 cells transiently transfected with HER3 in 200 µl via intraperitoneal injection. Subsequently, mice were boosted with $2 \times 10^6$ L929 cells transiently transfected with HER3 in 200 µl on days 14, 28, 49 and 63. For cohort #D, six C57Bl/6 mice were immunized with $2 \times 10^6$ L929 cells transiently transfected with HER3 via intraperitoneal injection on day 0, 14 and 28. Subsequently, mice were boosted with 20 µg Erbb-3-Fc protein dissolved in 125 µl TITERMAX™ Gold via intraperitoneal injection on day 49 and a final boost with 20 µg Erbb-3-Fc protein dissolved in 200 µl PBS via intraperitoneal injection on day 66. For cohort #F, six C57Bl/6 mice were immunized with 20 µg Erbb-3-Fc protein dissolved in 125 µl TITERMAX™ Gold via intraperitoneal injection. Subsequently, mice were boosted with 20 µg Erbb-3-Fc protein dissolved in 125 µl TITERMAX™ Gold via intraperitoneal injection at day 14 and 28 and a final boost was given with 20 µg Erbb-3-Fc protein dissolved in 200 µl PBS via intraperitoneal injection on day 42. For cohort #H, six C57Bl/6 mice were immunized by DNA vaccination at Genovac (Freiburg, Germany) according to their protocols. The endotoxin-free provided vectors used for the DNA vaccination encoded the transmembrane of PDGFR and extracellular part of HER3 cloned in pVax1. Subsequently, DNA boosts were given at day 14, 28 and 66.

Determination of Antibody Titers.

Anti-HER2 titers in the serum from immunized C57Bl/6 mice were determined by ELISA against ECD-Erbb-2 protein (Bendermedsystems) and FACS analysis on the HER2 negative K562, the HER2 low expressing cell line MCF-7 and HER2 amplified SKBR-3 and BT-474 cells. Anti-HER3 titers in the serum from immunized C57Bl/6 mice were determined by ELISA against Erbb-3-Fc protein and FACS analysis on the HER3 negative K562, the HER2 low expressing cell line MCF-7 and HER2 amplified SKBR-3 and BT-474 cells.

Serum titers against HER2 and HER3 before sacrificing the animals are described in Table 1 and Table 2 respectively. Animals in all cohorts developed antibody responses against HER2 or HER3.

Recovery of Lymphoid Tissue.

Spleen and draining lymph nodes were removed from all mice vaccinated with DNA (cohorts #G and #H). Single cell suspensions were generated from all tissues and subsequently tissues were lysed in Trizol reagent. From cohorts #A until #F spleens were removed from all mice except for one mouse of cohort #C that died after the first boost. Single cell suspensions were generated from all spleens and the total B cell fraction was isolated using the MACS separation procedure either by CD19 enrichment (cohorts #A, E, F) or depletion of non-B cells (cohorts #B, C, D).

Generation of Phage Display Libraries from Immunized Mice

One phage library was built for each mouse. To this end the material from all mice per group (5 or 6 mice per group) was used to prepare phage libraries using the following approach. From each individual mouse RNA was isolated and cDNA was synthesized and VH-family specific PCRs were performed. Subsequently all VH-family PCR products per mouse were purified and the DNA concentration was determined and digested and ligated in a phage-display vector containing the common-light chain to generate a mouse-human chimeric phage library. All phage libraries contained >$10^6$ clones with an insert frequency of >85%.

Selection of Phages Carrying Fab Fragments Specifically Binding to HER2 and HER3

Antibody fragments were selected using antibody phage display libraries. Immunized libraries and synthetic libraries (as described in de Kruif et al. Mol. Biol. (1995), 248, 97-105) were used for selections.

HER2 Phage Selection and Screening

Phage libraries were rescued with VCS-M13 helper phage (Stratagene) and selected for two rounds in immunotubes (Nunc) coated recombinant protein. In the first round ECD-Erbb-2 protein (Bendermedsystems) was coated onto immunotubes whereas in the second round Erbb-2-Fc (RND systems) was coated onto immunotubes. The immunotubes were blocked with 4% non fat dry milk (ELK). Phage antibody libraries were also blocked with 4% ELK prior to the addition of the phage library to the immunotubes. Incubation with the phage library with the coated protein in the immune tubes was performed for 2 H at room temperature under rotating conditions. Immunotubes were then washed five to ten times with 0.05% Tween-20 in PBS followed by 5 to 10 times in PBS. Bound phages were eluted using 50 mM glycine (pH 2.2) and added to E. coli XL-1 Blue and incubated at 37° C. for phage infection. Subsequently infected bacteria were plated on agar plates containing Ampicillin, tetracyclin and glucose and incubated at 37° C. overnight. After the first round, colonies were scraped off the plates and combined and thereafter rescued and amplified to prepare an enriched first round library. The enriched library was then selected on Erbb-2-Fc (RND systems) using the protocol described above. After the second round selection individual clones were picked and rescued to prepare a phage monoclonal miniprep. Positive phage clones binding Erbb2 were then identified in FACS for binding to the breast cancer cell line BT-474. The VH genes of all Erbb2 specific clones were sequenced. VH gene rearrangements were established with VBASE2 software to identify unique clones. All unique clones were then tested in phage format for binding in FACS to HEK293T cells (negative control), HEK293T cells transiently transfected with ErbB-2 and BT-474 cells.

HER3 Phage Selection and Screening

Phage libraries were rescued with VCS-M13 helper phage (Stratagene) and selected for two rounds in immunotubes (Nunc) coated with recombinant protein. In both selection rounds round Erbb-3-Fc (RND systems) was coated onto immunotubes. To overcome a selection bias towards the Fc part of the fusion protein, both selection rounds on Erbb-3-Fc were performed in the presence of 150 µg/ml human IgG. The immunotubes were blocked with 4% ELK. Phage antibody libraries were blocked with 4% ELK prior to the addition of the phage library to the immunotubes. Incubation with the phage library was performed for 2 H under rotating conditions. Immunotubes were then washed five to ten times with 0.05% Tween-20 in PBS followed by 5 to 10 times in PBS. Bound phages were eluted using 50 mM glycine (pH 2.2) and added to E. coli XL-1 Blue and incubated for phage infection. Subsequently infected bacteria were plated on agar plates containing Ampicillin, tetracyclin and glucose and incubated at 37° C. overnight. After the first round, colonies were scraped off the plates and combined and phages were rescued and amplified to prepare an enriched first round library. The enriched library was then selected on Erbb-3-Fc (RND systems) using the protocol described above. After the second round selection individual clones were picked and rescued to prepare a phage monoclonal miniprep. Positive phage clones were identified in FACS for binding to the breast cancer cell line BT-474. The VH genes of all positive clones were sequenced. VH gene rearrangements were established with VBASE2 software to identify unique clones. All unique clones were tested in phage format for binding in FACS to K562 cells (negative control), stable K562-HER3 cells and BT-474 cells.

In total 36 selections were performed on Erbb2 and Erbb3 antigen formats. All selection screening procedures resulted in 89 unique Fab clones directed against HER2 and 137 unique Fab clones directed against HER3. A Fab was considered unique based on its unique HCDR3 sequence, an indication of a unique VDJ recombination event. In some cases clonal variants were obtained, with an identical HCDR3 but differences in the CDR1 and/or CDR2. From the immunized mice libraries clusters of clonal variants containing substitutions in the VH gene reflecting affinity variants were selected.

Antibody Selection/Characterization

Generation of Monoclonal Antibodies

VH genes of unique antibodies, as judged by VH gene sequence and some sequence variants thereof, derived from the immunized mouse phage libraries were cloned in the backbone IgG1 vector. Two different production cell lines were used during the process; HEK293T and 293F Freestyle cells. Adherent HEK293T cells were cultivated in 6-well plates to a confluency of 80%. The cells were transiently transfected with the individual DNA-FUGENE mixture and further cultivated. Seven days after transfection, supernatant was harvested and medium was refreshed. Fourteen days after transfection supernatants were combined and filtrated through 0.22 µM (Sartorius). The sterile supernatant was stored at 4° C. Suspension adapted 293F Freestyle cells were cultivated in T125 flasks at a shaker plateau until a density of $3.0 \times 10^6$ cells/ml. Cells were seeded at a density of $0.3$-$0.5 \times 10^6$ viable cells/ml in each well of a 24-deep well plate. The cells were transiently transfected with the individual sterile DNA: PEl mixture and further cultivated. Seven days after transfection, supernatant was harvested and filtrated through 0.22 µM (Sartorius). The sterile supernatant was stored at 4° C.

Generation of Bispecific Antibodies

Bispecific antibodies were generated using the proprietary CH3 technology to ensure efficient hetero-dimerisation and formation of a bispecific antibody. The CH3 technology uses charge-based point mutations in the CH3 region to allow efficient pairing of two different heavy chain molecules as previously described (PCT/NL2013/050294; published as WO 2013/157954 A1).

IgG Purification for Functional Screening

The purification of IgG was performed at small scale (<500 µg), medium scale (<10 mg) and large scale (>10 mg) using affinity chromatography. Small scale purifications were performed under sterile conditions in 24 well filter plates using vacuum filtration. First the pH of the medium was adjusted to pH 8.0 and subsequently the small scale productions were incubated with protein A SEPHAROSE™ CL-4B beads (50% v/v) (Pierce) for 2 H at 25° C. on a shaking platform at 600 rpm (Heidolph plate shaker). Next the beads were harvested by vacuum filtration. Beads were washed twice with PBS pH 7.4. IgG was eluted at pH 3.0 with 0.1 M citrate buffer and the IgG fraction was immediately neutralized by Tris pH 8.0. Buffer exchange was performed by centrifugation using multiscreen ULTRAEL® 10 multiplates MILLIPORE®. The samples ended up in a final buffer of PBS pH 7.4

Validation of HER2/HER3 Specific IgGs

Antibodies were tested for binding in FACS to BT-474, HEK293T and HEK293T overexpressing HER2 or HER3. Therefore cells were harvested using trypsin and diluted to $10^6$ cells/ml in FACS buffer (PBS/0.5% BSA/0.5 mM EDTA). $1$-$2 \times 10^5$ cells were added to each well in a U-bottom 96 well plate. Cells were centrifuged for 2 minutes at 300 g at 4° C. Supernatant was discarded by inverting plate(s). 50 µl of each IgG sample was added at a concentration of 10 µg/ml and incubated for 1H on ice. Cells were centrifuged once, supernatant was removed and cells were washed twice with FACS buffer. 50 µl diluted 1:100 mouse anti human IgG PE (INVITROGEN®) was added and incubated for 30-60 minutes on ice in the dark. After adding FACS buffer, cells were centrifuged once, supernatant was removed and cells were washed twice with FACS buffer. Cells were analysed on a FACSCanto Flow cytometer in a HTS setting. Binding of the antibodies to cells was assessed by mean fluorescence intensity (MFI).

To test for non-specific binding reactivity ELISA assays were used. HER2 and HER3 antibodies were tested for reactivity against the antigens fibrinogen, hemoglobulin and tetanus toxin. To test specific binding to HER2 and HER3, the antibodies were tested for binding to purified recombinant extracellular domains of EGFR, HER2, HER3 and HER4. Antigens were coated overnight to MAXISORP™ ELISA plates. Wells of the ELISA plates were blocked with PBS (pH 7.2) containing 5% BSA for 1 hour at 37° C. Selected antibodies were tested in duplo at a concentration of 10 µg/ml diluted in PBS-2% BSA and allowed to bind for 2 hours at 25° C. As a control the procedure was performed simultaneously with an antibody specific for the coated antigens and a negative control antibody. The ELISA plates were washed 5 times with PBS-T (PBS-0.05% v/v Tween 20). Bound IgG was detected with 1:2000 diluted HRP-conjugate (Goat anti-mouse BD) and was allowed to bind for 2 hours at 25° C. The ELISA plates were washed 5 times with PBS-T (PBS-0.05% Tween 20) and bound IgG was detected by means of OD492 nm measurement.

Epitope Grouping of HER2/HER3 Specific IgGs

The panel of anti-HER2 antibodies was binned based on their reactivity to the HER2 ECD derived from other species (mouse, chicken) and on their binding to specific domains in the HER2 molecule i.e. domains I, II, III and IV using chimeric constructs.

The panel of anti-HER3 antibodies was binned based on their reactivity to the HER3 ECD derived from other species (cyno, rat) and on their binding to specific domains in the HER3 molecule i.e. domains I, II, III and IV using chimeric constructs.

For this purpose CHO-K1 cells were transiently transfected with the relevant constructs using lipofectamin/DNA mixes. In the chimeric swapped domain construct, domains of chicken HER2 or rat HER3 are replaced by the human counterpart. Binding of the specific antibodies was measured by FACS. Expression of the constructs was confirmed using an anti-myc antibody. FACS staining with trastuzumab was included as a control for specific binding to domain IV. Antibodies in each group could be ranked based on the intensity of staining (MFI). The HER2 panel of 65 antibodies could be mapped into seven bins (Table 3).
 1. Domain I specific (25)
 2. Domain II specific (2)
 3. Domain III specific (23)
 4. Domain IV specific (7)
 5. Domain IV specific and cross reactive to mouse (2)
 6. Reactive to all constructs (2)
 7. Only reactive to human HER2 (4)

Competition with Trastuzumab

Two antibodies mapped to HER2 domain IV inhibited proliferation of SKBR-3 cells. Both antibodies shared a similar CDR3 except for one amino acid difference. One antibody, PG1849 was investigated for its capacity to compete with trastuzumab in a competition ELISA. In this ELISA Fc-HER2 was coated and incubated with a concentration of 15 µg/ml IgG antibody. After an incubation of 15 minutes phages were allowed to incubate for another hour. Thereafter, phages were detected. Table 4 demonstrates that PG1849 and trastuzumab could bind simultaneously to HER2 since no loss of signal appeared during the ELISA. True competition only was observed when the same phage and antibody were combined in the assay.

The HER3 panel of 124 antibodies could be mapped into five bins (Table 5):
 1. High Domain III reactivity, rat and mouse reactive and minor reactivity to domain IV (8)
 2. High Domain III reactivity, rat, human and cyno reactive, minor reactivity to domain IV (8)
 3. Only reactivity to rat, cyno and human HER3 (43)
 4. Only reactive to human HER3 (32)
 5. Reactive to all constructs (33)

Cell Line Proliferation Assays

SK-BR-3 cells were cultured in DMEM-F/12 supplemented with L-glutamine and 10% heat inactivated FBS. BxPC-3-luc2 cells were cultured in RPMI1640 supplemented with 10% heat inactivated FBS. MCF-7 cells were cultured in RPMI1640 supplemented with 100 µM, NEAA1 mM sodium pyruvate, 4 µg/ml insulin and 10% heat inactivated FBS.

For the proliferation assay of SK-BR-3 cells, subconfluent cell cultures were washed with PBS, trypsinized and trypsin was inactivated by adding culture medium. Cells were diluted to $6 \times 10^4$ cells/ml in culture medium. Antibodies were diluted to concentrations of 10 and 1 µg/ml and added in a volume of 100 µl in 96-well black bottom plates (ABgene AB-0932). Cells were added at density of 6000 cells/well. The cells were cultivated for 3 days at 37° C., 5% CO, in 95% relative humidity. ALAMAR BLUE™ (INVITROGEN®) was added according to the manufacturer's instructions and incubated for 6 hours at 37° C., 5% CO, in 95% relative humidity in the dark. Fluorescence was measured at 550 nm excitation and 590 nm emission wavelength. The extent of growth inhibition was compared to that of the same concentration of trastuzumab (Table 6).

For the proliferation assay of MCF-7 and BxPC-3-luc2 cells, subconfluent cell cultures were washed with PBS, trypsinized and trypsin was inactivated by adding culture medium. Cells were washed twice in large volumes of assay medium (RPMI 1640 medium containing 0.05% BSA and 10 µg/ml Holo Transferrin). MCF-7 cells were diluted to $5 \times 10^4$ cells/ml in culture medium. Antibodies were diluted to concentrations of 10 and 1 µg/ml and added in a volume of 100 µl in 96-well black bottom plates (ABgene AB-0932). Cells were added at a density of 5000 cells/well in the presence of 1 ng/ml final concentration human Recombinant Human NRG1-beta 1/HRG1-beta 1 EGF Domain; (396-HB-050 RND). Human NRG1-beta 1/HRG1-beta 1 EGF Domain will hereinafter be referred to as HRG. The cells were cultivated for 5 days at 37° C., 5% CO, in 95% relative humidity. ALAMAR BLUE™ (INVITROGEN®) was added according to the manufacturer's instructions and incubated for 24 hours at 37° C., 5% CO2, in 95% relative humidity in the dark. Fluorescence was measured at 550 nm excitation with 590 nm emission wave length. The extent of growth inhibition was compared to that of the same concentration of #Ab6 (Table 7).

BxPC-3-luc-2 proliferation assays were used to screen the bispecific antibodies. BxPC-3-luc-2 cells were diluted to $8 \times 10^4$ cells/ml in culture medium. Antibodies were diluted to concentrations of 10 and 1 µg/ml and added in a volume of 100 µl in 96-well black bottom plates (ABgene AB-0932). Cells were added at density of 8000 cells/well in the absence or presence of 10 ng/ml final concentration human HRG. The cells were cultivated for 4 days at 37° C., 5% CO, in 95% relative humidity. ALAMAR BLUE™ (INVITROGEN®) was added according to the manufacturer's instructions and incubated for 4 hours at 37° C., 5% CO, in 95% relative humidity in the dark. Fluorescence was measured at 550 nm excitation with 590 nm emission wave length.

To minimalize edge effects, the outer wells of the 96 well plates were fully filled with PBS.

Affinity Ranking of HER2 Specific IgGs

Figure 1:
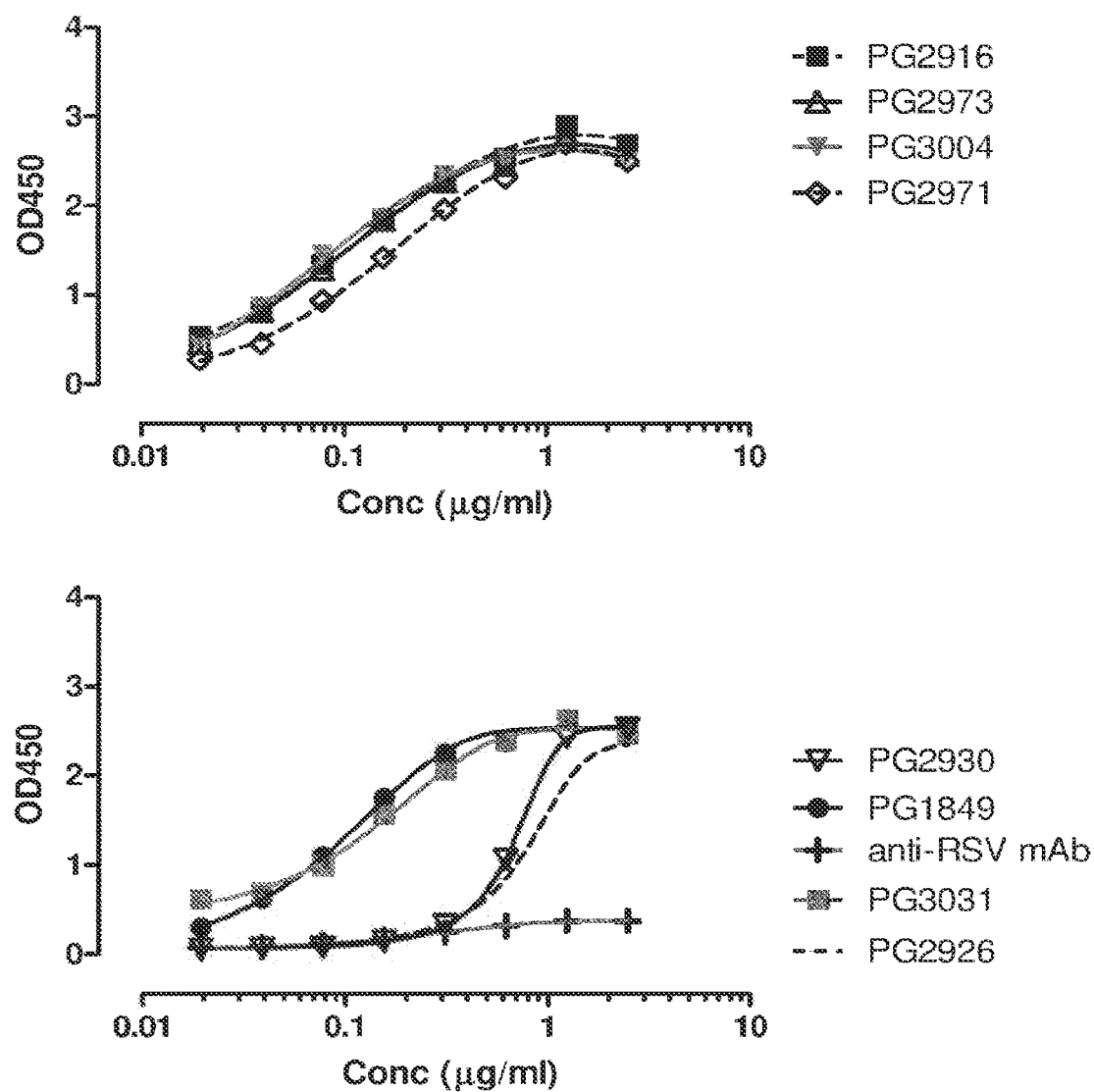
FIG. 1: Antigen titration on monomeric HER2 of a panel of HER2 arms that are also present in active HER2×HER3 bispecific antibodies in combination with one arm of PG3178. All HER2 monoclonals of the HER2×HER3 panel except for PG3025 were tested on an HER2 antigen titration ELISA.

We used the method described by Devash (PNAS, 1990) to rank the antibodies in a limited antigen-ELISA. The use of decreased antigen coating concentrations eliminates observed cross-reactivity reactions and can be used to detect high-affinity/avidity antibodies. Therefore the antigen concentration on the solid support was gradually decreased to investigate the weak immunoreactivities. A serial titration of ECD-Erbb-2 protein starting from 2.5 µg/ml until 0.019 µg/ml was coated overnight to MAXISORP™ ELISA plates. Wells of the ELISA plates were blocked with PBS (pH 7.2) containing 5% BSA for 1 hour at 37° C. Selected antibodies were tested in duplo at a concentration of 10 µg/ml diluted in PBS-2% BSA and allowed to bind for 2 hours at 25° C. As a control the procedure was performed simultaneously with an antibody specific for the coated antigens and a negative control antibody. The ELISA plates were washed 5 times with PBS-T (PBS-0.05% v/v Tween 20). Bound IgG was detected with 1:2000 diluted HRP-conjugate (Goat anti-mouse IgG, BD Biosciences) and was allowed to bind for 2 hours at 25° C. The ELISA plates were washed 5 times with PBS-T (PBS-0.05% Tween 20) and bound IgG was detected by means of OD492 nm measurement. PG1849, PG2916, PG2926, PG2930, PG2971, PG2973, PG3004 and PG3031 were tested in an HER2 antigen titration ELISA (FIG. 1).

Binding of HER2 VH Genes with Various Kappa Light Chains

To investigate the binding of HER2 VHs derived from different phage display libraries a panel of HER2 antibodies was cloned and expressed in the context of another VK kappa chain, i.e. the VL of MEHD7945A. Produced IgGs were subjected to FACS analysis on K562 cells and stable K562-HER2 cells. VH genes derived from the combinatorial libraries and non-combinatorial libraries are listed in Table 8. The VH chains MF2971, MF3958, MF2916, MF2973, MF3004, MF3025, MF3031 all could be combined with the MEHD7945A light chain without loosing significant antigen specificity and binding as observed when combined with the common light chain IGKV1-39. VH chain MF1849 was not able to combine with the variant kappa light chain and retain antigen specificity and binding.

Other HER2 and HER3 Antibodies

Antibodies that inhibit the function of HER2 or HER3 are known in the art. Further antibodies were constructed according to published information and expressed in 293F Freestyle cells. The anti-HER2 antibodies pertuzumab and trastuzumab were generated based on the information disclosed in US2006/0212956 A1 (Genentech). The anti-HER3 antibody #Ab6, was based on the information disclosed in WO 2008/100624 (Merrimack Pharmaceuticals, Inc.) and recloned in a IgG1 back bone vector. The information of the 1-53 and U1-59 anti-HER3 antibodies was obtained from U.S. Pat. No. 7,705,103 B2 (U3 Pharma AG). The information of the anti-HER3 LJM716 antibody was obtained from US 2012/0107306. The information for the construction of the two-in-one anti-EGFR anti-HER3 antibody MEHD7945A was obtained from WO2010/108127.

Screening of HER2×HER3 Bispecific Antibodies

VH from the HER2 and HER3 antibody panel were recloned into the charged engineered vectors such that upon expression of the antibody heavy chains heterodimerization of heavy chains is forced resulting in the generation of bispecific antibodies after transfection. Three different strategies were used in combining HER2 and HER3 arms in bispecific IgG format:

1. HER2 (blocking ligand independent growth)×HER3 (blocking ligand independent growth)
2. HER2 (blocking ligand independent growth)×HER3 (blocking ligand dependent growth)
3. HER2 from different epitope bins×HER3 (blocking ligand dependent growth)

In some bispecific combinations, antibodies generated in group 2 and 3 overlapped with group 1.

Figure 2:
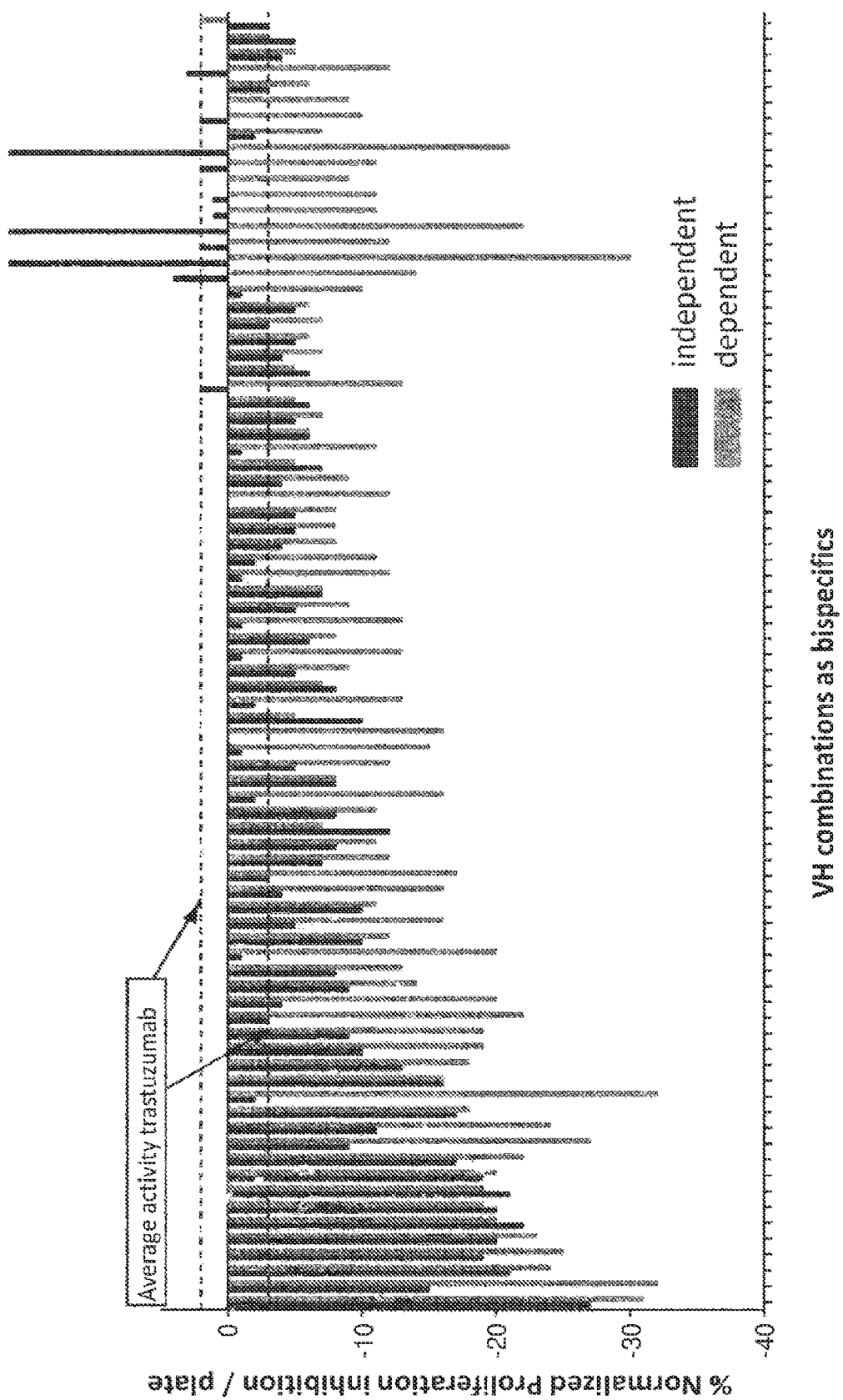
FIG. 2: Functional activity of HER2×HER3 bispecific antibodies on BxPC3 cells with or without ligand stimulation. Dotted lines represent activity of trastuzumab, the reference antibody in this assay, with or without ligand stimulation.

A total of 495 bispecific antibodies was produced in 24-well format and purified. All antibodies were tested for their capacity to inhibit the proliferation of the HER2- and HER3-expressing pancreatic BxPC-3-luc-2 cell line (Caliper). The potency of the antibodies was determined in a HRG-dependent and HRG-independent setting in a black and white screening with antibodies being present at a concentration of 10 and 1 µg/ml. Trastuzumab was included as a reference antibody as well as a negative control antibody at the same concentrations. The functional activity of the top 80 HER2×HER3 bispecifics (based on combined inhibition) at 1 µg/ml is shown in FIG. 2.

Figure 3:
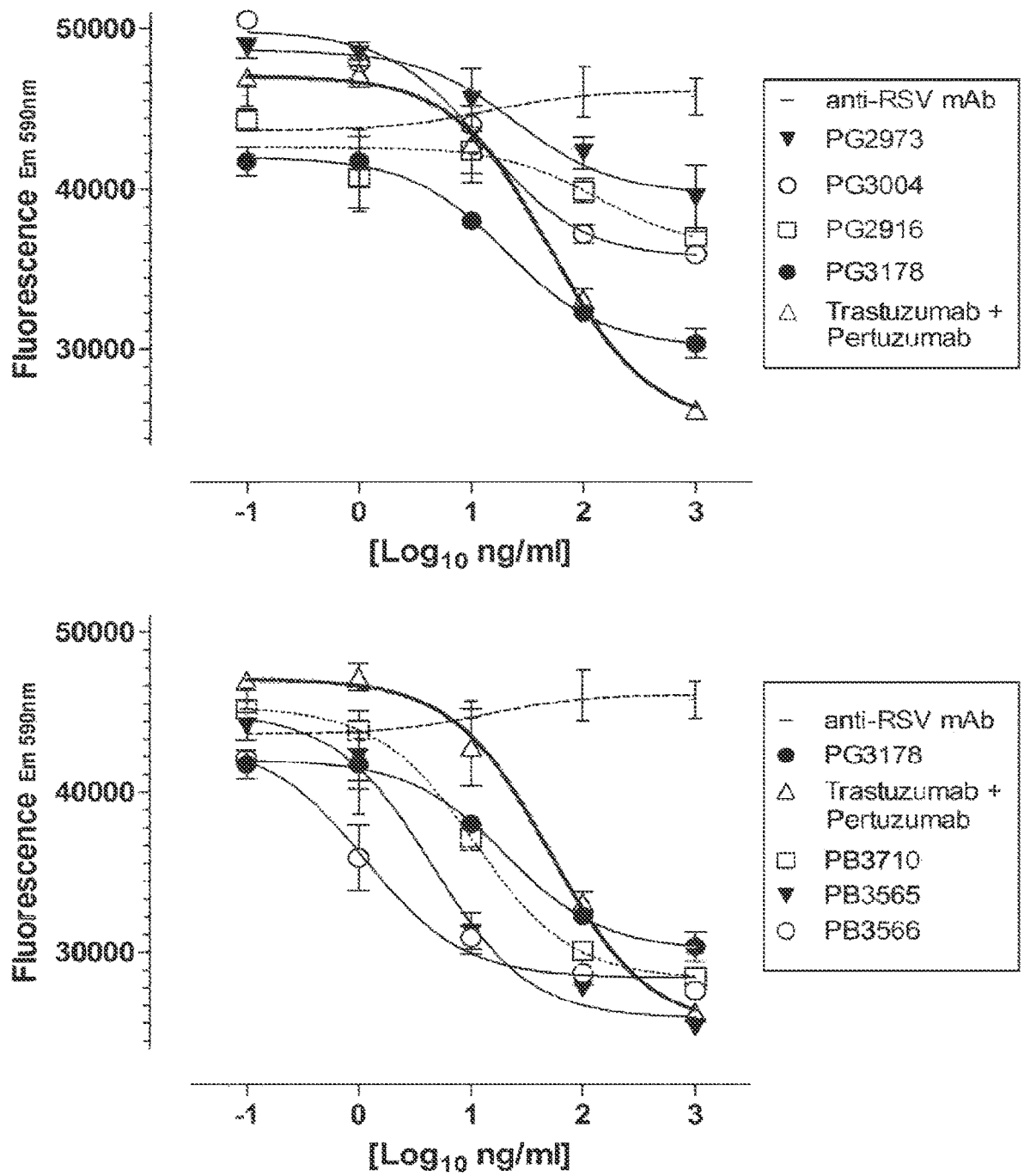
FIG. 3: Titration curves of HER2 and HER3 monoclonal antibodies (Upper panel) and HER2×HER3 bispecific antibodies thereof (Lower panel) in the MCF-7 assay

Antibodies (40 in total) that showed a higher inhibitory activity compared to the positive control antibody were selected, reproduced and purified in a 24-well format and tested again in the black-and-white BxPC-3-luc-2 screen at 10 and 1 µg/ml concentrations. These antibodies were further titrated in HRG-dependent MCF-7 assay and compared against the combination of trastuzumab and pertuzumab (1:1) and a negative control antibody. FIG. 3 shows an example of titration curves of three bispecific antibodies in comparison to the parental HER3 antibody and the combination of trastuzumab+pertuzumab. The parental monoclonal antibodies are shown in the top panel and the bispecific antibodies are shown in the lower panel. (FIG. 3).

The $IC_{50}$ for the bispecific antibodies, monoclonals and comparator antibodies was calculated using non-linear regression analysis with Prism software. Graph pad software lists the $IC_{50}$ values of the bispecific antibodies in the MCF-7 assay and their inhibitory activity in the BxPC3 assay for comparison. A panel of 12 HER2×HER3 bispecific antibodies had more potent inhibiting activity compared to trastuzumab+pertuzumab. In addition the bispecific antibodies were equally or more potent than the parental monoclonal PG3178 (Table 9).

The bispecific antibodies that inhibited ligand dependent cell growth were composed of HER2 arms in combination with the HER3 arms 3178, 3163, 3099 and 3176. Both the HER2 and HER3 arms of the most potent bispecifics were as a bivalent monoclonal also capable of inhibiting ligand-independent SKBR-3 proliferation (both the HER2 and HER3 arms) (Table 6) or ligand dependent MCF-7 proliferation (HER3 arms) (Table 7). The majority of the potent antibodies was composed of a HER2 arm recognizing domain I in combination with anti-HER3 antibody 3178.

Inhibition of BxPC-3-Luc2 Tumor Growth

The antibodies described in Table 9 were tested in a BxPC-3-luc2 pancreatic xenograft model. The BxPC-3-luc2 cell line expresses both HER2 and HER3 and is considered a HER2 low expressing cell line. CB17 SCID female mice, 8-10 weeks old at the beginning of the study were engrafted orthotopically in the pancreas with $1\times10^6$ tumor cells in 20 µl. To this aim mice were anesthetized and laid on the right side to expose the left side and a 0.5 cm incision was made on the left flank region. The pancreas and spleen were exteriorized and $1\times10^6$ tumor cells in 20 µl was injected into the sub-capsulary space of the pancreas tail. One week after implantation, bioluminescence (BLI) data were generated. 15 minutes prior to the imaging, all of the mice received i.p. injections of 150 mg/kg Luciferin (D-Luciferin-EF Potassium Salt, Cat. #E6552, Promega). BLI imaging was performed once or twice weekly using the left side view. Outlier animals—based on BLI/tumor volume—were removed and the mice were randomly distributed into groups of 7 mice each. On experimental day 8, the treatment was started. The animals in the antibody treatment group were dosed weekly for 3 consecutive weeks (days 0, 7, 14 and 21) with 30 mg/kg of antibody. At day 0 of the treatment the animals received twice the loading dose, i.e. 60 mg/kg of antibody. The final imaging was carried out at day 31.

Two BxPC-3-luc2 xenograft models were run with a different panel of bispecific antibodies and parental antibodies In the first BxPC-3-luc2 xenograft model (FIG. 4), one group received the negative control anti-RSV antibody (Ctrl IgG), one group received the control antibody trastuzumab and one group received the positive control antibody trastuzumab+pertuzumab (1:1 v/v). The seven remaining groups received one of the monoclonal (PG) or bispecific (PB) antibodies PG3004, PG3178, PB3566, PB3710, PB3443, PB3448 and PB3441. Details of the composition of the bispecific antibodies are depicted in Table 9.

Figure 4:
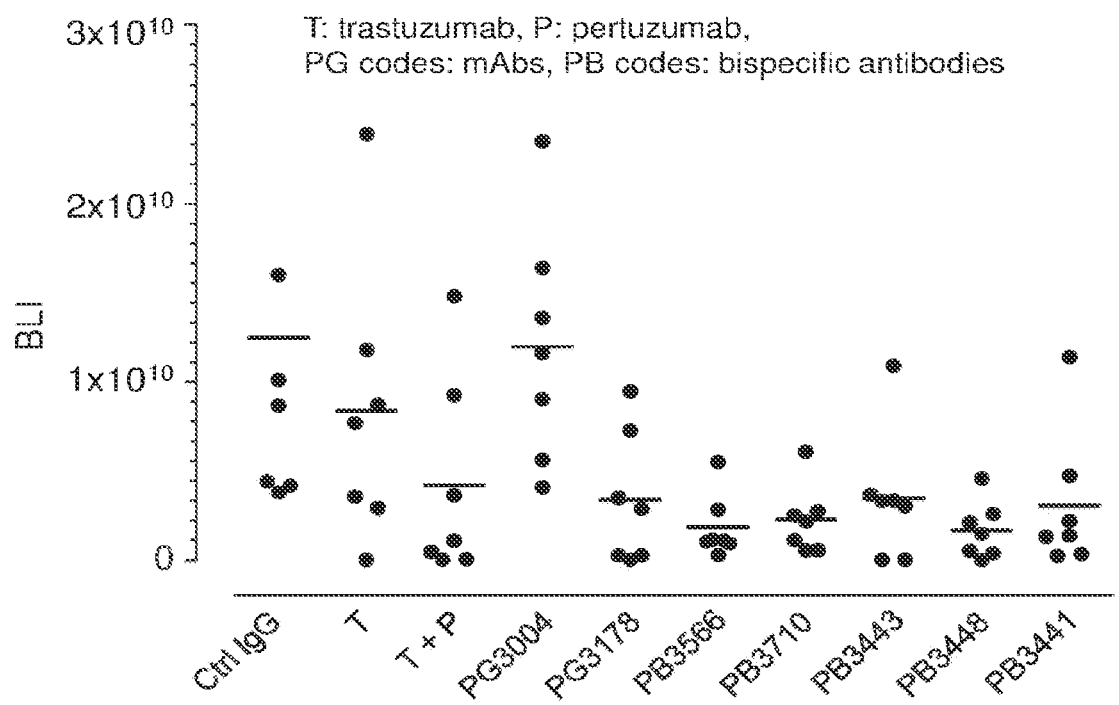
FIG. 4: Antibody treatment effect on BxPC3-luc2 tumor size at day 31 in an orthotopic murine model. BLI, tumor growth as measured by bioluminescence.

All five bispecific antibodies tested were able to inhibit tumor growth. The mean tumor mass (BLI) of bispecific HER2×HER3 antibody treated animals was similar to that in the animals treated with the combination of trastuzumab+pertuzumab. (FIG. 4)

Figure 5:
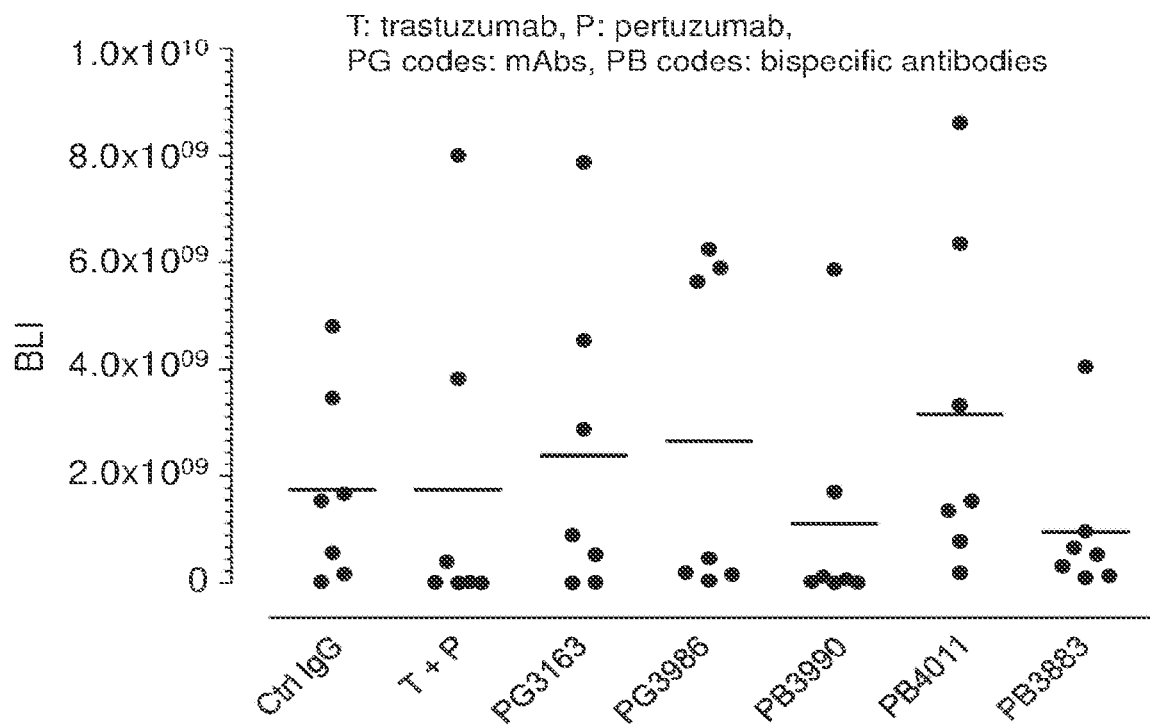
FIG. 5: Antibody treatment effect on BxPC3-luc2 tumor size at day 31 in an orthotopic murine model. BLI, tumor growth as measured by bioluminescence.
Figure 7A:
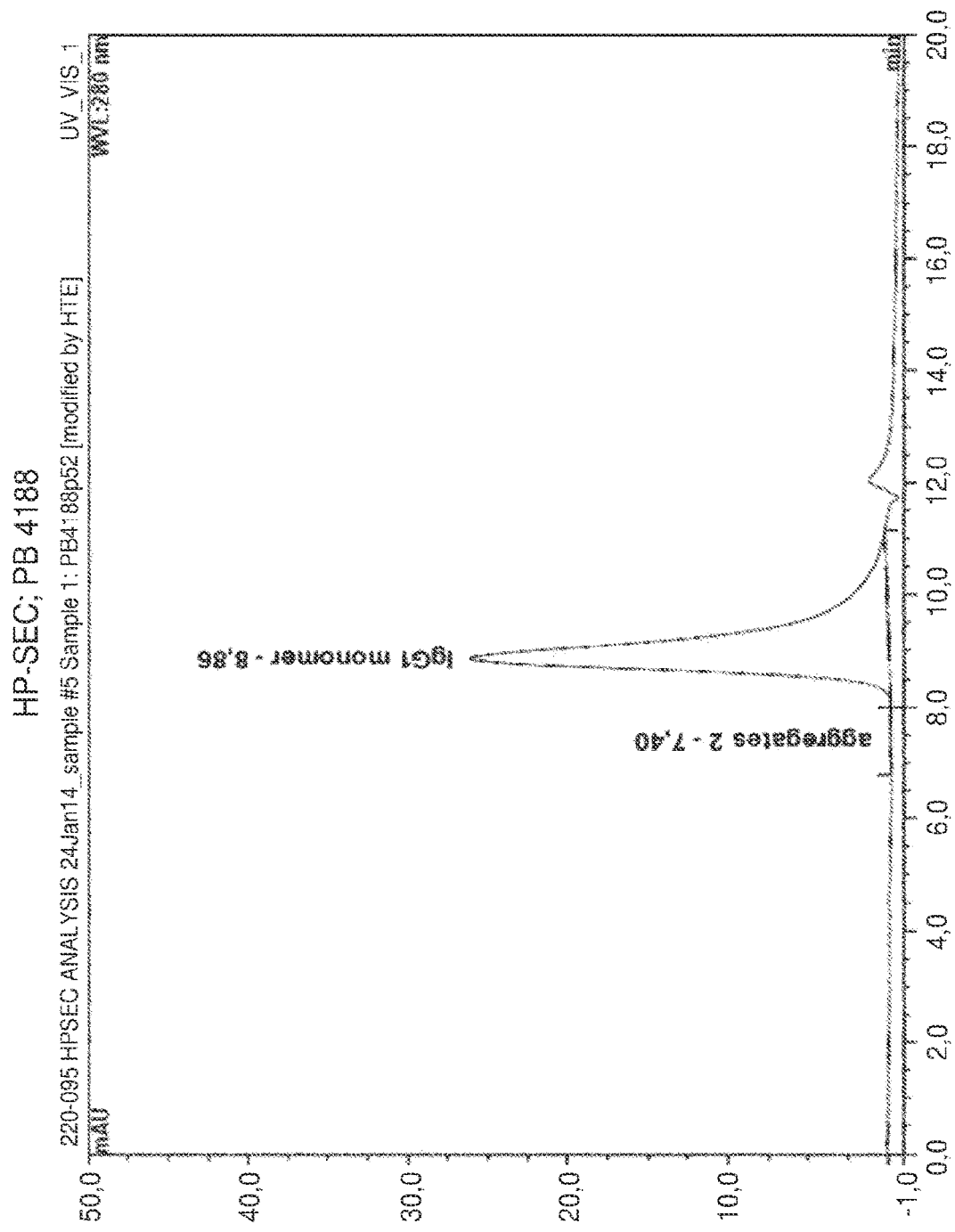
FIG. 7A-7E: Analytical characterization by HP-SEC and CIEX-HPLC. PB4188 (7A and 7B), anti-HER2 parental monoclonal antibody (7C and 7D), anti-RSV monoclonal reference IgG (7E and 7F).
Figure 7B:
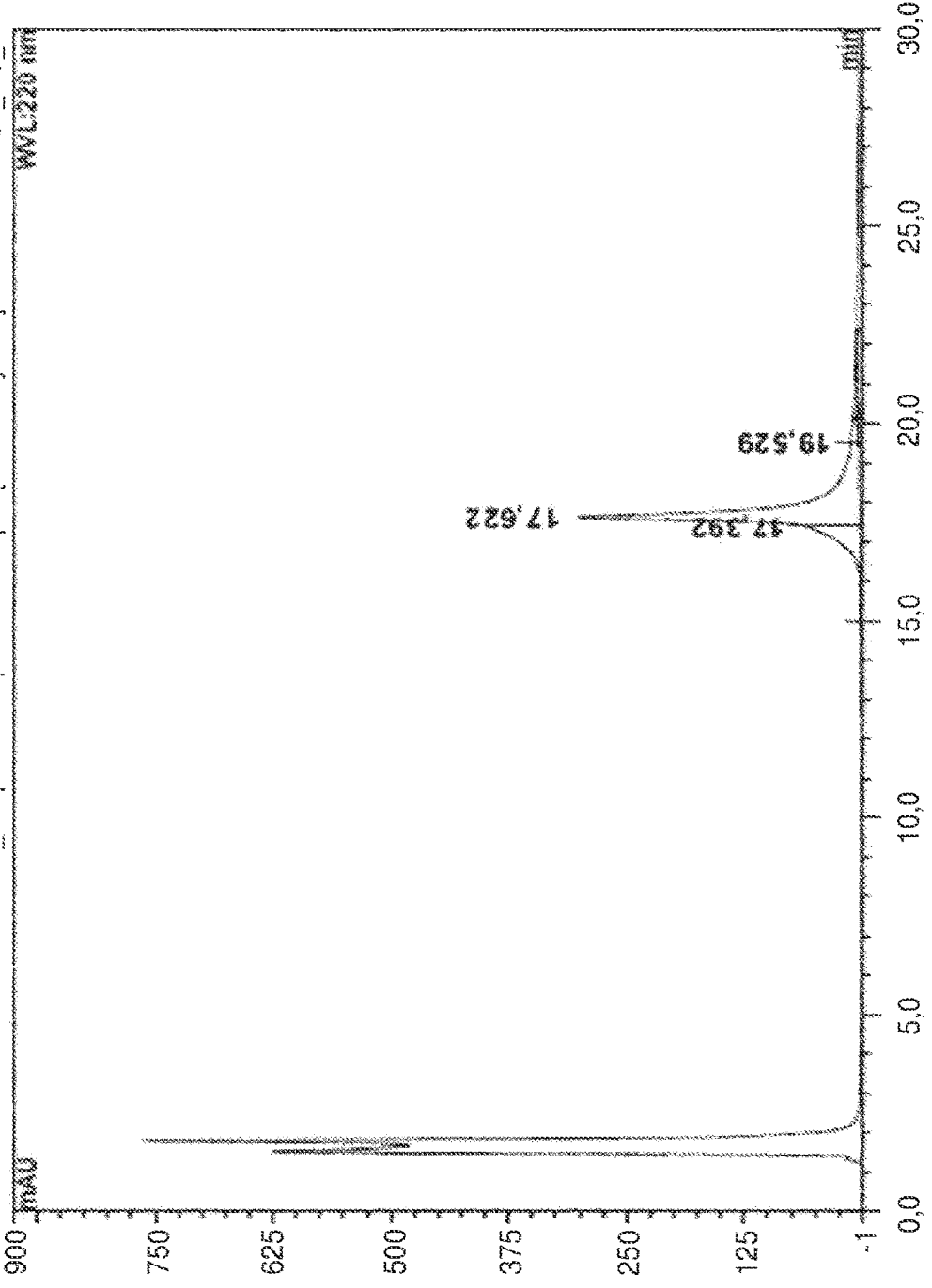
Figure 7C:
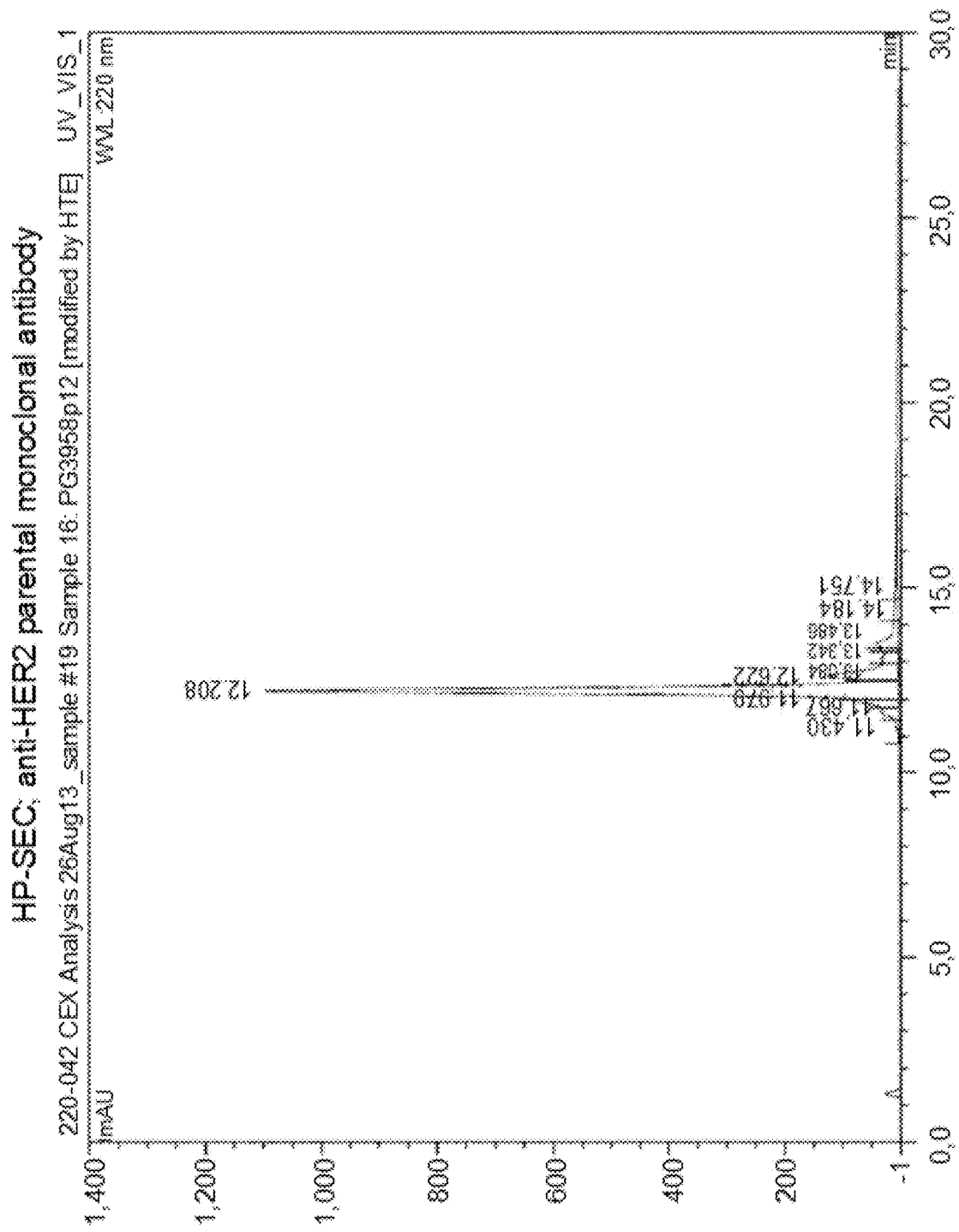
Figure 7D:
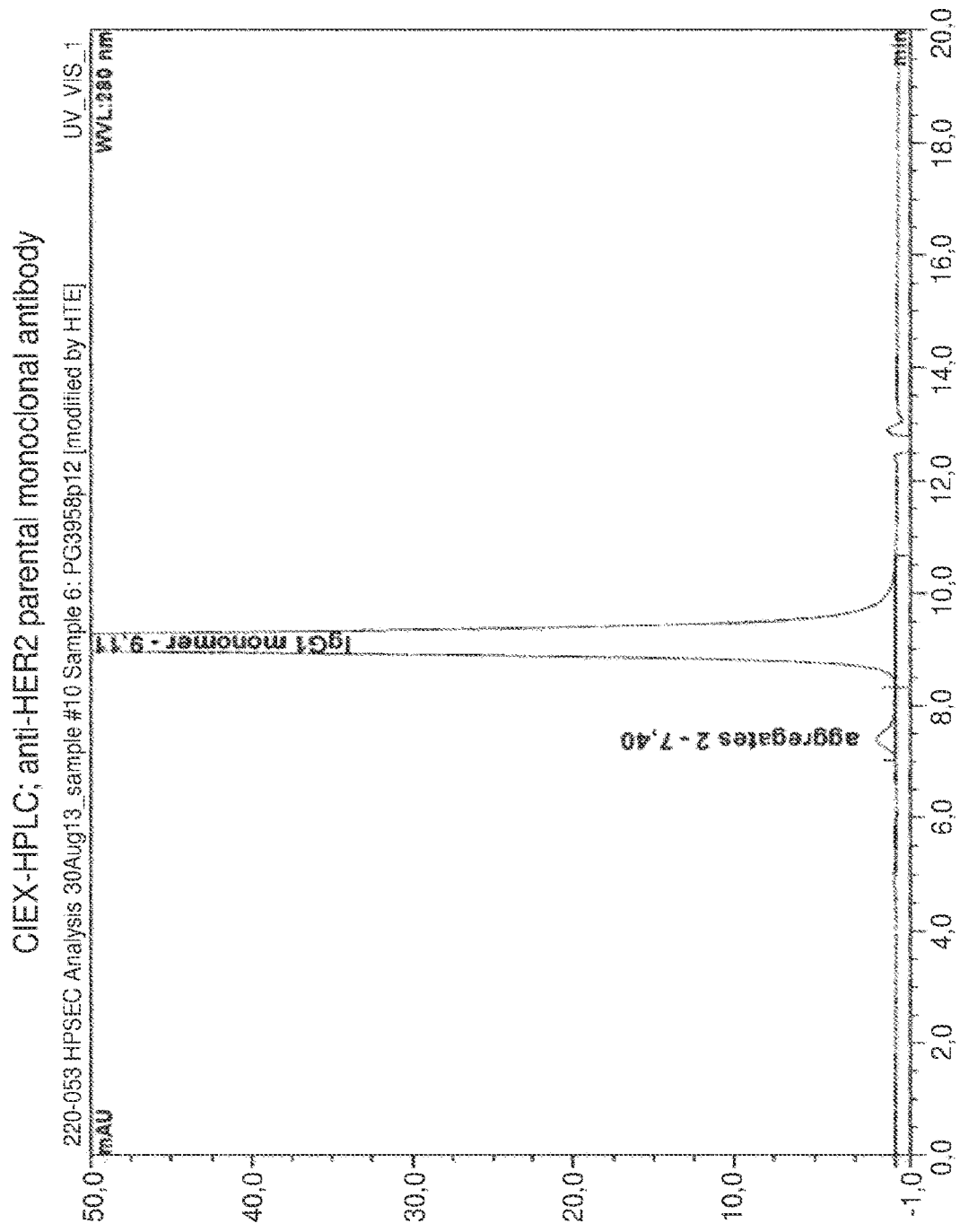
Figure 7E:
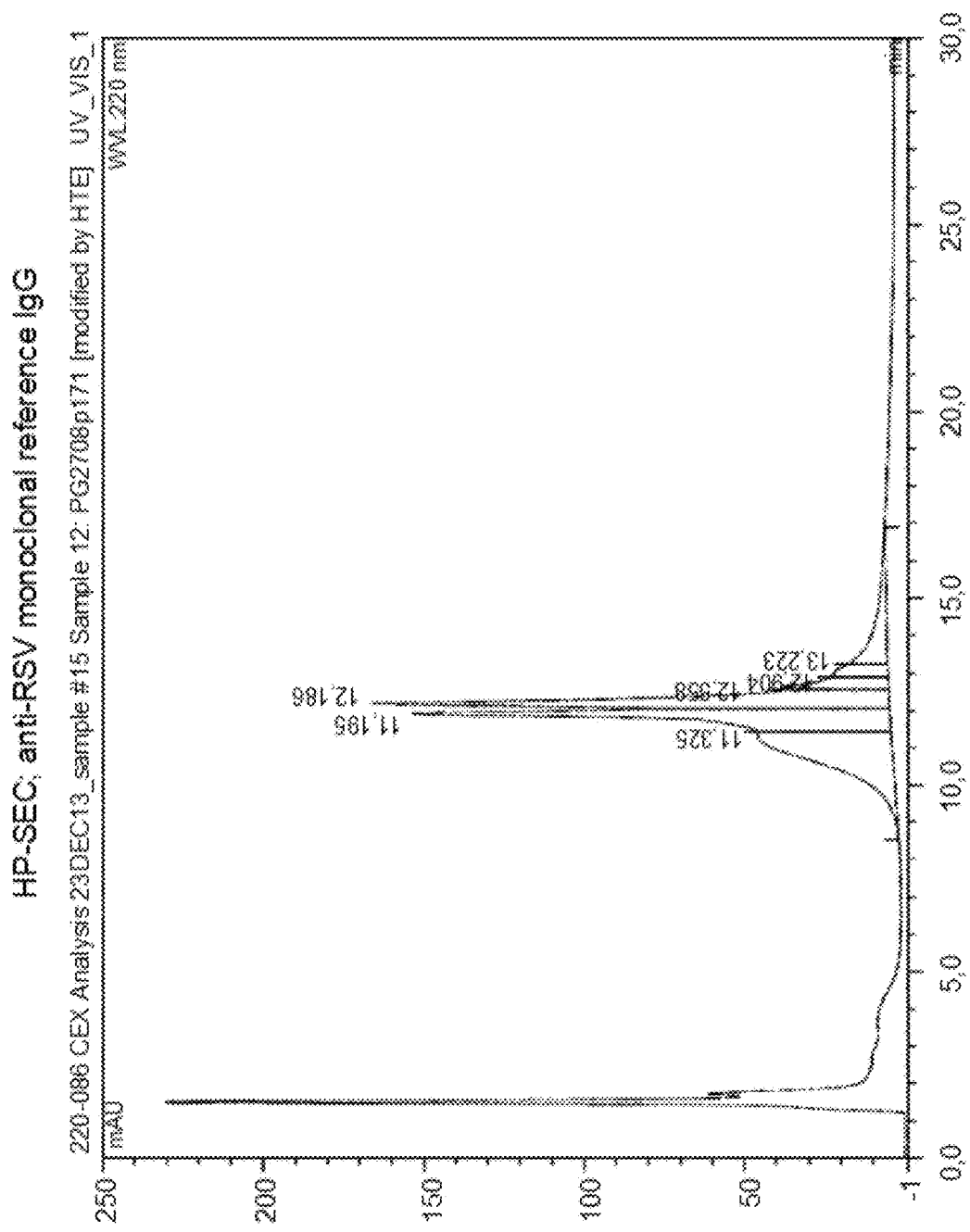
Figure 7F:
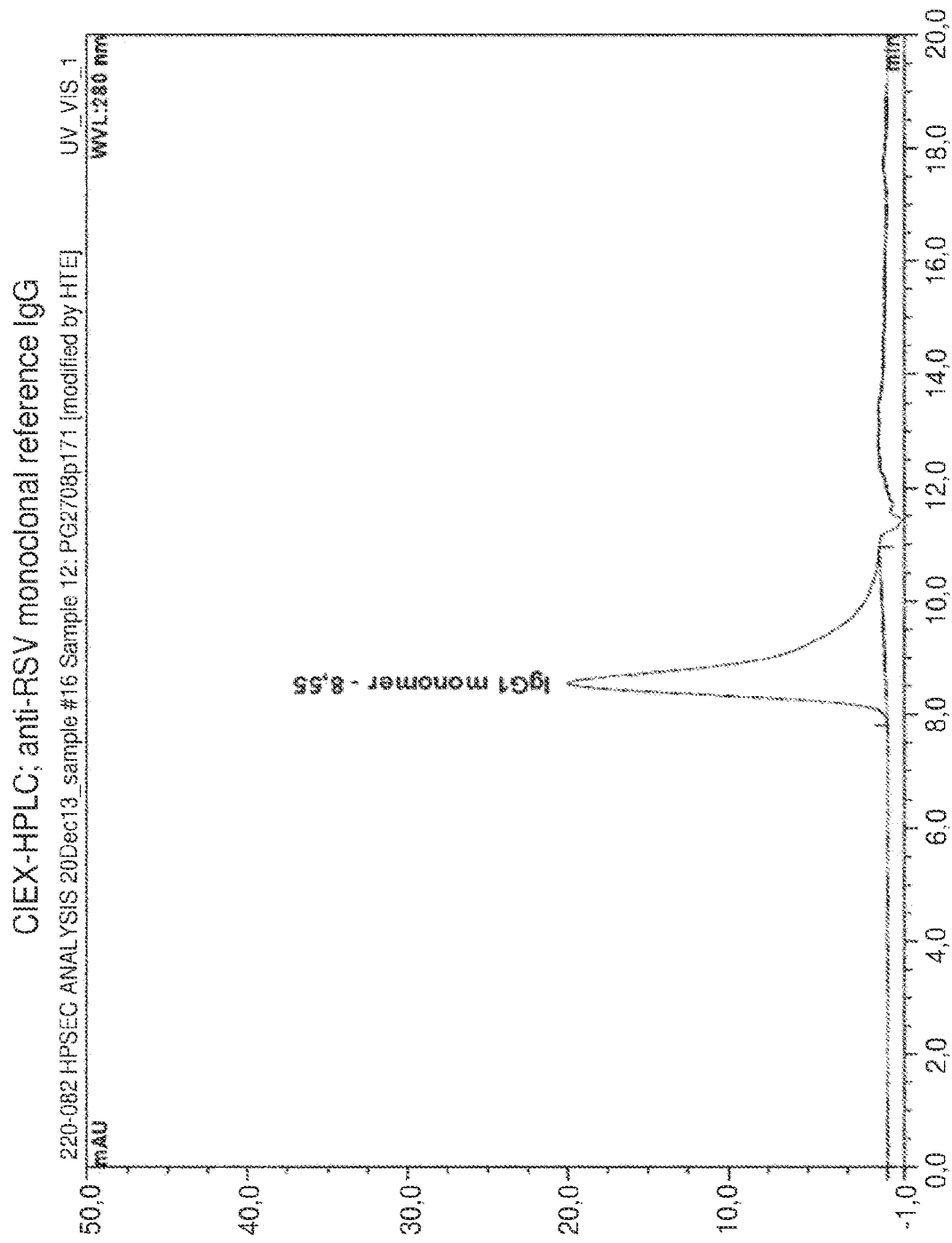

In the second BxPC-3-luc2 xenograft model (FIG. 5), one group received the negative control anti-RSV antibody (Ctrl IgG) and one group received the positive control antibody combination trastuzumab+pertuzumab (1:1 v/v). The five remaining groups received one of the antibodies PG3163, PB3986, PB3990, PB4011 and PB3883. For details about the bispecific PB antibodies: Table 9. These bispecific antibodies contained three different HER3 binding arms combined with the same HER2 arm MF2971 and an additional HER2 arm combined with the HER3 binding arm MF3163. In this experiment the tumors in the control group did not show the same level of accelerated growth as in the first experiment complicating interpretation of the results. Nevertheless, in comparison to trastuzumab+pertuzumab the PB3883 and PB3990 HER2×HER3 bispecifics had similar inhibitory activities (FIG. 5).

Based on the in vivo and in vitro data a bispecific panel of antibodies was selected of which the HER2 arms were composed of MF2971, MF3004, MF1849 and the HER3 arm was composed of MF3178. The MF2971 and MF3004 arm were of mouse origin and were humanized.

Binding of Bispecific HER2×HER3 Antibody Compared to Parental Monoclonal Antibodies Binding of HER2×HER3 bispecific antibodies as compared to their parental counterparts was determined by FACS analysis. A FACS was performed on BxPC-3-luc2 cells and MCF-7 cells with a serial titration of antibodies ranging from 2.5 µg g/ml-0, 01 µg g/ml. The tested antibody panel was composed of the bispecific antibody PB3566 and its parental antibodies the anti-HER3 antibody PG3178 and the anti-HER2 antibody PG3004. The MFI data were plotted and the graphs on both cell lines show that the bispecific PB3566 binds more effectively to both tumor cell lines compared to the anti-HER3 antibody PG3178 and the anti-HER2 antibody PG3004. (FIG. 6)

Humanization of MF2971 and MF3004

MF2971 and MF3004 were humanized according to technology known in the art. A total of seven humanised/de-immunised variant sequences of MF2971 were expressed, validated and characterised in vitro as monoclonal and in bispecific format combination with the HER3-specific antibody MF3178. The same was done for seven variant sequences of MF3004, which were created by replacing the HCDR3 of MF2971 in the seven MF2971 variants with the HCDR3 of MF3004. The expression, integrity, thermal stability and functional activity of all humanized variants was analysed. Based on production, integrity, stability and functionality integrity, a variant of MF2971 (2971-var2) was chosen as the optimal humanized variant of the VH to be used in a bispecific format with MF3178. This 2971-var2 was renamed MF3958. The bispecific HER2×HER3 combination MF3958×MF3178 resulted in PB4188.

Large Scale Production, Purification and Analytical Studies of PB4188

Suspension adapted 293F Freestyle cells were cultivated in Erlenmeyer flasks at a shaker plateau until a density of $3.0 \times 10^6$ cells/ml. Cells were seeded in a 4 L erlen flasks at a density of $0.3-0.5 \times 10^6$ viable cells/ml. The cells were transiently transfected with the individual sterile DNA: PEI mixture and further cultivated. Seven days after transfection, conditioned medium containing bispecific antibody was harvested by low-speed centrifugation, 5 minutes 1000 g, followed by high speed centrifugation, 5 minutes at 4000 g. Collected conditioned medium was concentrated over a 5 kDa Satorius hydrosart cassette to about 600 ml and subsequently diafiltrated against 4 L PBS. Antibodies were bound on column to ~35 ml MabSelectSure XL (11C). A-specifically bound proteins were removed by washing the column in reversed flow mode with 150 ml PBS, 150 ml PBS containing 1 M NaCl, 100 ml PBS. The bound antibodies were eluted using 100 mM citrate pH 3.0 in reversed flow mode and 5 ml fractions were collected in 10 ml tubes containing 4 ml 1Tris pH 8.0 for neutralization. The eluted antibodies were further purified by gel-filtration using superdex 200 50/1000. The purified antibody was filter-sterilized using a 0.22 m syringe filter. IgG concentration was determined by OD280 measurement and the protein concentration was calculated based on the amino acid sequence. Protein was tested for aggregation (HPSEC), purity (SDS-PAGE, nMS, IEX and IEF). Protein samples were stored at −80° C.

IgG Purification for Analytical and Xenograft Studies.

Medium scale purifications were performed on an AKTA 100 Explorer using HiTrap MabSelect Sure columns and HiTrap desalting columns. Samples were loaded at 5 ml/min. The column was washed with 2 column volumes of PBS. IgG was eluted at pH 3.0 with 0.1 M citrate buffer. Next the sample was desalted and ended up in a final buffer of PBS pH 7.4. IgGs were filtered through a 0.45 µM filter (Sartorius). The IgG concentration was measured using Octet with protein A sensors. Protein was tested for aggregation (HPSEC), purity (SDS-PAGE, nMS, IEX and IEF). Protein samples were stored at −80° C.

Analytical Characteristics of PB4188

The PB4188 (MF3958×MF3178) was subjected to analysis by HP-SEC and CIEX-HPLC (TSK gel-STAT 7 µm column, 4.6 mm ID×10 cm L). The analytical profile of PB4188 was in general consistent with the behavior of normal monospecific IgG1, such as the parental HER2 arm PG3958 and the anti-RSV monoclonal control antibody (FIG. 7).

Affinity Determination

The monovalent binding affinity of PB4188 and PB3448 for recombinant HER2 and HER3 was determined by SPR (BIACORE™ T100). BIACORE™ T100 (GE Healthcare, Uppsala, Sweden) was used to conduct all experiments described. Sensor surface preparation and interaction analyses were performed at 25° C. Buffer and BIACORE™ reagents were purchased from GE Healthcare. ErbB2-Fc and ERbB3-Fc(RND) was coated to the surface of a CM5 sensor chip in potassium acetate buffer (pH5.5) at the target immobilization level of 500 RU. Running buffer was HBS (hepes-buffered saline): 10 mM HEPES pH 7.4, 150 mM NaCl, 0.005% Tween-20; 0.2 µm) filter-sterilized. The bispecific antibodies were diluted to 100, 50, 20, 10, 1 and 0.1 nM in HBS and run at high (30 µl/min) flow rate over the antigen-coupled surface of the CM5 sensor chip. With the BIA evaluation software, a curve fitting model for 1:1 monovalent interaction allowed for determination of the HER2 arms affinities (mono-valent interaction), the affinities of the HER2 arms, could be determined. Due to the low-off rate of the HER3 arm the affinity could not be determined. To determine the affinity of the HER3 arm PB4188 was coated to a CM5 sensor chip at the target immobilization level of 500 RU. Her2-Fc and Her3-Fc antigens were diluted to 100, 50, 20, 10, 1 and 0.1 nM in HBS and run at high flow rate (40 µl/min) over the PB4188 surface. To determine the $k_{on}$ and $k_{off}$ values, the BIA evaluation software was used in conjunction with a model that takes into account that a monovalent molecule was coated to the sensor chip surface and that the ErbB3-Fc antigen was a bivalent molecule. The affinities of PB4188 and PB3448 are shown in Table 10.

PB4188 Affinity Determination on Cells

Figure 20A:
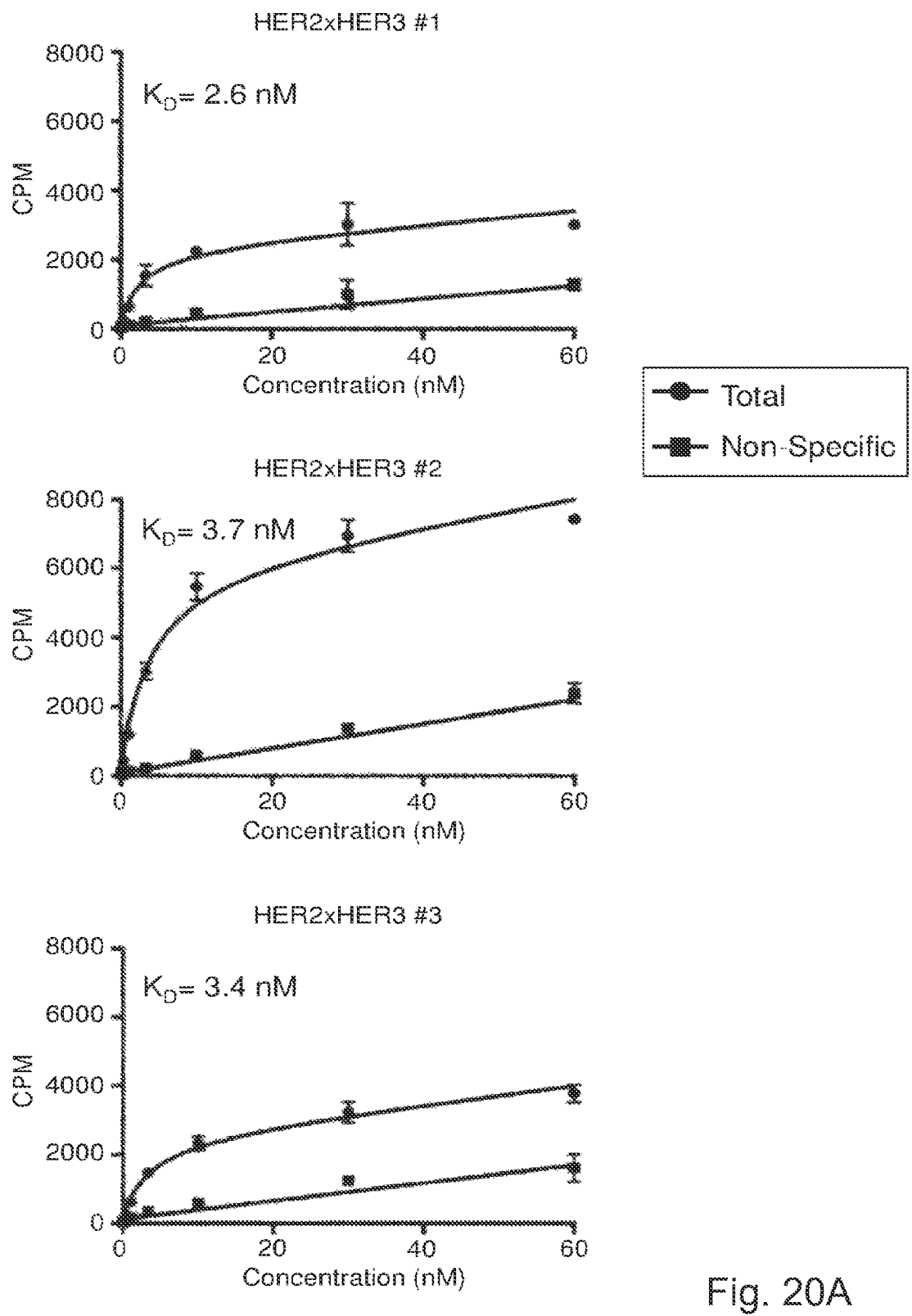
FIGS. 20A and 20B: Steady state cell affinity measurements of $^{125}$I-labeled IgG HER2×HER3 (PB4188) towards BT-474 cells (20A; three independent assays) and SK-BR-3 cells (20B; three independent assays). Non-specific binding was determined using a 100-fold excess of unlabeled HER2×HER3.
Figure 20B:
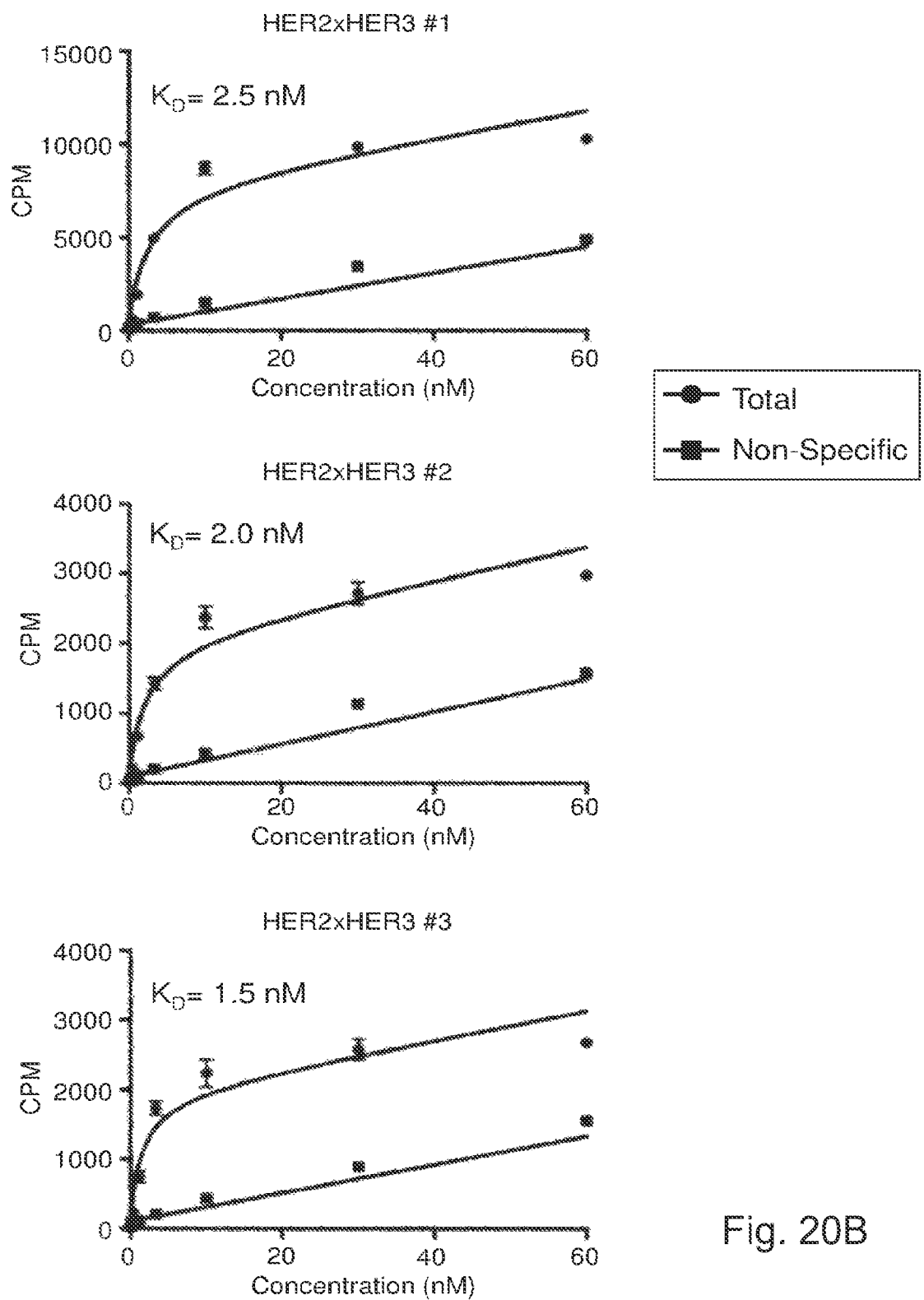

Binding affinities were also determined via steady state cell affinity measurements using BT-474 and SK-BR-3 cells. Four IgG were analyzed: 1) PB4188 (bispecific HER2×HER3), containing anti-HER2 antibody 3958 and anti-HER3 antibody 3178; 2) PB9215 (bispecific HER3×TT), containing anti-HER3 antibody 3178 and anti-TT (tetanus toxoid) antibody 1337; 3) PB9216 (bispecific HER2×TT), containing anti-HER2 antibody 3958 and anti-TT antibody 1337; 4) HERCEPTIN® (monospecific HER2). The IgG were radioactively labeled with $^{125}$I using IODO-GEN® Precoated Iodonation Tubes (Pierce) and associated instructions. The labeled IgG were diluted to an activity of ~1-2× $10^8$ cpm/ml in 25 mM Tris-HCl, 0.4 M NaCl, 0.25% BSA, 5 mM EDTA, 0.05% NaN$_3$. Protein concentrations were determined with the BCA Protein Assay Kit (Pierce). Flow cytometry analysis of the labeled and non-labeled IgG using BT-474 and SK-BR-3 cells showed no or only minor signs of reduction in binding after labeling. Steady state cell affinity measurements were performed as follows. Cells were seeded in 96-well plates and incubated at 4° C. with various concentrations of labeled IgG. Unbound radioactivity was removed after 4 hours and the cell-bound radioactivity was measured using a gamma well counter. Non-specific binding was measured by adding a receptor-blocking concentration (100-fold excess) of unlabeled antibody. Each condition was tested in triplicate and three independent experiments were performed per antibody. KD values were calculated based on a non-linear regression model that compensates for non-specific binding, using Prism 6.0d (GraphPad Software). Graphs including fitted curves are given in FIG. 20 for binding of the HER2×HER3 IgG (PB4188) to both cell lines. KD data for all 24 assays, including mean values, are given in Table 12.

In summary, the mean KD values as determined using BT-474 and SK-BR-3 cells were 3.2 and 2.0 nM for HER2× HER3, 3.7 and 1.3 nM for HERCEPTIN®, 3.9 and 2.3 nM for HER2×TT, and 0.23 and 0.99 nM for HER3×TT, respectively. Thus PB4188 shows a higher affinity for HER3 compared to HER2 which is in contrast to the HER2×HER3 bispecific molecule MM-111 that targets HER2 with a higher affinity compared to HER3.

Anti-Proliferative Activity on HER2 Amplified Breast Cancer Cells

JIMT-1 in Soft Agar

Figure 8:
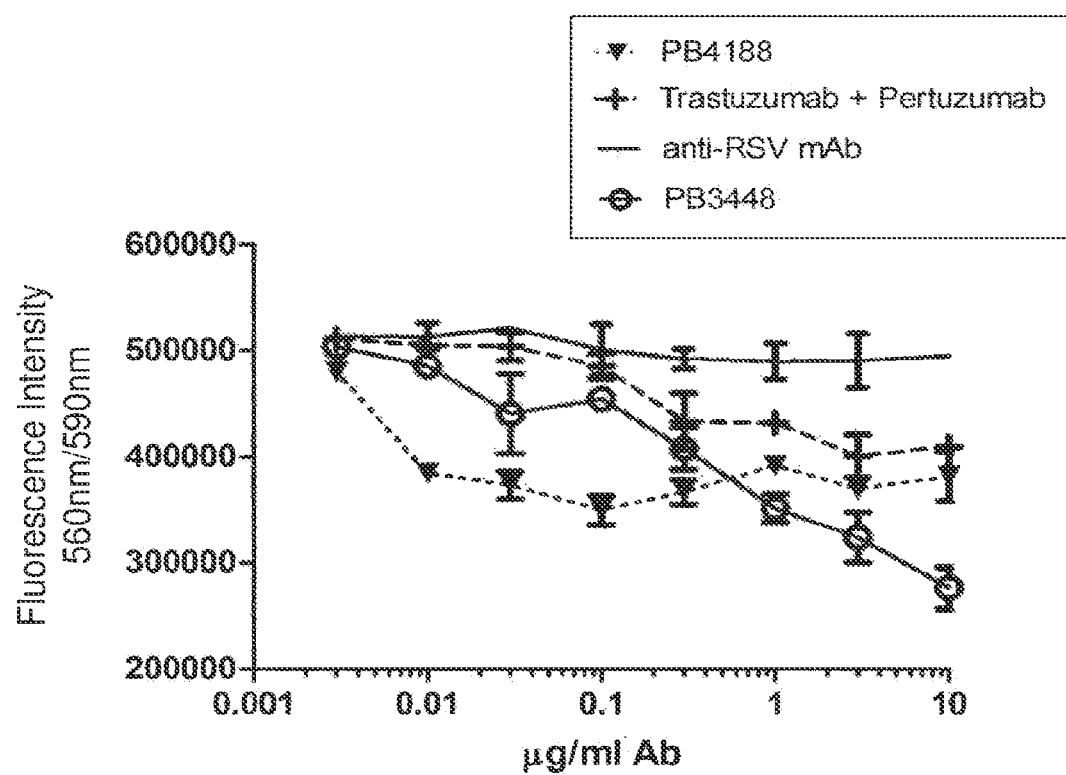
FIG. 8: Inhibition of JIMT-1 cell proliferation in soft agar by a serial titration of antibody.

PB3448 and PB4188 were tested for their potency to inhibit the growth of the trastuzumab resistant JIMT-1 cells in soft agar. To this aim 96 well suspension cell culture plates were prepared. 100 µL of the soft agar bottom layer (0.6% final concentration in complete medium) was poured and left to solidify. 50 µL of the soft agar top layer (0.4% final concentration) containing 10.000 JIMT-1 cells/well were then added on top, solidified and such 96 well plates incubated overnight at 37° C., 10% CO2. Next day, a negative control antibody, pertuzumab+trastuzumab (1:1 v/v), PB3448 and PB4188 were added in DMEM medium in a semi-log titration ranging from 10-0,003 µg/ml. Subsequently, the assay was incubated in cell culture incubators for 8 days. Finally, the cells were incubated with Alamar Blue for 3-5 h at 37° C. and fluorescence intensity was determined (excitation: 560 nm; emission: 590 nm). An example of dose dependent inhibition of JIMT-1 proliferation by PB3448 and PB4188 is shown. (FIG. 8).

BT-474 and SEBR-3 in MATRIGEL®

Figure 9A:
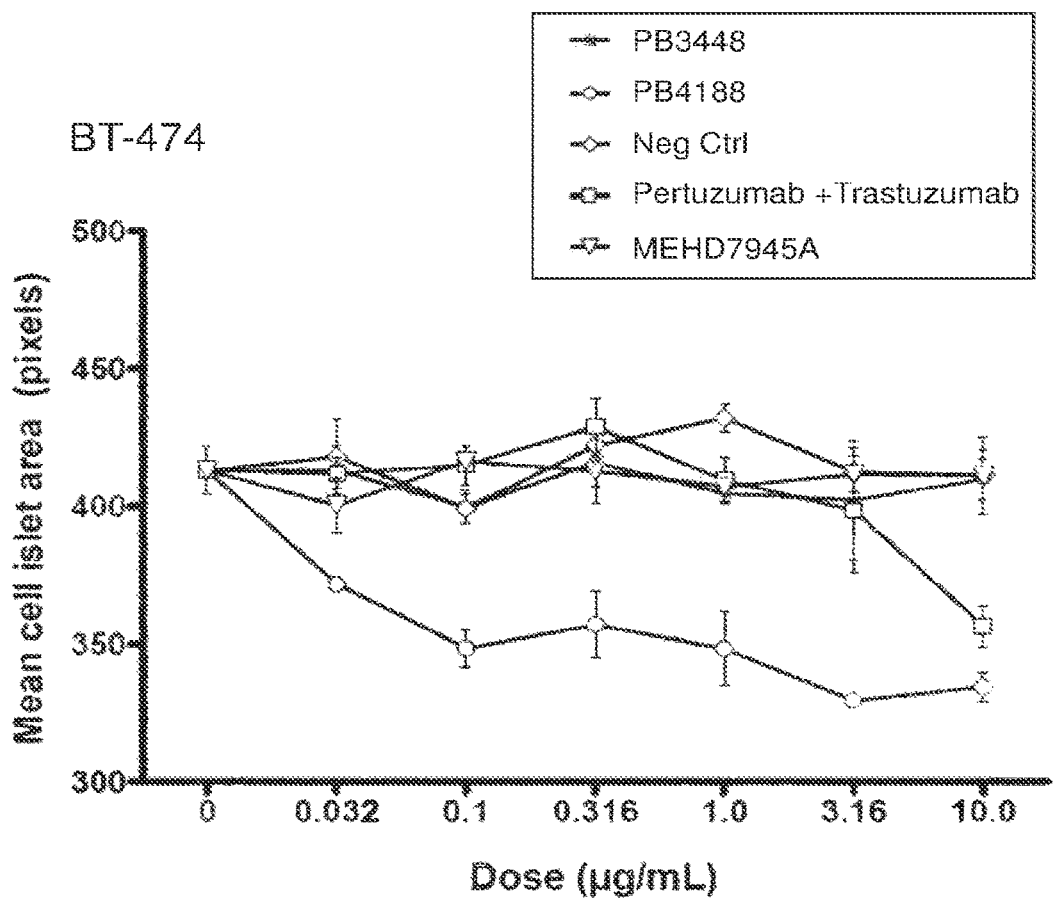
FIGS. 9A and 9B: Inhibition of BT-474 (9A) and SKBR3 (9B) cell proliferation in MATRIGEL® by a serial titration of antibody.
Figure 9B:
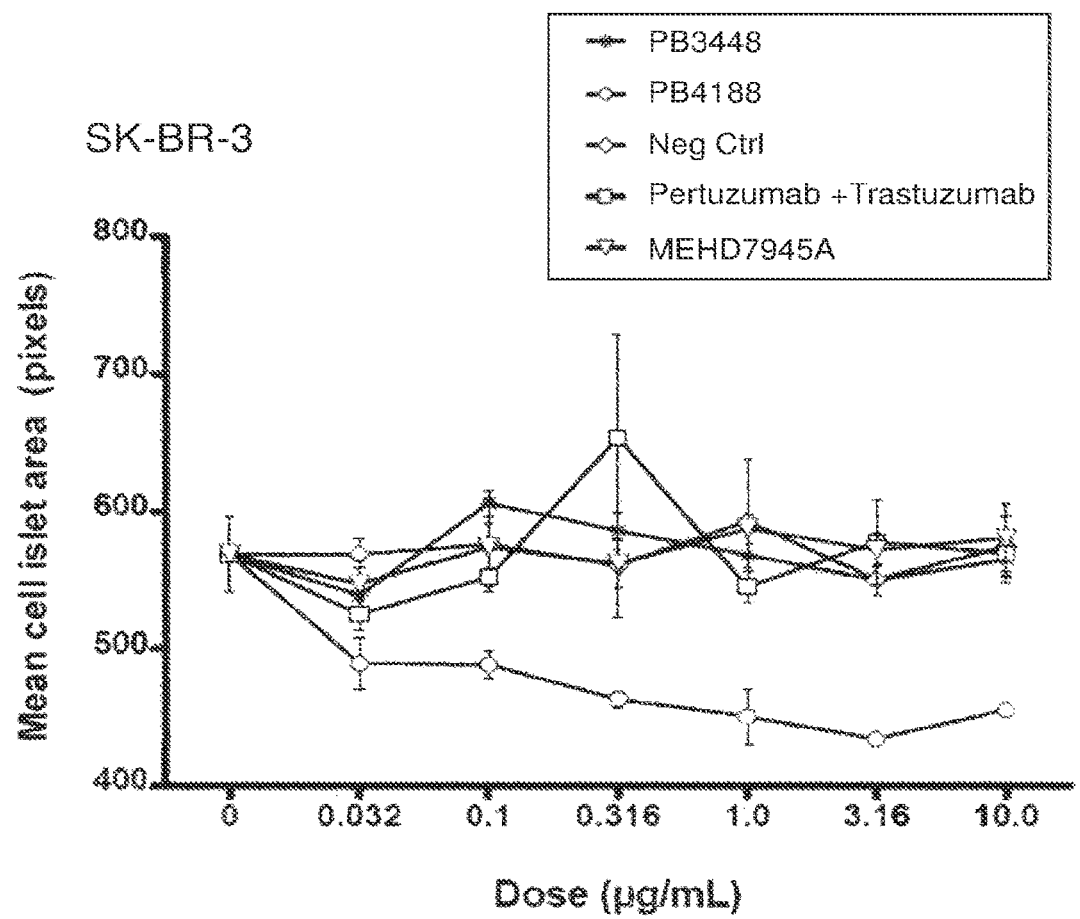

PB3448 and PB4188 were tested for their potency to inhibit the growth of BT-474 and SKBR-3 cells. The cells were tested at the company Ocello based in Leiden, the Netherlands that grows cells in three dimensional MATRIGEL® and uses principle component analysis to distinguish non-treated cells from treated cells. 2000 SK-BR-3 or 2250 BT474 cells were seeded in 15 µl MATRIGEL® per well of a 384 well plate (Greiner 781091). The next day a semi-log titration ranging from 10 to 0.003 µg/ml of antibodies were added in culture medium in the absence or presence of 5 ng/ml HRG. The test antibodies included a negative control antibody, pertuzumab+trastuzumab (1:1 v/v), PB3448, PB4188 and the bispecific anti-EGFR×HER3 two-in-one antibody MEHD7945A. In addition a dose-dependent titration of HRG was included as a positive control. Each dose was tested in quadruplicate. Cells were incubated for 7 days in a cell culture incubator at 37° C., 5% CO2. Next, the cells were fixed and actin cytoskeleton of the cells was stained with phalloidin and the nuclei are stained with Hoechst. Next, fluorescent images were taken at different levels through the gel (Z-stack) and the images were superimposed. A broad range of morphological features were measured (800 in total). Only features that differed between medium and HRG treatments were selected for analysis. Features that were associated with growth, mean spheroid area and nuclei per spheroid were most significantly different between medium and HRG treatments. Both multiparameter and single parameter analyses were made. For single parameter measurements, t-tests were performed to compare treatments (HRG or antibody) to medium. P-values for each point were determined. Principal component analysis (PCA), a method for finding low-dimensional combinations of high-dimensional data that capture most of the variability was used in relation to antibody concentration, to plot the data. FIG. 9 demonstrates the effect of pertuzumab+ trastuzumab (1:1 v/v), PB3448 and PB4188 in the presence of HRG. In both HER2 amplified breast cancer cell lines PB4188 showed superior activity compared to pertuzumab+ trastuzumab, PB3448 and the two-in-one antibody MEHD7945A in the presence of HRG.

Figure 10A:
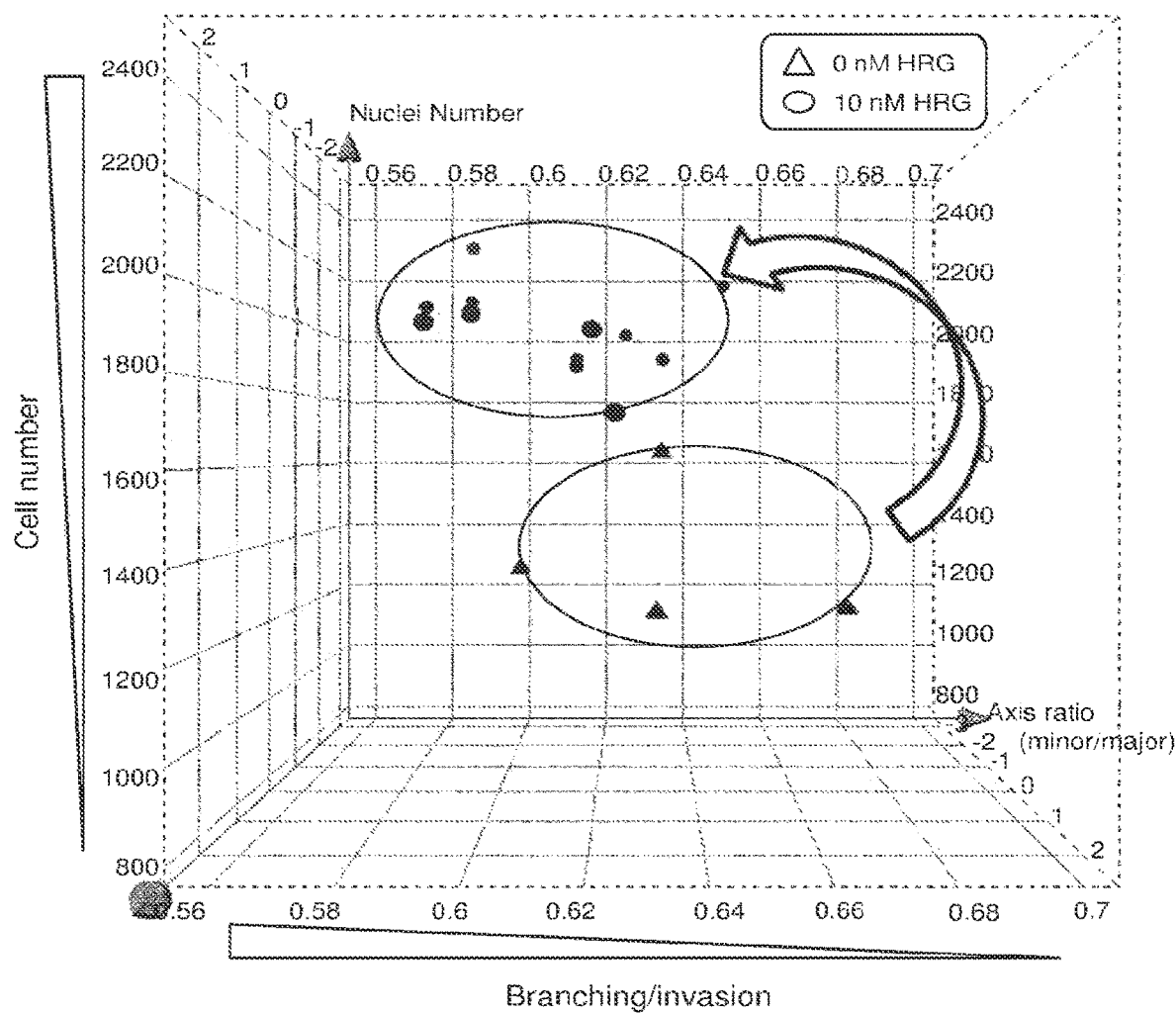
FIG. 10a: HRG induced proliferation and branching/invasion of SKBR-3 cells in MATRIGEL®.
Figure 10B:
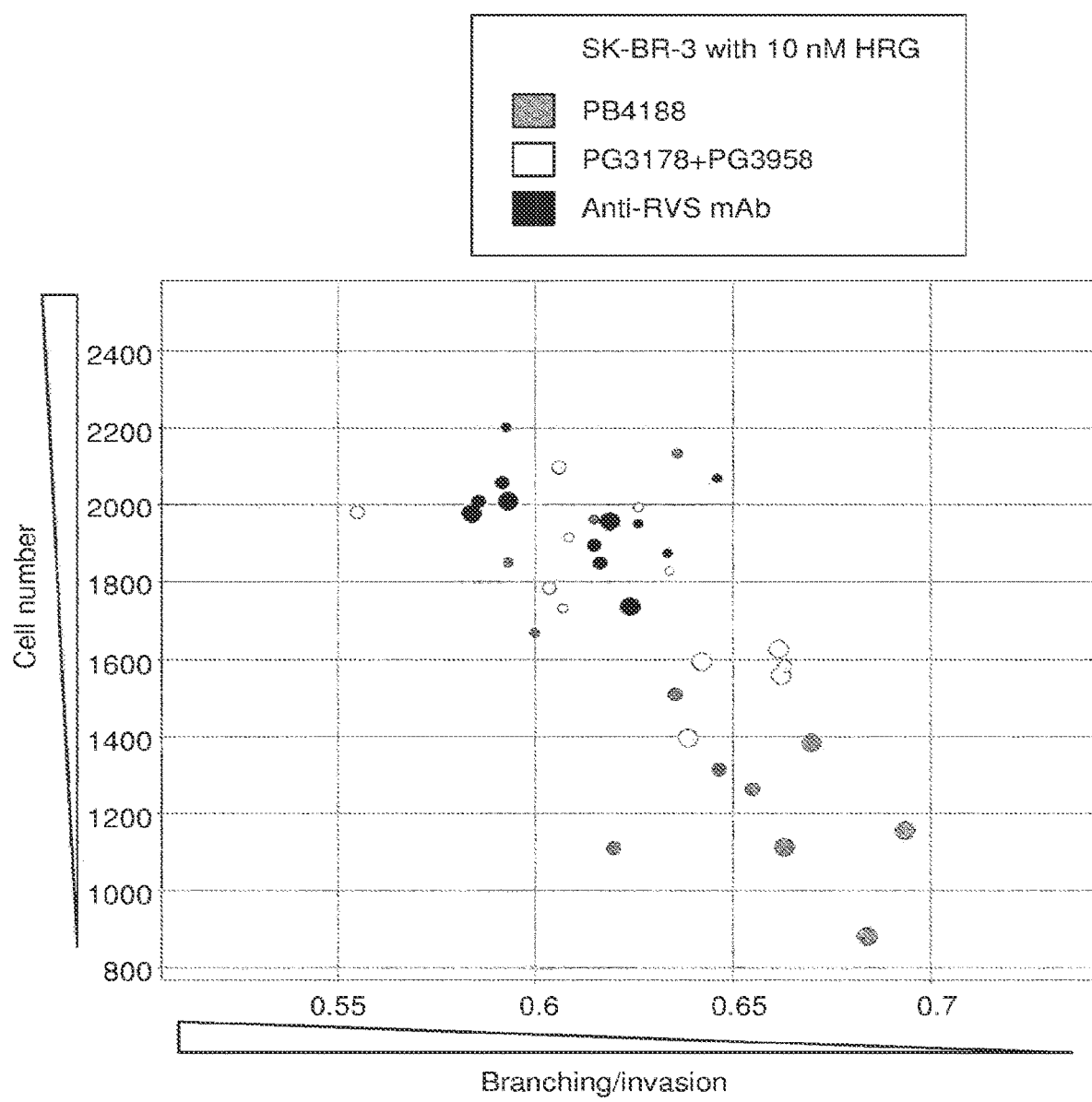
FIG. 10b: Inhibition of HRG induced proliferation and branching/invasion of SKBR-3 cells in MATRIGEL® by PB4188 in contrast to the parental monoclonal antibodies.
Figure 10C:
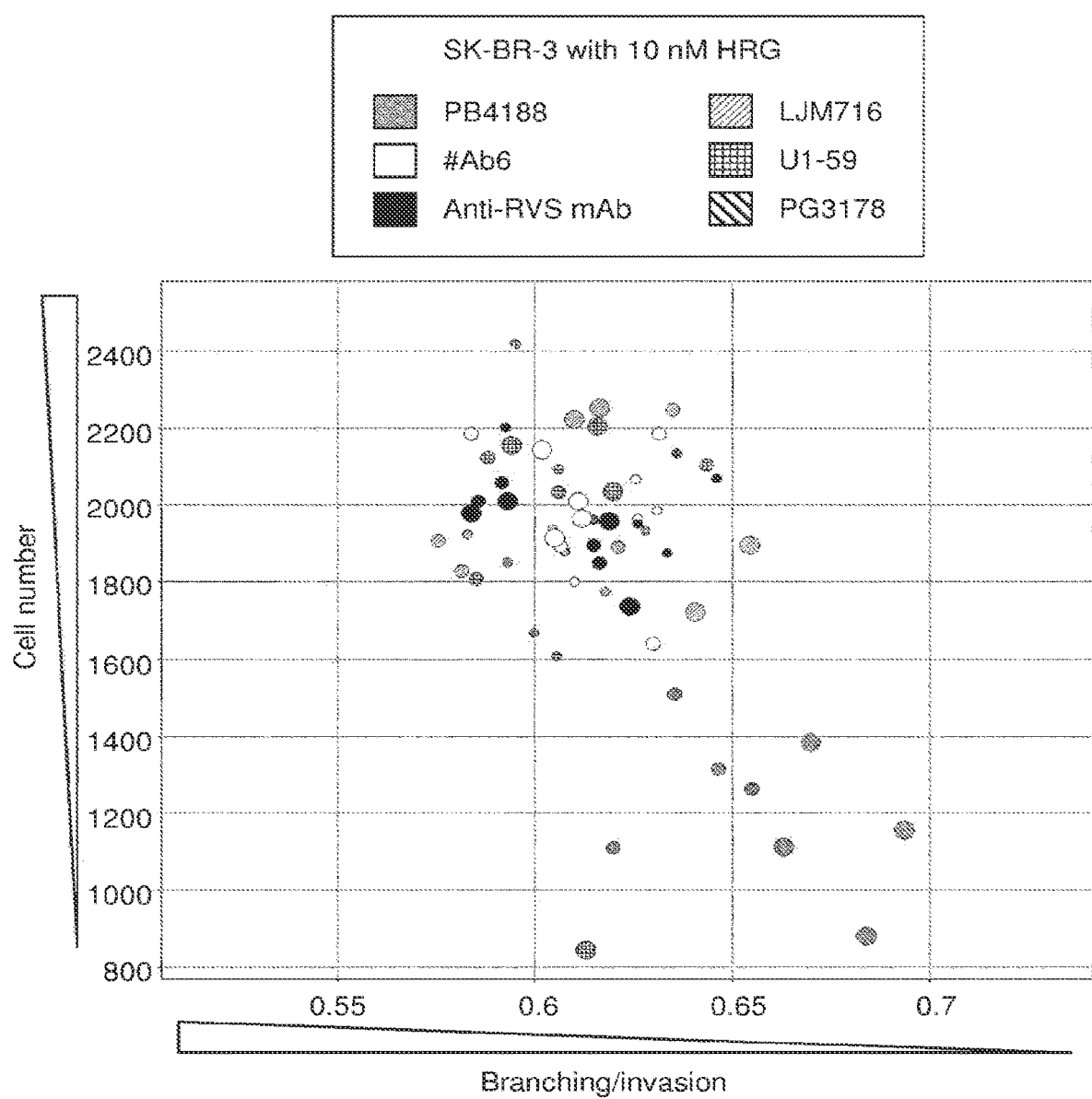
FIG. 10c: Inhibition of HRG induced proliferation and branching/invasion of SKBR-3 cells in MATRIGEL® by PB4188 in contrast to anti-HER3 monoclonal antibodies.
Figure 10D:
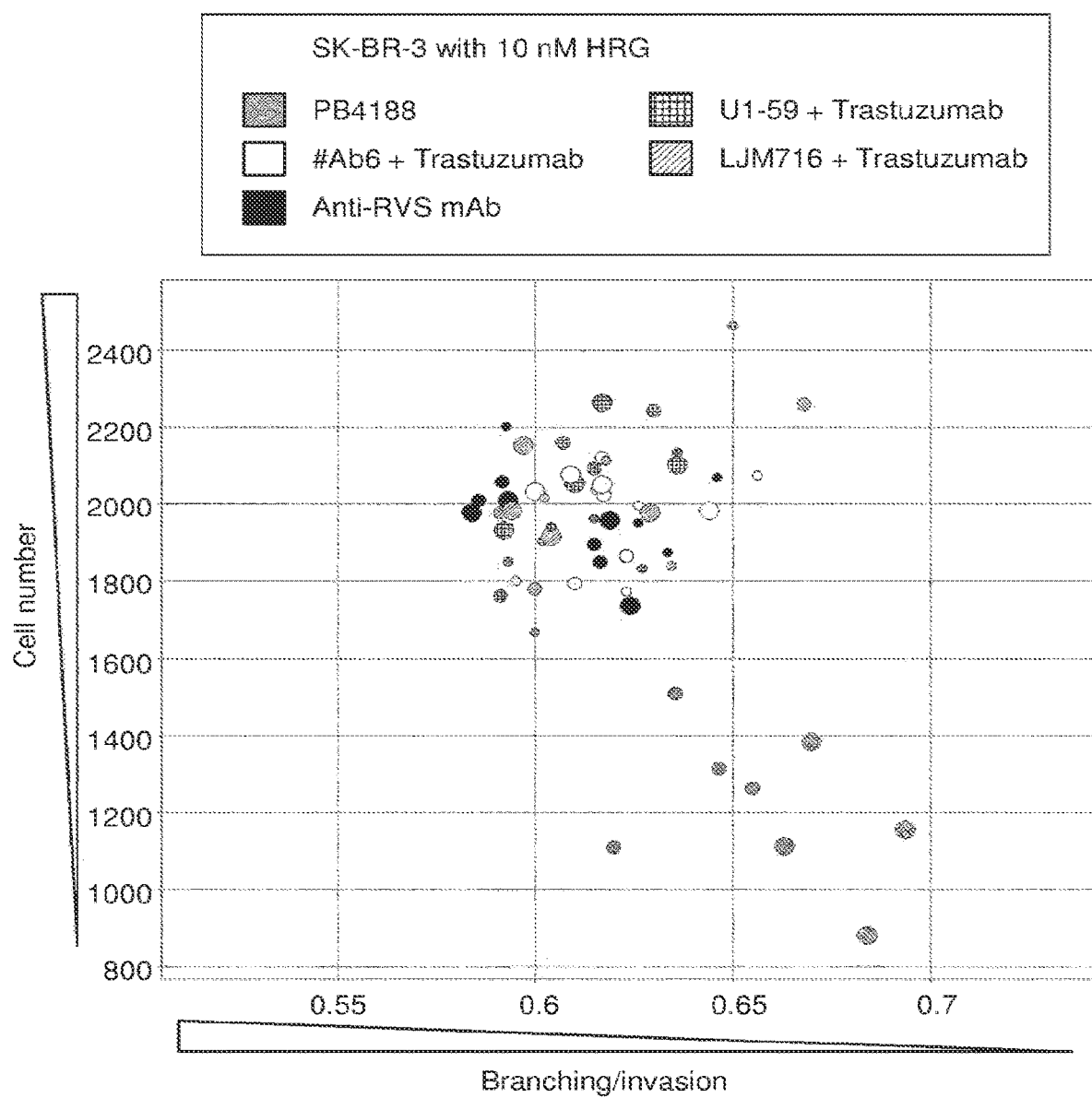
FIG. 10d: Inhibition of HRG induced proliferation and branching/invasion of SKBR-3 cells in MATRIGEL® by PB4188 in contrast to combinations of anti-HER3 monoclonal antibodies with trastuzumab.
Figure 10E:
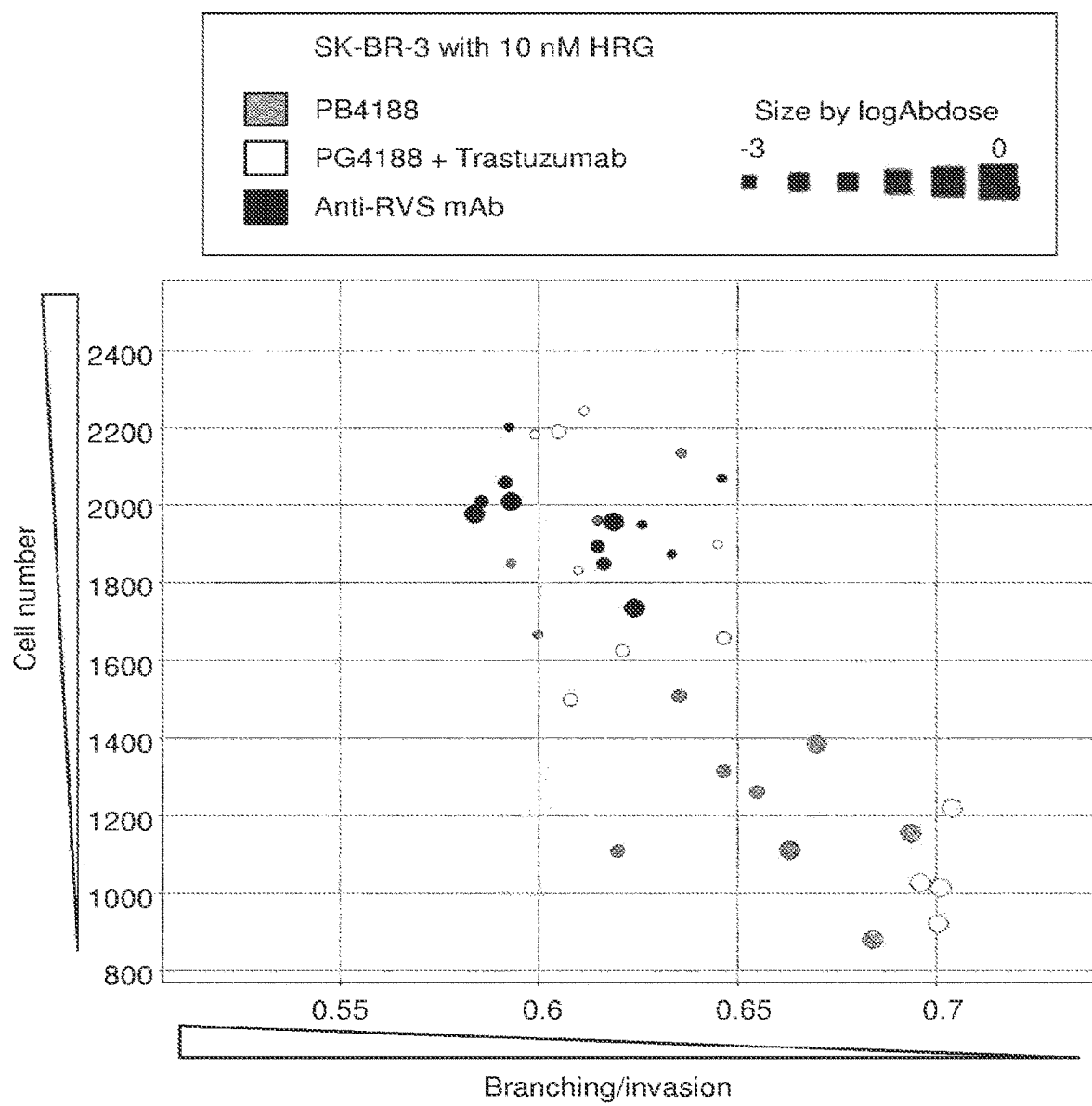
FIG. 10e: Inhibition of HRG induced proliferation and branching/invasion of SKBR-3 cells in MATRIGEL® by PB4188 and the combination PB4188 plus trastuzumab

Superior Anti-Proliferative Activity of PB4188 in the Presence of HRG on HER2 Amplified Breast Cancer Cells The activity of PB4188 in the presence of 10 ng/ml HRG on SKBR-3 and BT-474 was compared to a panel of HER2, HER3 antibodies and combinations thereof. The assay was performed in MATRIGEL®, as described above, and morphological features were analyzed. PCA data plotted in FIG. 10a show the HRG-induced proliferation and branching/invasion of SKBR-3 cells in MATRIGEL®. FIG. 10b shows that antibody PB4188 can completely revert the HRG induced phenotype, whereas the combination of the parental monoclonal antibodies (PG3958+PG3178) has no effect. Moreover, PB4188 was far more effective compared to all anti-HER3 antibodies tested (FIG. 10c). In addition, combinations of the individual anti-HER3 antibodies with trastuzumab (the current standard of care in metastatic breast cancer (mBC)) were not able to revert the HRG induced phenotype (FIG. 10d). Adding trastuzumab to PB4188 in the presence of HRG reduced the proliferation and branching/invasion of SK-BR-3 cells compared to PB4188 alone (FIG. 10e).

Superior Anti-Proliferative Activity of PB4188 on HER2 Amplified Gastric Cancer Cells Compared to HER2 and HER3 Monoclonal Antibodies.

Figure 11A:
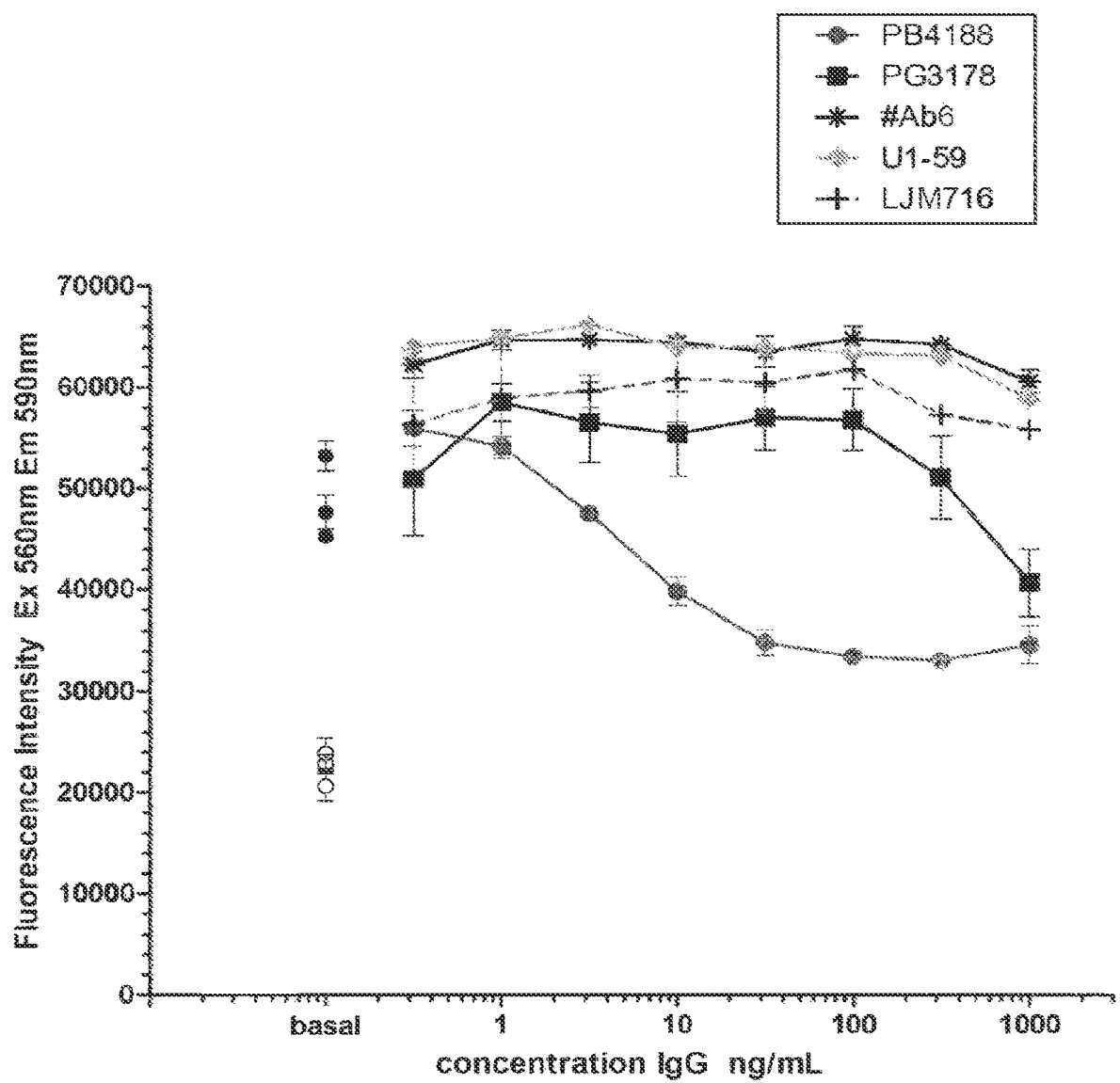
FIGS. 11A and 11B: Superior inhibitory activity of PB4188 in HER2$^{+++}$ N87 cells in the presence of 100 ng/ml HRG.
Figure 11B:
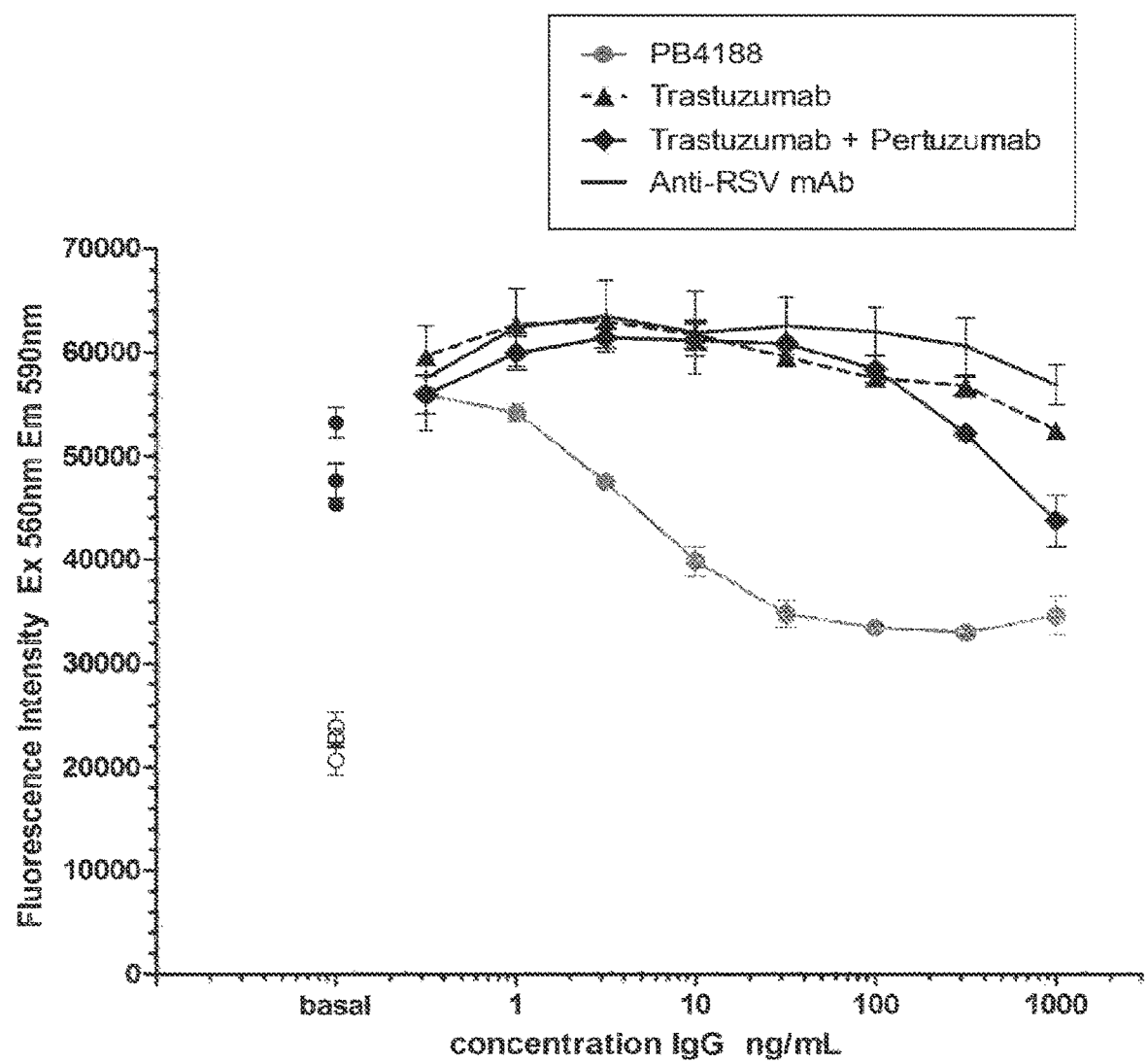

Upregulation of NRG1-β1 is a key resistance mechanism against HER2 targeted therapies (Wilson, 2012). To evaluate whether upregulation of NRG1-β1 would interfere with the anti-proliferative potency of PB4188 a panel of antibodies was tested at 100 ng/ml HRG on the N87 (HER2 amplified) gastric cancer cell line. N87 cells were cultured in RPMI 1640 supplemented with 10% heat inactivated FBS. For the proliferation assay subconfluent cell cultures of N87 cells were washed with PBS trypsinized and trypsin was inactivated by adding culture medium. Cells were washed twice in large volumes of assay medium (RPMI 1640 medium containing 0.05% BSA and 10 µg/ml Holo Transferrin). Antibodies were diluted in a semi-log titration that varied from 1-0,0001 µg/ml. Cells were added at a density of 10000 cells/well in the presence of 100 ng/ml final concentration of HRG. The cells were cultivated for 3 days at 37° C., 5% CO2, in 95% relative humidity. ALAMAR BLUE™ (INVITROGEN®) was added according to the manufacturer's instructions and incubated for 6 hours at 37° C., 5% CO2, in 95% relative humidity in the dark. Fluorescence was measured at 550 nm excitation with 590 nm emission wavelength. PB4188 showed superior activity over anti-HER2 or anti-HER3 monoclonal antibodies (FIG. 11).

HER2λHER3 Bispecific Antibodies Induce ADCC

Figure 12:
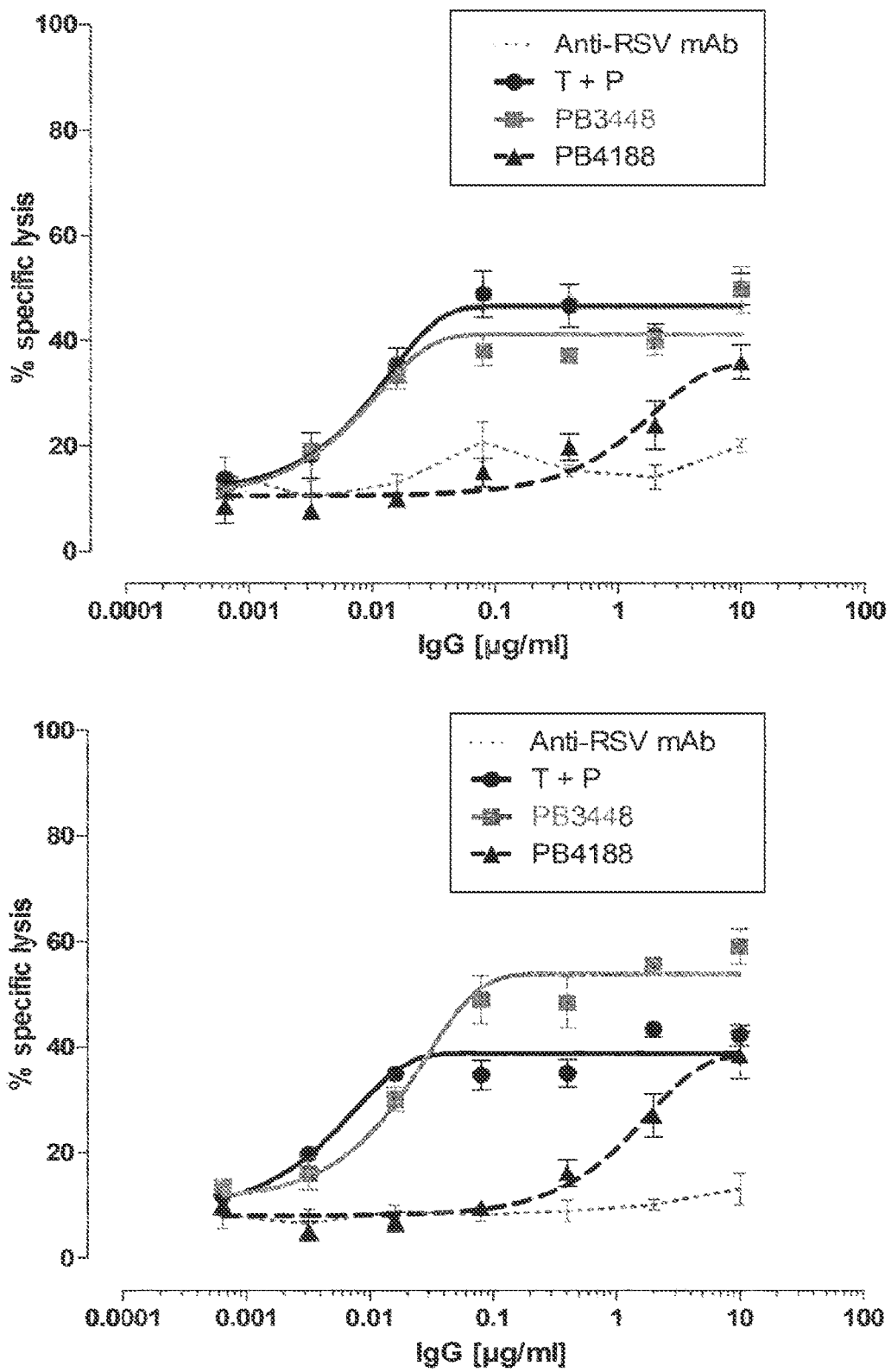
FIG. 12: ADCC activity of PB4188 and PB3448 in a dose titration

ADCC activity is an important anti-tumour mechanism of action for therapeutic antibodies in cancer. Human monoclonal antibodies directed to the HER family of receptors like cetuximab and trastuzumab induce ADCC. The baseline and enhanced ADCC activity of PB4188 and PB3448 were determined in validated in vitro ADCC assays. Trastuzumab and a negative control antibody were included as control antibodies in the experiment. Whole blood and PBMC fractions were obtained from healthy donors. Each antibody was tested against the HER2 high (SK-BR-3) and HER2 low (MCF-7) expressing target cells. Target cells were loaded with $^{51}$Cr (Amersham) and opsonized with the indicated concentrations of antibody. Whole-blood or PBMC fraction were used as effector cells in a 200 µL reaction in RPMI 1640+10% heat inactivated FCS. Cells were incubated together for 4 h, and lysis was estimated by measuring radioactivity in the supernatant using a γ-scintillator. Percentage of specific lysis was calculated as follows: (experimental cpm−basal cpm)/(maximal cpm−basal cpm)×100, with maximal lysis determined in the presence of 5% Triton X-100 and basal lysis in the absence of antibody and effectors. As shown in FIG. 12 bispecific antibody PB3448 showed similar ADCC activity compared to the combination pertuzumab+trastuzumab. Bispecific antibody PB4188 was effective at high antibody concentrations (10 µg/ml).

HER2×HER3 Bispecific Antibodies Show Higher ADCC Compared to the Combination of Parental Antibodies In a different ADCC setup, the ADCC Reporter Bioassay (Promega) was used. The bioassay uses engineered Jurkat cells stably expressing the FcγRIIIa receptor, V158 (high affinity) or F158 (low affinity) variant, and an NFAT response element driving expression of firefly luciferase. The assay was validated by comparing data obtained with the ADCC Reporter Bioassay to the classical $^{51}$Cr release assay. The ADCC assays were performed using the Promega ADCC Bioassay kit using 384 white well plates. In this experimental setup SKBR-3 cells were plated at a density of 1000 cells/well in 30 µl assay medium (RPMI with 4% low IgG serum) 20-24H before the bioassay. The next day, the culture medium was removed. Next, a serial dilution of antibodies, PB4188 and its parental anti-HER2 PG3958 and anti-HER3 PG3178 as well as the combination thereof was generated in duplo. 10 µl antibody dilutions were added to the wells. The starting concentration of the antibody was 10 µg/ml and a 10 points semi-log fold serial dilution was generated to provide a full dose-response curve. Finally, 5 µl of ADCC Bioassay effector cells (15000 cells/well, V158) were added. The cells were incubated for 6H at 37° C.

Figure 13:
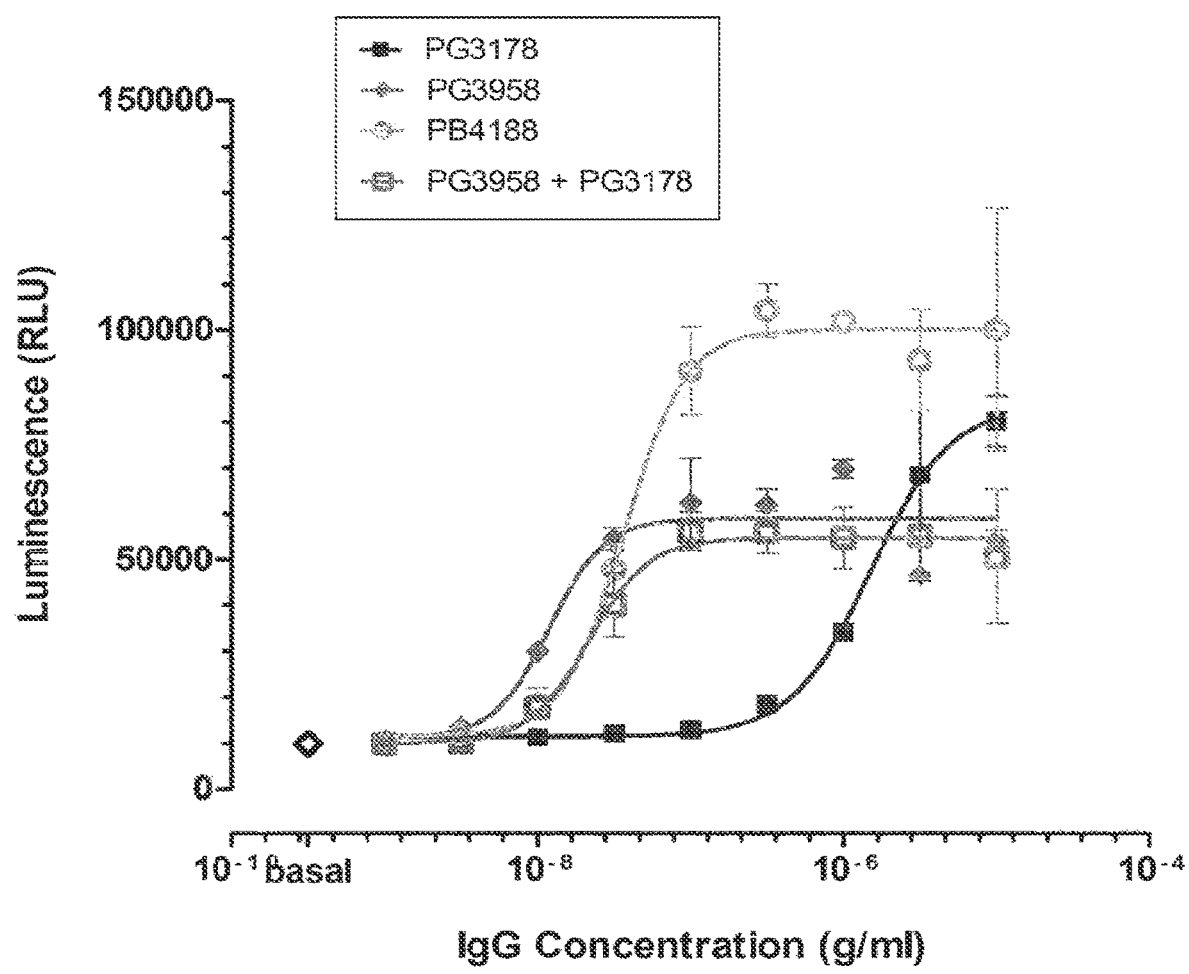
FIG. 13: Increased ADCC activity of bispecific antibody compared to monoclonal parental antibodies or a combination thereof

Next, 15 µl BIO-Glo luciferase substrate was added and 5 minutes later luminescence was detected in a plate reader. The obtained data are shown in FIG. 13. The PB4188 bispecific anti-HER2×HER3 antibodies showed a higher ADCC potency compared to the parental HER2 and HER3 monoclonals or a combination thereof.

ADCC Enhancement of PB4188

Figure 14:
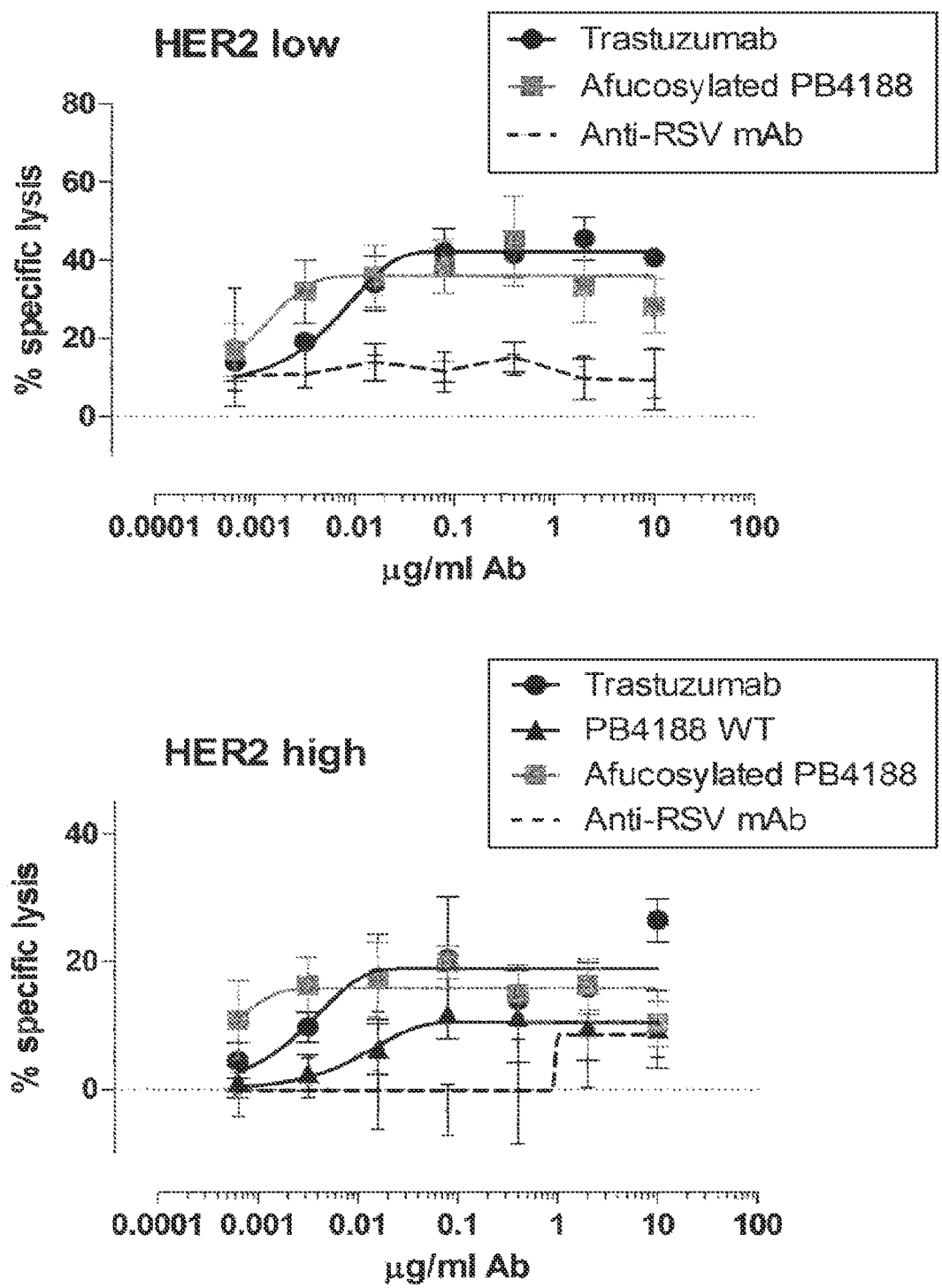
FIG. 14: ADCC activity of afucosylated PB4188 compared to trastuzumab on low (upper panel) and high (lower panel) HER2 expressing cells

ADCC activity can be enhanced by different techniques, one of them being the removal of fucose. Removal of fucose has resulted in increased anti-tumour activity in several in vivo models [Junttila, 2010]. To maximize PB4188 activity, afucosylation technology was applied (Cheng Liu and Andreia Lee. ADCC Enhancement Technologies for Next Generation Therapeutic Antibody. Antibody therapeutics—Trends in Bio/Pharmaceutical Industry 2009 [13-17]), thereby preventing fucosylation of the N-linked carbohydrate structure in the Fc region. The ADCC potency of afucosylated PB4188 compared to the wildtype PB4188 was determined in an ADCC $^{51}$Cr release assay using HER2 low expressing cells (MCF-7) and HER2 amplified cells (SK-BR-3). Both antibodies were applied in a serial dilution and a negative control antibody and trastuzumab were included in the assay. FIG. 14 shows the increase in ADCC potency of afucosylated PB4188 compared to the wild type version and/or trastuzumab in both high and low HER2 expressing cells.

Figure 15A:
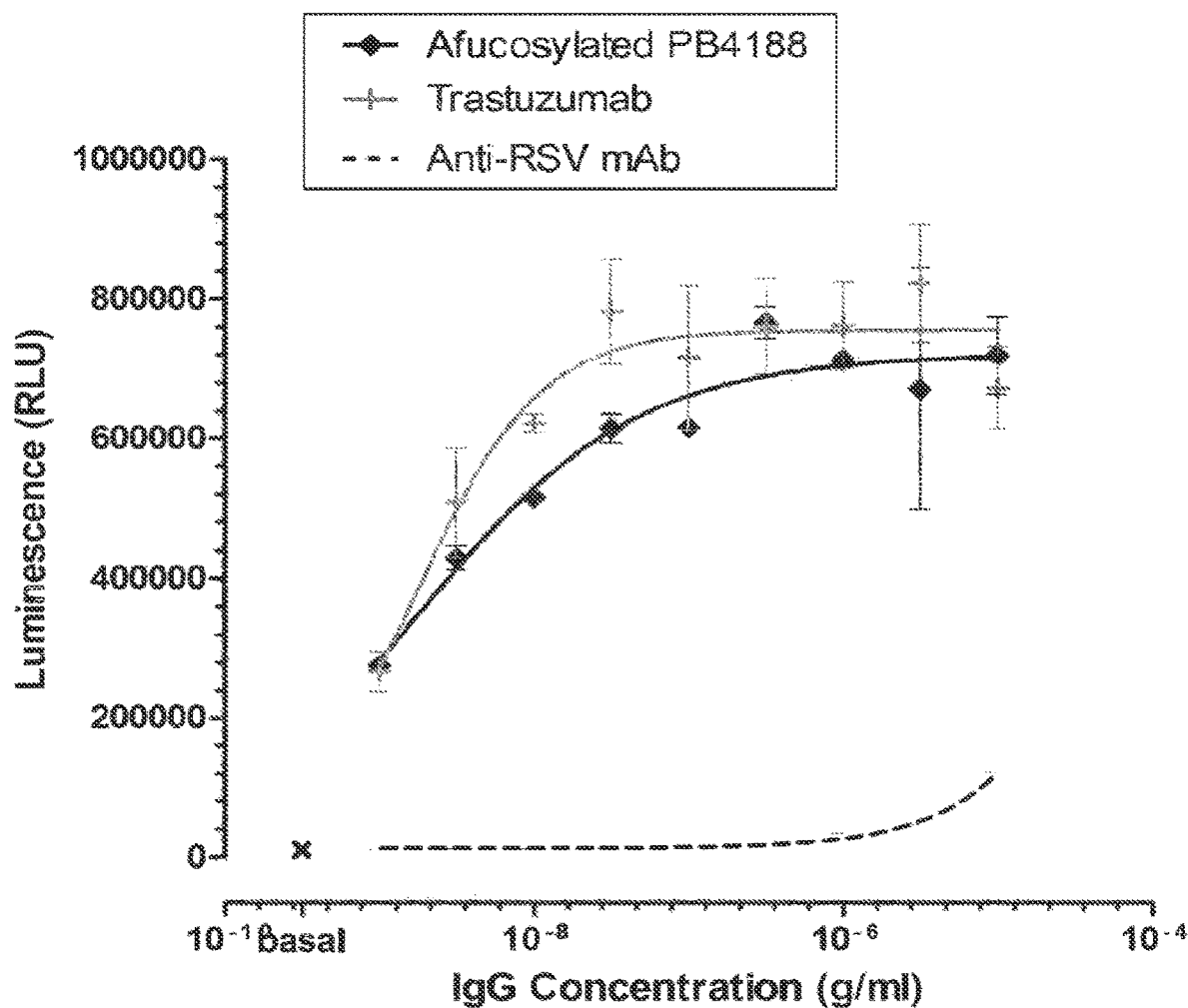
FIGS. 15A and 15B: ADCC activity of afucosylated PB4188 on SKBR-3 HER2$^{+++}$ cells in the presence of reporter cells expressing a high or low FcγR variant
Figure 15B:
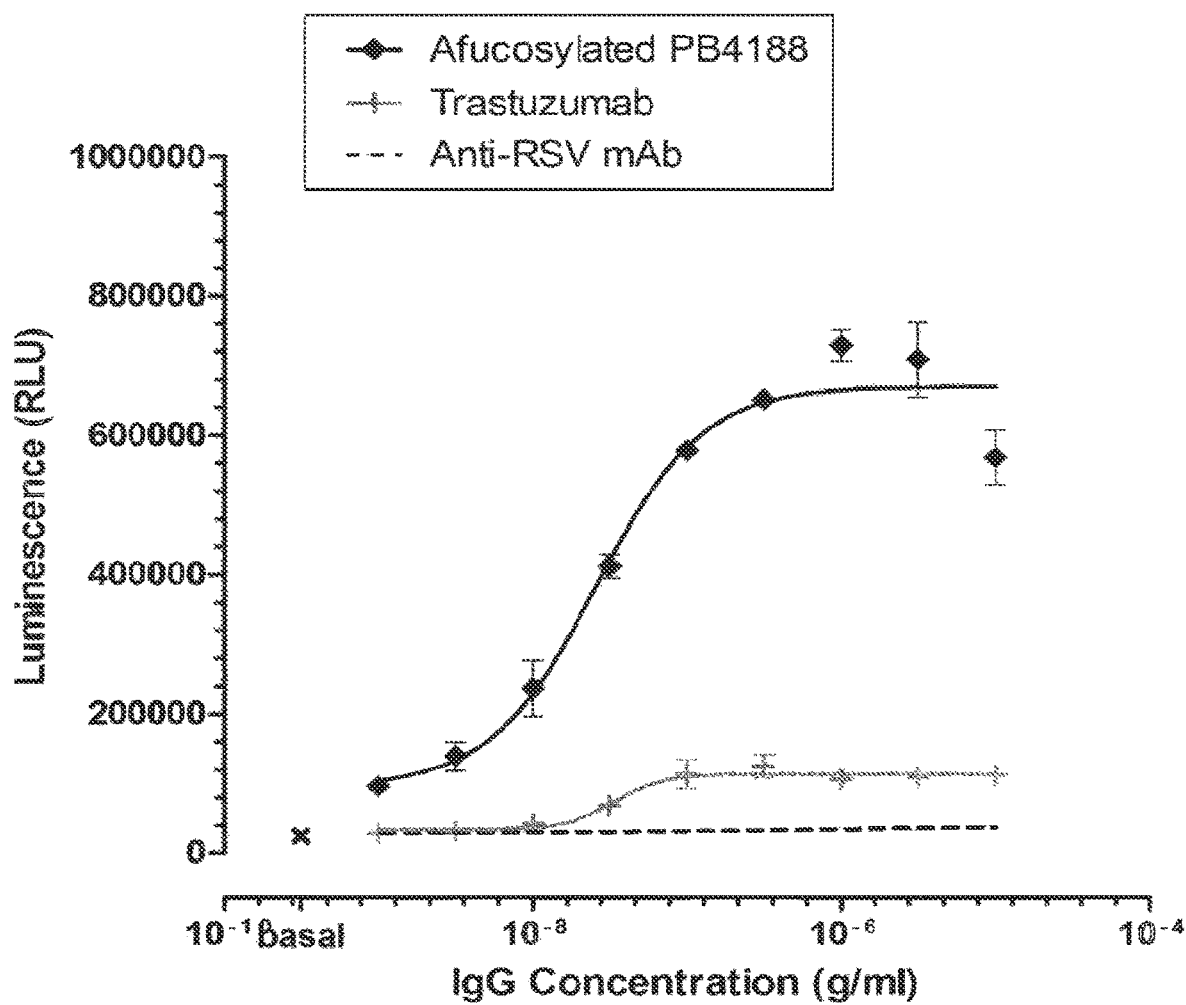

Afucosylated PB4188 Shows Superior ADCC Activity with Low Affinity FcγRIII Receptors Afucosylated PB4188 activity was tested on ADCC reporter cells containing either the V158 (high affinity) FcγRIIIa receptor variant or the F158 (low affinity) FcγRIIIa receptor variant. A serial titration of antibody, i.e. control antibody, trastuzumab and afucosylated PB4188, was added in combination with ADCC reporter cells harbouring the different FcγRIIIa variants to adherent SK-BR-3 cells. ADCC activity was measured by measuring luciferase activity. Afucosylated PB4188 showed equal activity compared to trastuzumab in combination with the high affinity V158 FcγRIIIa receptor variant. In contrast afucosylated PB4188 displayed superior ADCC activity compared to trastuzumab in combination with the low affinity F158 FcγRIIIa receptor variant. (FIG. 15)

JIMT-1 Xenograft Study

JIMT-1 human breast carcinoma cells were grown in DMEM containing 10% fetal bovine serum, 100 units/mL penicillin G sodium, 100 µg/mL streptomycin sulfate, 25 µg/mL gentamicin, and 2 mM glutamine until the time of implantation. At the day of implantation JIMT-1 breast cells were harvested during log phase growth and resuspended in cold PBS. Female CB.17 SCID mice (Charles River) were 8 weeks old on Day 1 of the study and had a body weight range of 16.5 to 20.7 g. Each mouse was injected subcutaneously in the right flank with $5 \times 10^6$ tumor cells (0.2 mL cell suspension). The tumors were measured with a caliper in two dimensions to monitor size as the mean volume twice per week. Once tumors had reached approximately 100-150 mm$^3$ in size animals were enrolled in the efficacy study. Outlier animals—tumor volume—were removed and the mice were randomly distributed into groups of 10 mice each. Mice were injected once weekly (antibody) or daily (lapatinib) for a period of four weeks. Details of the treatment groups are depicted in Table 11.

Figure 17A:
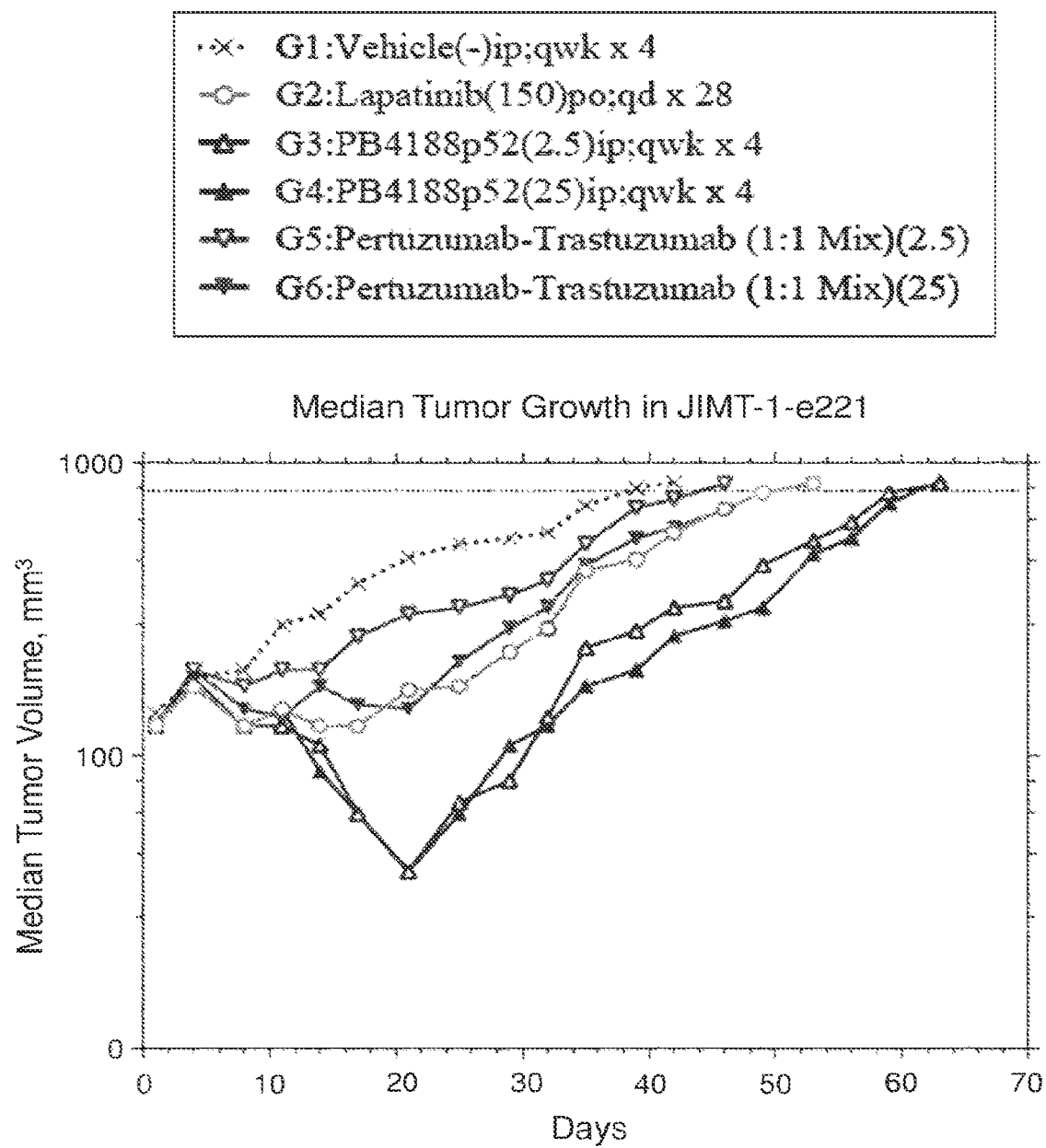
FIGS. 17A and 17B: Antibody treatment effect on tumor size in a JIMT-1 murine xenograft model. Tumor growth measured by tumor volume caliper measurement of the different treatment groups. 17A: tumor growth during 60 days; 17B: tumor growth inhibition (TGI) at the end of treatment period (29 days).
Figure 17B:
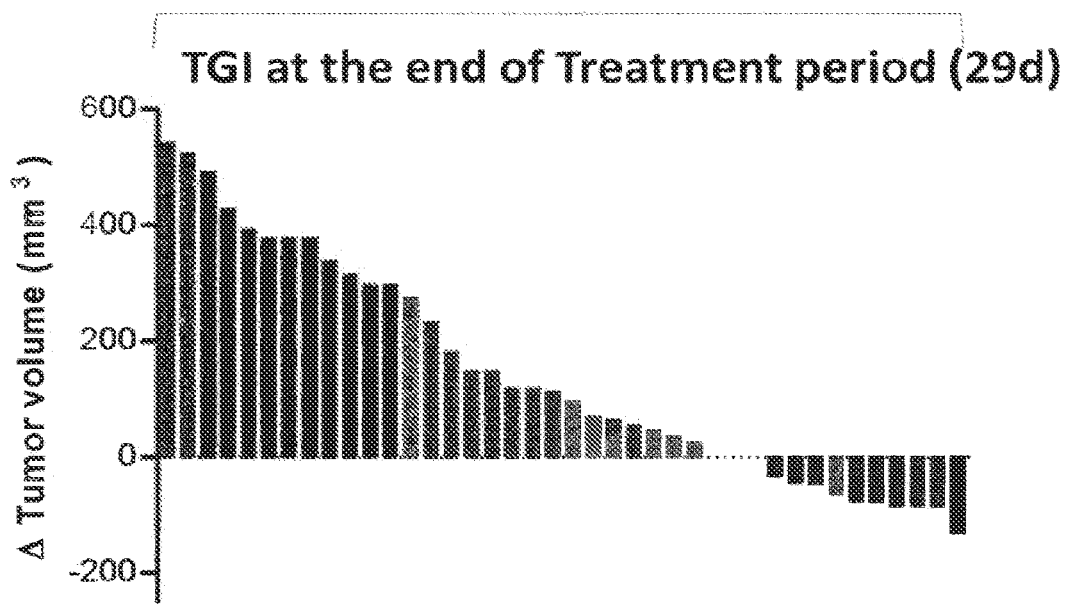
Figure 18:
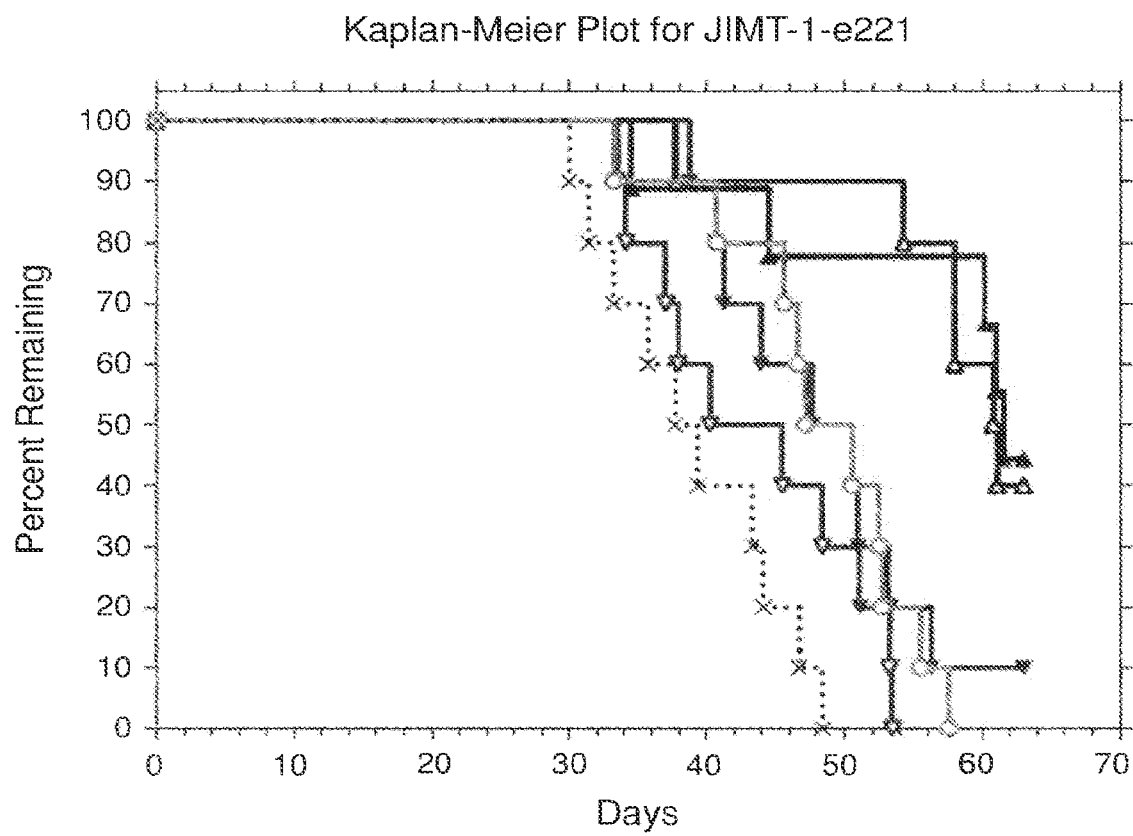
FIG. 18: Kaplan-Meier survival curves of the different treatment groups in the JIMT-1 murine xenograft model.

Tumor sizes were measured weekly by caliper measurement. The efficacy study revealed that PB4188 at both dosing schedules was equal effective and more potent than lapatinib or the combination pertuzumab and trastuzumab. The data are shown in FIGS. 17 and 18.

PB4188 can Overcome HRG Mediated Resistance

Figure 19:
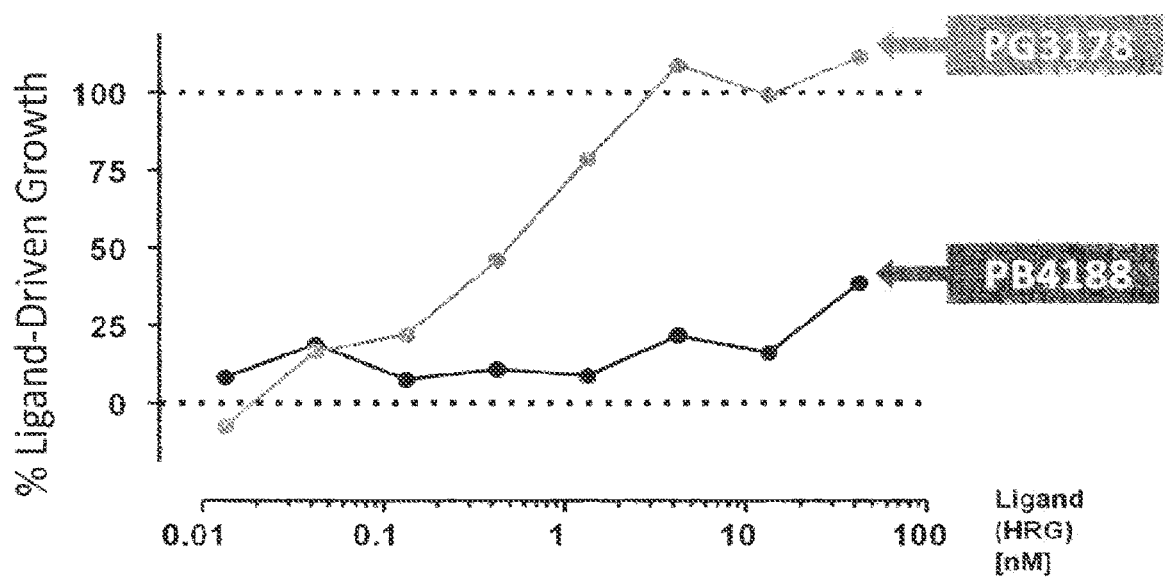
FIG. 19: Inhibition of N87 ligand driven growth. HRG driven proliferation of N87 can be overcome over a wide range of HRG by PB4188 in contrast to the parental anti-HER3 antibody. Data shown at antibody concentration of 40 ng/ml.

Upregulation of NRG1-β1 is a key resistance mechanism against HER2 targeted therapies (Wilson, 2012). PB4188 was tested in comparison to its parental anti-HER3 monoclonal antibody PG3178 in a serial titration in the presence of an increasing concentration of HRG (NRG1-β1 EGF). To this aim N87 cells were cultured in RPMI 1640 supplemented with 10% heat inactivated FBS. For the proliferation assay subconfluent cell cultures of N87 cells were washed with PBS trypsinized and trypsin was inactivated by adding culture medium. Cells were washed twice in large volumes of assay medium (RPMI 1640 medium containing 0.05% BSA and 10 µg/ml Holo Transferrin). Antibodies were diluted in a semi-log titration ranging from 1 to 0.0001 µg/ml. Cells were added at a density of 10000 cells/well in the presence an increasing concentration of HRG (0.04-39.5 nM). The cells were cultivated for 3 days at 37° C., 5% CO2, in 95% relative humidity. ALAMAR BLUE™ (INVITROGEN®) was added according to the manufacturer's instructions and incubated for 6 hours at 37° C., 5% CO2, in 95% relative humidity in the dark. Fluorescence was measured at 550 nm excitation with 590 nm emission wavelength. PB4188 showed superior activity compared to the parental anti-HER3 monoclonal antibody (FIG. 19).

Hence, in case of an escape mechanism, such as for instance upregulation of NRG1-β1, a bispecific antibody according to the invention is preferred.

Epitope Mapping of HER2/HER3 Specific IgGs

Shotgun Mutagenesis Experiments

Alanine scanning mutagenesis was used to map the epitopes of PG3958 and PG3178 for HER2 and respectively HER3. In the shotgun mutagenesis assay, clones are generated whereby each amino acid residue of the HER2/HER3 extracellular domain (ECD) is substituted for alanine. Next, a cell array was prepared by reverse transfection (patent US2011/0077163A1). Therefore, DNA of each clone was mixed with lipofectamin and the mixture was placed in a dedicated well of a 384 well plate. HEK293T cells were added to each well and expression of protein was measured 24H later. Subsequently, the reactivity of antibodies was measured by immunofluorescent staining leading to binding maps and identification of critical residues for antibody binding. Expression levels of the HER2 and HER3 ECD constructs were verified by FACS analysis using commercially available monoclonal antibodies (R&D mAb 1129 (HER2) and R&D mAb 66223 (HER3)).

HER2

Figure 21A:
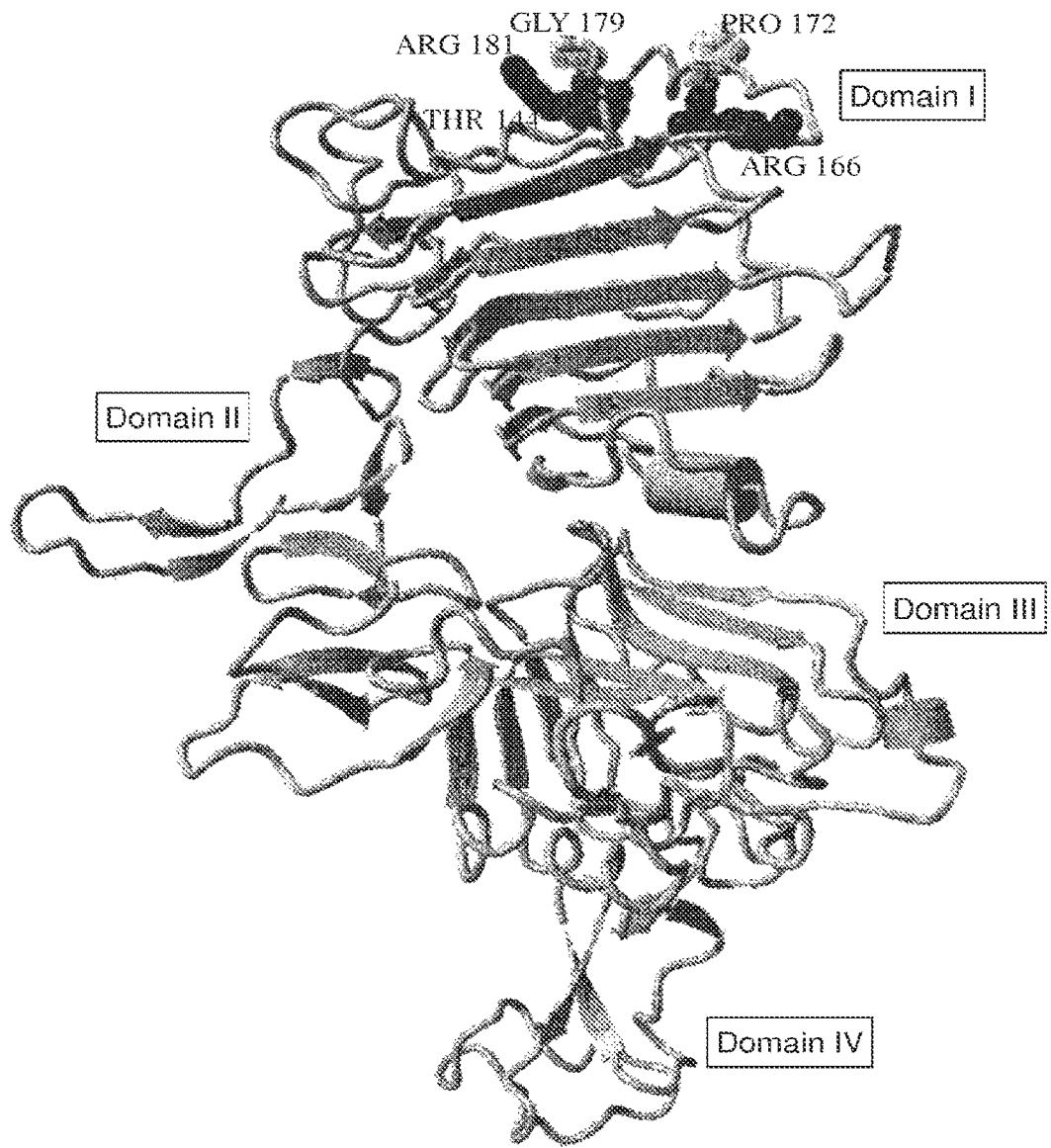
FIG. 21A: Epitope mapping HER2. Critical residues identified are represented as black spheres on the HER2 crystal structure, secondary critical residues identified are represented as gray spheres (PDB ID #1S78).
Figure 21B:
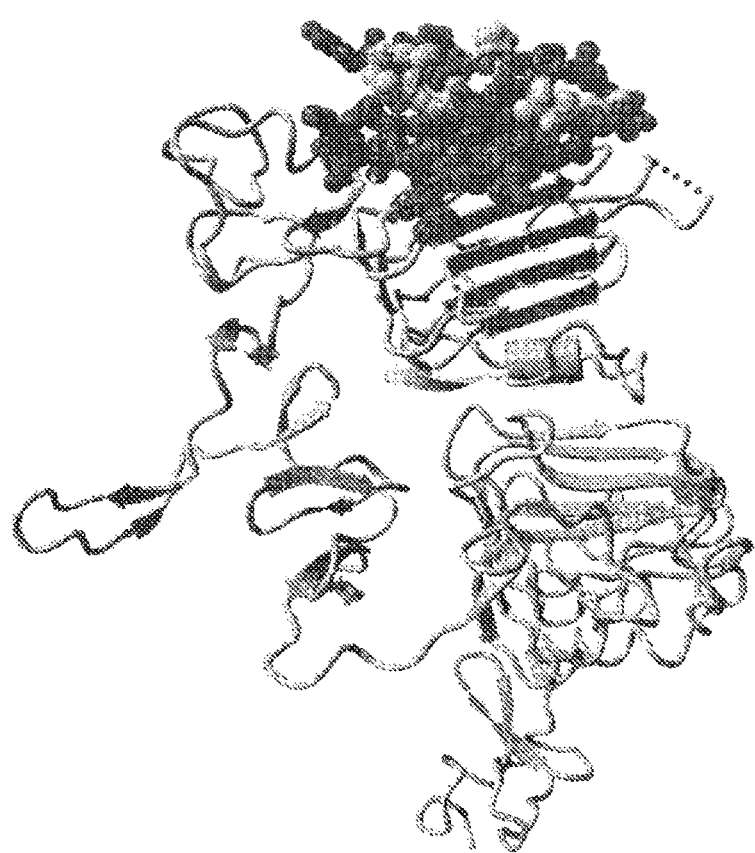
FIG. 21B a) HER2 crystal structure (PDB #1S78) showing verified PG3958 epitope residues as light gray spheres and surrounding residues (+/−five amino acid residues) as dark gray spheres. b) Solvent exposed surface of epitope region showing verified epitope residues in gray and surrounding residues (+/−five residues) in black. c) Detailed view of epitope region with verified epitope residues in light gray and surrounding residues (+/−five residues) in dark gray. d) Primary amino acid sequence of HER2 PG3958 epitope region indicating verified epitope residues (gray underlined), surrounding residues (black) and distant residues (gray italic, not shown in a, b and c). Figures and analyses were made with Yasara (www.yasara.org).
Figure 21B:
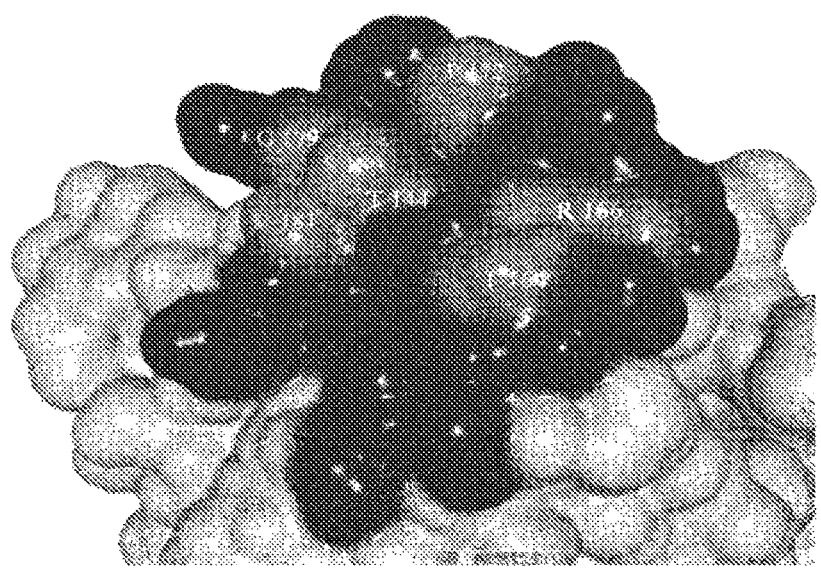
Figure 21B:
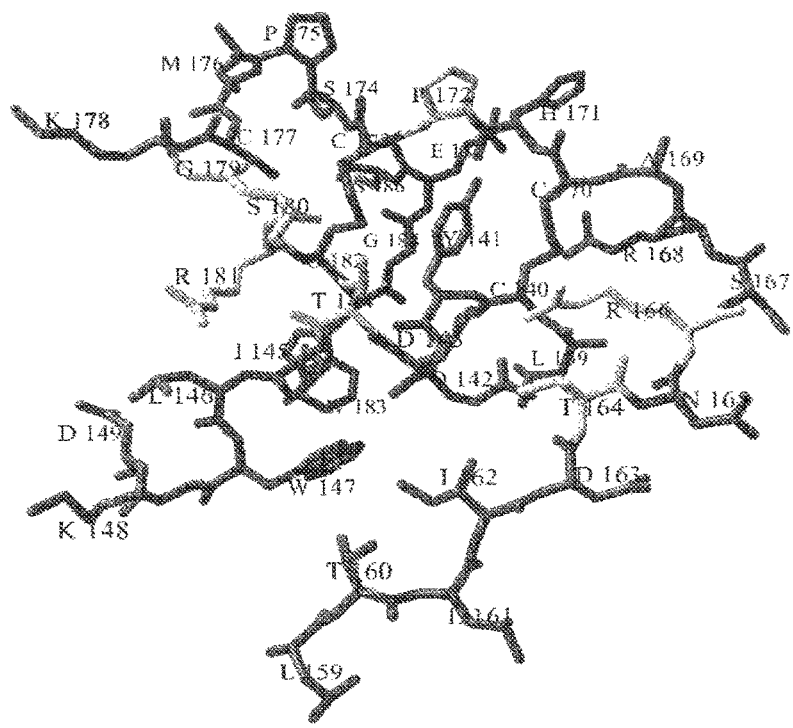
Figure 21C:
FIG. 21C.
Figure 21C:
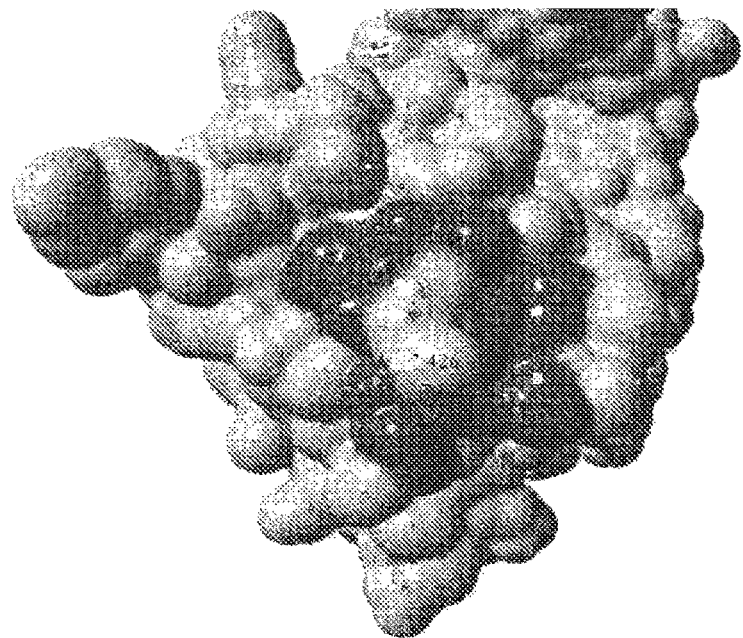
Figure 21C:
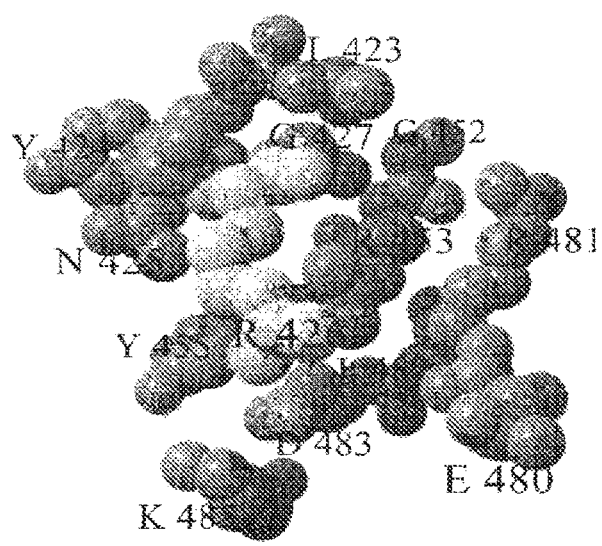

Binding of monovalent PG3958 Fab to HER2 ECD mutants was tested at a concentration of 0.25 µg/ml in the assay and stringent washing conditions were used (pH 9.0, 350 mM NaCl). This resulted in the identification of three 'critical' residues (T144, R166, R181) in HER2 that showed less than 35% residual binding of the PG3958 Fab compared to WT HER2 while retaining control mAb binding. Two residues (P172, G179) that are positioned near the critical residues in the HER2 structure showed significant, but less severe loss of binding and were designated 'secondary critical' residues (Table 13 and FIG. 21A). All these surface-exposed residues are located in Domain I of HER2 and together they form a discontinuous patch on the surface of the HER2 molecule.

Confirmation Experiments HER2 Epitope

Constructs encoding Wildtype (WT) HER2 ECD and the HER2 ECD variants listed in Table 13 were expressed in CHO-K1 cells. Three Domain I residues that are surface exposed and structurally near the determined critical residues were selected for further analysis. T164, S180 and D143 point mutations to tyrosine were generated in the HER2 ECD construct and the resulting constructs were also expressed in CHO-K1. The L159A HER2 ECD variant was expressed in CHO-K1 cells as control sample.

The bispecific PG3958×TT antibody tested for binding to the ECD variants in a FACS titration experiment. The anti-HER2 antibody trastuzumab which binds domain IV of HER2 was used to verify HER2 ECD expression at the cell surface. Mean MFI values were plotted and for each curve the AUC was calculated using GraphPad Prism 5 software. WT HER2 binding was used to normalize the data. The FACS data showed that in addition to T144A, R166A, R181A, P172A, G179A the mutations T164Y and S180Y resulted in significant reduction in binding of the PG3958×TT antibody (FIG. 22). The D143Y mutation resulted in severe loss of expression as demonstrated by the decreased binding of the control mAb, so its potential role in the PG3958 epitope could not be determined.

HER3

Binding analysis of PG3178 IgG at 0.25 µg/ml to HER3 ECD mutants in FACS resulted in the identification of two so-called 'critical' residues (F409, R426) for which mutation to alanine caused substantial loss of binding compared to WT HER3, while binding of the control mAb was retained (Table 14 and FIG. 23). Both residues are located in Domain III of HER3 and spatially distant. Moreover, F409 is buried in the HER3 hydrophobic core, which makes it unlikely to be part of the PG3178 epitope.

Confirmation Experiments HER3 Epitope

CHO-K1 cells were transfected with HER3 ECD mutation constructs (listed in Table 14), WT HER3 ECD and two control constructs (H407A and Y424A). PG3178 binding to the HER3 ECD variants was tested in a FACS titration experiment. Two control antibodies, binding Domain I (MM-121) and Domain III (MEHD7945A) of HER3 were included to verify HER3 ECD expression on the cell surface.

Mean MFI values were plotted and for each curve the AUC was calculated using GraphPad Prism 5 software. WT HER3 binding was used to normalize the data. The R426A mutation was shown to be critical for PG3178 binding whereas the binding to F409A could not be confirmed due to loss of cell surface expression (FIG. 24).

PB4188 Activity on Cardiomyocytes In Vitro

HER2 is involved in growth, repair, and survival of adult cardiomyocytes as part of a signalling network that involves the heregulin receptor complex HER2:HER4. Cardiotoxicity is a known risk factor in HER2 targeting and the frequency of complications is increased when trastuzumab is used in conjunction with anthracyclines thereby inducing cardiac stress. A model system based on human stem cell derived cardiomyocytes was used to test the potential toxicity of PB4188 and benchmark it against trastuzumab and the combination of trastuzumab and pertuzumab in the presence of the anthracyclin doxorubicin. Human stem cell derived cardiomyocytes (Pluriomics BV) were seeded at a concentration of 20.000 well in white flat-bottom assay plates (corning 655098). On day 5 of culture the medium was replaced for glucose and galactose free culture medium supplemented with 10 ng/ml HRG. On day 7 test antibodies were added in combination with doxorubicin (3 μM). Cell viability was assayed on day 9 using the Promega Cell titer Glo assay. The monospecific antibodies were tested at single concentrations of 68 nM whereas PB4188 was tested at three concentrations in the presence of 3 μM doxorubicin. FIG. 25 shows that the viability of the cardiomyocyte was unaffected by all PB4188 concentrations tested. In contrast, trastuzumab and the combination of trastuzumab and pertuzumab both reduced cardiomyocyte cell viability.

PB4188 Binding to Cells with Different HER2 Levels

The binding of PB4188 in comparison to trastuzumab and the HER3 antibody U1-59 was analyzed by FACS on breast and gastric cancer cell lines expressing different levels of HER2. Cells were considered HER2+++ if they express millions of HER2 copies and/or are HER2 gene amplified. The following cell lines were used: MCF-7 (HER 2+); MDA-MB-468 (HER2+, MKN-45 (HER2+), MDA-MB-175 (HER2+), MDA-MB-453 (HER2++), MDA-MB-361 (HER2++), ZR-75-1 (HER2++), JIMT-1 (HER2+++), BT-474 (HER2+++), SKBR-3 (HER2+++), SK-OV-3 (HER2+++), N87 (HER2+++). Cells of an exponentially grown culture were harvested by trypsin and diluted to $10^6$ cells/ml in FACS buffer (PBS/0.5% BSA/0.5 mM EDTA). 1-2 $10^5$ cells were added to each well in a U-bottom 96 well plate. Cells were centrifuged for 2 minutes at 300 g at 4° C. Supernatant was discarded by inverting plate(s) above, followed by flicking once. 50 μl of each IgG sample was added in a serial dilution from 3.16 ng-10 μg/ml and incubated for 1H on ice. Cells were centrifuged once, supernatant was removed and cells were washed twice with FACS buffer. 50 μl diluted 1:100 mouse anti human IgG gamma PE (INVITROGEN®) was added and incubated for 30-60 minutes on ice in the dark. Cells were centrifuged once, supernatant was removed and cells were washed twice with FACS buffer. Cells were analysed on a FACSCanto Flow cytometer in a HTS setting. The quantity of antibody bound was was assessed by median fluorescence. Data were plotted and the area under the curve (AUC, a cumulative measurement of the median fluorescence intensity) was determined for each antibody per cell line tested (FIG. 26).

From this experiment it is concluded that PB4188 has a higher binding affinity for HER2+++ cells, HER++ cells and HER+ cells as compared to trastuzumab.

Simultaneous Binding with Trastuzumab

PB4188 and Trastuzumab do not Compete for Binding to HER2

PB4188 binds domain I of the HER2 protein whereas the binding epitope of trastuzumab is localized in domain IV. To demonstrate that both antibodies do not compete for HER2 binding, a binding assay with HER2 amplified SKBR-3 breast cells was performed. First unlabeled antibody was allowed to bind SKBR-3 at saturating concentrations. Next FITC-labeled PB4188 was added in a titration range and fluorescence was measured by FACS. FIG. 27 demonstrates that PB4188$^{FITC}$ bound as effectively to cells in the presence of trastuzumab or the negative control. Pre-incubation of SKBR-3 cells with PB4188 prevented PB4188$^{FITC}$ from binding. Thus, trastuzumab and PB4188 do not compete for binding to HER2

Targeting Domain I of HER2 by a HER2xHER3 Bispecific Molecule can Overcome Heregulin Resistance To test whether the orientation of PB4188 on the HER2xHER3 dimer was preferred for inhibiting cell proliferation under HRG stress conditions, bispecific antibodies were generated composed of the 3178 HER3 arm and HER2 arms targeting either domain I, II, III or IV. Two HER2xHER3 bispecific antibodies were generated for each of the HER2 domains I-IV. The HER2 arms included: MF3958 and MF3003 targeting domain I; MF2889 and MF2913 targeting domain II; MF1847 and MF3001 targeting domain III and MF1849 and MF1898 targeting domain IV. Each HER2 Fab arm was combined with the 3178 HER3 Fab arm and tested for their potency to inhibit cell proliferation in the presence of high concentrations of heregulin. Antibody titrations were performed on HER2 low expressing MCF-7 cells and the HER2 overexpressing N87 and SK-BR-3 cells. Subconfluent cell cultures of N87, SK-BR-3, and MCF-7 cells were washed with PBS trypsinized and trypsin was inactivated by adding culture medium. Cells were washed twice in large volumes of assay medium (RPMI 1640 medium containing 0.05% BSA and 10 μg/ml Holo Transferrin). Antibodies were diluted in a semi-log titration. Cells were added at a density of 10000 cells/well (N87, SKB-BR-3) and 5000 cells/well MCF-7 in the presence the experimentally defined stress concentration of HRG (10 nM SK-BR-3, 100 nM N87 and MCF-7). The cells were cultivated for 3-4 days at 37° C., 5% CO2, in 95% relative humidity. ALAMAR BLUE™ (INVITROGEN®) was added to assess the proliferation. Absorbance was measured at 550 nm excitation with 590 nm emission wave length. In all assays tested, only the bispecific antibodies targeting domain I of HER2 were able to inhibit proliferation in the presence of a high heregulin concentration (FIG. 28).

Drug Combinations with PB4188 In Vitro.

To investigate the possibility to combine PB4188 with small molecule drugs PB4188 was combined with drugs interfering at different levels of the PI3K or MAPK pathway. Moreover, combination with chemotherapeutic drugs and cyclin inhibitors were tested. Combinations were tested on HER2 overexpressing cells growing in the presence of HRG in MATRIGEL® (SK-BR-3 and BT-474) or in the presence of HRG stress concentrations (N87 and SK-BR-3 as described in proliferation assays). The inhibitory effect of drug combinations was tested by imaging or by measuring proliferation using Alamar Blue as described herein before. First, the EC20 PB4188 and drugs tested was determined. Next, checkerboard titrations were performed with PB4188 and the drugs. Synergies were observed in all cell lines tested with tyrosine kinase inhibitors (afatinib, lapatinib, neratinib), the PI3Ka inhibitor BYL719, the Akt inhibitor MK-2206, the mTOR inhibitor everolimus, the Src inhibitor saracatinib, the microtubuli disrupting drug paclitaxel, and the HDAC inhibitor vorinostat (which is misspelled in FIG. 40 as "voronistat"). FIG. 29 shows an example of the synergistic combination of PB4188 with lapatinib on SKBR-3 cells grown in MATRIGEL® resulting in morphological changes and reduction of cell growth. The extent of growth inhibition obtained with each combination was calculated. Potency shifting can be shown using isobolograms (Greco et al 1995) which shows how much less drug is required in a combination to achieve a desired level when compared to the single agent required to reach that effect. The inhibition values of the combination experiments were used by CHALICE™ Analyzer software to generate the isobolograms. Isobolograms of the different drug combinations on HER2 amplified cells are shown in FIG. 40. Isobologram analysis indicated that PB4188 displayed synergistic drug combinations with afatinib, lapatinib, neratinib, BYL719, MK-2206, everolimus, saracatinib, vorinostat and paclitaxel.

These data demonstrate that drugs acting on the PI3K pathway are particular effective in combination with PB4188. In addition, combinations with Tyrosine Kinase Inhibitors are effective. Moreover, a combination with the growth and migration/invasion drug saracatinib can be favourable in the metastatic setting.

PB4188 In Vitro Inhibition of Phosphorylation

Cells of an exponentially grown culture were harvested and seeded in 6 well plates ($3.75 \times 10^6$ cells for N87 and $1.5 \times 10^6$ cells for SKBR-3) in starvation medium (N87 cells: RPMI-1640, 0.05% BSA, 10 g/ml Holo-transferrin; SKBR-3 cells: DMEM/F-12, 2 mM L-glutamine, 0.05% BSA, 10 g/ml Holo-transferrin) and incubated incubated overnight at 37° C., 5% CO2, in 95% relative humidity. The next day, antibodies were added to a final concentration of 5 nM and cells were incubated for one hour at 37° C., 5% CO2, in 95% relative humidity. HRG was then added to a final concentration of 100 ng/ml. After 1, 3, 6 or 24 hours at 37° C., 5% CO2, in 95% relative humidity, plates were placed on ice, cells were washed twice with cold PBS. Subsequently 0.3 ml ice-cold lysis buffer was added (Cell signaling RTK #9803 or IC #7018) and cells were lysed for a minimum of 30 minutes on ice. Next, protein concentrations were measured using BCA (Pierce #23235). Protein concentrations were adjusted to 2 mg/ml with lysis buffer. Next, lysates were applied to PathScan RTK Signaling Antibody Arrays (Cell signaling #7949) or PathScan Intracellular Signaling Antibody Arrays. All incubations were performed with sealed wells on an orbital shaker at room temperature. Lysates (75 l) were diluted 2 times to 0.8 mg/ml concentration with 75 µl Array Diluent Buffer supplemented with protease inhibitor cocktail and kept on ice. Array wells were blocked with 100 µl Array block buffer for 15 minutes. Block buffer was removed and Lysates were applied to the wells and allowed to incubate for 2 hours. Lysate was aspirated and wells were washed 4 times with 100 µl Wash buffer. Next, 100 µl detection antibody cocktail was added per well and incubated for 1 hour. Antibody cocktail was aspirated and wells were washed 4 times with 100 µl Wash buffer. 75 µl DYLIGHT80™ Streptavidin was added to each well. DYLIGHT80™ Streptavidin was aspirated and wells were washed 4 times with 100 µl Wash buffer. The multi-gasket was removed and slides were washed for 10 seconds in 10 ml in deionized water. Slides were allowed to dry and processed for imaging on an ODYSSEE®Clx. Spot fluorescence intensity was calculated using Image Studio software.

In N87 and SKBR-3, PB4188 completely blocks AKT phosphorylation during the first 6H of incubation, in contrast to the combination of trastuzumab+pertuzumab. In addition a strong inhibition is observed in ERK and S6 phosphorylation in contrast to the combination of trastuzumab+pertuzumab. PB4188 does not inhibit phosphorylation of HER2 (FIG. 30)

Western Blot Analyses

To verify the phosphorylation inhibition observed in the RTK and intracellular Pathscan arrays Western blots were performed of cells treated with PB4188, the combination pertuzumab and trastuzumab and a control antibody in the presence of HRG stress concentrations. Cells of an exponentially grown culture were harvested and seeded in 10 cm dishes ($20 \times 10^6$ cells for N87 and $7 \times 10^6$ cells for SKBR-3) in starvation medium (N87 cells: RPMI-1640, 0.05% BSA, 10 g/ml Holo-transferrin; SKBR-3 cells: DMEM/F-12, 2 mM L-glutamine, 0.05% BSA, 10 g/ml Holo-transferrin). The next day, antibodies were added to a final concentration of 5 nM and cells were incubated for one hour. HRG was then added to a final concentration of 100 ng/ml. After 1, 3, 6 or 24 hours, dishes were placed on ice, cells were washed twice with cold PBS, transferred to Eppendorf tubes and lysed with 250 µl of RIPA lysis buffer (20 mM Tris-HCl pH 7.5, 150 mM NaCl, 1 mM Na2EDTA, 1 mM EGTA, 1% NP-40, 1% sodium deoxycholate, 0.1% SDS, 2.5 mM sodium pyrophosphate, 1 mM beta-glycerophosphate, 1 mM Na3VO4, 1 µg/ml leupeptin). Lysis was allowed to proceed for 30 minutes on ice. Cell lysates were centrifuged and supernatants were collected in new Eppendorf tubes. Protein concentration was determined using the BCA method (Pierce). 30 µg of the lysate was separated on a 4-12% Bis-Tris NuPage gel (INVITROGEN®) and proteins on the gel were transferred to a nitrocellulose membrane. Membranes were blocked for one hour with TBS-T containing 5% BSA and stained with the indicated antibodies according to the manufacturer's instructions (Cell Signaling Technology). Membranes were then incubated with a HRP-conjugated secondary antibody, incubated with ECL substrate and subjected to autoradiography using X-ray films (Amersham). All detection antibodies were from Cell Signaling Technology: Phospho-Akt (ser 473) #4060, Total Akt #4691, Phospho-HER2 (Tyr 1221/1222) #2243, Total HER2 #2242, Phospho-HER3 (Tyr 1289) #4791, Total HER3 #4754, Phospho-ERK1/2 (Thr 202/Tyr 204) #4377, Total ERK1/2 #4695, Phospho-S6 RP (Ser 235/236) #2211, Total S6 RP #2217, Goat anti-rabbit HRP-linked #7074.

The results show that PB4188 shows a prolonged inhibition of HER3 phosphorylation resulting in the inhibition of both the MAPK and PI3 kinase pathway with a profound effect on AKT phosphorylation inhibition (FIG. 31).

PB4188 In Vivo Pharmacodynamics

Phosphoprotein Analysis by Luminex

Tumors (100 mm$^3$) of JIMT-1 transplanted mice treated with 2 doses of PB4188 and 4 doses of PB4188 were removed 24H after dosing. Tumors were flash-frozen and processed to powder. Tumor lysates were prepared to a concentration of 50 mg tumor/mL using cold BioRad Lysis Buffer (supplemented with 0.4% BioRad Factor 1, 0.2% BioRad Factor 2, and 2 mM PMSF) to the frozen powder samples, incubated at 4° C. on a rocker for 60 minutes to ensure complete lysis. The samples were centrifuged at 4° C. for 10 minutes at 16000×g, and aliquoted. Total protein was determined using the Biorad DC Protein Assay reagents according to manufacturer's instructions. Luminex Assay: The JIMT-1 tumor lysate samples were processed and analyzed for: Total AKT AKT(Ser473) and AKT(Thr308using commercially available Luminex kits from Millipore (Cat #48-618MAG (Lot No. 2532050), 46-645MAG (Lot No.

46645M-1K). Each sample was tested in duplicate. Dilutions were prepared in sample diluent to load a target of approximately 25 µg protein per well for all total and phosphorylated analyte determinations. The Millipore kits were used according to the manufacturer's specifications.

Tumors treated with PB4188 showed an increase in Akt expression in comparison to untreated tumors. Phosphorylation of AKT was completely inhibited by PB4188 both after a two-weekly dose as after a four-weekly dose (FIG. 32).

Phosphoprotein Analysis by VeraTag Assay

Tumors (100 mm$^3$ or 400 mm$^3$) of JIMT-1 transplanted mice treated with 1 or 2 doses doses of PB4188 were removed and fixed in 10% neutral buffered formalin. Mice bearing 100 mm$^3$ tumors were sacrificed 24H after a single PB4188 dose (25 mg/kg) whereas mice bearing 400 mm$^3$ tumors received 2 weekly doses of 25 mg/kg and were sacrificed 4H after dosing. Next, samples were paraffin-embedded. Sections of 7 µm in thickness were sliced with a microtome (LEICA) and placed on positively charged glass slides (VWR) with serial number labeled. Slides were air-dried for 30 min and then baked in a heated oven set at 60° C. Next samples were processed for different VeraTag analysis. Total HER2 analysis (HT2) according to U.S. patent application Ser. No. 12/340,436, total HER3 analysis (H3T) according to U.S. Pat. No. 8,349,574; U.S. Patent Appl. No. 2013/0071859 and finally HER2-HER3 heterodimer (H23D), HER3pY1289 (H3pY1289) and HER3-PI3 kinase (H3PI3K) according to Int'l Patent Appl. No. PCT/US2014/033208. In both dosing regimens a significant PB4188 mediated reduction in HER2:HER3 dimers became apparent in comparison to untreated controls. There was no difference observed in total HER2, HER3 or phosphorylated HER3 between PB4188 treated tumors and controls. Tumors that were analyzed 4H after PB4188 dosing showed a significant reduction in HER3-p85 (PI3K) compared with untreated controls.

PB4188 Reduces Cell Cycle Progression in HRG-Stimulated Cancer Cells

The ability of PB4188 to influence cell cycle progression was investigated in cancer cell lines expressing various protein levels of HER2. HER2+(MCF-7), HER2+++(JIMT-1, SK-BR-3 and N87 cells) cells were seeded in assay medium (MCF-7 cells: RPMI-1640, 0.05% BSA, 10 µg/ml Holo-transferrin, 1 mM sodium pyruvate, MEM NEAA; JIMT-1: DMEM, 0.05% BSA, 10 µg/ml Holo-transferrin; SK-BR-3 cells: DMEM/F-12, 2 mM L-glutamine, 0.05% BSA, 10 µg/ml Holo-transferrin; N87 cells: RPMI-1640, 0.05% BSA, 10 µg/ml Holo-transferrin). Per well of 24-well plate, 300.000 MCF-7, or 400.000 N87 or 150.000 SK-BR-3 or 150.000 JIMT-1 or cells seeded in 1 ml assay medium and incubated overnight at 37° C., 5% CO2, in 95% relative humidity. The next day, PB4188 or pertuzumab+trastuzumab or PG3178 or PG1337 were added to the cells in the presence of a final concentration of HRG of 1 or 100 ng/ml. After 24 hrs (for JIMT-1, N87 or SK-BR-3 cells) or 48 hrs (for MCF-7 cells) incubation at 37° C., 5% CO2, in 95% relative humidity, cells were supplemented with EdU (10 µM final concentration) for 2 hrs before being harvested and stained for EdU incorporation using the Click-iT EdU AlexaFluor488 kit according to the manufacturer instructions (LifeTechnologies, cat.no. C10425). At least 30 min before analyzing the cells by flow cytometry on FACSCanto, cells were incubated with 200 nM FxCycle far red dye (LifeTechnologies, cat.no. F10348) and 100 µg/ml RNAse A (LifeTechnologies, cat.no. 12091-039). Events were acquired in the AlexFluor488 channel (for EdU detection) and in the APC channel (for total DNA stain with the FxCycle dye). Data were analyzed by gating single cells on a FSC-width vs FSC-height scatter plot, and subgating the G0/G1, S and G2M phases of the cell cycle on an APC vs AlexaFluor488 scatter plot, as EdU$^{neg}$APC$^{low}$, EdU$^{pos}$ and EdU$^{neg}$APC$^{high}$ populations, respectively.

Data are represented as the proliferation index calculated by dividing the percentage of cells in the S and G2/M phases by the percentage of cells in the G0/G1 phase. FIG. 34 shows that PB4188 is consistently more potent than PG3178 or pertuzumab+trastuzumab in inhibiting proliferation induced by a standard (1 ng/ml) or a high (100 ng/ml) concentration of HRG. At high concentrations of HRG PB4188 still inhibits the cell cycle progression.

PB4188 Induces Receptor Internalization

Internalization pattern of antibodies was measured using pH-sensitive dyes. This has been described in the art in WO2013134686 A1 where such dyes, when coupled to an antibody, display an increased fluorescence signal when exposed to lower pH. This occurs when the dye-coupled antibodies internalize from the surface of target cells into mildly acidic endosomes (pH 6-6.5) to acidic lysosomes (pH lower than 5.5). To investigate whether PB4188 internalizes in cancer cells, the antibody was coupled to the pH sensor dye with succinimidyl ester reactive group (Promega, cat.no. CS1783A01) according to the manufacturer's instructions. As comparators, anti-HER2 (trastuzumab, pertuzumab, PG3958), anti-HER3 (PG3178, #Ab6) and negative control (anti-tetanus toxin, PG1337) dye labeled antibodies were included. HER2-overexpressing SKBR-3 and N87 cancer cells of an exponentially grown culture were harvested and seeded on 96 well plates (15×10$^3$ cells per well) in 100 µl assay medium (N87 cells: RPMI-1640, 0.05% BSA, 10 µg/ml Holo-transferrin; SKBR-3 cells: DMEM/F-12, 2 mM L-glutamine, 0.05% BSA, 10 µg/ml Holo-transferrin) containing 1 ng/ml HRG and incubated overnight at 37° C., 5% CO2, in 95% relative humidity. The next day, 20 µl pH-sensitive dye-labelled antibodies were added to reach a final concentration of 100 nM and cells were incubated overnight at 37° C., 5% CO2, in 95% relative humidity. The next day, cells were harvested by collecting non-adherent cells and trypsinizing adherent cells. After washing cells with FACS buffer (PBS 0.5% BSA 0.1% sodium azide), cells were stained with APC-labelled anti-human IgG (Jackson Immunoresearch, cat.no. 109-136-098, 1:100 dilution). Cells were analyzed by flow cytometry on FACSCanto (BD Biosciences) measuring median fluorescence intensities (MFI) of the PE and APC channels to determine internalization and residual surface binding of antibodies, respectively. Data shown in FIG. 35 show that PB4188 internalizes to the same extend as trastuzumab whereas the combination trastuzumab+pertuzumab leads to enhanced internalization. The combination of trastuzumab+pertuzumab reduces the ADCC in comparison to trastuzumab alone (FIG. 36). It is therefore anticipated that the level of PB4188 internalization leaves the ADCC potency unaffected.

Generation and Characterization of Anti-HER3 Antibody 3178 Variants

Variants of anti-HER3 antibody MF3178 were designed with the aim to improve antibody properties. Mutations were introduced in the VH gene framework region 1 (FR1), complementarity determining region 1 (CDR1), FR2, CDR2 and/or FR3, while CDR3 and FR4 were not modified. The design included, but was not limited to, mutations that were introduced to remove post-translational modification (PTM) motifs (e.g. by changing the deamidation motif NS to NQ), to reduce surface hydrophobicity (e.g. by changing I to T) or to increase the iso-electric point (pI; e.g. by changing Q to K). All 20 variants (See FIG. 37) were expressed as bispecific antibody combined with a Tetanus Toxoid (TT) arm and tested in the MCF-7 functional assay and all 20 variants had a similar potency as the MF3178 antibody in this format. All 20 variants were also tested in this format in FACS in a titration for binding to MCF-7 and all variants had very similar binding profiles suggesting that the affinities of all variants are similar. Three lead variants MF6058, MF6061 and MF6065 were selected for further experiments that contain ten, three and seven amino acid mutations, respectively (see sequences in FIG. 16E and FIG. 37). The corresponding monospecific IgG1 PG6058, PG6061 and PG6065 were produced and purified at large scale. As shown in FIG. 38, the inhibitory activity of the three variants in the HRG-dependent N87 cell line proliferation assay is similar to that of PG3178. The CIEX-HPLC profile of the three variants was similar to that of PG3178 with respect to charge heterogeneity as well as peak width and symmetry, as shown in FIG. 39. The retention time (tR) of the main peak correlated roughly with the pI of the antibodies, i.e. higher pI resulted in longer retention time. In the design of bispecific antibodies or mixtures of antibodies, selecting antibody variants with optimal tR is valuable since purification of the desired antibody components using CIEX can be facilitated.

Serum titers of the different cohorts of immunized mice as determined by FACS. D=day of antibody titer determination. Table 1: response against HER2. Table 2: response against HER3. Cell lines used are indicated (MCF7, SKBR3, BT474). The different mice are in the columns

TABLE 1 anti-HER2 response

| ErbB2 | K562 | | | | | | MCF7 | | | | | | SKBR3 |
|---|---|---|---|---|---|---|---|---|---|---|---|---|---|
| A, D35 | 236 | 168 | 315 | 148 | 116 | 145 | 5909 | 5728 | 6147 | 5491 | 4838 | 4930 | 67748 |
| C, D42 | 163 | 144 | 154 | 152 | 166 | | 2574 | 3212 | 2140 | 2346 | 2172 | | 15448 |
| E, D35 | 129 | 134 | 152 | 132 | 147 | 157 | 6214 | 5542 | 5625 | 5634 | 4812 | 3905 | 27730 |
| G, D52 | 145 | 129 | 126 | 133 | 163 | | 5752 | 5088 | 4268 | 4899 | 5240 | | 22769 |
| | Average | 130.8 | | | | | Average | 194.4 | | | | | Average |
| | D 0 | | | | | | D 0 | | | | | | D 0 |
| | 5× | 654 | | | | | 5× | 972.2 | | | | | 5× |
| | 10× | 1308 | | | | | 10× | 1944 | | | | | 10× |
| | 20× | 2616 | | | | | 20× | 3889 | | | | | 20× |
| | 30× | 3924 | | | | | 30× | 5833 | | | | | 30× |

| ErbB2 | | | | | | BT474 | | | | | |
|---|---|---|---|---|---|---|---|---|---|---|---|
| A, D35 | 29537 | 45315 | 44737 | 33508 | 38355 | 38707 | 18928 | 27240 | 24784 | 17659 | 18713 |
| C, D42 | 17188 | 12627 | 12432 | 12067 | | 10259 | 9669 | 7789 | 6618 | 6030 | |
| E, D35 | 19765 | 26863 | 26232 | 19478 | 13968 | 22716 | 17413 | 19139 | 18317 | 16397 | 12787 |
| G, D52 | 26157 | 16726 | 14633 | 15783 | | 19413 | 16640 | 16424 | 16959 | 18633 | |
| | 300.2 | | | | | Average | 241 | | | | |
| | | | | | | D 0 | | | | | |
| | 1501 | | | | | 5× | 1205 | | | | |
| | 3002 | | | | | 10× | 2410 | | | | |
| | 6004 | | | | | 20× | 4819 | | | | |
| | 9005 | | | | | 30× | 7229 | | | | |

TABLE 2 anti-HER3 response

| ErbB3 | K562 | | | | | | MCF7 | | | | | |
|---|---|---|---|---|---|---|---|---|---|---|---|---|
| B, D56 | 332 | 356 | 453 | 535 | 417 | 645 | 1630 | 1236 | 3251 | 1401 | 1297 | 1814 |
| D, D56 | 336 | 445 | 277 | 185 | 319 | | 1159 | 3260 | 959 | 643 | 2362 | |
| F, D35 | 265 | 245 | 249 | 285 | 291 | 262 | 4370 | 3985 | 3445 | 3428 | 3579 | 2718 |
| H, D52 | 263 | 289 | 233 | 271 | 242 | | 4083 | 4239 | 2970 | 4167 | 4584 | |
| | Average | 130 | | | | | Average | 172 | | | | |
| | D 0 | | | | | | D 0 | | | | | |
| | 2.5× | 326 | | | | | 2.5× | 430 | | | | |
| | 5× | 651 | | | | | 5× | 859 | | | | |
| | 10× | 1303 | | | | | 10× | 1718 | | | | |
| | 20× | 2605 | | | | | 20× | 3437 | | | | |

| ErbB3 | SKBR3 | | | | | | BT474 | | | | | |
|---|---|---|---|---|---|---|---|---|---|---|---|---|
| B, D56 | 1666 | 1100 | 3072 | 1199 | 1268 | 1503 | 1675 | 1204 | 3393 | 1380 | 1295 | 1725 |
| D, D56 | 964 | 2180 | 721 | 510 | 1577 | | 1030 | 3754 | 945 | 584 | 2042 | |
| F, D35 | 4139 | 3378 | 2676 | 2659 | 2674 | 2414 | 4618 | 3690 | 3522 | 3144 | 3208 | 2776 |
| H, D52 | 5183 | 4319 | 3256 | 5408 | 5474 | | 6326 | 4920 | 4542 | 6653 | 6938 | |
| | Average | 200 | | | | | Average | 222 | | | | |
| | D 0 | | | | | | D 0 | | | | | |

TABLE 2-continued anti-HER3 response

| | | | |
|---|---|---|---|
| 2.5x | 501 | 2.5x | 556 |
| 5x | 1002 | 5x | 1112 |
| 10x | 2004 | 10x | 2223 |
| 20x | 4008 | 20x | 4446 |

TABLE 3

Binning of HER2 antibodies depending on their reactivity with chicken-human-HER2 chimera's and reactivity to mouse HER2. 'Number' indicates the number of unique antibodies in each group

| Group | Domain reactivity | Number |
|---|---|---|
| 1 | Domain I specific | 25 |
| 2 | Domain II specific | 2 |
| 3 | Domain III specific | 23 |
| 4 | Domain IV specific | 7 |
| 5 | Domain IV specific + murine cross-reactive | 2 |
| 6 | Reactive to all constructs | 2 |
| 7 | Human WT reactive only | 4 |

TABLE 4

Competition ELISA using IgGs and phage antibodies. Four IgG antibodies are used in the competition assay: two HER2 antibodies recognizing domain IV (trastuzumab and PG1849); one antibody recognizing domain II (PG2971) and one negative control anti-RSV antibody. Loss of signal is observed when the phage and antibody encoded by the same variable region genes are competing; i.e. MF1849 and PG1849 and MF2971 and PG2971.

| | — | MF1849 | MF2971 | MF2708 |
|---|---|---|---|---|
| Trastuzumab | 0.046 | 1.02 | 1.115 | 0.044 |
| PG1849 | 0.043 | 0.384 | 1.139 | 0.041 |
| PG2971 | 0.042 | 1.202 | 0.091 | 0.042 |
| Anti-RSV mAB | 0.044 | 0.94 | 1.003 | 0.047 |
| — | 0.045 | 1.432 | 1.481 | 0.038 |

TABLE 5

Binning of HER3 antibodies depending on their reactivity with rat-human-HER2 chimera's and reactivity to HER3 and HER3 of other species. 'Number' indicates the number of unique antibodies in each group

| Group | Reactivity | Number |
|---|---|---|
| 1 | High Domain III reactivity, rat and mouse reactive and minor reactivity to domain IV | 8 |
| 2 | High Domain III reactivity, rat, human and cyno reactive, minor reactivity to domain IV | 8 |
| 3 | Reactivity to rat, cyno and human HER3 | 43 |
| 4 | Reactive to human HER3 | 32 |
| 5 | Reactive to all constructs | 33 |

TABLE 6

Functional activity of the most potent HER2 monoclonals at 1 µg/ml IgG. Percentage activity compared to reference antibodies, i.e. trastuzumab in SKBR-3 and #Ab6 in MCF-7. For HER2 antibodies the domains of all antibodies except PG2926 were mapped to domains I, III or IV

| PG ID nr | Target | Epitope Bin | HER2 domain | SKBR-3 | MCF-7 |
|---|---|---|---|---|---|
| PG2916 | HER2 | 1 | I | 58% | 30% |
| PG2973 | HER2 | 1 | I | 49% | 58% |
| PG3004 | HER2 | 1 | I | 49% | 56% |
| PG1849 | HER2 | 5 | IV | 42% | 22% |
| PG3025 | HER2 | 1 | I | 38% | 28% |
| PG2971 | HER2 | 1 | I | 25% | 51% |
| PG3031 | HER2 | 1 | I | 33% | 38% |
| PG2926 | HER2 | 7 | NA | 0% | 35% |
| PG2930 | HER2 | 3 | III | 0% | 7% |

TABLE 7

Functional activity of the most potent HER3 monoclonals at 1 µg/ml IgG in a HRG dependent MCF-7 assay. Percentage activity compared to reference antibody #Ab6.

| PG ID nr | Target | Epitope group | MCF-7 |
|---|---|---|---|
| PG3178 | HER3 | 5 | 162% |
| PG3163 | HER3 | 5 | 119% |
| PG3176 | HER3 | 5 | 68% |
| PG3099 | HER3 | 3 | ND |

TABLE 8

FACS stainings of HER2 antibodies whereby the HER2 VH is combined with a different light chain than the common light chain indicated in FIG. 16. MFI, indicates Mean Fluorescence Intensity in FACS. The HER2 MF number is indicated in between brackets, HER2 binding clones in the context of the different light chain are indicated in bold.

| PGnumber | MFI K562 cells (neg control) | MFI K562 HER2 |
|---|---|---|
| PG4462 (MF2971) | 267 | 14900 |
| PG4463 (MF3958) | 248 | 15600 |
| PG4474 (MF2916) | 254 | 14700 |
| PG4478 (MF2973) | 254 | 18000 |
| PG4481 (MF3004) | 267 | 16200 |
| PG4482 (MF3025) | 299 | 12000 |
| PG4483 (MF3031) | 260 | 14900 |
| PG4465 (MF1849) | 270 | 249 |
| Anti-HER2 mAb | 309 | 7618 |
| Anti-RSV mAb | 263 | 276 |

TABLE 9

Functional activity of lead HER2 x HER5 bispecific antibodies (indicated using the PB prefix; each PB comprises an HER2 arm and an HER3 arm as indicated in the table) compared to comparator antibodies in the HRG dependent MCF-7 and BxPCS assays. Based on binding profiles using chimeric constructs HER2 and HER5 antibodies could be separated over different bins. For HER2 antibodies the domains all antibodies except PG2926 could be mapped to domains I, III or IV.

| Name | HER2 arm | HER2 domain | HER3 arm | HER3 bin | MCF-7 IC50 (pM) | BxPC3 % Inhibition |
|---|---|---|---|---|---|---|
| PB3441 | 2926 | NA | 3178 | 5 | 51.7 | −24% |
| PB3443 | 2930 | III | 3178 | 5 | 136 | −31% |
| PB3448 | 1849 | IV | 3178 | 5 | 371 | −22% |
| PB3565 | 2973 | I | 3178 | 5 | 30.9 | −19% |
| PB3566 | 3004 | I | 3178 | 5 | 7.9 | −20% |
| PB3567 | 2971 | I | 3178 | 5 | 46.5 | −17% |
| PB3709 | 3025 | I | 3178 | 5 | 34.5 | −19% |
| PB3710 | 2916 | I | 3178 | 5 | 74.2 | −19% |
| PB3883 | 2971 | I | 3176 | 5 | 113 | −19% |
| PB3986 | 3025 | I | 3163 | 5 | 30.7 | −21% |
| PB3990 | 2971 | I | 3163 | 5 | 13 | −18% |
| PB4011 | 2971 | I | 3099 | 3 | 40.2 | ND |
| PB3437 | 3031 | I | 3178 | 5 | 14 | −10% |
| PG3178 | NA | NA | 3178 | 5 | 139 | −17% |
| #Ab6 | | | | | 504 | −7% |
| trastuz. + pertuz. | | | | | 352 | ND |
| trastuzumab | | | | | 500 | −3% |

TABLE 10

Monovalent binding affinities of PB4188 and PB3448 for HER2 and HER3 as measured in BIACORE™. Both bispecific antibodies share the same HER3 arm. ND, not done.

| PB | KD on Her2 (nM) | KD on Her3 (nM) |
|---|---|---|
| PB3448 | 5.4* | ND |
| PB4188 | 0.16* | 3.9 |

TABLE 11

JIMT-1 xenograft study treatment groups

Regimen 1

| Gr. | N | Agent | Vehicle | mg/kg | Route | Schedule |
|---|---|---|---|---|---|---|
| 1# | 10 | PBS | X | — | ip | qwk × 4 (start on day 1) |
| 2 | 10 | lapatinib | — | 150 | po | qd × 28 (start on day 1) |
| 3 | 10 | PB4188 | — | 2.5 | ip | qwk × 4 (start on day 1) |
| 4 | 10 | PB4188 | — | 25 | ip | qwk × 4 (start on day 1) |
| 5 | 10 | Pertuzumab + Trastuzumab | — | 2.5 | ip | qwk × 4 (start on day 1) |
| 6 | 10 | Pertuzumab + Trastuzumab | — | 25 | ip | qwk × 4 (start on day 1) |

TABLE 12

Affinities of $^{125}$I-labeled IgG HER2xHER3 IgG (PB4188), HER3xTT (PB9215), HER2xTT (PB9216) and HERCEPTIN® H(monospecific for HER2), as determined using steady state cell affinity measurements with BT-474 cells and SK-BR-3 cells. Data were obtained from three independent experiments.

| | BT-474 | SK-BR-3 |
|---|---|---|
| HERCEPTIN® | 3.7 ± 0.5 nM | 1.3 ± 0.1 nM |
| PB4188 | 3.2 ± 0.5 nM | 2.0 ± 0.4 nM |
| HER2xTT | 3.9 ± 0.6 nM | 2.3 ± 0.7 nM |
| HER3xTT | 0.23 ± 0.08 nM | 0.99 ± 0.4 nM |

TABLE 13

The mean binding protein reactivities (and ranges) listed for all critical residues identified. Critical residues involved in PG3958Fab binding were identified as those mutated in clones that were negative for PG3958Fab binding (<35% WT) but positive for the control mAb 1129 binding (>80% WT). Two additional critical residues were identified which did not meet the threshold guidelines, but whose mutation reduced antibody binding by a lesser extent. Residue numbering is that of PDB ID #1S78.

| HER2 Residue | Mutation | PG3958 Fab binding % of wt binding (range) | Control mAb binding % of wt binding (range) | Designation |
|---|---|---|---|---|
| 144 | T144A | 31.9 (11) | 82.1 (13) | Critical |
| 166 | R166A | 32.2 (5) | 93.7 (17) | Critical |
| 181 | R181A | 10.1 (5) | 98.6 (34) | Critical |
| 172 | P172A | 52.5 (2) | 94.9 (24) | Secondary |
| 179 | G179A | 41.7 (18) | 87.9 (25) | Secondary |

TABLE 14

The mean binding protein reactivities (and ranges) are listed for both critical residues. Critical residues involved in PG3178 binding were identified as those mutated in clones that were negative for PG3178 mAb binding (<20% WT) but positive for the control mAb 66223 binding (>70% WT). Residue numbering is that of PDB ID #4P59.

| HER3 Residue | Mutation | PG3178 binding % of wt binding (range) | Control mAb binding % of wt binding (range) | Designation |
|---|---|---|---|---|
| 409 | F409A | 16.74 (8) | 79.63 (0) | Critical |
| 426 | R426A | 3.17 (5) | 93.08 (36) | Critical |

TABLE 15

List of exposed residues within 11.2 Å radius of Arg 426 in HER3:

| | |
|---|---|
| Leu 423 | L423 |
| Tyr 424 | Y424 |
| Asn 425 | N425 |
| Gly 427 | G427 |
| Gly 452 | G452 |
| Arg 453 | R453 |
| Tyr 455 | Y455 |
| Glu 480 | E480 |
| Arg 481 | R481 |
| Leu 482 | L482 |
| Asp 483 | D483 |
| Lys 485 | K485 |

REFERENCES

Arteaga C L, Sliwkowski M X, Osborne C K, Perez E A, Puglisi F, Gianni L. 2011. Treatment of HER2-positive breast cancer: current status and future perspectives. Nat Rev Clin Oncol. 2011 Nov. 29; 9(1):16-32.

Balko J M, Miller T W, Morrison M M, Hutchinson K, Young C, Rinehart C, Sánchez V, Jee D, Polyak K, Prat A, Perou C M, Arteaga C L, Cook R S. 2012. The receptor tyrosine kinase ErbB3 maintains the balance between luminal and basal breast epithelium. Proc Natl Acad Sci USA. January 3; 109(1):221-6.

Baselga J, Cortés J, Kim S B, Im S A, Hegg R, Im Y H, Roman L, Pedrini J L, Pienkowski T, Knott A, Clark E, Benyunes M C, Ross G, Swain S M. 2012. Pertuzumab plus trastuzumab plus docetaxel for metastatic breast cancer. N Engl J Med. January 12; 366(2):109-19.

de Kruif et al. Mol. Biol. (1995), 248, 97-105

Ewer M S, Ewer S M. Cardiotoxicity of anticancer treatments: What the cardiologist needs to know. Nat Rev Cardiol 2010; 7:564-75

Guarneri Jain K K, Casper E S, Geller N L, et al. A prospective randomized comparison of epirubicin and doxorubicin in patients with advanced breast cancer; J Clin Oncol 1985; 3:818-26

Junttila T T, Akita R W, Parsons K, Fields C, Lewis Phillips G D, Friedman L S, Sampath D, Sliwkowski M X. 2009. Ligand-independent HER2/HER3/PI3K complex is disrupted by trastuzumab and is effectively inhibited by the PI3K inhibitor GDC-0941. Cancer Cell. May 5; 15(5): 429-40.

Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489

Merchant et al. Nature Biotechnology, Vol. 16 Jul. 1998 pp 677-681

Nissim A, Hoogenboom H R, Tomlinson I M, Flynn G, Midgley C, Lane D, Winter G. 1994. Antibody fragments from a 'single pot' phage display library as immunochemical reagents. EMBO J. 1994 Feb. 1; 13(3):692-8.

Ocana A, Vera-Badillo F, Seruga B, Templeton A, Pandiella A, Amir E. 2013. HER3 overexpression and survival in solid tumors: a meta-analysis. J Natl Cancer Inst. February 20; 105(4):266-73.

Sergina N V, Rausch M, Wang D, Blair J, Hann B, Shokat K M, Moasser M M. 2007. Escape from HER-family tyrosine kinase inhibitor therapy by the kinase-inactive HER3. Nature. January 25; 445(7126):437-41.

Schaefer et al. Cancer Cell 20, 472-486, October 2011

Schoeberl B, Faber A C, Li D, Liang M C, Crosby K, Onsum M, Burenkova O, Pace E, Walton Z, Nie L, Fulgham A, Song Y, Nielsen U B, Engelman J A, Wong K K. 2010. An ErbB3 antibody, MM-121, is active in cancers with ligand-dependent activation. Cancer Res. March 15; 70(6):2485-94.

Shames et al. PLOS ONE, February 2013, Vol. 8, Issue 2, pp 1-10

Tanner M, Kapanen Al, Junttila T, Raheem O, Grenman S, Elo J, Elenius K, Isola J. 2004. Characterization of a novel cell line established from a patient with Herceptin-resistant breast cancer. Mol Cancer Ther. 2004 December; 3(12):1585-92.

Yarden Y, Pines G. 2012. The ERBB network: at last, cancer therapy meets systems biology. Nat Rev Cancer July 12; 12(8):553-63.

Thery J.-C. et al., Resistance to human epidermal growth factor receptor type 2-targeted therapies, Eur J Cancer (2014), Vol. 50, Issue 5, pages 892-901

Wadhwa D, Fallah-Rad N, Grenier D, et al. Trastuzumab mediated cardiotoxicity in the setting of the adjuvant chemotherapy for breast cancer: A retrospective study. Breast Cancer Res Treat 2009; 117:357-64.

Wehrman T S, Raab W J, Casipit C L, Doyonnas R, Pomerantz J H, Blau H M. 2006. A system for quantifying dynamic protein interactions defines a role for Herceptin in modulating ErbB2 interactions. Proc Natl Acad Sci USA. December 12; 103(50):19063-8.

Wilson T R, Fridlyand J, Yan Y, Penuel E, Burton L, Chan E, Peng J, Lin E, Wang Y, Sosman J, Ribas A, Li J, Moffat J, Sutherlin D P, Koeppen H, Merchant M, Neve R, Settleman J. 2012. Widespread potential for growth-factor-driven resistance to anticancer kinase inhibitors. Nature. July 26; 487(7408):505-9.

Yonesaka et al., Sci. transl. Med., Vol. 3, Issue 99 (2011); pp 1-11

Zhang H, Berezov A, Wang Q, Zhang G, Drebin J, Murali R, Greene M I. 2007. ErbB receptors: from oncogenes to targeted cancer therapies. J Clin Invest. August; 117(8): 2051-8.

Greco, Bravo, Parsons (1995) The search for synergy: a critical review from a response surface perspective. Pharmacol. Rev 47 (2): 331-85

---

The invention claimed is:

1. A method of treating a human subject having an ErbB-2, ErbB-3 or ErbB-2/ErbB-3 positive tumor comprising administering to the subject a bispecific antibody comprising:
   a first binding arm that specifically binds to the extracellular domain of a human ErbB2 polypeptide and comprises a heavy chain variable region comprising the CDR1, CDR2, and CDR3 sequences of AYYIN (SEQ ID NO:49), RIYPGSGYTSYAQKFQG (SEQ ID NO:50), and PPVYYDSAWFAY (SEQ ID NO:51), respectively, and a light chain variable region comprising the CDR1, CDR2, and CDR3 sequences of a light chain comprising SEQ ID NO: 87; and
   a second binding arm that specifically binds to the extracellular domain of a human ErbB3 polypeptide and comprises a heavy chain variable region comprising the CDR1, CDR2, and CDR3 sequences GYYMH (SEQ ID NO:64), WINPNSGGTNY AQKFQG (SEQ ID NO:65), and DHGSRHFWSYWGFDY (SEQ ID NO:66), respectively, and a light chain variable region comprising the CDR1, CDR2, and CDR3 sequences of a light chain comprising SEQ ID NO: 87.

2. The method of claim 1, wherein the antibody comprises the light chain comprising the amino acid sequence

```
                                        (SEQ ID NO: 87)
DIQMTQSPSSLSASVGDRVTITCRASQSISSYLNWYQQKPGKAPKLLIY

AASSLOSGVPSRFSGSGSGTDFTLTISSLQPEDFATYYCQQSYSTPPTF

GQGTKVEIKRTVAAPSVFIFPPSDEQLKSGTASVVCLLNNEYPREAKVQ

WKVDNALQSGNSQESVTEQDSKDSTYSLSSTLTLSKADYEKHKVYACEV

THQGLSSPVTKSFNRGEC.
```

3. The method of claim 1, wherein the first binding arm comprises a heavy chain variable region comprising SEQ ID NO: 48, the second binding arm comprises a heavy chain variable region comprising SEQ ID NO: 63, and both the first and second binding arms comprise a light chain variable region comprising SEQ ID NO: 87.

4. The method of claim 1, wherein the first binding arm comprises a heavy chain comprising SEQ ID NO: 88, the second binding arm comprises a heavy chain comprising SEQ ID NO: 89, and both the first and second binding arms comprise a light chain comprising SEQ ID NO: 87.

5. The method of claim 1, wherein the bispecific antibody comprises two different immunoglobulin heavy chains with compatible heterodimerization domains.

6. The method of claim 5, wherein the compatible heterodimerization domains are compatible immunoglobulin heavy chain CH3 heterodimerization domains.

7. The method of claim 1, wherein the subject is administered a pharmaceutical composition comprising the bispecific antibody.

8. The method of claim 1, further comprising administering to the subject at least one additional therapeutic agent, selected from BYL719, MK-2206, everolimus, saracatinib, paclitaxel, and vorinostat.

9. The method of claim 1, wherein the tumor is an ErbB-2/ErbB-3 positive tumor.

10. The method of claim 1, wherein the tumor is an ErbB-2 positive tumor.

11. The method of claim 1, wherein the tumor is an ErbB-3 positive tumor.

12. The method of claim 8, wherein the tumor is an ErbB-2/ErbB-3 positive tumor.

13. The method of claim 8, wherein the tumor is an ErbB-2 positive tumor.

14. The method of claim 8, wherein the tumor is an ErbB-3 positive tumor.

15. The method of claim 1, wherein the tumor is a breast tumor, gastric tumor, colorectal tumor, colon tumor, gastroesophageal tumor, esophageal tumor, endometrial tumor, ovarian tumor, liver tumor, lung tumor including non-small cell lung tumor, clear cell sarcoma, salivary gland tumor, head and neck tumor, brain tumor, bladder tumor, pancreatic tumor, prostate tumor, kidney tumor, skin tumor, or melanoma.

16. The method of claim 1, wherein the subject has an ErbB-2, ErbB-3 or ErbB-2/ErbB-3 positive tumor having less than 1,000,000 ErbB-2 cell-surface receptors per tumor cell.

17. A method of treating a human subject having an ErbB-2, ErbB-3 or ErbB-2/ErbB-3 positive tumor comprising administering to the subject a bispecific antibody comprising a first and second binding arm;
wherein the first binding arm specifically binds to the extracellular domain of a human ErbB2 polypeptide and comprises a heavy chain variable region comprising SEQ ID NO: 48, and the second binding arm specifically binds to the extracellular domain of a human ErbB3 polypeptide and comprises a heavy chain variable region comprising SEQ ID NO: 63, and wherein both the first and second binding arms comprise a light chain variable region comprising SEQ ID NO: 87.

18. The method of claim 1, wherein the antibody comprises the light chain variable region comprising the amino acid sequence

```
                                       (SEQ ID NO: 176)
DIQMTQSPSSLSASVGDRVTITCRASQSISSYLNWYQQKPGKAPKLLIY

AASSLOSGVPSRFSGSGSGTDFTLTISSLQPEDFATYYCQQSYSTPPTF

GQGTKVEIK.
```

19. The method of claim 1, wherein the bispecific antibody is an IgG antibody.

20. The method of claim 1, wherein CDR numbering of the heavy chain CDR1, CDR2, and CDR3 sequence is according to Kabat.

* * * * *

UNITED STATES PATENT AND TRADEMARK OFFICE
CERTIFICATE OF CORRECTION

PATENT NO. : 12,139,548 B2
APPLICATION NO. : 18/047933
DATED : November 12, 2024
INVENTOR(S) : Cecilia Anna Wilhelmina Geuijen et al.

Page 1 of 2

It is certified that error appears in the above-identified patent and that said Letters Patent is hereby corrected as shown below:

In the Claims

In Column 131, Claim 2, Lines 8-15, delete:
"DIQMTQSPSSLSASVGDRVTITCRASQSISSYLNWYQQKPGKAPKLLIYAASSLOSGVPSRFS GSGSGTDFTLTISSLQPEDFATYYCQQSYSTPPTFGQGTKVEIKRTVAAPSVFIFPPSDEQLKSG TASVVCLLNNEYPREAKVQWKVDNALQSGNSQESVTEQDSKDSTYSLSSTLTLSKADYEKH KVYACEVTHQGLSSPVTKSFNRGEC."
And insert:
-- DIQMTQSPSSLSASVGDRVTITCRASQSISSYLNWYQQKPGKAPKLLIYAASSLQSGVPSRF SGSGSGTDFTLTISSLQPEDFATYYCQQSYSTPPTFGQGTKVEIKRTVAAPSVFIFPPSDEQLKS GTASVVCLLNNFYPREAKVQWKVDNALQSGNSQESVTEQDSKDSTYSLSSTLTLSKADYEKH KVYACEVTHQGLSSPVTKSFNRGEC --, therefor.

In Column 131, Claim 3, Lines 20-21, delete:
"first and second binding arms comprise a light chain variable region comprising SEQ ID NO: 87."
And insert:
-- first and second binding arms comprise a light chain comprising SEQ ID NO: 87. --, therefor.

In Column 132, Claim 17, Lines 29-31, delete:
"wherein both the first and second binding arms comprise a light chain variable region comprising SEQ ID NO: 87."
And insert:
-- wherein both the first and second binding arms comprise a light chain comprising SEQ ID NO: 87. --, therefor.

In Column 132, Claim 18, Lines 37-41, delete:
"DIQMTQSPSSLSASVGDRVTITCRASQSISSYLNWYQQKPGKAPKLLIYAASSLOSGVPSRFS GSGSGTDFTLTISSLQPEDFATYYCQQSYSTPPTF GQGTKVEIK."

Signed and Sealed this
Twenty-fifth Day of March, 2025

Coke Morgan Stewart
*Acting Director of the United States Patent and Trademark Office*

CERTIFICATE OF CORRECTION (continued)
U.S. Pat. No. 12,139,548 B2

And insert:
-- DIQMTQSPSSLSASVGDRVTITCRASQSISSYLNWYQQKPGKAPKLLIYAASSLQSGVPSR FSGSGSGTDFTLTISSLOPEDFATYYCQQSYSTPPTF GQGTKVEIK. --, therefor.

SEQUENCE LISTING

```
Sequence total quantity: 176
SEQ ID NO: 1            moltype = DNA  length = 36
FEATURE                 Location/Qualifiers
source                  1..36
                        mol_type = other DNA
                        note = primer
                        organism = synthetic construct
SEQUENCE: 1
aagctggcta gcaccatgga gctggcggcc ttgtgc                          36

SEQ ID NO: 2            moltype = DNA  length = 32
FEATURE                 Location/Qualifiers
source                  1..32
                        mol_type = other DNA
                        note = primer
                        organism = synthetic construct
SEQUENCE: 2
aataattcta gactggcacg tccagaccca gg                              32
```

| SEQ ID NO: 3 | moltype = DNA length = 36 |
|---|---|
| FEATURE | Location/Qualifiers |
| source | 1..36 |
| | mol_type = other DNA |
| | note = primer |
| | organism = synthetic construct |

SEQUENCE: 3
aagctggcta gcaccatgga gctggcggcc tggtac      36

| SEQ ID NO: 4 | moltype = DNA length = 32 |
|---|---|
| FEATURE | Location/Qualifiers |
| source | 1..32 |
| | mol_type = other DNA |
| | note = primer |
| | organism = synthetic construct |

SEQUENCE: 4
aataattcta gactggcacg tccagaccca gg      32

| SEQ ID NO: 5 | moltype = DNA length = 36 |
|---|---|
| FEATURE | Location/Qualifiers |
| source | 1..36 |
| | mol_type = other DNA |
| | note = primer |
| | organism = synthetic construct |

SEQUENCE: 5
aagctggcta gcaccatgag ggcgaacggc gctctg      36

| SEQ ID NO: 6 | moltype = DNA length = 33 |
|---|---|
| FEATURE | Location/Qualifiers |
| source | 1..33 |
| | mol_type = other DNA |
| | note = primer |
| | organism = synthetic construct |

SEQUENCE: 6
aataattcta gattacgttc tctgggcatt agc      33

| SEQ ID NO: 7 | moltype = DNA length = 370 |
|---|---|
| FEATURE | Location/Qualifiers |
| source | 1..370 |
| | mol_type = other DNA |
| | note = MF2926:heavy chain variable region sequence of an erB-2 binding antibody |
| | organism = synthetic construct |
| CDS | 20..370 |

SEQUENCE: 7
```
gcccagccg gccatggccc aggtccagct gcagcagtct ggacctgagc tggtgaaacc   60
tggggcttca gtgatgattt cctgcaaggc ttctggttac tcattcactg gctaccacat  120
gaactgggtg aagcaaagtc ctgaaaagag ccttgagtgg attggagaca taaatcctag  180
cattggtacg actgcccaca accagatttt cagggccaag gccacaatga ctgttgacaa  240
atcctccaac acagcctaca tgcagctcaa gagcctgaca tctgaagact ctggagtctt  300
ttactgtgtt agaagagggg actggtcctt cgatgtctgg ggcacaggga ccacggtcac  360
cgtctccagt                                                         370
```

| SEQ ID NO: 8 | moltype = AA length = 117 |
|---|---|
| FEATURE | Location/Qualifiers |
| source | 1..117 |
| | mol_type = protein |
| | organism = synthetic construct |

SEQUENCE: 8
```
QVQLQQSGPE LVKPGASVMI SCKASGYSFT GYHMNWVKQS PEKSLEWIGD INPSIGTTAH   60
NQIFRAKATM TVDKSSNTAY MQLKSLTSED SGVFYCVRRG DWSFDVWGTG TTVTVSS    117
```

| SEQ ID NO: 9 | moltype = AA length = 16 |
|---|---|
| FEATURE | Location/Qualifiers |
| source | 1..16 |
| | mol_type = protein |
| | note = MF2926 CDR1 |
| | organism = synthetic construct |

SEQUENCE: 9
GYHMNWVKQS PEKSLE      16

| SEQ ID NO: 10 | moltype = AA length = 6 |
|---|---|
| FEATURE | Location/Qualifiers |
| source | 1..6 |
| | mol_type = protein |
| | note = MF2926 CDR2 |
| | organism = synthetic construct |

SEQUENCE: 10

```
NQIFRA                                                                       6

SEQ ID NO: 11           moltype = AA  length = 8
FEATURE                 Location/Qualifiers
source                  1..8
                        mol_type = protein
                        note = MF2926 CDR3
                        organism = synthetic construct
SEQUENCE: 11
RGDWSFDV                                                                     8

SEQ ID NO: 12           moltype = DNA  length = 379
FEATURE                 Location/Qualifiers
source                  1..379
                        mol_type = other DNA
                        note = MF2930: heavy chain variable region sequence of an
                         erbB-2 binding antibody
                        organism = synthetic construct
CDS                     20..379
SEQUENCE: 12
ggcccagccg gccatggccg aggtccagct gcagcagtct ggggctgaac tggtgaagcc            60
tggagcctca gtgatgatgt cctgtaaggt ttctggctac accttcactt cctatcctat           120
agcgtggatg aagcaggttc atggaaagag cctagagtgg attggaaatt ttcatccta            180
cagtgatgat actaagtaca atgaaaactt caagggcaag gccacattga ctgtagaaaa           240
atcctctagc acagtctact ggagctcag ccgattaaca tctgatgact ctgctgttta            300
ttactgtgca agaagtaacc cattatatta ctttgctatg gactactggg gtcaaggaac           360
ctcggtcacc gtctccagt                                                       379

SEQ ID NO: 13           moltype = AA  length = 120
FEATURE                 Location/Qualifiers
source                  1..120
                        mol_type = protein
                        organism = synthetic construct
SEQUENCE: 13
EVQLQQSGAE LVKPGASVMM SCKVSGYTFT SYPIAWMKQV HGKSLEWIGN FHPYSDDTKY            60
NENFKGKATL TVEKSSSTVY LELSRLTSDD SAVYYCARSN PLYYFAMDYW GQGTSVTVSS           120

SEQ ID NO: 14           moltype = AA  length = 16
FEATURE                 Location/Qualifiers
source                  1..16
                        mol_type = protein
                        note = MF2930 CDR1
                        organism = synthetic construct
SEQUENCE: 14
SYPIAWMKQV HGKSLE                                                           16

SEQ ID NO: 15           moltype = AA  length = 6
FEATURE                 Location/Qualifiers
source                  1..6
                        mol_type = protein
                        note = MF2930 CDR2
                        organism = synthetic construct
SEQUENCE: 15
NENFKG                                                                       6

SEQ ID NO: 16           moltype = AA  length = 11
FEATURE                 Location/Qualifiers
source                  1..11
                        mol_type = protein
                        note = MF2930 CDR3
                        organism = synthetic construct
SEQUENCE: 16
SNPLYYFAMD Y                                                                11

SEQ ID NO: 17           moltype = DNA  length = 385
FEATURE                 Location/Qualifiers
source                  1..385
                        mol_type = other DNA
                        note = MF1849: heavy chain variable region sequence of an
                         erbB-2 binding antibody
                        organism = synthetic construct
CDS                     20..385
SEQUENCE: 17
ggcccagccg gccatggccc aggtgcagct ggtggagtct ggggggaggcg tggtccagcc           60
tggggaggtcc ctgagactct cctgtgcagc ctctggattc accttcagta gctatggcat         120
gcactgggtc cgccaggctc caggcaaggg gctggagtgg gtggcagtta tatcatatga          180
tggaagtaat aaatactatg cagactccgt gaagggccga ttcaccatct ccagagacaa          240
ttccaagaac acgctgtatc tgcaaatgaa cagcctgaga gctgaggaca cggccgtgta          300
ttactgtgca aaaggtgact acggttctta ctcttcttac gcctttgatt attggggcca          360
```

```
aggtaccctg gtcaccgtct ccagt                                             385

SEQ ID NO: 18           moltype = AA   length = 122
FEATURE                 Location/Qualifiers
source                  1..122
                        mol_type = protein
                        organism = synthetic construct
SEQUENCE: 18
QVQLVESGGG VVQPGRSLRL SCAASGFTFS SYGMHWVRQA PGKGLEWVAV ISYDGSNKYY         60
ADSVKGRFTI SRDNSKNTLY LQMNSLRAED TAVYYCAKGD YGSYSSYAFD YWGQGTLVTV        120
SS                                                                      122

SEQ ID NO: 19           moltype = AA   length = 5
FEATURE                 Location/Qualifiers
source                  1..5
                        mol_type = protein
                        note = MF1849 CDR1
                        organism = synthetic construct
SEQUENCE: 19
SYGMH                                                                     5

SEQ ID NO: 20           moltype = AA   length = 17
FEATURE                 Location/Qualifiers
source                  1..17
                        mol_type = protein
                        note = MF1849 CDR2
                        organism = synthetic construct
SEQUENCE: 20
VISYDGSNKY YADSVKG                                                       17

SEQ ID NO: 21           moltype = AA   length = 13
FEATURE                 Location/Qualifiers
source                  1..13
                        mol_type = protein
                        note = MF1849 CDR3
                        organism = synthetic construct
SEQUENCE: 21
GDYGSYSSYA FDY                                                           13

SEQ ID NO: 22           moltype = DNA   length = 385
FEATURE                 Location/Qualifiers
source                  1..385
                        mol_type = other DNA
                        note = MF2973: heavy chain variable region sequence of an
                         erbB-2 binding antibody
                        organism = synthetic construct
CDS                     20..385
SEQUENCE: 22
ggcccagccg gccatggccc aggtgcagct gaagcagtct ggggctgagc tggtgaggcc         60
tggggcttca gtgaagttgt cctgcaaggc ttctggctac atttttcactg ctactatat       120
aaactggttg aggcagaggc ctggacaggg acttgaatgg attgcaaaaa tttatcctgg       180
aagtggtaat acttactaca atgaaaagtt caggggcaag gccacactga ctgcagaaga       240
atcctccagc actgcctaca tgcagctcag cagcctgaca tctgaggact ctgctgtcta       300
tttctgtgca agagggcccc actatgatta cgacggcccc tggtttgttt actggggcca       360
agggactctg gtcaccgtct ccagt                                             385

SEQ ID NO: 23           moltype = AA   length = 122
FEATURE                 Location/Qualifiers
source                  1..122
                        mol_type = protein
                        organism = synthetic construct
SEQUENCE: 23
QVQLKQSGAE LVRPGASVKL SCKASGYIFT GYYINWLRQR PGQGLEWIAK IYPGSGNTYY         60
NEKFRGKATL TAEESSSTAY MQLSSLTSED SAVYFCARGP HYDYDGPWFV YWGQGTLVTV        120
SS                                                                      122

SEQ ID NO: 24           moltype = AA   length = 16
FEATURE                 Location/Qualifiers
source                  1..16
                        mol_type = protein
                        note = MF2973 CDR1
                        organism = synthetic construct
SEQUENCE: 24
GYYINWLRQR PGQGLE                                                        16

SEQ ID NO: 25           moltype = AA   length = 6
FEATURE                 Location/Qualifiers
source                  1..6
                        mol_type = protein
```

```
                        note = MF2973 CDR2
                        organism = synthetic construct
SEQUENCE: 25
NEKFRG                                                                    6

SEQ ID NO: 26           moltype = AA  length = 13
FEATURE                 Location/Qualifiers
source                  1..13
                        mol_type = protein
                        note = MF1973 CDR3
                        organism = synthetic construct
SEQUENCE: 26
GPHYDYDGPW FVY                                                           13

SEQ ID NO: 27           moltype = DNA  length = 382
FEATURE                 Location/Qualifiers
source                  1..382
                        mol_type = other DNA
                        note = MF3004: heavy chain variable region sequence of an
                          erbB-2 binding antibody
                        organism = synthetic construct
CDS                     20..382
SEQUENCE: 27
ggcccagccg gccatggccc aggtgcagct gaagcagtct ggggctgagc tggtgaggcc         60
tggggcttca gtgaagctgt cctgcaaggc ttctggctac actttcactg gctactatat        120
aaactgggtg aagcagaggc ctggacaggg acttgagtgg attgcaagga tttatcctgg        180
aagtggttat acttactaca atgaaaagtt caagggcaag gccacactga ctgcagaaga        240
atcctccagc actgcctaca tgcacctcag cagcctgaca tctgaggact ctgctgtcta        300
tttctgtgca agaccccact atggttacga cgactggtac ttcggtgtct ggggcacagg        360
caccacggtc accgtctcca gt                                                 382

SEQ ID NO: 28           moltype = AA  length = 121
FEATURE                 Location/Qualifiers
source                  1..121
                        mol_type = protein
                        organism = synthetic construct
SEQUENCE: 28
QVQLKQSGAE LVRPGASVKL SCKASGYTFT GYYINWVKQR PGQGLEWIAR IYPGSGYTYY         60
NEKFKGKATL TAEESSSTAY MHLSSLTSED SAVYFCARPH YGYDDWYFGV WGTGTTVTVS        120
S                                                                       121

SEQ ID NO: 29           moltype = AA  length = 16
FEATURE                 Location/Qualifiers
source                  1..16
                        mol_type = protein
                        note = MF3004 CDR1
                        organism = synthetic construct
SEQUENCE: 29
GYYINWVKQR PGQGLE                                                        16

SEQ ID NO: 30           moltype = AA  length = 6
FEATURE                 Location/Qualifiers
source                  1..6
                        mol_type = protein
                        note = MF3004 CDR2
                        organism = synthetic construct
SEQUENCE: 30
NEKFKG                                                                    6

SEQ ID NO: 31           moltype = AA  length = 12
FEATURE                 Location/Qualifiers
source                  1..12
                        mol_type = protein
                        note = MF3004 CDR3
                        organism = synthetic construct
SEQUENCE: 31
PHYGYDDWYF GV                                                            12

SEQ ID NO: 32           moltype = DNA  length = 382
FEATURE                 Location/Qualifiers
source                  1..382
                        mol_type = other DNA
                        note = MF2971: heavy chain variable region sequence of an
                          erbB-2 binding antibody
                        organism = synthetic construct
CDS                     20..382
SEQUENCE: 32
ggcccagccg gccatggccc aggtgcagct gaagcagtct ggggctgagc tggtgaggcc         60
tggggcttca gtgaaactgt cctgcaaggc ttctggctac actttcactg cctactatat        120
```

```
aaactgggtg aagcagaggc ctggacaggg acttgagtgg attgcaagga tttatcctgg    180
aagtggctat acttactaca atgagatttt caagggcagg ccacactga ctgcagacga    240
atcctccagc actgcctaca tgcaactcag cagcctgaca tctgaggact ctgctgtcta    300
tttctgtgca agacctccgg tctactatga ctcggcctgg tttgcttact ggggccaagg    360
gactctggtc accgtctcca gt                                            382

SEQ ID NO: 33              moltype = AA  length = 121
FEATURE                    Location/Qualifiers
source                     1..121
                           mol_type = protein
                           organism = synthetic construct
SEQUENCE: 33
QVQLKQSGAE LVRPGASVKL SCKASGYTFT AYYINWVKQR PGQGLEWIAR IYPGSGYTYY    60
NEIFKGRATL TADESSSTAY MQLSSLTSED SAVYFCARPP VYYDSAWFAY WGQGTLVTVS    120
S                                                                   121

SEQ ID NO: 34              moltype = AA  length = 16
FEATURE                    Location/Qualifiers
source                     1..16
                           mol_type = protein
                           note = MF2971 CDR1
                           organism = synthetic construct
SEQUENCE: 34
AYYINWVKQR PGQGLE                                                   16

SEQ ID NO: 35              moltype = AA  length = 6
FEATURE                    Location/Qualifiers
source                     1..6
                           mol_type = protein
                           note = MF2971 CDR2
                           organism = synthetic construct
SEQUENCE: 35
NEIFKG                                                              6

SEQ ID NO: 36              moltype = AA  length = 12
FEATURE                    Location/Qualifiers
source                     1..12
                           mol_type = protein
                           note = MF2971 CDR3
                           organism = synthetic construct
SEQUENCE: 36
PPVYYDSAWF AY                                                       12

SEQ ID NO: 37              moltype = DNA  length = 382
FEATURE                    Location/Qualifiers
source                     1..382
                           mol_type = other DNA
                           note = MF3025: heavy chain variable region sequence of an
                            erbB-2 binding  antibody
                           organism = synthetic construct
CDS                        20..382
SEQUENCE: 37
ggcccagccg gccatggccc aggtgcagct gaagcagtct ggggctgagc tggtgaggcc    60
tgggacttca gtgaagctgt cctgcaaggc ttctggctac actttcactg gctactatat    120
aaactgggtg aagcagaggc ctggacaggg acttgagtgg attgcaagga tttatcctgg    180
aagtggttat acttactaca atgagaagtt caagggcaag ccacactga ctgcagaaga    240
atcctccaac actgcctata tgcacctcag cagcctgaca tctgaggact ctgctgtcta    300
tttctgtgca aggccccact atggttacga cgactggtac ttcgctgtct ggggcacagg    360
gaccacggtc accgtctcca gt                                            382

SEQ ID NO: 38              moltype = AA  length = 121
FEATURE                    Location/Qualifiers
source                     1..121
                           mol_type = protein
                           organism = synthetic construct
SEQUENCE: 38
QVQLKQSGAE LVRPGTSVKL SCKASGYTFT GYYINWVKQR PGQGLEWIAR IYPGSGYTYY    60
NEKFKGKATL TAEESSNTAY MHLSSLTSED SAVYFCARPH YGYDDWYFAV WGTGTTVTVS    120
S                                                                   121

SEQ ID NO: 39              moltype = AA  length = 16
FEATURE                    Location/Qualifiers
source                     1..16
                           mol_type = protein
                           note = MF3025 CDR1
                           organism = synthetic construct
SEQUENCE: 39
GYYINWVKQR PGQGLE                                                   16
```

```
SEQ ID NO: 40              moltype = AA  length = 6
FEATURE                    Location/Qualifiers
source                     1..6
                           mol_type = protein
                           note = MF3025 CDR2
                           organism = synthetic construct
SEQUENCE: 40
NEKFKG                                                                    6

SEQ ID NO: 41              moltype = AA  length = 12
FEATURE                    Location/Qualifiers
source                     1..12
                           mol_type = protein
                           note = MF3025 CDR3
                           organism = synthetic construct
SEQUENCE: 41
PHYGYDDWYF AV                                                            12

SEQ ID NO: 42              moltype = DNA  length = 385
FEATURE                    Location/Qualifiers
source                     1..385
                           mol_type = other DNA
                           note = MF2916: heavy chain variable region sequence of an
                            erbB-2 binding antibody
                           organism = synthetic construct
CDS                        20..385
SEQUENCE: 42
ggcccagccg gccatggccc aggtccagct gcagcagtct ggggctgagc tggtgaggcc        60
tggggcttca gtgaagctgt cctgcaaggc ttctggctac actttcactg gctactatat       120
aaactggtg aagcagaggc ctggacaggg acttgagtgg attgcaagga tttatcctgg        180
cagtggtcat acttcctaca atgagaagtt caagggcaag gccacactga ctacagaaaa       240
atcctccagc actgcctaca tgcagctcag cagcctgaca tctgaggact ctgctgtcta       300
tttctgtgca agacctatct actttgatta cgcagggggg tacttcgatg tctggggcac       360
aagaaccctcg gtcaccgtct ccagt                                            385

SEQ ID NO: 43              moltype = AA  length = 122
FEATURE                    Location/Qualifiers
source                     1..122
                           mol_type = protein
                           organism = synthetic construct
SEQUENCE: 43
QVQLQQSGAE LVRPGASVKL SCKASGYTFT GYYINWVKQR PGQGLEWIAR IYPGSGHTSY        60
NEKFKGKATL TTEKSSSTAY MQLSSLTSED SAVYFCARPI YFDYAGGYFD VWGTRTSVTV       120
SS                                                                     122

SEQ ID NO: 44              moltype = AA  length = 16
FEATURE                    Location/Qualifiers
source                     1..16
                           mol_type = protein
                           note = MF2916 CDR1
                           organism = synthetic construct
SEQUENCE: 44
GYYINWVKQR PGQGLE                                                        16

SEQ ID NO: 45              moltype = AA  length = 6
FEATURE                    Location/Qualifiers
source                     1..6
                           mol_type = protein
                           note = MF2916 CDR2
                           organism = synthetic construct
SEQUENCE: 45
NEKFKG                                                                    6

SEQ ID NO: 46              moltype = AA  length = 13
FEATURE                    Location/Qualifiers
source                     1..13
                           mol_type = protein
                           note = MF2916 CDR3
                           organism = synthetic construct
SEQUENCE: 46
PIYFDYAGGY FDV                                                           13

SEQ ID NO: 47              moltype = DNA  length = 382
FEATURE                    Location/Qualifiers
source                     1..382
                           mol_type = other DNA
                           note = MF3958: heavy chain variable region sequence of an
                            erbB-2 binding antibody
                           organism = synthetic construct
```

```
CDS                        20..382
SEQUENCE: 47
ggcccagccg gccatggccc aggtgcagct ggtgcagtct ggcgccgaag tgaagaaacc    60
tggcgccagc gtgaagctga gctgcaaggc cagcggctac accttcaccg cctactacat   120
caactgggtc cgacaggccc caggccaggg cctggaatgg atcggcagaa tctaccccgg   180
ctccggctac accagctacg cccagaagtt ccagggcaga gccaccctga ccgccgacga   240
gagcaccagc accgcctaca tggaactgag cagcctgcgg agcgaggata ccgccgtgta   300
cttctgcgcc agaccccccg tgtactacga cagcgcttgg tttgcctact ggggccaggg   360
caccctggtc accgtctcca gt                                            382

SEQ ID NO: 48              moltype = AA  length = 121
FEATURE                    Location/Qualifiers
source                     1..121
                           mol_type = protein
                           organism = synthetic construct
SEQUENCE: 48
QVQLVQSGAE VKKPGASVKL SCKASGYTFT AYYINWVRQA PGQGLEWIGR IYPGSGYTSY    60
AQKFQGRATL TADESTSTAY MELSSLRSED TAVYFCARPP VYYDSAWFAY WGQGTLVTVS   120
S                                                                   121

SEQ ID NO: 49              moltype = AA  length = 5
FEATURE                    Location/Qualifiers
source                     1..5
                           mol_type = protein
                           note = MF3958 CDR1
                           organism = synthetic construct
SEQUENCE: 49
AYYIN                                                                 5

SEQ ID NO: 50              moltype = AA  length = 17
FEATURE                    Location/Qualifiers
source                     1..17
                           mol_type = protein
                           note = MF3958 CDR2
                           organism = synthetic construct
SEQUENCE: 50
RIYPGSGYTS YAQKFQG                                                   17

SEQ ID NO: 51              moltype = AA  length = 12
FEATURE                    Location/Qualifiers
source                     1..12
                           mol_type = protein
                           note = MF3958 CDR3
                           organism = synthetic construct
SEQUENCE: 51
PPVYYDSAWF AY                                                        12

SEQ ID NO: 52              moltype = DNA  length = 382
FEATURE                    Location/Qualifiers
source                     1..382
                           mol_type = other DNA
                           note = MF3031: heavy chain variable region sequence of an
                            erbB-2 binding antibody
                           organism = synthetic construct
CDS                        20..382
SEQUENCE: 52
ggcccagccg gccatggccc aggtccagct gcagcagtct ggggctgagc tggtgaggcc    60
tggggcttca gtgaagctgt cctgcaaggc ttctggctac actttcactg cctactatat   120
aaactgggtg aagcagaggc ctggacaggg acttgagtgg attgcaaaga tttatcctgg   180
aagtggttat acttactaca atgagaattt caggggcaag gccacactga ctgcagaaga   240
atcctccagt actgcctaca tacaactcag cagcctgaca tctgaggact ctgctgtcta   300
tttctgtgca agaggcgtct atgattacga cggggcctgg tttgcttact ggggccaagg   360
gactctggtc accgtctcca gt                                            382

SEQ ID NO: 53              moltype = AA  length = 121
FEATURE                    Location/Qualifiers
source                     1..121
                           mol_type = protein
                           organism = synthetic construct
SEQUENCE: 53
QVQLQQSGAE LVRPGASVKL SCKASGYTFT AYYINWVKQR PGQGLEWIAK IYPGSGYTYY    60
NENFRGKATL TAEESSSTAY IQLSSLTSED SAVYFCARGV YDYDGAWFAY WGQGTLVTVS   120
S                                                                   121

SEQ ID NO: 54              moltype = AA  length = 16
FEATURE                    Location/Qualifiers
source                     1..16
                           mol_type = protein
                           note = MF3031 CDR1
```

```
                                   -continued
                       organism = synthetic construct
SEQUENCE: 54
AYYINWVKQR PGQGLE                                                  16

SEQ ID NO: 55          moltype = AA   length = 6
FEATURE                Location/Qualifiers
source                 1..6
                       mol_type = protein
                       note = MF3031 CDR2
                       organism = synthetic construct
SEQUENCE: 55
NENFRG                                                             6

SEQ ID NO: 56          moltype = AA   length = 12
FEATURE                Location/Qualifiers
source                 1..12
                       mol_type = protein
                       note = MF3031 CDR3
                       organism = synthetic construct
SEQUENCE: 56
GVYDYDGAWF AY                                                      12

SEQ ID NO: 57          moltype = DNA  length = 382
FEATURE                Location/Qualifiers
source                 1..382
                       mol_type = other DNA
                       note = MF3991: heavy chain  variable region sequence of an
                        erbB-2 binding antibody
                       organism = synthetic construct
CDS                    20..382
SEQUENCE: 57
ggcccagccg gccatggccc aggtgcagct ggtgcagtct ggcgccgaag tgaagaaacc   60
tggcgccagc gtgaagctga gctgcaaggc cagcggctac accttcaccg cctactacat   120
caactgggtc cgacaggccc caggccaggg cctggaatgg atcggcagaa tctaccccgg   180
ctccggctac accagctacg cccagaagtt ccagggcaga ccgccgacga                 240
gagcaccagc accgcctaca tggaactgag cagcctgcgg agcgaggata ccgccgtgta   300
cttctgcgcc agacccccact acggctacga cgactggtac ttcggcgtgt ggggccaggg   360
caccctggtc accgtctcca gt                                            382

SEQ ID NO: 58          moltype = AA   length = 121
FEATURE                Location/Qualifiers
source                 1..121
                       mol_type = protein
                       organism = synthetic construct
SEQUENCE: 58
QVQLVQSGAE VKKPGASVKL SCKASGYTFT AYYINWVRQA PGQGLEWIGR IYPGSGYTSY   60
AQKFQGRATL TADESTSTAY MELSSLRSED TAVYFCARPH YGYDDWYFGV WGQGTLVTVS   120
S                                                                   121

SEQ ID NO: 59          moltype = AA   length = 5
FEATURE                Location/Qualifiers
source                 1..5
                       mol_type = protein
                       note = MF3991 CDR1
                       organism = synthetic construct
SEQUENCE: 59
AYYIN                                                              5

SEQ ID NO: 60          moltype = AA   length = 17
FEATURE                Location/Qualifiers
source                 1..17
                       mol_type = protein
                       note = MF3991 CDR2
                       organism = synthetic construct
SEQUENCE: 60
RIYPGSGYTS YAQKFQG                                                 17

SEQ ID NO: 61          moltype = AA   length = 12
FEATURE                Location/Qualifiers
source                 1..12
                       mol_type = protein
                       note = MF3991 CDR3
                       organism = synthetic construct
SEQUENCE: 61
PHYGYDDWYF GV                                                      12

SEQ ID NO: 62          moltype = DNA  length = 391
FEATURE                Location/Qualifiers
source                 1..391
```

```
                        mol_type = other DNA
                        note = MF3178: heavy chain variable region sequence of an
                          erbB-3 binding antibody
                        organism = synthetic construct
CDS                     20..391
SEQUENCE: 62
ggcccagccg gccatggccc aggtgcagct ggtgcagtct ggggctgagg tgaagaagcc    60
tggggcctca gtgaaggtct cctgcaaggc ttctggatac accttcaccg gctactatat   120
gcactgggtg cgacaggccc ctggacaagg gcttgagtgg atgggatgga tcaaccctaa   180
cagtggtggc acaaactatg cacagaagtt tcagggcagg gtcacgatga ccagggacac   240
gtccatcagc acagcctaca tggagctgag caggctgaga tctgacgaca cggctgtgta   300
ttactgtgca agagatcatg gttctcgtca tttctggtct tactggggct tgattattgg   360
gggccaaggt accctggtca ccgtctccag t                                   391

SEQ ID NO: 63           moltype = AA  length = 124
FEATURE                 Location/Qualifiers
source                  1..124
                        mol_type = protein
                        organism = synthetic construct
SEQUENCE: 63
QVQLVQSGAE VKKPGASVKV SCKASGYTFT GYYMHWVRQA PGQGLEWMGW INPNSGGTNY    60
AQKFQGRVTM TRDTSISTAY MELSRLRSDD TAVYYCARDH GSRHFWSYWG FDYWGQTLV    120
TVSS                                                                124

SEQ ID NO: 64           moltype = AA  length = 5
FEATURE                 Location/Qualifiers
source                  1..5
                        mol_type = protein
                        note = MF3178 CDR1
                        organism = synthetic construct
SEQUENCE: 64
GYYMH                                                                5

SEQ ID NO: 65           moltype = AA  length = 17
FEATURE                 Location/Qualifiers
source                  1..17
                        mol_type = protein
                        note = MF3178 CDR2
                        organism = synthetic construct
SEQUENCE: 65
WINPNSGGTN YAQKFQG                                                   17

SEQ ID NO: 66           moltype = AA  length = 15
FEATURE                 Location/Qualifiers
source                  1..15
                        mol_type = protein
                        note = MF3178 CDR3
                        organism = synthetic construct
SEQUENCE: 66
DHGSRHFWSY WGFDY                                                     15

SEQ ID NO: 67           moltype = DNA  length = 385
FEATURE                 Location/Qualifiers
source                  1..385
                        mol_type = other DNA
                        note = MF3176: heavy chain variable region sequence of an
                          erbB-3 binding antibody
                        organism = synthetic construct
CDS                     20..385
SEQUENCE: 67
ggcccagccg gccatggccg aggtgcagct gttggagtct gggggaggct tggtacagcc    60
tggggggtcc ctgagactct cctgtgcagc ctctggattc acctttagca gctatgccat   120
gagctgggtc cgccaggctc cagggaaggg gctgagtggg tctcagcta ttagtggtag    180
tggtgtagc acatactacg cagactccgt gaagggccgg ttcaccatct ccagagacaa    240
ttccaagaac acgctgtatc tgcaaatgaa cagcctgaga gccgaggaca cggctgtgta    300
ttactgtgca agagattggt ggtacccgcc gtactactgg ggctttgatt attggggcca    360
aggtaccctg gtcaccgtct ccagt                                          385

SEQ ID NO: 68           moltype = AA  length = 122
FEATURE                 Location/Qualifiers
source                  1..122
                        mol_type = protein
                        organism = synthetic construct
SEQUENCE: 68
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARDW WYPPYYWGFD YWGQTLVTV    120
SS                                                                   122

SEQ ID NO: 69           moltype = AA  length = 5
```

| FEATURE | Location/Qualifiers |
|---|---|
| source | 1..5<br>mol_type = protein<br>note = MF3176 CDR1<br>organism = synthetic construct |

SEQUENCE: 69
SYAMS								5

| SEQ ID NO: 70 | moltype = AA   length = 17 |
|---|---|
| FEATURE | Location/Qualifiers |
| source | 1..17<br>mol_type = protein<br>note = MF3176 CDR2<br>organism = synthetic construct |

SEQUENCE: 70
AISGSGGSTY YADSVKG						17

| SEQ ID NO: 71 | moltype = AA   length = 13 |
|---|---|
| FEATURE | Location/Qualifiers |
| source | 1..13<br>mol_type = protein<br>note = MF3176 CDR3<br>organism = synthetic construct |

SEQUENCE: 71
DWWYPPYYWG FDY							13

| SEQ ID NO: 72 | moltype = DNA   length = 391 |
|---|---|
| FEATURE | Location/Qualifiers |
| source | 1..391<br>mol_type = other DNA<br>note = MF3163: heavy chain variable region sequence of an erbB-3 binding antibody<br>organism = synthetic construct |
| CDS | 20..391 |

SEQUENCE: 72
```
ggcccagccg gccatggccc aggtgcagct ggtgcagtct ggggctgagg tgaagaagcc    60
tggggcctca gtgaaggtct cctgcaaggc ttctggatac accttcaccg gctactatat   120
gcactgggtg cgacaggccc ctggacaagg gcttgagtgg atgggatgga tcaacccta a  180
cagtggtggc acaaactatg cacagaagtt cagggcgagtt catgacgatga ccagggacac   240
gtccatcagc acagcctaca tggagctgag caggctgaga tctgacgaca cggccgtgta   300
ttactgtgca aaagattctt actctcgtca tttctactct tggtgggcct ttgattattg   360
gggccaaggt accctggtca ccgtctccag t                                   391
```

| SEQ ID NO: 73 | moltype = AA   length = 124 |
|---|---|
| FEATURE | Location/Qualifiers |
| source | 1..124<br>mol_type = protein<br>organism = synthetic construct |

SEQUENCE: 73
QVQLVQSGAE VKKPGASVKV SCKASGYTFT GYYMHWVRQA PGQGLEWMGW INPNSGGTNY	60
AQKFQGRVTM TRDTSISTAY MELSRLRSDD TAVYYCAKDS YSRHFYSWWA FDWGQGTLV	120
TVSS								124

| SEQ ID NO: 74 | moltype = AA   length = 5 |
|---|---|
| FEATURE | Location/Qualifiers |
| source | 1..5<br>mol_type = protein<br>note = MF3163 CDR1<br>organism = synthetic construct |

SEQUENCE: 74
GYYMH								5

| SEQ ID NO: 75 | moltype = AA   length = 17 |
|---|---|
| FEATURE | Location/Qualifiers |
| source | 1..17<br>mol_type = protein<br>note = MF3163 CDR2<br>organism = synthetic construct |

SEQUENCE: 75
WINPNSGGTN YAQKFQG						17

| SEQ ID NO: 76 | moltype = AA   length = 15 |
|---|---|
| FEATURE | Location/Qualifiers |
| source | 1..15<br>mol_type = protein<br>note = MF3163 CDR3<br>organism = synthetic construct |

SEQUENCE: 76
DSYSRHFYSW WAFDY						15

```
SEQ ID NO: 77              moltype = DNA  length = 382
FEATURE                    Location/Qualifiers
source                     1..382
                           mol_type = other DNA
                           note = MF3099: heavy chain variable region sequence of an
                             erbB-3 binding antibody
                           organism = synthetic construct
CDS                        20..382
SEQUENCE: 77
ggcccagccg gccatggccg aggtccagct gcagcagcct ggggctgagc tggtgaggcc    60
tgggacttca gtgaagttgt cctgcaaggc ttctggctac accttcacca gctactggat   120
gcactgggta aagcagaggc ctggacaagg ccttgagtgg atcggaattc ttgatccttc   180
tgatagttat actacctaca atcaaaagtt caagggcaac gccacattaa cagtagacac   240
atcctccagc atagcctaca tgcagctcag cagcctgaca tctgaggact ctgcgctcta   300
ttactgtgca agagggggag attacgacga gggaggtgct atggactact ggggtcaagg   360
aacctcggtc accgtctcca gt                                            382

SEQ ID NO: 78              moltype = AA  length = 121
FEATURE                    Location/Qualifiers
source                     1..121
                           mol_type = protein
                           organism = synthetic construct
SEQUENCE: 78
EVQLQQPGAE LVRPGTSVKL SCKASGYTFT SYWMHWVKQR PGQGLEWIGI LDPSDSYTTY     60
NQKFKGKATL TVDTSSSIAY MQLSSLTSED SALYYCARGG DYDEGGAMDY WGQGTSVTVS    120
S                                                                   121

SEQ ID NO: 79              moltype = AA  length = 5
FEATURE                    Location/Qualifiers
source                     1..5
                           mol_type = protein
                           note = MF3099 CDR1
                           organism = synthetic construct
SEQUENCE: 79
SYWMH                                                                 5

SEQ ID NO: 80              moltype = AA  length = 17
FEATURE                    Location/Qualifiers
source                     1..17
                           mol_type = protein
                           note = MF3099 CDR2
                           organism = synthetic construct
SEQUENCE: 80
ILDPSDSYTT YNQKFKG                                                   17

SEQ ID NO: 81              moltype = AA  length = 12
FEATURE                    Location/Qualifiers
source                     1..12
                           mol_type = protein
                           note = MF3099 CDR3
                           organism = synthetic construct
SEQUENCE: 81
GGDYDEGGAM DY                                                        12

SEQ ID NO: 82              moltype = DNA  length = 391
FEATURE                    Location/Qualifiers
source                     1..391
                           mol_type = other DNA
                           note = MF3307: heavy chain variable region sequence of an
                             erbB-3 binding antibody
                           organism = synthetic construct
CDS                        20..391
SEQUENCE: 82
ggcccagccg gccatggccc aggtgcagct ggtgcagtct ggggctgagg tgaagaagcc    60
tggggcctca gtgaaggtct cctgcaaggc ttctggatac accttcaccg gctactatat   120
gcactgggtg cgacaggccc ctggacaagg cttgagtgg atgggatgga tcaaccctaa    180
cagtggtggc acaaactatg cacagaagtt tcagggcagg gtcacgatga ccagggacac   240
gtccatcagc acagcctaca tggagctgag caggctgaga tctgacgaca cggccgtgta   300
ttactgtgca agaggttctc gtaaacgtct gtctaactac ttcaacgcct tgattattg    360
gggccaaggt accctggtca ccgtctccag t                                  391

SEQ ID NO: 83              moltype = AA  length = 124
FEATURE                    Location/Qualifiers
source                     1..124
                           mol_type = protein
                           organism = synthetic construct
SEQUENCE: 83
QVQLVQSGAE VKKPGASVKV SCKASGYTFT GYYMHWVRQA PGQGLEWMGW INPNSGGTNY     60
```

```
AQKFQGRVTM TRDTSISTAY MELSRLRSDD TAVYYCARGS RKRLSNYFNA FDYWGQGTLV   120
TVSS                                                               124

SEQ ID NO: 84           moltype = AA  length = 5
FEATURE                 Location/Qualifiers
source                  1..5
                        mol_type = protein
                        note = MF3307 CDR1
                        organism = synthetic construct
SEQUENCE: 84
GYYMH                                                              5

SEQ ID NO: 85           moltype = AA  length = 17
FEATURE                 Location/Qualifiers
source                  1..17
                        mol_type = protein
                        note = MF3307 CDR2
                        organism = synthetic construct
SEQUENCE: 85
WINPNSGGTN YAQKFQG                                                 17

SEQ ID NO: 86           moltype = AA  length = 15
FEATURE                 Location/Qualifiers
source                  1..15
                        mol_type = protein
                        note = MF3307 CDR3
                        organism = synthetic construct
SEQUENCE: 86
GSRKRLSNYF NAFDY                                                   15

SEQ ID NO: 87           moltype = AA  length = 214
FEATURE                 Location/Qualifiers
source                  1..214
                        mol_type = protein
                        note = Common Light Chain
                        organism = synthetic construct
SEQUENCE: 87
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 88           moltype = AA  length = 450
FEATURE                 Location/Qualifiers
source                  1..450
                        mol_type = protein
                        note = heavy chain for erbB-2 binding
                        organism = synthetic construct
SEQUENCE: 88
QVQLVQSGAE VKKPGASVKL SCKASGYTFT AYYINWVRQA PGQGLEWIGR IYPGSGYTSY   60
AQKFQGRATL TADESTSTAY MELSSLRSED TAVYFCARPP VYYDSAWFAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTPPPSRE   360
EMTKNQVSLT CEVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 89           moltype = AA  length = 453
FEATURE                 Location/Qualifiers
source                  1..453
                        mol_type = protein
                        note = heavy chain for erbB-3 binding
                        organism = synthetic construct
SEQUENCE: 89
QVQLVQSGAE VKKPGASVKV SCKASGYTFT GYYMHWVRQA PGQGLEWMGW INPNSGGTNY   60
AQKFQGRVTM TRDTSISTAY MELSRLRSDD TAVYYCARDH GSRHFWSYWG FDYWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK RVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTKPP   360
SREEMTKNQV SLKCLVKGFY PSDIAVEWES NGQPENNYKT TPPVLDSDGS FFLYSKLTVD   420
KSRWQQGNVF SCSVMHEALH NHYTQKSLSL SPG                               453

SEQ ID NO: 90           moltype = DNA  length = 379
FEATURE                 Location/Qualifiers
source                  1..379
                        mol_type = other DNA
                        note = MF2889: heavy chain variable region sequence of an
```

```
                        erbB-2 binding antibody
                        organism = synthetic construct
CDS                     20..379
SEQUENCE: 90
ggcccagccg gccatggccg aggtccagct gcagcagtct ggagctgagc tggtaaggcc    60
tgggacttca gtgaaggtgt cctgcaaggc ttctggatac gccttcacta attatttgat   120
agagtgggta aagcagaggc ctggccaggg ccttggagtg attggagtga tttatcctga   180
aggtggtggt actatctaca atgagaagtt caagggcaag gcaacactga ctgcagacaa   240
atcctccagc actgcctaca tgcagctcag cggcctgaca tctgaggact ctgcggtcta   300
tttctgtgca agaggagact atgattacaa atatgctatg gactactggg gtcaaggaac   360
ctcggtcacc gtctccagt                                                379

SEQ ID NO: 91           moltype = AA  length = 120
FEATURE                 Location/Qualifiers
source                  1..120
                        mol_type = protein
                        organism = synthetic construct
SEQUENCE: 91
EVQLQQSGAE LVRPGTSVKV SCKASGYAFT NYLIEWVKQR PGQGLEWIGV IYPEGGGTIY    60
NEKFKGKATL TADKSSSTAY MQLSGLTSED SAVYFCARGD YDYKYAMDYW GQGTSVTVSS   120

SEQ ID NO: 92           moltype = AA  length = 5
FEATURE                 Location/Qualifiers
source                  1..5
                        mol_type = protein
                        note = CDR1
                        organism = synthetic construct
SEQUENCE: 92
NYLIE                                                                 5

SEQ ID NO: 93           moltype = AA  length = 17
FEATURE                 Location/Qualifiers
source                  1..17
                        mol_type = protein
                        note = CDR2
                        organism = synthetic construct
SEQUENCE: 93
VIYPEGGGTI YNEKFKG                                                   17

SEQ ID NO: 94           moltype = AA  length = 11
FEATURE                 Location/Qualifiers
source                  1..11
                        mol_type = protein
                        note = CDR3
                        organism = synthetic construct
SEQUENCE: 94
GDYDYKYAMD Y                                                         11

SEQ ID NO: 95           moltype = DNA  length = 370
FEATURE                 Location/Qualifiers
source                  1..370
                        mol_type = other DNA
                        note = MF2913: heavy chain variable region sequence of an
                          erbB-2 binding antibody
                        organism = synthetic construct
CDS                     20..370
SEQUENCE: 95
ggcccagccg gccatggccg aggtcaagct gcagcagtct ggacctgagc tggtgaagcc    60
tggcgcttca gtgaagatat cctgcaaggc ttctggttac tcattcactg actacaaaat   120
ggactgggtg aagcagagcc atggaaagag cctcgaatgg attggaaata ttaatcctaa   180
cagtggtggt gttatctaca accagaagtt caggggcaag gtcacattga ctgttgacag   240
gtcctccagc gcagcctaca tggagctccg cagcctgaca tctgaggaca ctgcagtcta   300
ttattgttca agaggactgt gggatgctat ggactcctgg ggtcaaggaa cctcggtcac   360
cgtctccagt                                                          370

SEQ ID NO: 96           moltype = AA  length = 117
FEATURE                 Location/Qualifiers
source                  1..117
                        mol_type = protein
                        organism = synthetic construct
SEQUENCE: 96
EVKLQQSGPE LVKPGASVKI SCKASGYSFT DYKMDWVKQS HGKSLEWIGN INPNSGGVIY    60
NQKFRGKVTL TVDRSSSAAY MELRSLTSED TAVYYCSRGL WDAMDSWGQG TSVTVSS      117

SEQ ID NO: 97           moltype = AA  length = 16
FEATURE                 Location/Qualifiers
source                  1..16
                        mol_type = protein
                        note = CDR1
```

-continued

```
                            organism = synthetic construct
SEQUENCE: 97
DYKMDWVKQS HGKSLE                                                      16

SEQ ID NO: 98               moltype = AA  length = 6
FEATURE                     Location/Qualifiers
source                      1..6
                            mol_type = protein
                            note = CDR2
                            organism = synthetic construct
SEQUENCE: 98
NQKFRG                                                                  6

SEQ ID NO: 99               moltype = AA  length = 8
FEATURE                     Location/Qualifiers
source                      1..8
                            mol_type = protein
                            note = CDR3
                            organism = synthetic construct
SEQUENCE: 99
GLWDAMDS                                                                8

SEQ ID NO: 100              moltype = DNA  length = 382
FEATURE                     Location/Qualifiers
source                      1..382
                            mol_type = other DNA
                            note = MF1847: heavy chain variable region sequence of an
                              erbB-2 binding antibody
                            organism = synthetic construct
CDS                         20..382
SEQUENCE: 100
ggcccagccg gccatggccc aggtgcagct ggtggagtct gggggaggcg tggtccagcc        60
tgggaggtcc ctgagactct cctgtgcagc ctctggattc accttcagta gctatggcat       120
gcactgggtc cgccaggctc caggcaaggg gctggagtgg gtggcagtta tatcatatga       180
tggaagtaat aaatactatg cagactccgt gaagggccga ttcaccatct ccagagacaa       240
ttccaagaac acgctgtatc tgcaaatgaa cagcctgaga gctgaggaca cggccgtgta       300
ttactgtgca aaaggttggt ggcatccgct gctgtctggc tttgattatt ggggccaagg       360
taccctggtc accgtctcca gt                                                382

SEQ ID NO: 101              moltype = AA  length = 121
FEATURE                     Location/Qualifiers
source                      1..121
                            mol_type = protein
                            organism = synthetic construct
SEQUENCE: 101
QVQLVESGGG VVQPGRSLRL SCAASGFTFS SYGMHWVRQA PGKGLEWVAV ISYDGSNKYY        60
ADSVKGRFTI SRDNSKNTLY LQMNSLRAED TAVYYCAKGW WHPLLSGFDY WGQGTLVTVS       120
S                                                                      121

SEQ ID NO: 102              moltype = AA  length = 5
FEATURE                     Location/Qualifiers
source                      1..5
                            mol_type = protein
                            note = CDR1
                            organism = synthetic construct
SEQUENCE: 102
SYGMH                                                                   5

SEQ ID NO: 103              moltype = AA  length = 17
FEATURE                     Location/Qualifiers
source                      1..17
                            mol_type = protein
                            note = CDR2
                            organism = synthetic construct
SEQUENCE: 103
VISYDGSNKY YADSVKG                                                     17

SEQ ID NO: 104              moltype = AA  length = 12
FEATURE                     Location/Qualifiers
source                      1..12
                            mol_type = protein
                            note = CDR3
                            organism = synthetic construct
SEQUENCE: 104
GWWHPLLSGF DY                                                          12

SEQ ID NO: 105              moltype = DNA  length = 370
FEATURE                     Location/Qualifiers
source                      1..370
```

```
                            mol_type = other DNA
                            note = MF3001: heavy chain variable region sequence of an
                              erbB-2 binding antibody
                            organism = synthetic construct
CDS                         20..370
SEQUENCE: 105
ggcccagccg gccatggccg aggtccagct gcagcagtct ggggctgaac tggcaaaacc    60
tggggcctca gtgaagctgt cctgcaagac ttctggctac aactttccta tctactggat   120
gcactgggta aaacagaggc ctggacgggg tctggaatgg attggatata ttaatcctag   180
tactggttat attaagaaca atcagaagtt caaggacaag gccaccttga ctgcagacaa   240
atcctccaac acagcctaca tgcagctgaa cagcctgaca tatgaggact ctgcagtcta   300
ttactgtaca agagaaggga taactgggtt tacttactgg ggccaaggga ctctggtcac   360
cgtctccagt                                                          370

SEQ ID NO: 106              moltype = AA  length = 117
FEATURE                     Location/Qualifiers
source                      1..117
                            mol_type = protein
                            organism = synthetic construct
SEQUENCE: 106
EVQLQQSGAE LAKPGASVKL SCKTSGYNFP IYWMHWVKQR PGRGLEWIGY INPSTGYIKN     60
NQKFKDKATL TADKSSNTAY MQLNSLTYED SAVYYCTREG ITGFTYWGQG TLVTVSS      117

SEQ ID NO: 107              moltype = AA  length = 16
FEATURE                     Location/Qualifiers
source                      1..16
                            mol_type = protein
                            note = CDR1
                            organism = synthetic construct
SEQUENCE: 107
IYWMHWVKQR PGRGLE                                                    16

SEQ ID NO: 108              moltype = AA  length = 6
FEATURE                     Location/Qualifiers
source                      1..6
                            mol_type = protein
                            note = CDR2
                            organism = synthetic construct
SEQUENCE: 108
NQKFKD                                                                6

SEQ ID NO: 109              moltype = AA  length = 8
FEATURE                     Location/Qualifiers
source                      1..8
                            mol_type = protein
                            note = CDR3
                            organism = synthetic construct
SEQUENCE: 109
EGITGFTY                                                              8

SEQ ID NO: 110              moltype = DNA  length = 385
FEATURE                     Location/Qualifiers
source                      1..385
                            mol_type = other DNA
                            note = MF1898: heavy chain variable region sequence of an
                              erbB-2 binding antibody
                            organism = synthetic construct
CDS                         20..385
SEQUENCE: 110
ggcccagccg gccatggccc aggtgcagct ggtggagtct ggggaggcg tggtccagcc     60
tgggaggtcc ctgagactct cctgtgcagc ctctggattc accttcagta gctatggcat   120
gcactgggtc cgccaggctc caggcaaggg gctggagtgg gtggcagtta tcatcatga   180
tggaagtaat aaatactatg cagactccgt gaagggccga ttcaccatct ccagagacaa   240
ttccaagaac acgctgtatc tgcaaatgaa cagcctgaga gctgaggaca cggccgtgta   300
ttactgtgca aaagatggtt tccgtcgtac tactctgtct ggctttgatt attggggcca   360
aggtaccctg gtcaccgtct ccagt                                         385

SEQ ID NO: 111              moltype = AA  length = 122
FEATURE                     Location/Qualifiers
source                      1..122
                            mol_type = protein
                            organism = synthetic construct
SEQUENCE: 111
QVQLVESGGG VVQPGRSLRL SCAASGFTFS SYGMHWVRQA PGKGLEWVAV ISYDGSNKYY     60
ADSVKGRFTI SRDNSKNTLY LQMNSLRAED TAVYYCAKDG FRRTTLSGFD YWGQGTLVTV   120
SS                                                                  122

SEQ ID NO: 112              moltype = AA  length = 5
FEATURE                     Location/Qualifiers
```

```
source            1..5
                  mol_type = protein
                  note = CDR1
                  organism = synthetic construct
SEQUENCE: 112
SYGMH                                                                    5

SEQ ID NO: 113    moltype = AA  length = 17
FEATURE           Location/Qualifiers
source            1..17
                  mol_type = protein
                  note = CDR2
                  organism = synthetic construct
SEQUENCE: 113
VISYDGSNKY YADSVKG                                                      17

SEQ ID NO: 114    moltype = AA  length = 13
FEATURE           Location/Qualifiers
source            1..13
                  mol_type = protein
                  note = CDR3
                  organism = synthetic construct
SEQUENCE: 114
DGFRRTTLSG FDY                                                          13

SEQ ID NO: 115    moltype = DNA  length = 379
FEATURE           Location/Qualifiers
source            1..379
                  mol_type = other DNA
                  note = MF3003 heavy chain variable region sequence of an
                   erbB-2 binding antibody
                  organism = synthetic construct
CDS               20..379
SEQUENCE: 115
ggcccagccg gccatggccc aggtgcagct gaagcagtct ggacctgagc tggtgaagcc        60
tggggcctca gtgaagattt cctgcaaggc ttctggcgac gcattcagtt actcctggat       120
gaactgggtg aagcagaggc ctggaaaggg tcttgagtgg attggacgga tttatcctgg       180
agatggagat attaactaca atgggaagtt caagggcaag gccacactga ctgcagacaa       240
atcctccagc acagcccacc tgcaactcaa cagcctgaca tctgaggact ctgcggtcta       300
cttctgtgca agaggacagc tcggactaga ggcctggttt gcttattggg gccaggggac       360
tctggtcacc gtctccagt                                                   379

SEQ ID NO: 116    moltype = AA  length = 120
FEATURE           Location/Qualifiers
source            1..120
                  mol_type = protein
                  organism = synthetic construct
SEQUENCE: 116
QVQLKQSGPE LVKPGASVKI SCKASGDAFS YSWMNWVKQR PGKGLEWIGR IYPGDGDINY        60
NGKFKGKATL TADKSSSTAH LQLNSLTSED SAVYFCARGQ LGLEAWFAYW GQGTLVTVSS       120

SEQ ID NO: 117    moltype = AA  length = 16
FEATURE           Location/Qualifiers
source            1..16
                  mol_type = protein
                  note = CDR1
                  organism = synthetic construct
SEQUENCE: 117
YSWMNWVKQR PGKGLE                                                       16

SEQ ID NO: 118    moltype = AA  length = 6
FEATURE           Location/Qualifiers
source            1..6
                  mol_type = protein
                  note = CDR2
                  organism = synthetic construct
SEQUENCE: 118
NGKFKG                                                                   6

SEQ ID NO: 119    moltype = AA  length = 11
FEATURE           Location/Qualifiers
source            1..11
                  mol_type = protein
                  note = CDR3
                  organism = synthetic construct
SEQUENCE: 119
GQLGLEAWFA Y                                                            11

SEQ ID NO: 120    moltype = DNA  length = 391
```

| FEATURE | Location/Qualifiers |
|---|---|
| source | 1..391<br>mol_type = other DNA<br>note = MF6058: heavy chain variable region sequence of erbB-3 binding antibody<br>organism = synthetic construct |
| CDS | 20..391 |

SEQUENCE: 120

```
gcccagccg gccatggccc aggtgcagct ggtgcagtct ggggctgacg tgaagaagcc    60
tggggcctca gtgaaggtca cgtgcaaggc ttctggatac accttcaccg gctactatat   120
gcactgggtg cgacaggccc ctggacaagc tcttgagtgg atgggatgga tcaaccctca   180
aagtggtggc acaaactatg caaagaagtt cagggcagg gtctctatga ccagggagac    240
gtccacaagc acagcctaca tgcagctgag caggctgaga tctgacgaca cggctacgta   300
ttactgtgca agagatcatg gttctcgtca tttctggtct tactggggct ttgattattg   360
ggggccaaggt accctggtca ccgtctccag t                                 391
```

| SEQ ID NO: 121<br>FEATURE<br>source | moltype = AA length = 124<br>Location/Qualifiers<br>1..124<br>mol_type = protein<br>organism = synthetic construct |
|---|---|

SEQUENCE: 121

```
QVQLVQSGAD VKKPGASVKV TCKASGYTFT GYYMHWVRQA PGQALEWMGW INPQSGGTNY    60
AKKFQGRVSM TRETSTSTAY MQLSRLRSDD TATYYCARDH GSRHFWSYWG FDYWGQGTLV   120
TVSS                                                                124
```

| SEQ ID NO: 122<br>FEATURE<br>source | moltype = AA length = 5<br>Location/Qualifiers<br>1..5<br>mol_type = protein<br>note = CDR1<br>organism = synthetic construct |
|---|---|

SEQUENCE: 122

```
GYYMH                                                                 5
```

| SEQ ID NO: 123<br>FEATURE<br>source | moltype = AA length = 17<br>Location/Qualifiers<br>1..17<br>mol_type = protein<br>note = CDR2<br>organism = synthetic construct |
|---|---|

SEQUENCE: 123

```
WINPQSGGTN YAKKFQG                                                   17
```

| SEQ ID NO: 124<br>FEATURE<br>source | moltype = AA length = 15<br>Location/Qualifiers<br>1..15<br>mol_type = protein<br>note = CDR3<br>organism = synthetic construct |
|---|---|

SEQUENCE: 124

```
DHGSRHFWSY WGFDY                                                     15
```

| SEQ ID NO: 125<br>FEATURE<br>source | moltype = DNA length = 391<br>Location/Qualifiers<br>1..391<br>mol_type = other DNA<br>note = MF6061: heavy chain variable region sequence of an erbB-3 binding antibody<br>organism = synthetic construct |
|---|---|
| CDS | 20..391 |

SEQUENCE: 125

```
gcccagccg gccatggccc aggtgcagct ggtgcagtct ggggctgagg tgaagaagcc    60
tggggcctca gtgaaggtct cctgcaaggc ttctggatac accttcaccg gctactatat   120
gcactgggtg cgacaggccc ctggacaagc gcttgagtgg atgggatgga tcaaccctca   180
gagtggtggc acaaactatg cacagaagtt taagggcagg gtcacgatga ccagggacac   240
gtccaccagc acagcctaca tggagctgag caggctgaga tctgacgaca cggctgtgta   300
ttactgtgca agagatcatg gttctcgtca tttctggtct tactggggct ttgattattg   360
gggccaaggt accctggtca ccgtctccag t                                  391
```

| SEQ ID NO: 126<br>FEATURE<br>source | moltype = AA length = 124<br>Location/Qualifiers<br>1..124<br>mol_type = protein<br>organism = synthetic construct |
|---|---|

SEQUENCE: 126

```
QVQLVQSGAE VKKPGASVKV SCKASGYTFT GYYMHWVRQA PGQGLEWMGW INPQSGGTNY    60
AQKFKGRVTM TRDTSTSTAY MELSRLRSDD TAVYYCARDH GSRHFWSYWG FDYWGQGTLV   120
TVSS                                                                124
```

```
SEQ ID NO: 127          moltype = AA   length = 5
FEATURE                 Location/Qualifiers
source                  1..5
                        mol_type = protein
                        note = CDR1
                        organism = synthetic construct
SEQUENCE: 127
GYYMH                                                                    5

SEQ ID NO: 128          moltype = AA   length = 17
FEATURE                 Location/Qualifiers
source                  1..17
                        mol_type = protein
                        note = CDR2
                        organism = synthetic construct
SEQUENCE: 128
WINPQSGGTN YAQKFKG                                                      17

SEQ ID NO: 129          moltype = AA   length = 15
FEATURE                 Location/Qualifiers
source                  1..15
                        mol_type = protein
                        note = CDR3
                        organism = synthetic construct
SEQUENCE: 129
DHGSRHFWSY WGFDY                                                        15

SEQ ID NO: 130          moltype = DNA   length = 391
FEATURE                 Location/Qualifiers
source                  1..391
                        mol_type = other DNA
                        note = MF6065: heavy chain variable region sequence of an
                         erbB-3 binding antibody
                        organism = synthetic construct
CDS                     20..391
SEQUENCE: 130
ggcccagccg gccatggccc aggtgcagct ggtgcagtct ggggctgagg tgaagaagcc        60
tggggcctca gtgaaggtct cctgcaaggc ttctggatac accttcacct cttactatat       120
gcactgggtg cgacaggccc ctggacaagg gcttgagtgg atgggatgga tcaaccctca       180
gggggggttct acaaactatg cacagaagtt tcagggcagg gtcacgatga ccagggacac       240
gtccaccagc acagtgtaca tggagctgag caggctgaga tctgaggaca cggctgtgta       300
ttactgtgca agagatcatg gttctcgtca tttctggtct tactgggggct ttgattattg       360
gggccaaggt accctggtca ccgtctccag t                                      391

SEQ ID NO: 131          moltype = AA   length = 124
FEATURE                 Location/Qualifiers
source                  1..124
                        mol_type = protein
                        organism = synthetic construct
SEQUENCE: 131
QVQLVQSGAE VKKPGASVKV SCKASGYTFT SYYMHWVRQA PGQGLEWMGW INPQGGSTNY        60
AQKFQGRVTM TRDTSTSTVY MELSRLRSED TAVYYCARDH GSRHFWSYWG FDYWGQGTLV       120
TVSS                                                                   124

SEQ ID NO: 132          moltype = AA   length = 5
FEATURE                 Location/Qualifiers
source                  1..5
                        mol_type = protein
                        note = CDR1
                        organism = synthetic construct
SEQUENCE: 132
SYYMH                                                                    5

SEQ ID NO: 133          moltype = AA   length = 17
FEATURE                 Location/Qualifiers
source                  1..17
                        mol_type = protein
                        note = CDR2
                        organism = synthetic construct
SEQUENCE: 133
WINPQGGSTN YAQKFQG                                                      17

SEQ ID NO: 134          moltype = AA   length = 15
FEATURE                 Location/Qualifiers
source                  1..15
                        mol_type = protein
                        organism = synthetic construct
SEQUENCE: 134
```

-continued

```
DHGSRHFWSY WGFDY                                                   15

SEQ ID NO: 135          moltype = AA  length = 48
FEATURE                 Location/Qualifiers
source                  1..48
                        mol_type = protein
                        note = PG3958 epitope
                        organism = synthetic construct
SEQUENCE: 135
LCYQDTILWK DIFHKNNQLA LTLIDTNRSR ACHPCSPMCK GSRCWGES               48

SEQ ID NO: 136          moltype = DNA  length = 363
FEATURE                 Location/Qualifiers
source                  1..363
                        mol_type = other DNA
                        note = MF6055
                        organism = synthetic construct
CDS                     1..363
SEQUENCE: 136
caggtgcagc tggtgcagtc tggggctgac gtgaagaagc ctggggcctc agtgaaggtc   60
tcctgcaagg cttctggata caccttcacc ggctactata tgcactgggt gcgacaggcc  120
cctggacaag ctcttgagtg gatgggatgg atcaacccct ctagtggtgg cacaaactat  180
gcaaagaagt tcagggcag gtcacgatg accaggaga cgtccacaag cacagcctac     240
atggagctga gcaggctgag atctgacgac acggctacgt attactgtgc aagagatcat  300
ggttctcgtc atttctggtc ttactggggc tttgattatt ggggccaagg taccctggtc  360
acc                                                                363

SEQ ID NO: 137          moltype = AA  length = 121
FEATURE                 Location/Qualifiers
source                  1..121
                        mol_type = protein
                        organism = synthetic construct
SEQUENCE: 137
QVQLVQSGAD VKKPGASVKV SCKASGYTFT GYYMHWVRQA PGQALEWMGW INPSSGGTNY   60
AKKFQGRVTM TRTSTSTAY MELSRLRSDD TATYYCARDH GSRHFWSYWG FDYWGQGTLV   120
T                                                                  121

SEQ ID NO: 138          moltype = DNA  length = 363
FEATURE                 Location/Qualifiers
source                  1..363
                        mol_type = other DNA
                        note = MF6056
                        organism = synthetic construct
CDS                     1..363
SEQUENCE: 138
caggtgcagc tggtgcagtc tggggctgac gtgaagaagc ctggggcctc agtgaaggtc   60
acgtgcaagg cttctggata caccttcacc ggctactata tgcactgggt gcgacaggcc  120
cctggacaag ctcttgagtg gatgggatgg atcaaccctt ctagtggtgg cacaaactat  180
gcaaagaagt tcagggcag gtctctatg accaggaga cgtccacaag cacagcctac     240
atgcagctga gcaggctgag atctgacgac acggctacgt attactgtgc aagagatcat  300
ggttctcgtc atttctggtc ttactggggc tttgattatt ggggccaagg taccctggtc  360
acc                                                                363

SEQ ID NO: 139          moltype = AA  length = 121
FEATURE                 Location/Qualifiers
source                  1..121
                        mol_type = protein
                        organism = synthetic construct
SEQUENCE: 139
QVQLVQSGAD VKKPGASVKV TCKASGYTFT GYYMHWVRQA PGQALEWMGW INPSSGGTNY   60
AKKFQGRVSM TRTSTSTAY MQLSRLRSDD TATYYCARDH GSRHFWSYWG FDYWGQGTLV   120
T                                                                  121

SEQ ID NO: 140          moltype = DNA  length = 363
FEATURE                 Location/Qualifiers
source                  1..363
                        mol_type = other DNA
                        note = MF6057
                        organism = synthetic construct
CDS                     1..363
SEQUENCE: 140
caggtgcagc tggtgcagtc tggggctgat gtgaagaagc ctggggcctc agtgaaggtc   60
acgtgcaagg cttctggata caccttcacc ggctactata tgcactgggt gcgacaggcc  120
cctggacaag gccttgagtg gatgggatgg atcaaccctt cagtggtgg cacaaactat   180
gcacagaagt tcagggcag gtcacgatg accaggaca cgtccatcag cacagcctac     240
atgcagctga gcaggctgag atctgacgac acggctgtgt attactgtgc aagagatcat  300
ggttctcgtc atttctggtc ttactggggc tttgattatt ggggccaagg taccctggtc  360
acc                                                                363
```

```
SEQ ID NO: 141          moltype = AA   length = 121
FEATURE                 Location/Qualifiers
source                  1..121
                        mol_type = protein
                        organism = synthetic construct
SEQUENCE: 141
QVQLVQSGAD VKKPGASVKV TCKASGYTFT GYYMHWVRQA PGQGLEWMGW INPQSGGTNY    60
AQKFQGRVTM TRDTSISTAY MQLSRLRSDD TAVYYCARDH GSRHFWSYWG FDYWGQGTLV   120
T                                                                   121

SEQ ID NO: 142          moltype = DNA   length = 363
FEATURE                 Location/Qualifiers
source                  1..363
                        mol_type = other DNA
                        note = MF6058
                        organism = synthetic construct
CDS                     1..363
SEQUENCE: 142
caggtgcagc tggtgcagtc tggggctgac gtgaagaagc ctggggcctc agtgaaggtc    60
acgtgcaagg cttctggata caccttcacc ggctactata tgcactgggt gcgacaggcc   120
cctggacaag ctcttgagtg gatgggatgg atcaaccctc aaagtggtgg cacaaactat   180
gcaaagaagt tccagggcag ggtctctatg accagggaca cgtccacaca cacagcctac   240
atgcagctga gcaggctgag atctgacgac acggctacgt attactgtgc aagagatcat   300
ggttctcgtc atttctggtc ttactgggc tttgattatt ggggccaagg taccctggtc    360
acc                                                                 363

SEQ ID NO: 143          moltype = AA   length = 121
FEATURE                 Location/Qualifiers
source                  1..121
                        mol_type = protein
                        organism = synthetic construct
SEQUENCE: 143
QVQLVQSGAD VKKPGASVKV TCKASGYTFT GYYMHWVRQA PGQALEWMGW INPQSGGTNY    60
AKKFQGRVSM TRETSTSTAY MQLSRLRSDD TATYYCARDH GSRHFWSYWG FDYWGQGTLV   120
T                                                                   121

SEQ ID NO: 144          moltype = DNA   length = 363
FEATURE                 Location/Qualifiers
source                  1..363
                        mol_type = other DNA
                        note = MF6059
                        organism = synthetic construct
CDS                     1..363
SEQUENCE: 144
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag ggcttgagtg gatgggatgg atcaaccctc gcagtggttc tacaaactat   180
gcacagaagt tccagggcag ggtcacgatg accagggaca cgtccatcag cacagcctac   240
atggagctga gcaggctgag atctgacgac acggctgtgt attactgtgc aagagatcat   300
ggttctcgtc atttctggtc ttactgggc tttgattatt ggggccaagg taccctggtc    360
acc                                                                 363

SEQ ID NO: 145          moltype = AA   length = 121
FEATURE                 Location/Qualifiers
source                  1..121
                        mol_type = protein
                        organism = synthetic construct
SEQUENCE: 145
QVQLVQSGAE VKKPGASVKV SCKASGYTFT GYYMHWVRQA PGQGLEWMGW INPSGSTNY    60
AQKFQGRVTM TRDTSISTAY MELSRLRSDD TAVYYCARDH GSRHFWSYWG FDYWGQGTLV   120
T                                                                   121

SEQ ID NO: 146          moltype = DNA   length = 363
FEATURE                 Location/Qualifiers
source                  1..363
                        mol_type = other DNA
                        note = MF6060
                        organism = synthetic construct
CDS                     1..363
SEQUENCE: 146
caggtgcagc tggtgcagtc tggggctgac gtgaagaagc ctggggcctc agtgaaggtc    60
tcctgcaagg cttctggata caccttcacc ggctactata tgcactgggt gcgacaggcc   120
cctggacaag ctcttgagtg gatgggatgg atcaaccctc aaagtggtgg cacaaactat   180
gcaaagaagt tccagggcag ggtcacgatg accagggaca cgtccacaag cacagcctac   240
atggagctga gcaggctgag atctgacgac acggctacgt attactgtgc aagagatcat   300
ggttctcgtc atttctggtc ttactgggc tttgattatt ggggccaagg taccctggtc    360
acc                                                                 363

SEQ ID NO: 147          moltype = AA   length = 121
```

```
FEATURE                 Location/Qualifiers
source                  1..121
                        mol_type = protein
                        organism = synthetic construct
SEQUENCE: 147
QVQLVQSGAD VKKPGASVKV SCKASGYTFT GYYMHWVRQA PGQALEWMGW INPQSGGTNY   60
AKKFQGRVTM TRETSTSTAY MELSRLRSDD TATYYCARDH GSRHFWSYWG FDYWGQGTLV  120
T                                                                 121

SEQ ID NO: 148          moltype = DNA   length = 363
FEATURE                 Location/Qualifiers
source                  1..363
                        mol_type = other DNA
                        note = MF6061
                        organism = synthetic construct
CDS                     1..363
SEQUENCE: 148
caggtgcagc tggtgcagtc tggggctgag gtgaagaagc ctggggcctc agtgaaggtc   60
tcctgcaagg cttctggata caccttcacc ggctactata tgcactgggt gcgacaggcc  120
cctggacaag ggcttgagtg gatgggatgg atcaaccctc agagtggtgg cacaaactat  180
gcacagaagt ttaagggcag ggtcacgatg accaggaca cgtccaccag cacagcctac   240
atggagctga gcaggctgag atctgacgac acggctgtgt attactgtgc aagagatcat  300
ggttctcgtc atttctggtc ttactggggc tttgattatt ggggccaagg taccctggtc  360
acc                                                               363

SEQ ID NO: 149          moltype = AA   length = 121
FEATURE                 Location/Qualifiers
source                  1..121
                        mol_type = protein
                        organism = synthetic construct
SEQUENCE: 149
QVQLVQSGAE VKKPGASVKV SCKASGYTFT GYYMHWVRQA PGQGLEWMGW INPQSGGTNY   60
AQKFKGRVTM TRDTSTSTAY MELSRLRSDD TAVYYCARDH GSRHFWSYWG FDYWGQGTLV  120
T                                                                 121

SEQ ID NO: 150          moltype = DNA   length = 363
FEATURE                 Location/Qualifiers
source                  1..363
                        mol_type = other DNA
                        note = MF6062
                        organism = synthetic construct
CDS                     1..363
SEQUENCE: 150
caggtgcagc tggtgcagtc tggggctgag gtgaagaagc ctggggcctc agtgaaggtc   60
tcctgcaagg cttctggata caccttcacc ggctactata tgcactgggt gcgacaggcc  120
cctggacaag ggcttgagtg gatgggatgg atcaaccctg cagtggttc tacaaactat   180
gcacagaagt ttcagggcag ggtcacgatg accaggaca cgtccacaag cacagcctac   240
atggagctga gcaggctgag atctgacgac acggctgtgt attactgtgc aagagatcat  300
ggttctcgtc atttctggtc ttactggggc tttgattatt ggggccaagg taccctggtc  360
acc                                                               363

SEQ ID NO: 151          moltype = AA   length = 121
FEATURE                 Location/Qualifiers
source                  1..121
                        mol_type = protein
                        organism = synthetic construct
SEQUENCE: 151
QVQLVQSGAE VKKPGASVKV SCKASGYTFT GYYMHWVRQA PGQGLEWMGW INPGSGSTNY   60
AQKFQGRVTM TRDTSTSTAY MELSRLRSDD TAVYYCARDH GSRHFWSYWG FDYWGQGTLV  120
T                                                                 121

SEQ ID NO: 152          moltype = DNA   length = 363
FEATURE                 Location/Qualifiers
source                  1..363
                        mol_type = other DNA
                        note = MF6063
                        organism = synthetic construct
CDS                     1..363
SEQUENCE: 152
caggtgcagc tggtgcagtc tggggctgag gtgaagaagc ctggggcctc agtgaaggtc   60
tcctgcaagg cttctggata caccttcacc ggctactata tgcactgggt gcgacaggcc  120
cctggacaag ggcttgagtg gatgggatgg atcaaccctc agagtggtgg cacaaactat  180
gcaaagaagt ttcagggcag ggtcacgatg accaggaca cgtccaccag cacagcctac   240
atggagctga gcaggctgag atctgacgac acggctgtgt attactgtgc aagagatcat  300
ggttctcgtc atttctggtc ttactggggc tttgattatt ggggccaagg taccctggtc  360
acc                                                               363

SEQ ID NO: 153          moltype = AA   length = 121
FEATURE                 Location/Qualifiers
```

```
source                  1..121
                        mol_type = protein
                        organism = synthetic construct
SEQUENCE: 153
QVQLVQSGAE VKKPGASVKV SCKASGYTFT GYYMHWVRQA PGQGLEWMGW INPQSGGTNY    60
AKKFQGRVTM TRDTSTSTAY MELSRLRSDD TAVYYCARDH GSRHFWSYWG FDYWGQGTLV   120
T                                                                  121

SEQ ID NO: 154          moltype = DNA  length = 363
FEATURE                 Location/Qualifiers
source                  1..363
                        mol_type = other DNA
                        note = MF6064
                        organism = synthetic construct
CDS                     1..363
SEQUENCE: 154
caggtgcagc tggtgcagtc tggggctgag gtgaagaagc ctggggcctc agtgaaggtc    60
tcctgcaagg cttctggata cacctteacc ggctactata tgcactgggt gcgacaggcc   120
cctggaaagg ggcttgagtg gatgggatgg atcaaccctc agagtggtgg cacaaactat   180
gcacagaagt tccagggcag ggtcacgatg accagggaca cgtccaccag cacagcctac   240
atggagctga gcaggctgag atctgacgac acggctgtgt attactgtgc aagagatcat   300
ggttctcgtc atttctggtc ttactggggc tttgattatt ggggccaagg tacccctggtc   360
acc                                                                363

SEQ ID NO: 155          moltype = AA  length = 121
FEATURE                 Location/Qualifiers
source                  1..121
                        mol_type = protein
                        organism = synthetic construct
SEQUENCE: 155
QVQLVQSGAE VKKPGASVKV SCKASGYTFT GYYMHWVRQA PGKGLEWMGW INPQSGGTNY    60
AQKFQGRVTM TRDTSTSTAY MELSRLRSDD TAVYYCARDH GSRHFWSYWG FDYWGQGTLV   120
T                                                                  121

SEQ ID NO: 156          moltype = DNA  length = 363
FEATURE                 Location/Qualifiers
source                  1..363
                        mol_type = other DNA
                        note = MF6065
                        organism = synthetic construct
CDS                     1..363
SEQUENCE: 156
caggtgcagc tggtgcagtc tggggctgag gtgaagaagc ctggggcctc agtgaaggtc    60
tcctgcaagg cttctggata cacctteacc tcttactata tgcactgggt gcgacaggcc   120
cctggacaag ggcttgagtg gatgggatgg atcaaccctc aggggggttc tacaaactat   180
gcacagaagt tccagggcag ggtcacgatg accagggaca cgtccaccag cacagtgtac   240
atggagctga gcaggctgag atctgaggac acggctgtgt attactgtgc aagagatcat   300
ggttctcgtc atttctggtc ttactggggc tttgattatt ggggccaagg tacccctggtc   360
acc                                                                363

SEQ ID NO: 157          moltype = AA  length = 121
FEATURE                 Location/Qualifiers
source                  1..121
                        mol_type = protein
                        organism = synthetic construct
SEQUENCE: 157
QVQLVQSGAE VKKPGASVKV SCKASGYTFT SYYMHWVRQA PGQGLEWMGW INPQGGSTNY    60
AQKFQGRVTM TRDTSTSTVY MELSRLRSED TAVYYCARDH GSRHFWSYWG FDYWGQGTLV   120
T                                                                  121

SEQ ID NO: 158          moltype = DNA  length = 363
FEATURE                 Location/Qualifiers
source                  1..363
                        mol_type = other DNA
                        note = MF6066
                        organism = synthetic construct
CDS                     1..363
SEQUENCE: 158
caggtgcagc tggtgcagtc tggggctgag gtgaagaagc ctggggcctc agtgaaggtc    60
tcctgcaagg cttctggata cacctteacc ggctactata tgcactgggt gcgacaggcc   120
cctggacaag ggcttgagtg gatgggatgg atcaaccctc agagtggttc tacaaactat   180
gcacagaagt tccagggcag ggtcacgatg accagggaca cgtccaccag cacagcctac   240
atggagctga gctctctgag atctgaggac acggctgtgt attactgtgc aagagatcat   300
ggttctcgtc atttctggtc ttactggggc tttgattatt ggggccaagg tacccctggtc   360
acc                                                                363

SEQ ID NO: 159          moltype = AA  length = 121
FEATURE                 Location/Qualifiers
source                  1..121
```

```
                        mol_type = protein
                        organism = synthetic construct
SEQUENCE: 159
QVQLVQSGAE VKKPGASVKV SCKASGYTFT GYYMHWVRQA PGQGLEWMGW INPQSGSTNY      60
AQKFQGRVTM TRDTSTSTAY MELSSLRSED TAVYYCARDH GSRHFWSYWG FDYWGQGTLV     120
T                                                                     121

SEQ ID NO: 160          moltype = DNA   length = 363
FEATURE                 Location/Qualifiers
source                  1..363
                        mol_type = other DNA
                        note = MF6067
                        organism = synthetic construct
CDS                     1..363
SEQUENCE: 160
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctc agagtggtgg cacaaactat      180
gcacagaagt tccagggcag ggtcacgatg accaggggaca cgtccaccag cacagtctac    240
atggagctga gctctctgag atctgacgac acggctgtgt attactgtgc aagagatcat    300
ggttctcgtc atttctggtc ttactggggc tttgattatt ggggccaagg tacccctgtc    360
acc                                                                   363

SEQ ID NO: 161          moltype = AA   length = 121
FEATURE                 Location/Qualifiers
source                  1..121
                        mol_type = protein
                        organism = synthetic construct
SEQUENCE: 161
QVQLVQSGAE VKKPGASVKV SCKASGYTFT GYYMHWVRQA PGQGLEWMGW INPQSGGTNY      60
AQKFQGRVTM TRDTSTSTVY MELSSLRSDD TAVYYCARDH GSRHFWSYWG FDYWGQGTLV     120
T                                                                     121

SEQ ID NO: 162          moltype = DNA   length = 363
FEATURE                 Location/Qualifiers
source                  1..363
                        mol_type = other DNA
                        note = MF6068
                        organism = synthetic construct
CDS                     1..363
SEQUENCE: 162
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctc agagtggtgg cacaaactat      180
gcacagaagt tccagggcag ggtcacgatg accaggggaca cgtccaccag cacagcctac    240
atggagctga gcaggctgag atctgacgac acggctgtgt attactgtgc aagagatcat    300
ggttctcgtc atttctggtc ttactggggc tttgattatt ggggccaagg tacccctgtc    360
acc                                                                   363

SEQ ID NO: 163          moltype = AA   length = 121
FEATURE                 Location/Qualifiers
source                  1..121
                        mol_type = protein
                        organism = synthetic construct
SEQUENCE: 163
QVQLVQSGAE VKKPGASVKV SCKASGYTFT GYYMHWVRQA PGQGLEWMGW INPQSGGTNY      60
AQKFQGRVTM TRDTSTSTAY MELSRLRSDD TAVYYCARDH GSRHFWSYWG FDYWGQGTLV     120
T                                                                     121

SEQ ID NO: 164          moltype = DNA   length = 363
FEATURE                 Location/Qualifiers
source                  1..363
                        mol_type = other DNA
                        note = MF6069
                        organism = synthetic construct
CDS                     1..363
SEQUENCE: 164
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctc agagtggtgg cacaaactat      180
gcacagaagt tccagggcag ggtcacgatg accaggggaca cgtccatcag cacagcctac    240
atggagctga gcaggctgag atctgacgac acggctgtgt attactgtgc aagagatcat    300
ggttctcgtc atttctggtc ttactggggc tttgattatt ggggccaagg tacccctgtc    360
acc                                                                   363

SEQ ID NO: 165          moltype = AA   length = 121
FEATURE                 Location/Qualifiers
source                  1..121
                        mol_type = protein
```

```
                         organism = synthetic construct
SEQUENCE: 165
QVQLVQSGAE VKKPGASVKV SCKASGYTFT GYYMHWVRQA PGQGLEWMGW INPQSGGTNY      60
AQKFQGRVTM TRDTSISTAY MELSRLRSDD TAVYYCARDH GSRHFWSYWG FDYWGQGTLV     120
T                                                                    121

SEQ ID NO: 166           moltype = DNA   length = 363
FEATURE                  Location/Qualifiers
source                   1..363
                         mol_type = other DNA
                         note = MF6070
                         organism = synthetic construct
CDS                      1..363
SEQUENCE: 166
caggtgcagc tggtgcagtc tggggctgag gtgaagaagc ctggggcctc agtgaaggtc      60
tcctgcaagg cttctggata caccttcacc tcttactata tgcactgggt gcgacaggcc    120
cctggacaag ggcttgagtg gatgggatgg atcaacccct ctgggggttc tacaaactat    180
gcacagaagt tcagggcag gtcacgatg accagggaca cgtccaccag cacagtgtac       240
atggagctga gcaggctgag atctgaggac acggctgtgt attactgtgc aagagatcat    300
ggttctcgtc atttctggtc ttactggggc tttgattatt ggggccaagg taccctggtc    360
acc                                                                  363

SEQ ID NO: 167           moltype = AA   length = 121
FEATURE                  Location/Qualifiers
source                   1..121
                         mol_type = protein
                         organism = synthetic construct
SEQUENCE: 167
QVQLVQSGAE VKKPGASVKV SCKASGYTFT SYYMHWVRQA PGQGLEWMGW INPSGGSTNY      60
AQKFQGRVTM TRDTSTSTVY MELSRLRSED TAVYYCARDH GSRHFWSYWG FDYWGQGTLV     120
T                                                                    121

SEQ ID NO: 168           moltype = DNA   length = 363
FEATURE                  Location/Qualifiers
source                   1..363
                         mol_type = other DNA
                         note = MF6071
                         organism = synthetic construct
CDS                      1..363
SEQUENCE: 168
caggtgcagc tggtgcagtc tggggctgag gtgaagaagc ctggggcctc agtgaaggtc      60
tcctgcaagg cttctggata caccttcacc ggctactata tgcactgggt gcgacaggcc    120
cctggacaag ggcttgagtg gatgggatgg atcaacccct ctagtggttc tacaaactat    180
gcacagaagt tcagggcag gtcacgatg accagggaca cgtccaccag cacagcctac       240
atggagctga gctctctgag atctgaggac acggctgtgt attactgtgc aagagatcat    300
ggttctcgtc atttctggtc ttactggggc tttgattatt ggggccaagg taccctggtc    360
acc                                                                  363

SEQ ID NO: 169           moltype = AA   length = 121
FEATURE                  Location/Qualifiers
source                   1..121
                         mol_type = protein
                         organism = synthetic construct
SEQUENCE: 169
QVQLVQSGAE VKKPGASVKV SCKASGYTFT GYYMHWVRQA PGQGLEWMGW INPSSGSTNY      60
AQKFQGRVTM TRDTSTSTAY MELSSLRSED TAVYYCARDH GSRHFWSYWG FDYWGQGTLV     120
T                                                                    121

SEQ ID NO: 170           moltype = DNA   length = 363
FEATURE                  Location/Qualifiers
source                   1..363
                         mol_type = other DNA
                         note = MF6072
                         organism = synthetic construct
CDS                      1..363
SEQUENCE: 170
caggtgcagc tggtgcagtc tggggctgag gtgaagaagc ctggggcctc agtgaaggtc      60
tcctgcaagg cttctggata caccttcacc ggctactata tgcactgggt gcgacaggcc    120
cctggacaag ggcttgagtg gatgggatgg atcaacccct ctagtggtgg cacaaactat    180
gcacagaagt tcagggcag gtcacgatg accagggaca cgtccaccag cacagtctac       240
atggagctga gctctctgag atctgacgac acggctgtgt attactgtgc aagagatcat    300
ggttctcgtc atttctggtc ttactggggc tttgattatt ggggccaagg taccctggtc    360
acc                                                                  363

SEQ ID NO: 171           moltype = AA   length = 121
FEATURE                  Location/Qualifiers
source                   1..121
                         mol_type = protein
                         organism = synthetic construct
```

```
SEQUENCE: 171
QVQLVQSGAE VKKPGASVKV SCKASGYTFT GYYMHWVRQA PGQGLEWMGW INPSSGGTNY    60
AQKFQGRVTM TRDTSTSTVY MELSSLRSDD TAVYYCARDH GSRHFWSYWG FDYWGQGTLV   120
T                                                                   121

SEQ ID NO: 172          moltype = DNA  length = 363
FEATURE                 Location/Qualifiers
source                  1..363
                        mol_type = other DNA
                        note = MF6073
                        organism = synthetic construct
CDS                     1..363
SEQUENCE: 172
caggtgcagc tggtgcagtc tggggctgag gtgaagaagc ctggggcctc agtgaaggtc    60
tcctgcaagg cttctggata cacccttcacc ggctactata tgcactgggt gcgacaggcc   120
cctggacaag ggcttgagtg gatgggatgg atcaacccctt ctagtggtgg cacaaactat   180
gcacagaagt tcagggcag ggtcacgatg accaggggaca cgtccaccag cacagcctac    240
atggagctga gcaggctgag atctgacgac acggctgtgt attactgtgc aagagatcat    300
ggttctcgtc atttctggtc ttactggggc tttgattatt ggggccaagg tacccctggtc   360
acc                                                                 363

SEQ ID NO: 173          moltype = AA  length = 121
FEATURE                 Location/Qualifiers
source                  1..121
                        mol_type = protein
                        organism = synthetic construct
SEQUENCE: 173
QVQLVQSGAE VKKPGASVKV SCKASGYTFT GYYMHWVRQA PGQGLEWMGW INPSSGGTNY    60
AQKFQGRVTM TRDTSTSTAY MELSRLRSDD TAVYYCARDH GSRHFWSYWG FDYWGQGTLV   120
T                                                                   121

SEQ ID NO: 174          moltype = DNA  length = 363
FEATURE                 Location/Qualifiers
source                  1..363
                        mol_type = other DNA
                        note = MF6074
                        organism = synthetic construct
CDS                     1..363
SEQUENCE: 174
caggtgcagc tggtgcagtc tggggctgag gtgaagaagc ctggggcctc agtgaaggtc    60
tcctgcaagg cttctggata cacccttcacc ggctactata tgcactgggt gcgacaggcc   120
cctggacaag ggcttgagtg gatgggatgg atcaacccctt ctagtggtgg cacaaactat   180
gcacagaagt tcagggcag ggtcacgatg accaggggaca cgtccaccag cacagcctac    240
atggagctga gcaggctgag atctgacgac acggctgtgt attactgtgc aagagatcat    300
ggttctcgtc atttctggtc ttactggggc tttgattatt ggggccaagg tacccctggtc   360
acc                                                                 363

SEQ ID NO: 175          moltype = AA  length = 121
FEATURE                 Location/Qualifiers
source                  1..121
                        mol_type = protein
                        organism = synthetic construct
SEQUENCE: 175
QVQLVQSGAE VKKPGASVKV SCKASGYTFT GYYMHWVRQA PGQGLEWMGW INPSSGGTNY    60
AQKFQGRVTM TRDTSISTAY MELSRLRSDD TAVYYCARDH GSRHFWSYWG FDYWGQGTLV   120
T                                                                   121

SEQ ID NO: 176          moltype = AA  length = 107
FEATURE                 Location/Qualifiers
source                  1..107
                        mol_type = protein
                        note = Common Light Chain Variable Region
                        organism = synthetic construct
SEQUENCE: 176
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPTFGQ GTKVEIK                 107
```